(12) United States Patent
Sakai et al.

(10) Patent No.: US 9,089,139 B2
(45) Date of Patent: Jul. 28, 2015

(54) AGRI-HORTICULTURAL PEST CONTROL COMPOSITIONS COMPRISING 4-(3-BUTYNYL)AMINOPYRIMIDINE DERIVATIVES

(75) Inventors: Masaaki Sakai, Ibaraki, PA (US);
Tomoaki Matsumura, Ibaraki (JP);
Satohiro Midorikawa, Ibaraki (JP);
Takashi Nomoto, Tokyo (JP); Tomoko Muraki, Ibaraki (JP); Ryutaro Katsuki, Ibaraki (JP)

(73) Assignee: SDS Biotech K. K., Tokyo (JP)

( * ) Notice: Subject to any disclaimer, the term of this patent is extended or adjusted under 35 U.S.C. 154(b) by 0 days.

(21) Appl. No.: 13/979,306

(22) PCT Filed: Dec. 27, 2011

(86) PCT No.: PCT/JP2011/080219
§ 371 (c)(1),
(2), (4) Date: Jul. 11, 2013

(87) PCT Pub. No.: WO2012/096129
PCT Pub. Date: Jul. 19, 2012

(65) Prior Publication Data
US 2013/0296271 A1  Nov. 7, 2013

(30) Foreign Application Priority Data
Jan. 14, 2011 (JP) ................... 2011-006485

(51) Int. Cl.
*A61K 31/517* (2006.01)
*A01N 55/00* (2006.01)
(Continued)

(52) U.S. Cl.
CPC ............... *A01N 55/00* (2013.01); *A01N 37/34* (2013.01); *A01N 37/50* (2013.01); *A01N 37/52* (2013.01); *A01N 43/42* (2013.01); *A01N 43/50* (2013.01); *A01N 43/54* (2013.01); *A01N 43/56* (2013.01); *A01N 43/653* (2013.01); *A01N 43/78* (2013.01); *A01N 43/82* (2013.01); *A01N 43/84* (2013.01); *A01N 43/90* (2013.01); *A01N 47/24* (2013.01); *A01N 47/34* (2013.01); *A01N 47/44* (2013.01); *A01N 53/00* (2013.01); *A01N 57/26* (2013.01); *A01N 59/16* (2013.01)

(58) Field of Classification Search
CPC ....... A01N 43/40; A01N 43/42; A01N 43/90; A61K 31/519; A61K 31/538; A61K 31/5383; A61K 31/517
See application file for complete search history.

(56) References Cited

U.S. PATENT DOCUMENTS

2012/0136150 A1* 5/2012 Sakai et al. .................. 544/229

FOREIGN PATENT DOCUMENTS

WO WO 03/076415 9/2003
WO WO 2006/047397 5/2006
(Continued)

OTHER PUBLICATIONS

International Search Report for PCT/JP2011/080219, mailed Mar. 27, 2012, 2 pages.
(Continued)

*Primary Examiner* — Marcos Sznaidman
*Assistant Examiner* — Rayna B Rodriguez
(74) *Attorney, Agent, or Firm* — Swanson & Bratschun, L.L.C.

(57) ABSTRACT

Agri-horticultural pest control compositions having outstanding control effect on pests, in particular, agri-horticultural pests, which comprise as active ingredients one or more 4-(3-butynyl)aminopyrimidine derivatives represented by the general formula [I], namely,

[Formula 1]

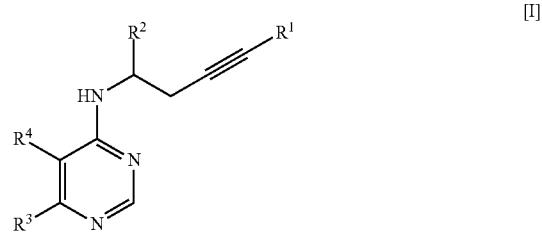

[I]

where $R^1$ is typically selected from among:
a) phenyl
c) —$SiR^5R^6R^7$ ($R^5$, $R^6$, and $R^7$ which may be the same or different represent a linear or branched alkyl having 1-6 carbon atoms, a linear or branched haloalkyl having 1-3 carbon atoms which is substituted by one halogen atom, a linear or branched cyanoalkyl having 1-3 carbon atoms which is substituted by one cyano group, and phenyl);
d) hydropgen atom;
$R^2$ typically represents a hydrogen atom;
$R^3$ typically represents a hydrogen atom;
$R^4$ represents a hydrogen atom
and one or more agri-horticultural pest control compounds selected from among agri-horticultural antimicrobial compounds, say, multi-site contact active compounds, nucleic acids synthesis inhibitory active compounds, mitosis and cell division inhibitory active compounds, and/or agri-horticultural insecticidal, miticidal or nematicidal compounds, say, acetylcholinesterase inhibitors, GABA-gated chloride antagonists, and sodium channel modulators. Since the 4-(3-butynyl)aminopyrimidine derivatives and the existing antimicrobial active compounds and/or insecticidal active compounds are used in admixture, the 4-(3-butynyl)aminopyrimidine derivatives which are useful as pest control agents, particularly as agri-horticultural pest control agents, need be used in smaller amounts and yet their antimicrobial or insecticidal activity can be improved.

6 Claims, No Drawings

(51) Int. Cl.
*A01N 37/34* (2006.01)
*A01N 37/50* (2006.01)
*A01N 37/52* (2006.01)
*A01N 43/42* (2006.01)
*A01N 43/50* (2006.01)
*A01N 43/54* (2006.01)
*A01N 43/56* (2006.01)
*A01N 43/653* (2006.01)
*A01N 43/78* (2006.01)
*A01N 43/84* (2006.01)
*A01N 43/90* (2006.01)
*A01N 47/24* (2006.01)
*A01N 47/34* (2006.01)
*A01N 47/44* (2006.01)
*A01N 43/82* (2006.01)
*A01N 53/00* (2006.01)
*A01N 57/26* (2006.01)
*A01N 59/16* (2006.01)

(56) References Cited

FOREIGN PATENT DOCUMENTS

| WO | WO 2007/046809 | | 4/2007 |
| WO | WO 2007/135029 | | 11/2007 |
| WO | WO 2010/025451 | | 3/2010 |
| WO | WO 2011/007839 A1 | | 1/2011 |
| WO | WO 2011078939 | * | 1/2011 |
| WO | WO 2011/036074 A1 | | 3/2011 |

OTHER PUBLICATIONS

Taylor et al. (1992) Journal of Organic Chemistry 57(11):3218-3225 "Novel 5-Desmethylene Analogues of 5,10-Dideaza-5,6,7,8-tetrahydrofolic Acid as Potential Anticancer Agents".

European Search Report issued Aug. 19, 2014 in EP 11855768.5.

* cited by examiner

AGRI-HORTICULTURAL PEST CONTROL COMPOSITIONS COMPRISING 4-(3-BUTYNYL)AMINOPYRIMIDINE DERIVATIVES

RELATED APPLICATIONS

This application is a 35 U.S.C. §371 national phase application of PCT/JP2011/080219 (WO 2012/096129), filed on Dec. 27, 2011, entitled "4-(3-Butynyl)Aminopyrimidine Derivative-Containing Pest Control Composition for Agricultural or Horticultural Use", which application claims the benefit of JP Patent Application Serial No. 2011-006485, filed Jan. 14, 2011, which are each incorporated herein by reference in their entirety.

TECHNICAL FIELD

The present invention relates to agri-horticultural pest control compositions characterized by comprising one or more 4-(3-butynyl)aminopyrimidine derivatives and agri-horticultural antimicrobial compounds or insecticidal compounds as active ingredients.

BACKGROUND

The chemicals to be used in the present invention which comprise one or more 4-(3-butynyl)aminopyrimidine derivatives in admixture with agri-horticultural antimicrobial compounds or pesticidal compounds are not known in the art. On the other hand, many compounds having agri-horticultural antimicrobial activity (e.g., multi-site contact active compounds, nucleic acids synthesis inhibitory active compounds, mitosis and cell division inhibitory active compounds, succinate dehydrogenase inhibitory active compounds, strobilurin compounds, other electron transport chain inhibitory active compounds, amino acids and protein synthesis inhibitory active compounds, sterol biosynthesis inhibitory active compounds, signal transduction inhibitory active compounds, lipid biosynthesis inhibitory active compounds, cell wall biosynthesis inhibitory active compounds, melanine synthesis inhibitory active compounds, host plant defence inducing compounds, compounds having unknown mode of actions, biocides and other compounds having insecticidal, miticidal or nematicidal activity, such as acetylcholinesterase inhibitors (Carbamates), acetylcholinesterase inhibitors (Organophosphates), GABA-gated chloride antagonists, sodium channel modulators, nicotinic acetylcholine receptor agonists, nicotinic acetylcholine receptor allosteric activators, chloride channel activators, juvenile hormone mimics, multi-site inhibitors, selective homopteran feeding blockers, mite growth inhibitors, microbial disruptors of insect midgut membranes, mitochondrial ATP synthase inhibitory compounds, oxidative phosphorylation decoupling compounds, nicotinic acetylcholine receptor channel blockers, chitin biosynthesis inhibitory compounds, ecdysis/metamorphosis disrupting compounds, octopamine receptor agonistic compounds, electron transport chain inhibitory compounds, mitochondrial complex IV electron transport inhibitors, voltage-dependent sodium channel blockers, acetyl CoA carboxylase inhibitory compounds, ryanodine receptor modulators, and compounds having unknown mode of actions) have been either developed for commercial sale or known by being disclosed in the following non-patent document.

CITATION LIST

Non-Patent Literature

NON-PATENT DOCUMENT 1: Handbook on Agrichemicals, published by the Japan Plant Protection Association, 2009; Directory of Agrichemicals, published by the same Association, 2009; A Comprehensive List of Kumiai Agrichemicals, published by JA ZENNO, 2009; and SHIBUYA INDEX published by JA ZENNO, 2009.

SUMMARY OF INVENTION

Technical Problem

Lots of agri-horticultural antimicrobials, insecticides, miticides, and nematicides are currently used in order to control disease and insect damage on useful crops but their control efficacy is not completely satisfactory. As for major blights such as powdery mildew and aphids, chemical-resistant microorganisms or a population of chemical-resistant individuals that resist antimicrobials or insecticides have spread, making some chemicals unsuitable for use. In order to improve the antimicrobially or insecticidally active abilities of such chemicals, attempts are being made to develop agrichemical preparations by mixing them with other antimicrobial or insecticidal active compounds but in most cases, the result has been either a reduction in the inherent chemical's activity or a mere additive effect. Environmental considerations are also demanding new antimicrobials and insecticides by which pathological microorganisms and harmful insects can be efficiently controlled at lower chemicals doses. Moreover, in order to increase the efficiency of blight and harmful insect control operations, it is also desired to increase the effectiveness of actions, expand the scope of diseases and insects that can be controlled, and prolong the season that is suitable for use. Having solved these problems, the present invention provides agri-horticultural pest control compositions having superior antimicrobial activity and insecticidal activity.

An object of the present invention is to provide agri-horticultural antimicrobial and insecticidal compositions that exhibit superior antimicrobial and insecticidal activities against disease damage to useful crops even if they are applied at low chemicals doses.

Solution to Problem

With a view to inventing agri-horticultural antimicrobial and insecticidal compositions that would display superior blight and harmful insect control effects, the present inventors combined one or more 4-(3-butynyl)aminopyrimidine derivatives of the general formula [I] with one or more agri-horticultural antimicrobial compounds or insecticidal compounds; as a result, they found that the resulting agri-horticultural pest control compositions of the present invention have superior pest control effects due to the synergism far beyond the additive effects of the individual bactericidal active compounds and insecticidal active compounds; the problem of the present invention has thus been solved.

The agri-horticultural pest control compositions of the present invention comprise one or more 4-(3-butynyl)aminopyrimidine derivatives represented by the general formula

[I] and one or more existing agri-horticultural pest control compounds as active ingredients.

[Formula 1]

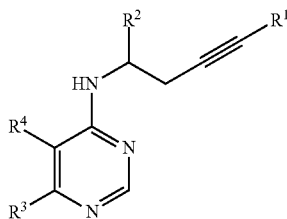

The above-mentioned 4-(3-butynyl)aminopyrimidine derivatives include not only the 4-(3-butynyl)aminopyrimidine derivatives that are represented by the general formula [I] but also their salts (e.g., sodium salt, potassium salt, magnesium salt, calcium salt, and aluminum salt), hydrates, solvates, and substances of crystalline polymorphism. Furthermore, all possible stereoisomers or optical isomers that occur to the compounds of the present invention, as well as mixtures containing two or more of such isomers at any desired ratios are encompassed within the scope of the invention compounds (the 4-(3-butynyl)aminopyrimidine derivatives represented by the formula [I].)

The substituents of various types referred to in the aforementioned compounds [I] are defined as follows.

$R^1$ is a substituent selected from either of the following a) to d):

a) a group having as a bond any ring-forming atom (carbon or hetero atom) that composes a monocyclic or bicyclic ring optionally containing 0-3 hetero atoms, said group being selected from the group consisting of phenyl, benzyl, oxazolyl, isoxazolyl, furyl, benzofuryl, isobenzofuryl, dihydrobenzofuryl, thiazolyl, isothiazolyl, naphthyl, pyrimidinyl, pyrazinyl, quinoxalyl, quinazolyl, pyridyl, quinolyl, isoquinolyl, benzothiazolyl, benzisothiazolyl, pyrrolyl, indolyl, isoindolyl, benzoxazolyl, benzisooxazolyl, thienyl, benzothienyl, imidazolyl, benzimidazolyl, pyrazolyl, and pyridonyl;

b) a linear or branched alkyl having 1-6 carbon atoms, a linear or branched alkenyl having 2-8 carbon atoms, a linear or branched alkynyl having 2-8 carbon atoms, a cycloalkyl having 3-8 carbon atoms, or a cycloalkenyl having 3-8 carbon atoms;

c) —$SiR^5R^6R^7$ (where $R^5$, $R^6$ and $R^7$ are a linear or branched alkyl having 1-6 carbon atoms, a linear or branched haloalkyl having 1-3 carbon atoms which is substituted by one halogen atom, a linear or branched cyanoalkyl having 1-3 carbon atoms which is substituted by one cyano group, and phenyl, provided that two or all of these may be the same substituent or all may be different substituents);

d) a hydrogen atom.

In the case of a) or b), $R^1$ may be substituted by —C(O)OR, —C(O)R, —R, —OR, —SR, —$SO_2R$, —OC(O)R, —C(O)NHR, —C(O)$NR_2$, —$NHSO_2R$, —$NRSO_2R$, —NHR, —$NR_2$, —NHC(O)R, —NRC(O)R, —NHC(O)OR, —NRC(O)OR, —N(OR)C(O)OR, —$NHSO_2R$, —$NRSO_2R$, —$SO_2NHR$, —$SO_2NR_2$ (where R is a linear or branched alkyl having 1-8 carbon atoms, a linear or branched alkenyl having 2-8 carbon atoms, a linear or branched alkynyl having 2-8 carbon atoms, or a cycloalkyl having 3-8 carbon atoms), —$SiR^5R^6R^7$, —$OSiR^5R^6R^7$ (where $R^5$, $R^6$ and $R^7$ are a linear or branched alkyl having 1-6 carbon atoms, a linear or branched haloalkyl having 1-3 carbon atoms which is substituted by one halogen atom, a linear or branched cyanoalkyl having 1-3 carbon atoms which is substituted by one cyano group, and phenyl, provided that two or all of these may be the same substituent or all may be different substituents), haloalkyl (a linear or branched alkyl group having 1-4 carbon atoms which is substituted by 1-9 halogen atoms which may be the same or different), haloalkenyl (a linear or branched alkenyl group having 2-6 carbon atoms which is substituted by 1-4 halogen atoms which may be the same or different), haloalkoxy (a linear or branched alkoxy group having 1-4 carbon atoms which is substituted by 1-9 halogen atoms which may be the same or different), acylalkoxy (a linear or branched alkoxy group having 1-3 carbon atoms which is substituted by one or two acyl groups represented by (a linear or branched aliphatic hydrocarbon group having 1-8 carbon atoms)-CO—), acyloxyalkyl (a linear or branched alkyl group having 1-3 carbon atoms which is substituted by one or two acyloxy groups represented by (a linear or branched aliphatic hydrocarbon group having 1-8 carbon atoms)-CO—O—), alkylsulfonylalkyl (a linear or branched alkyl group having 1-3 carbon atoms which is substituted by one or two linear or branched alkylsulfonyl groups having 1-8 carbon atoms), siloxyalkyl (a linear or branched alkyl group having 1-3 carbon atoms which is substituted by one or two —$OSiR^5R^6R^7$ (where $R^5$, $R^6$ and $R^7$ are a linear or branched alkyl having 1-6 carbon atoms, a linear or branched haloalkyl having 1-3 carbon atoms which is substituted by one halogen atom, a linear or branched cyanoalkyl having 1-3 carbon atoms which is substituted by one cyano group, and phenyl, provided that two or all of these may be the same substituent or all may be different substituents)), hydroxyalkyl (a linear or branched alkyl group having 1-3 carbon atoms which is substituted by one or two hydroxyl groups), alkoxyalkyl (a linear or branched alkyl group having 1-3 carbon atoms which is substituted by one or two linear or branched alkoxy groups having 1-8 carbon atoms), haloalkoxyalkyl (a linear or branched alkyl group having 1-3 carbon atoms which is substituted by one or two linear or branched haloalkoxy groups having 1-4 carbon atoms which are substituted by 1-9 halogen atoms which may be the same or different), alkylthioalkyl (a linear or branched alkyl group having 1-3 carbon atoms which is substituted by one or two linear or branched alkylthio groups having 1-8 carbon atoms), dialkoxyacetal (a dialkoxymethyl group having two linear or branched alkoxy groups with 1-8 carbon atoms substituted on the methyl group), alkoxyalkoxy (a linear or branched alkoxy group having 1-3 carbon atoms which is substituted by one or two linear or branched alkoxy groups having 1-8 carbon atoms), cyanoalkyl (a linear or branched alkyl group having 1-3 carbon atoms which is substituted by one or two cyano groups), halogen, cyano, nitro, amino, hydroxy, pentahalosulfanyl, benzyl, benzyloxy, phenyl, phenoxy, pyridyl, oxazolyl, furyl, thiazolyl, naphthyl, pyrimidinyl, thienyl, benzothiazolyl, benzoxazolyl, benzodioxolyl, imide, formyl (—CHO), carboxyl (—COOH), formamide (—NHCHO), cyclic ether, and cyclic amine.

$R^2$ represents a hydrogen atom, —R, —OR, —C(O)OR, —C(O)NHR, —$CONR_2$ (where R is a linear or branched alkyl having 1-8 carbon atoms, a linear or branched alkenyl having 2-8 carbon atoms, a linear or branched alkynyl having 2-8 carbon atoms, or a cycloalkyl having 3-8 carbon atoms), hydroxyalkyl (a linear or branched alkyl group having 1-3 carbon atoms which is substituted by 1 or 2 hydroxyl groups), alkoxyalkyl (a linear or branched alkyl group having 1-3 carbon atoms which is substituted by 1 or 2 alkoxy groups having 1-8 carbon atoms), haloalkoxyalkyl (a linear or branched alkyl groups having 1-3 carbon atoms which is substituted by 1 or 2 linear or branched haloalkoxy groups having 1-4 carbon atoms which are substituted by 1-9 halogen atoms which may be the same or different), phenyl, heteroaryl, halogen, cyano, haloalkyl (a linear or branched alkyl group having 1-4 carbon atoms which is substituted by 1-9 halogen atoms which may be the same or different), or haloalkoxy (a linear or branched alkoxy group having 1-4 carbon atoms which is substituted by 1-9 halogen atoms which may be the same or different).

$R^3$ represents (1) a hydrogen atom, (2) a halogen atom, (3) an alkyl having 1-6 carbon atoms which is substituted by 1 to 4 acyloxys represented by (a linear or branched aliphatic hydrocarbon group having 1-8 carbon atoms)-CO—O—, 1-13 halogen atoms, or 1-4 hydroxyl groups, (4) an unsubstituted alkyl having 1-6 carbon atoms, (5) —OR, —SR, or —SO$_2$R (where R is a linear or branched alkyl having 1-8 carbon atoms, a linear or branched alkenyl having 2-8 carbon atoms, a linear or branched alkynyl having 2-8 carbon atoms, or a cycloalkyl having 3-8 carbon atoms), or (6) a haloalkyl (a linear or branched alkyl group having 1-4 carbon atoms which is substituted by 1-9 halogen atoms which may be the same or different).

$R^4$ represents a hydrogen atom, a halogen atom, an alkyl having 1-6 carbon atoms, a nitro, an amino, a phenyl, a benzyl or, taken together with $R^3$ and two carbon atoms of the pyrimidine ring, may form a thiophene ring, a pyridine ring, a pyrrole ring, an imidazole ring, a benzene ring, a naphthalene ring, a pyrimidine ring, a furan ring, a pyrazine ring, a pyrazole ring, or an oxazole ring.

Advantageous Effects of Invention

While the 4-(3-butynyl)aminopyrimidine derivatives themselves, which are represented by the general formula [I], exhibit outstanding control effects on pests, namely, all diseases and harmful insects that attack agri-horticultural plants as well as all pathogenic microorganisms that attack agri-horticultural plants, the pest control compositions of the present invention which comprise one or more of the 4-(3-butynyl)aminopyrimidine derivatives of the general formula [I] in admixture with one or more existing agri-horticultural pest control compounds exhibit particularly outstanding synergism, in particular, superb pest control activity.

DESCRIPTION OF EMBODIMENTS

Examples of the monocyclic or bicyclic ring in $R^1$ which optionally contains 0-3 hetero atoms include phenyl, benzyl, oxazolyl, isoxazolyl, furyl, benzofuryl, isobenzofuryl, dihydrobenzofuryl, thiazolyl, isothiazolyl, naphthyl, pyrimidinyl, pyrazinyl, quinoxalyl, quinazolyl, pyridyl, quinolyl, isoquinolyl, benzothiazolyl, benzisothiazolyl, pyrrolyl, indolyl, isoindolyl, benzoxazolyl, benzisooxazolyl, thienyl, benzothienyl, imidazolyl, benzimidazolyl, pyrazolyl, and pyridonyl groups, but phenyl, oxazolyl, thiazolyl, pyridyl and thienyl groups are preferred, with phenyl, pyridyl and thiazolyl groups being further preferred. Exemplary substituents include —C(O)OR, —C(O)R, —R, —OR, —SR, —SO$_2$R, —OC(O)R, —C(O)NHR, —C(O)NR$_2$, —NHSO$_2$R, —NRSO$_2$R, —NHR, —NR$_2$, —NHC(O)R, —NRC(O)R, —NHC(O)OR, —NRC(O)OR, —N(OR)C(O)OR, —NHSO$_2$R, —NRSO$_2$R, —SO$_2$NHR, —SO$_2$NR$_2$ (where R is a linear or branched alkyl having 1-8 carbon atoms, a linear or branched alkenyl having 2-8 carbon atoms, a linear or branched alkynyl having 2-8 carbon atoms, or a cycloalkyl having 3-8 carbon atoms), —SiR$^5$R$^6$R$^7$, —OSiR$^5$R$^6$R$^7$ (where R$^5$, R$^6$ and R$^7$ are a linear or branched alkyl having 1-6 carbon atoms, a linear or branched haloalkyl having 1-3 carbon atoms which is substituted by one halogen atom, a linear or branched cyanoalkyl having 1-3 carbon atoms which is substituted by one cyano group, and phenyl, provided that two or all of these may be the same substituent or all may be different substituents), haloalkyl (a linear or branched alkyl group having 1-4 carbon atoms which is substituted by 1-9 halogen atoms which may be the same or different), haloalkenyl (a linear or branched alkenyl group having 2-6 carbon atoms which is substituted by 1-4 halogen atoms which may be the same or different), haloalkoxy (a linear or branched alkoxy group having 1-4 carbon atoms which is substituted by 1-9 halogen atoms which may be the same or different), acylalkoxy (a linear or branched alkoxy group having 1-3 carbon atoms which is substituted by one or two acyl groups represented by (a linear or branched aliphatic hydrocarbon group having 1-8 carbon atoms)-CO—), acyloxyalkyl (a linear or branched alkyl group having 1-3 carbon atoms which is substituted by one or two acyloxy groups represented by (a linear or branched aliphatic hydrocarbon group having 1-8 carbon atoms)-CO—O—), alkylsulfonylalkyl (a linear or branched alkyl group having 1-3 carbon atoms which is substituted by one or two linear or branched alkylsulfonyl groups having 1-8 carbon atoms), siloxyalkyl (a linear or branched alkyl group having 1-3 carbon atoms which is substituted by one or two —OSiR$^5$R$^6$R$^7$ (where R$^5$, R$^6$ and R$^7$ are a linear or branched alkyl having 1-6 carbon atoms, a linear or branched haloalkyl having 1-3 carbon atoms which is substituted by one halogen atom, a linear or branched cyanoalkyl having 1-3 carbon atoms which is substituted by one cyano group, and phenyl, provided that two or all of these may be the same substituent or all may be different substituents)), hydroxyalkyl (a linear or branched alkyl group having 1-3 carbon atoms which is substituted by one or two hydroxyl groups), alkoxyalkyl (a linear or branched alkyl group having 1-3 carbon atoms which is substituted by one or two linear or branched alkoxy groups having 1-8 carbon atoms), haloalkoxyalkyl (a linear or branched alkyl group having 1-3 carbon atoms which is substituted by one or two linear or branched haloalkoxy groups having 1-4 carbon atoms which are substituted by 1-9 halogen atoms which may be the same or different), alkylthioalkyl (a linear or branched alkyl group having 1-3 carbon atoms which is substituted by one or two linear or branched alkylthio groups having 1-8 carbon atoms), dialkoxyacetal (a dialkoxymethyl group having two linear or branched alkoxy groups with 1-8 carbon atoms substituted on the methyl group), alkoxyalkoxy (a linear or branched alkoxy group having 1-3 carbon atoms which is substituted by one or two linear or branched alkoxy groups having 1-8 carbon atoms), cyanoalkyl (a linear or branched alkyl group having 1-3 carbon atoms which is substituted by one or two cyano groups), halogen, cyano, nitro, amino, hydroxy, pentahalosulfanyl, benzyl, benzyloxy, phenyl, phenoxy, pyridyl, oxazolyl, furyl, thiazoly, naphthyl, pyrimidinyl, thienyl, benzothiazolyl, benzoxazolyl, benzodioxolyl, imide, formyl (—CHO), carboxyl (—COOH), formamide (—NHCHO), cyclic ether, and cyclic amine; preferred are alkyl (e.g., methyl group, ethyl group, n-propyl group, or isopropyl group), alkoxy (e.g., methoxy group, ethoxy group, n-propoxy group, or isopropoxy group), acylalkoxy (e.g., acetylmethoxy group, propionylmethoxy group, or acetylethoxy group), halogen (e.g., fluorine atom, chlorine atom, or bromine atom), cyano, haloalkyl (e.g., monofluoromethyl group, difluoromethyl group, trifluoromethyl group, or heptafluoroisopropyl group), hydroxyalkyl (e.g., hydroxymethyl group or hydrdoxyethyl group), cyanoalkyl (e.g., cyanomethyl group or cyanoethyl group), alkoxyalkyl (e.g., methoxymethoxy group, ethoxymethoxy group, or methoxyethoxy group), haloalkoxyalkyl (e.g., monofluoromethoxymethyl group, difluoromethoxymethyl group, or trifluoromethoxymethyl group), haloalkoxy (e.g., monofluoromethoxy group, difluoromethoxy group, or trifluoromethoxy group), benzyloxy group, and phenoxy group.

Alternatively, $R^1$ may be a linear or branched alkyl having 1-6 carbon atoms, a linear or branched alkenyl having 2-8 carbon atoms, a linear or branched alkynyl having 2-8 carbon atoms, a cycloalkyl having 3-8 carbon atoms, or a cycloalkenyl having 3-8 carbon atoms, and examples include n-butyl group, s-butyl group, t-butyl group, n-hexyl group, 1-propenyl group, 2-propenyl group, and isopropenyl group, with n-butyl group, s-butyl group, t-butyl group, 1-propenyl group, and isopropenyl group being preferred. Exemplary substituents include —C(O)OR, —C(O)R, —R, —OR, —SR, —SO$_2$R, —OC(O)R, —C(O)NHR, —C(O)NR$_2$, —NHSO$_2$R, —NRSO$_2$R, —NHR, —NR$_2$, —NHC(O)R, —NRC(O)R, —NHC(O)OR, —NRC(O)OR, —N(OR)C(O)OR, —NHSO$_2$R, —NRSO$_2$R, —SO$_2$NHR, —SO$_2$NR$_2$ (where R is a linear or branched alkyl having 1-8 carbon atoms, a linear or branched alkenyl having 2-8 carbon atoms, a linear or branched alkynyl having 2-8 carbon atoms, or a cycloalkyl having 3-8 carbon atoms), —SiR$^5$R$^6$R$^7$, —OSiR$^5$R$^6$R$^7$ (where R$^5$, R$^6$ and R$^7$ are a linear or branched alkyl having 1-6 carbon atoms, a linear or branched haloalkyl having 1-3 carbon atoms which is substituted by one halogen atom, a linear or branched cyanoalkyl having 1-3 carbon atoms which is substituted by one cyano group, and phenyl, provided that two or all of these may be the same substituent or all may be different substituents), haloalkyl (a linear or branched alkyl group having 1-4 carbon atoms which is substituted by 1-9 halogen atoms which may be the same or different), haloalkenyl (a linear or branched alkenyl group having 2-6 carbon atoms which is substituted by 1-4 halogen atoms which may be the same or different), haloalkoxy (a linear or branched alkoxy group having 1-4 carbon atoms which is substituted by 1-9 halogen atoms which may be the same or different), acylalkoxy (a linear or branched alkoxy group having 1-3 carbon atoms which is substituted by one or two acyl groups represented by (a linear or branched aliphatic hydrocarbon group having 1-8 carbon atoms)-CO—), acyloxyalkyl (a linear or branched alkyl group having 1-3 carbon atoms which is substituted by one or two acyloxy groups represented by (a linear or branched aliphatic hydrocarbon group having 1-8 carbon atoms)-CO—O—), alkylsulfonylalkyl (a linear or branched alkyl group having 1-3 carbon atoms which is substituted by one or two linear or branched alkylsulfonyl groups having 1-8 carbon atoms), siloxyalkyl (a linear or branched alkyl group having 1-3 carbon atoms which is substituted by one or two —OSiR$^5$R$^6$R$^7$ (where R$^5$, R$^6$ and R$^7$ are a linear or branched alkyl having 1-6 carbon atoms, a linear or branched haloalkyl having 1-3 carbon atoms which is substituted by one halogen atom, a linear or branched cyanoalkyl having 1-3 carbon atoms which is substituted by one cyano group, and phenyl, provided that two or all of these may be the same substituent or all may be different substituents)), hydroxyalkyl (a linear or branched alkyl group having 1-3 carbon atoms which is substituted by one or two hydroxyl groups), alkoxyalkyl (a linear or branched alkyl group having 1-3 carbon atoms which is substituted by one or two linear or branched alkoxy groups having 1-8 carbon atoms), haloalkoxyalkyl (a linear or branched alkyl group having 1-3 carbon atoms which is substituted by one or two linear or branched haloalkoxy groups having 1-4 carbon atoms which are substituted by 1-9 halogen atoms which may be the same or different), alkylthioalkyl (a linear or branched alkyl group having 1-3 carbon atoms which is substituted by one or two linear or branched alkylthio groups having 1-8 carbon atoms), dialkoxyacetal (a dialkoxymethyl group having two linear or branched alkoxy groups with 1-8 carbon atoms substituted on the methyl group), alkoxyalkoxy (a linear or branched alkoxy group having 1-3 carbon atoms which is substituted by one or two linear or branched alkoxy groups having 1-8 carbon atoms), cyanoalkyl (a linear or branched alkyl group having 1-3 carbon atoms which is substituted by one or two cyano groups), halogen, cyano, nitro, amino, hydroxy, pentahalosulfanyl, benzyl, benzyloxy, phenyl, phenoxy, pyridyl, oxazolyl, furyl, thiazolyl, naphthyl, pyrimidinyl, thienyl, benzothiazolyl, benzoxazolyl, benzodioxolyl, imide, formyl (—CHO), carboxyl (—COOH), formamide (—NHCHO), cyclic ether, and cyclic amine; preferred are alkoxycarbonyl (e.g., methoxycarbonyl group or ethoxycarbonyl group), halogen (e.g., fluorine atom, chlorine atom, or bromine atom), cyano, hydroxyalkyl (e.g., hydroxymethyl group or hydroxyethyl group), alkoxyalkyl (e.g., methoxymethyl group, ethoxymethyl group, or methoxyethyl group), haloalkyl (e.g., monofluoromethyl group, difluoromethyl group, trifluoromethyl group, or heptafluoroisopropyl group), haloalkoxy (e.g., monofluoromethoxy group, difluoromethoxy group, or trifluoromethoxy group), haloalkoxyalkyl (e.g., monofluoromethoxymethyl group, difluoromethoxymethyl group, or trifluoromethoxymethyl group), cyanoalkyl (e.g., cyanomethyl group or cyanoethyl group), phenyl group, pyridyl group, furyl group, thiazolyl group, and pyrimidinyl group.

Alternatively, $R^1$ may be —SiR$^5$R$^6$R$^7$ (where R$^5$, R$^6$ and R$^7$ are a linear or branched alkyl having 1-6 carbon atoms, a linear or branched haloalkyl having 1-3 carbon atoms which is substituted by one halogen atom, a linear or branched cyanoalkyl having 1-3 carbon atoms which is substituted by one cyano group, and phenyl, provided that two or all of these may be the same substituent or all may be different substituents) and examples include a trimethylsilyl group, a triethylsilyl group, a triisopropylsilyl group, a t-butyldimethylsilyl group, a t-butyldiphenylsilyl group, a chloromethyldimethylsilyl group, and a cyanopropyldimethylsilyl group, with a trimethylsilyl group and a triethylsilyl group being preferred.

$R^2$ is preferably a hydrogen atom or a cyano group; the linear or branched alkyl having 1-8 carbon atoms is preferably a methyl group or an ethyl group; and the linear or branched alkenyl having 2-8 carbon atoms is preferably an ethynyl group or a propenyl group.

Examples of $R^2$ include —C(O)OR, —C(O)NHR, —CONR$_2$ (where R is a linear or branched alkyl having 1-6 carbon atoms, a linear or branched alkenyl having 2-8 carbon atoms, a linear or branched alkynyl having 2-8 carbon atoms, or a cycloalkyl having 3-8 carbon atoms), a phenyl group, and a heteroaryl group, with a phenyl group being preferred.

Examples of the halogen atom in $R^2$ include a chlorine atom, an iodine atom, a bromie atom, and a fluorine atom, with a chlorine atom and a fluorine atom being preferred.

Examples of the alkoxy group in $R^2$ include a methoxy group, an ethoxy group, a n-propoxy group, and an isopropoxy group, with a methoxy group and an ethoxy group being preferred.

The haloalkyl group in $R^2$ is preferably a monofluoromethyl group, a difluoromethyl group, or a trifluoromethyl group, and the haloalkoxy group in $R^2$ is preferably a monofluoromethoxy group, a difluoromethoxy group, or a trifluoromethoxy group.

Examples of the halogen atom in $R^3$ include a chlorine atom, an iodine atom, a bromie atom, and a fluorine atom, with a chlorine atom, a bromine atom, and an iodine atom being preferred.

Examples of the alkyl in $R^3$ which has 1-6 carbon atoms and is substituted by 1 to 4 acyloxys represented by (a linear or branched aliphatic hydrocarbon group having 1-8 carbon atoms)-CO—O—, 1-13 halogen atoms, or 1-4 hydroxyl groups include a chloromethyl group, a 1-chloroethyl group, a 1-bromoethyl group, a 1-fluoroethyl group, an acetyloxymethyl group, a 1-acetyloxyethyl group, a 1-propionyloxyethyl group, a 1-hydroxyethyl group, etc., with a 1-chloroethyl group, a 1-fluoroethyl group, a 1-acetyloxyethyl group or a 1-hydroxyethyl group being preferred.

Examples of the unsubstituted alkyl having 1-6 carbon atoms in $R^3$ include a methyl group and an ethyl group.

Other examples of $R^3$ include —OR, —SR, and —SO$_2$R (where R is a linear or branched alkyl having 1-8 carbon atoms, a linear or branched alkenyl having 2-8 carbon atoms, a linear or branched alkynyl having 2-8 carbon atoms, or a cycloalkyl having 3-8 carbon atoms), with a methoxy group, an ethoxy group, a methylthio group, and an ethylthio group being preferred.

Examples of the haloalkyl group as $R^3$ include a monofluoromethyl group, a difluoromethyl group, a trifluoromethyl group, a pentafluoroethyl group, a heptafluoropropyl group, and a heptafluoroisopropyl group, with a monofluoromethyl group, a difluoromethyl group, and a trifluoromethyl group being preferred.

Examples of the halogen atom in $R^4$ include a chlorine atom, an iodine atom, a bromine atom, and a fluorine atom, with a chlorine atom, a bromine atom, or an iodine atom being preferred.

Preferred examples of the linear or branched alkyl group having 1-6 carbon atoms in $R^4$ include a methyl group and an ethyl group.

The thiophene ring which $R^4$ may form when taken together with $R^3$ and two carbon atoms of the pyrimidine ring is exemplified by the one having the following formula (IV-1):

[Formula 2]

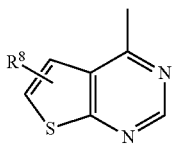

[IV-1]

(where $R^8$ represents a hydrogen atom, a methyl group, a fluorine atom, or a chlorine atom) and a thieno[2,3-d]pyrimidine ring where $R^8$ is a hydrogen atom or a chlorine atom is preferred.

The benzene ring which $R^4$ may form when taken together with $R^3$ and two carbon atoms of the pyrimidine ring is exemplified by the one having the following formula (IV-2):

[Formula 3]

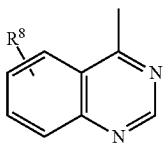

[IV-2]

(where $R^8$ represents a hydrogen atom, a methyl group, a fluorine atom, a chlorine atom, a bromine atom, an iodine atom, a methoxy group, a trifluoromethyl group, a cyano group, a nitro group, a methylthio group, a propargyl group, a propargyloxy group, a benzyl group, a benzyloxy group, a heteroaryl group, or a phenyl group) and a quinazoline ring where $R^8$ is a hydrogen atom, a fluorine atom, or a chlorine atom is preferred.

The term "alkyl" as used herein refers to a linear or branched alkyl group having 1-8 carbon atoms, and examples include a methyl group, ethyl group, n-propyl group, isopropyl group, n-butyl group, isobutyl group, s-butyl group, t-butyl group, n-pentyl group, isopentyl group, neopentyl group, n-hexyl group, n-heptyl group, n-octyl group, etc.

The term "alkenyl" as used herein refers to a linear or branched alkenyl group having 2-8 carbon atoms, and examples include an ethenyl group, 1-propenyl group, 2-propenyl group, isopropenyl group, 1-butenyl group, 2-butenyl group, 3-butenyl group, etc.

The term "alkynyl" as used herein refers to a linear or branched alkynyl group having 2-8 carbon atoms, and examples include an ethynyl group, 2-propynyl group, 2-butynyl group, 3-butynyl group, etc.

The term "cycloalkyl" as used herein refers to a cycloalkyl group having 3-8 carbon atoms, and examples include a cyclopropyl group, cyclobutyl group, cyclopentyl group, and cyclohexyl group.

The term "cycloalkenyl" as used herein refers to a cycloalkenyl group having 3-8 carbon atoms, and examples include a 1-cyclopentyl group, 2-cyclopentyl group, 3-cyclopentyl group, 1-cyclohexyl group, 2-cyclohexyl group, and 3-cyclohexyl group.

The term "hetero atom" as used herein encompasses a nitrogen atom, an oxygen atom, and a sulfur atom.

The term "halogen" as used herein encompasses a fluorine, a chlorine, a bromine, and an iodine.

The term "halo" used herein as a prefix in "halo . . . " (e.g. haloalkyl) encompasses a fluorine, a chlorine, a bromine, and an iodine.

The term "haloalkyl" as used herein refers to a linear or branched alkyl group having 1-4 carbon atoms which are substituted by 1-9 halogen atoms which may be the same or different, and examples include a monofluoromethyl group, monochloromethyl group, monobromomethyl group, difluoromethyl group, trifluoromethyl group, pentafluoroethyl group, n-heptafluoropropyl group, isoheptafluoropropyl group, etc.

The term "haloalkenyl" as used herein refers to a linear or branched alkenyl group having 2-6 carbon atoms which are substituted by 1-4 halogen atoms which may be the same or different, and examples include a 1,2-difluoroethenyl group, 2,2-difluoroethenyl group, 3,3-difluoro-2-propenyl group, etc.

The term "alkoxy" as used herein refers to an (alkyl)-O— group wherein the alkyl moiety has the same meaning as defined above, and examples include a methoxy group, ethoxy group, n-propoxy group, isopropoxy group, n-butoxy group, s-butoxy group, t-butoxy group, etc.

The term "haloalkoxy" as used herein refers to a (haloalkyl)-O— group wherein the haloalkyl moiety has the same meaning as defined above, and examples include a monofluoromethoxy group, difluoromethoxy group, trifluoromethoxy group, 2,2-difluoroethoxy group, 2,2,2-trifluoroethoxy group, etc.

The term "acyl" as used herein either independently or as a prefix in acylalkoxy, acyloxyalkyl, and acyloxy refers to a group represented by (a linear or branched aliphatic hydrocarbon group having 1-8 carbon atoms)-CO—, and examples include an acetyl group, propionyl group, butyryl group, isobutyryl group, etc. It should also be noted that the aliphatic hydrocarbon group as referred to herein means an alkyl, alkenyl, alkynyl, cycloalkyl, cycloalkenyl, and cycloalkynyl.

The term "acylalkoxy" as used herein refers to a linear or branched alkoxy group having 1-3 carbon atoms which is substituted by one or two of the acyl groups mentioned above, and examples include an acetylmethoxy group, acetylethoxy group, acetylpropoxy group, etc.

The term "acyloxy" as used herein refers to a (linear or branched aliphatic hydrocarbon group having 1-8 carbon atoms)-CO—O— group, and examples include an acetoxy group, propionyloxy group, isopropionyloxy group, pivaloyloxy group, etc.

The term "acyloxyalkyl" as used herein refers to a linear or branched alkyl groups having 1-3 carbon atoms which is substituted by one or two of the acyloxy groups mentioned above, and examples include an acetoxymethyl group, acetoxyethyl group, acetoxypropyl group, etc.

The term "alkylsulfonylalkyl" as used herein refers to an (alkyl)-$SO_2$— group wherein the alkyl moiety has the same meaning as defined above, and examples include a methylsulfonyl group, ethylsulfonyl group, n-propylsulfonyl group, isopropylsulfonyl group, etc.

The term "alkylsulfonylalkyl" as used herein refers to a linear or branched alkyl group having 1-3 carbon atoms which is substituted by one or two of the alkylsulfonyl groups mentioned above, and examples include a methylsulfonylmethyl group, methylsulfonylethyl group, methylsulfonylpropyl group, etc.

The term "siloxy" as used herein refers to —$OSiR^5R^6R^7$ (where $R^5$, $R^6$ and $R^7$ are a linear or branched alkyl having 1-6 carbon atoms, a linear or branched haloalkyl having 1-3 carbon atoms which is substituted by one halogen atom, a linear or branched cyanoalkyl having 1-3 carbon atoms which is substituted by one cyano group, and phenyl, provided that two or all of these may be the same substituent or all may be different substituents), and examples include a trimethylsiloxy group, triethylsiloxy group, triisopropylsiloxy group, t-butyldimethylsiloxy group, t-butyldiphenylsiloxy group, etc.

The term "siloxyalkyl" as used herein refers to a linear or branched alkyl group having 1-3 carbon atoms which is substituted by one or two of the siloxy groups mentioned above, and examples include a trimethylsiloxymethyl group, trimethylsiloxyethyl group, trimethylsiloxypropyl group, triethylsiloxymethyl group, t-butyldimethylsiloxymethyl group, etc.

The term "hydroxyalkyl" as used herein refers to a linear or branched alkyl group having 1-3 carbon atoms which is substituted by one or two hydroxyl groups, and examples include a hydroxymethyl group, hydroxyethyl group, hydroxypropyl group, etc.

The term "alkoxyalkyl" as used herein refers to a linear or branched alkyl group having 1-3 carbon atoms which is substituted by one or two of the alkoxy groups mentioned above, and examples include a methoxymethyl group, ethoxymethyl group, propoxymethyl group, isopropoxymethyl group, etc.

The term "alkylthio" as used herein refers to an (alkyl)-S— group wherein the alkyl moiety has the same meaning as defined above, and examples include a methylthio group, ethylthio group, propylthio group, etc.

The term "alkylthioalkyl" as used herein refers to a linear or branched alkyl group having 1-3 carbon atoms which is substituted by one or two of the alkylthio groups mentioned above, and examples include a methylthiomethyl group, ethylthiomethyl group, methylthioethyl group, ethylthioethyl group, etc.

The term "dialkoxyacetal" as used herein refers to a dialkoxymethyl group wherein two of the alkoxy groups mentioned above substitute for the methyl group, and examples include a dimethoxymethyl group, diethoxymethyl group, dipropoxymethyl group, etc.

The term "alkoxyalkoxy" as used herein refers to a linear or branched alkoxy group having 1-3 carbon atoms which is substituted by one or two of the alkoxy groups mentioned above, and examples include a methoxymethoxy group, methoxyethoxy group, methoxypropoxy group, etc.

The term "haloalkoxyalkyl" as used herein refers to a linear or branched alkyl group having 1-3 carbon atoms which is substituted by two or more of the haloalkoxy groups mentioned above, and examples include a monofluoromethoxymethyl group, difluoromethoxymethyl group, trifluoromethoxymethyl group, etc.

The term "cyanoalkyl" as used herein refers to a linear or branched alkyl group having 1-3 carbon atoms which is substituted by one or two cyano groups, and examples include a cyanomethyl group, cyanoethyl group, cyanopropyl group, etc.

The "phenyl", "thienyl", "pyridyl", "oxazolyl", "furanyl", "thiazolyl", "naphthyl", "pyrimidinyl", "benzothiazolyl", "benzoxazolyl", and "benzodioxolyl" as used herein may or may not have one or more substituents which may be the same or different.

The term "phenoxy" as used herein encompasses a phenoxy group having one or more substituents which may be the same or different, as well as an unsubstituted phenoxy group.

The term "benzyl" as used herein encompasses a benzyl group having one or more substituents which may be the same or different, as well as an unsubstituted benzyl group.

The term "benzyloxy" as used herein encompasses a benzyloxy group having one or more substituents which may be the same or different, as well as an unsubstituted benzyloxy group.

The term "propargyl" as used herein emcompasses a propargyl group having a substituent at the end of the alkyne, as well as an unsubstituted propargyl group.

The term "propargyloxy" as used herein encompasses a propargyloxy group having a substituent at the end of the alkyne, as well as an unsubstituted propargyloxy group.

The term "heteroaryl" as used herein encompasses oxazolyl, isoxazolyl, thiazolyl, isothiazolyl, pyrimidinyl, pyrazinyl, quinoxalyl, quinazolyl, quinolyl, isoquinolyl, indolyl, isoindolyl, imidazolyl, pyrazolyl, pyridyl, furyl, thienyl, and pyrrolyl. These groups may or may not have one or more substituents which may be the same or different.

The term "cyclic ether" as used herein encompasses epoxy, oxetane, tetrahydrofuran, tetrahydropyran, dioxolan, and dioxane.

The term "cyclic amine" as used herein encompasses pyrrolidinyl, imidazolidinyl, pyrazolidinyl, piperidinyl, piperazinyl, and morpholinyl.

The term "imide" as used herein encompasses a chained imide and a cyclic imide.

Since the compounds of the present invention which are represented by the formula [I] have an amino group, acid addition salts derived therefrom are also included in the present invention.

Acids that can form acid addition salts include, for example, inorganic acids such as hydrochloric acid, hydrobromic acid, nitric acid, sulfuric acid, and phosphoric acid; carboxylic acids such as formic acid, oxalic acid, fumaric acid, adipic acid, stearic acid, oleic acid, and aconitic acid; sulfonic acids such as methanesulfonic acid, benzenesulfonic acid, and p-toluenesulfonic acid; and saccharin.

Also included in the present invention are respective optical isomers, racemic bodies or mixtures thereof that derive from an asymmetric carbon atom as occurs when $R^2$ in the compound represented by the formula [I] is —R, —OR, —C(O)OR, —C(O)NHR, —CONR$_2$ (where R is a linear or branched alkyl having 1-8 carbon atoms, a linear or branched alkenyl having 2-8 carbon atoms, a linear or branched alkynyl having 2-8 carbon atoms, or a cycloalkyl having 3-8 carbon atoms), hydroxyalkyl (a linear or branched alkyl group having 1-3 carbon atoms which is substituted by 1 or 2 hydroxyl groups), alkoxyalkyl (a linear or branched alkyl group having 1-3 carbon atoms which is substituted by 1 or 2 alkoxy groups having 1-8 carbon atoms), phenyl, heteroaryl, halogen, cyano, haloalkyl (a linear or branched alkyl group having 1-4 carbon atoms which is substituted by 1-9 halogen atoms which may be the same or different), or haloalkoxy (a linear or branched alkoxy group having 1-4 carbon atoms which is substituted by 1-9 halogen atoms which may be the same or different).

Also included in the present invention are respective optical isomers, racemic bodies or mixtures thereof that derive from an asymmetric carbon atom as occurs when $R^3$ in the compound represented by the formula [I] is an alkyl having 1-6 carbon atoms which is substituted by 1 to 4 acyloxys represented by (a linear or branched aliphatic hydrocarbon group having 1-8 carbon atoms)-CO—O—, 1-13 halogen atoms, or 1-4 hydroxyl groups.

The present invention provides agri-horticultural pest control compositions characterized by comprising as active ingredients one or more of the 4-(3-butynyl)aminopyrimidine derivatives described above and one or more of the agri-horticultural antimicrobial compounds or insecticidal compounds described below. The agri-horticultural antimicrobial compounds are exemplified below.

Multi-site contact active compounds: chlorothalonil, dithianon, captan, folpet, iminoctadine albesilate, iminoctadine triacetate, ferbam, nabam, maneb, mancozeb, metiram, propineb, polycarbamate, thiram, ziram, zineb, cupric oxide, copper hydroxide, copper oxychloride, copper sulfate (anhydride), copper sulfate, sulphur, etc.

Nucleic acids synthesis inhibitory active compounds: metalaxyl, metalaxyl-M, oxadixyl, bupirimate, hymexazol, oxolinic acid, etc.

Mitosis and cell division inhibitory active compounds: benomyl, carbendazim, diethofencarb, thiophanate-methyl, zoxamide, pencycuron, fluopicolide, etc.

Succinate dehydrogenase inhibitory active compounds: furametpyr, penthiopyrad, thifluzamide, boscalid, oxycarboxin, carboxin, fluopyram, flutolanil, mepronil, sedaxane, isopyrazam, penflufen, bixafen, fluxapyroxad, etc.

Strobilurin compounds: azoxystrobin, picoxystrobin, kresoxim-methyl, trifloxystrobin, orysastrobin, metominostrobin, pyraclostrobin, famoxadone, fenamidone, pyribencarb, dimoxystrobin, pyrametostrobin, pyraoxystrobin, etc.

Other electron transport chain inhibitory active compounds: diflumetorim, cyazofamid, amisulbrom, meptyl dinocap, fluazinam, ferimzone, etc.

Amino acids and protein synthesis inhibitory active compounds: cyprodinil, mepanipyrim, pyrimethanil, blasticidin-S, streptomycin, kasugamycin, etc.

Sterol biosynthesis inhibitory active compounds: azaconazole, bitertanol, bromuconazole, cyproconazole, difenoconazole, epoxiconazole, fenbuconazole, furconazole, hexaconazole, imibenconazole, metconazole, myclobutanil, penconazole, propiconazole, simeconazole, tebuconazole, triadimefon, triadimenol, triticonazole, imazalil, triflumizole, pefurazoate, prochloraz, fenarimol, fenhexamid, fenpropimorph, piperalin, spiroxamine, etc.

Signal transduction inhibitory active compounds: iprodione, myclozolin, procymidone, vinclozolin, quinoxyfen, fludioxonil, proquinazid, etc.

Lipid biosynthesis inhibitory active compounds: iprobenfos, isoprothiolane, quintozene, propamocarb, prothiocarb, etc.

Cell wall biosynthesis inhibitory active compounds: validamycin, polyoxin B, dimethomorph, iprovalicarb, benthiavalicarb, mandipropamid, flumorph, valifenalate, etc.

Melanine synthesis inhibitory active compounds: pyroquilon, tricyclazole, carpropamid, diclocymet, fenoxanil, etc.

Host plant defence inducing compounds: acibenzolar-5-methyl, probenazole, isotianil, laminarin, etc.

Compounds having unknown mode of actions: cymoxanil, fosetyl-Al, triazoxide, methasulfocarb, flusulfamide, chinomethionat, ethaboxam, cyflufenamid, flutianil, metrafenone, tebufloquin, pyridylamidine, enestroburin, fluopyram, pyriofenone, etc.

The agri-horticultural insecticidal, miticidal, and nematicidal compounds are exemplified below:

Acetylcholinesterase inhibitors (Carbamates): aldicarb, benfuracarb, carbaryl, carbofuran, carbosulfan, fenobucarb, methiocarb, methomyl, oxamyl, thiodicarb, etc.

Acetylcholinesterase inhibitors (Organophosphates): acephate, chlorpyrifos, diazinon, dimethoate, malathion, methamidophos, monocrotophos, parathion-methyl, profenofos, terbufos, imicyafos, etc.

GABA-gated chloride antagonists: endosulfan, ethiprole, fipronil, acetoprole, etc.

Sodium channel modulators: bifenthrin, cypermethrin, esfenvalerate, etofenprox, lambda-cyhalothrin, tefluthrin, DDT, methoxychlor, etc.

Nicotinic acetylcholine receptor agonists: acetamiprid, clothianidin, dinotefuran, imidacloprid, nitenpyram, thiacloprid, thiamethoxam, etc.

Nicotinic acetylcholine receptor allosteric activators: spinetoram, spinosad, etc.

Chloride channel activators: abamectin, emamectin benzoate, milbemectin, lepimectin, etc.

Juvenile hormone mimics: kinoprene, methoprene, fenoxycarb, pyriproxyfen, etc.

Multi-site inhibitors: methyl bromide, chloropicrin, etc.

Selective homopteran feeding blockers: pymetrozine, flonicamid, etc.

Mite growth inhibitors: clofentezine, hexythiazox, etoxazole, etc.

Microbial disruptors of insect midgut membranes: *Bacillus thuringiensis*, etc.

Mitochondrial ATP synthase inhibitory compounds: diafenthiuron, azocyclotin, cyhexatin, fenbutatin oxide, propargite, tetradifon, etc.

Oxidative phosphorylation decoupling compounds: chlorfenapyr, etc.

Nicotinic acetylcholine receptor channel blockers: bensultap, cartap, thiocyclam, etc.

Chitin biosynthesis inhibitory compounds: chlorfluazuron, diflubenzuron, flufenoxuron, hexaflumuron, lufenuron, novaluron, teflubenzuron, triflumuron, buprofezin, bistrifluoron, noviflumuron, etc.

Ecdysis/metamorphosis disrupting compounds: cyromazine, chromafenozide, halofenozide, methoxyfenozide, tebufenozide, etc.

Octopamine receptor agonistic compounds: amitraz, etc.

Electron transport chain inhibitory compounds: fenazaquin, fenpyroximate, pyrimidifen, pyridaben, tebufenpyrad, tolfenpyrad, rotenone, hydramethylnon, acequinocyl, etc.

Mitochondrial complex IV electron transport inhibitors: Aluminium phosphide, etc.

Voltage-dependent sodium channel blockers: indoxacarb, metaflumizone, etc.

Acetyl CoA carboxylase inhibitory compounds: spirodiclofen, spiromesifen, spirotetramat, etc.

Ryanodine receptor modulators: chlorantraniliprole, flubendiamide, cyantraniliprol, etc.

Compounds having unknown mode of actions: azadirachtin, benzoximate, bifenazate, chinomethionat, dicofol, pyridalyl, pyrifluquinazon, fluensulfone, etc.

The 4-(3-butynyl)aminopyrimidine derivatives represented by the general formula [I] show superior control activity against pests. The term "pests" as used herein embrace all pathogenic microorganisms on agri-horticultural plants, as well as all harmful insects, mites, etc. on agri-horticultural plants.

(Pathogenic Microorganisms on Agri-Horticultgural Plants)

Examples of pathogenic microorganisms on agri-horticultgural plants include oomycetes, ascomycetes, deuteromycetes, basidiomycetes, and bacteria; plant disease damage caused by these pathogenic microorganisms can be controlled by agri-horticultural pest control compositions that contain the 4-(3-butynyl)aminopyrimidine derivatives that are used in the present invention. Listed below are the names of specific, but by no means limiting, examples of microorganisms.

Examples of pathogenic microorganisms undesirable for agri-horticultural purposes include: *Pyricularia oryzae, Cochliobolus miyabeanus, Rhizoctonia solani, Gibberella fujikuroi, Erysiphe graminis* f. sp. *tritici, Erysiphe graminis* f. sp. *hordei, Pseudocercosporella herpotrichoides, puccinia graminis, Colletotrichum graminicola, Septoria tritici, Phynchosporium secalis* f. sp. *hordei, Phytophthora infestans, Alternaria solani, Colletotrichum atramentarium, Thanatephorus cucumeris, Botrytis cinerea, Erysiphe pisi, Cercospora canescens, Sclerotinia sclerotiorum, Colletotrichum phaseolorum, Colletotrichum lindemuthianumn, Colletotrichum truncatum, Cercospora kikuchii, Phakopsora pachyrhizi, Gloeosporium conjac, Septoria perillae, Colletotrichum theae-sinensis, Cercospora beticola, Colletotrichum spinaciae, Peronospora effusa, Alternaria brassicae, Alternaria brassicicola, Xanthomonas campestris* pv. *campestris, Erwinia carotovora* sub. sp. *carotovora, Colletotrichum higginsianum, Alternaria cucumerina, Pseudoperonospora cubensis, Sphaerotheca fuliginea, Phytophthora melonis, Corynespora cassiicola, Colletotrichum lagenarium, Fusarium oxysporum* f. sp. *cucumerinum, Pythium cucurbitacearum, Phomopsis* sp., *Pseudomonas syringae, Sphaerotheca fuliginea, Phytophthora cryptogea, Colletotrichum orbiculare, Fusarium oxysporum* f. sp. *melonis, Fusarium oxysporum, Puccinia cnici-oleracei, Gloeosporium chrysanthemi* (or *Gloeosporium carthami*), *Fusarium avenaceum, Erysiphe heraclei, Sclerotinia intermedia, Alternaria dauci, Alternaria radicina, Oidiopsis sicula, Phytophthora capsici, Colletotrichum capsici, Fusarium oxysporum* f. sp. *lycopersici, Fulvia fulva, Thanatephorus cucumeris, Alternaria solani, Verticillium dahliae, Sphaerotheca aphanis, Phytophthora nicotianae* var. *parasitica, Pythium ultimum* var. *ultimum, Alternaria alternata, Mycosphaerella fragariae, Colletotrichum acutatum, Glomerella cingulata, Cercospora asparagi, Phomopsis asparagi, Puccinia asparagi-lucidi, Colletotrichum gloeosporioides, Phytophthora nicotianae, Cladosporium allii-cepae, Fusarium oxysporum* f. sp. *cepae, Septoria alliacea, Alternaria porri, Puccinia allii, Puccinia allii, Botrytis squamosa, Phytophthora porri, Colletotrichum circinans, Botrytis allii, Pleospora herbarum, Peronospora destructor, Botrytis byssoidea, Mycosphaerella allicina, Ciborinia allii, Colletotrichum circinans, Peronospora destructor, Phyllactinia kakicola, Colletotrichum* ssp. (or *Glomerella* sp.), *Cercospora kakivora, Cercospora kaki, Macrophoma kaki, Fusicladium levieri, Phoma kakivora, Cercospora fuliginosa, Physalospora kaki, Aureobasidium pullulans* (or *Capnophaeum fuliginodes, Cladosporium herbarum, Microxyphium* sp., *Scorias communis,* or *Tripospermum juglandis*), *Zygophiala jamaicensis, Gloeosporium kaki, Pestalotia diospyri, Glomerella cingulata, Mycosphaerella nawae, Podosphaera tridactyla* (or *Sphaerotheca pannosa*), *Botryosphaeria dothidea, Cladosporium carpophilum, Leucotelium prunipersicae, Rosellinia necatrix, Fusarium lateritium, Pseudocercospora circumscissa, Sphaceloma pruni-domesticae, Monilinia fructicola* (or *Monilinia laxa*), *Glomerella mume, Rhizopus nigricans, Phyllactinia mali, Phytophthora cactorum* (or *phytophthora syringae*), *Venturia pirina, Gymnosporangium asiaticum, Phyllactinia pyri, Venturia nashicola, Alternaria kikuchiana, Leptothyrium pomi, Physalospora piricola, Fusarium oxysporum* (or *Gibberella zeae*), *Stenella* sp., *Pseudocercospora circumscissa, Phyllosticta persicae, Gloeosporium laeticolor, Phomopsis* sp., *Gymnosporangium yamadae, Podosphaera leucotricha, Phytophthora cactorum* (or *phytophthora cambivora,* or *Phytophthora syringae*), *Diplocarpon mali, Cristulariella moricola, Venturia inaequalis, Zygophiala jamaicensis, Alternaria mali, Uncinula necator, Pseudocercospora vitis, Briosia ampelophaga, Elsinoe ampelina, Phyllosticta ampelicida, Phomopsis viticola, Plasmopara viticola, Capnodium salicinum, Morenoella quercina, Microsphaera alphitoides, Monochaetia monochaeta, Phytophthora citrophthora, Diaporthe citri, Mycosphaerella citri* (or *Mycosphaerella horii*), *Elsinoe fawcettii, Mycosphaerella pinodes,* etc.

(Harmful Insects, Mites, Etc. On Agri-Horticultural Plants)

Examples of harmful insects, mites, etc. on agri-horticultural plants include Hemiptera, Thysanoptera, Lepidoptera, Acari, and so forth; plant disease damage caused by these harmful insects, mites, etc. can be controlled by the 4-(3-butynyl)aminopyrimidine derivatives that are used in the present invention. Listed below are specific, but by no means limiting, examples of harmful insects, mites, etc.

Harmful insects, mites, etc. typically include: harmful insects of the order Lepidoptera, such as *Plutella xylostella, Agrotis ipsilon, Agrotis segetum, Helicoverpa armigera, Helicoverpa assulta, Helicoverpa zea, Heliothis virescens, Mamestra brassicae, Naranga aenescens, Autographa nigrisigna, Mythimna separata Spodoptera exigua, Spodoptera litura, Spodoptera littoralis, Spodoptera frugiperda, Spodoptera eridania, Manduca sexta, Endopiza viteana, Lyonetia prunifoliella malinella, Phyllonorycter ringoniella, Phyllocnistis citrella, Pectinophora gossypiella, Carposina sasakii, Adoxophyes orana fasciata, Adoxophyes honmai, Homona magnanima, Cydia pomonella, Grapholita molesta, Chilo suppressalis, Cnaphalocrocis medinalis, Hellula undalis, Ostrinia nubilalis, Pseudoplusia includens, Trichoplusia ni, Hyphantria cunea, Pieris rapae crucivora,* and *Parnara guttata;* harmful insects of the order Coleoptera, such as *Anomala cuprea, Anomala rufocuprea, Popillia japonica, Leptinotarsa decemlineata, Epilachna varivestis, Melanotus tamsuyensis, Lasioderma serricorne, Epuraea domina, Henosepilachna vigintioctopunctata, Tenebrio molitor, Tribolium castaneum, Anoplophora malasiaca, Monochamus alternatus, Callosobruchus chinensis, Aulacophora* femoralis, Oulema oryzae, Phyllotreta striolata, Cylas formicarius, Anthonomus grandis, Echinocnemus bipunctatus, Hypera postica, Lissorhoptrus oryzophilus, Sitophilus zeamais, Sphenophrus venatus vestitus, Sitophilus granarius, Diabrotica undecimpunctata, Diabrotica virgifera, Diabrotica barberi, and Paederus fuscipes; harmful insects of the order Hemiptera, such as Eurydema rugosum, Eysarcoris ventralis, Halyomorpha halys, Nezara viridula, Leptocorisa chinensis, Riptortus clavatus, Togo hemipterus, Stephanitis pyrioides, Epiacanthus stramineus, Empoasca onukii, Empoasca fabae, Nephotettix cincticeps, Laodelphax striatella, Nilaparvata lugens, Sogatella furcifera, Diaphorina citri, Cacopsylla pyrisuga, Bemisia tabaci, Bemisia argentifolii, Dialeurodes citri, Trialeurodes vaporariorum, Aphis gossypii, Aphis spiraecola, Myzus persicae, Drosicha corpulenta, Icerya purchasi, Planococcus citri, Pseudococcus comstocki, Ceroplastes rubens, Unaspis yanonensis, and Cimex lectularius; harmful insects of the order Thysanoptera, such as Frankliniella occidentalis, Frankliniella intonsa, Scirtothrips dorsalis, Thrips palmi, and Thrips tabaci; harmful insects of the order Diptera, such as Dacus dorsalis, Dacus cucurbitae, Ceratitis capitata, Hydrellia griseola, Liriomyza bryoniae, Liriomyza trifolii, Delia platura, Rhagoletis pomonella, Mayetiola destructor, Musca domestica, Stomoxys calcitrans, Melophagus ovinus, Hypoderma lineatum, Hypoderma bovis, Oestrus ovis, Glossina palpalis (or Glossina morsitans), Prosimulium yezoensis, Tabanus trigonus, Telmatoscopus albipunctatus, Leptoconops nipponensis, Culex pipiens pallens, Aedes albopictus, Aedes aegypti, and Anopheles hyracanus sinensis; harmful insects of the order Hymenoptera, such as Apethymus kuri, Athalia rosae ruficornis, Neodiprion sertifer, Eciton burchelli (or Eciton schmitti), Camponotus japonicus, Vespa mandarinia, Myrmecia spp., Solenopsis spp., and Monomorium pharaonis; harmful insects of the order Blattodea, such as Periplaneta fuliginosa, Periplaneta japonica, and Blattella germanica; harmful insects of the order Orthoptera, such as Teleogryllus emma, Gryllotalpa orientalis, Locusta migratoria, Oxya yezoensis, and Schistocerca gregaria; harmful insects of the order Isoptera, such as Coptotermes formosanus, Reticulitermes speratus, and Odontotermes formosanus; harmful insects of the order Siphonaptera, such as Ctenocephalides felis, Pulex irritans, and Xenopsylla cheopis; harmful insects of the order Mallophaga, such as Menacanthus stramineus and Bovicola bovis; and harmful insects of the order Phthiraptera, such as Haematopinus eurysternus, Haematopinus suis, Linognathus vituli, and Solenopotes capillatus. Harmful insects of the order Acari include spider mites such as Panonychus citri, Panonychus ulmi, Tetranychus kanzawai, and Tetranychus urticae; gall mites such as Acaphylla theae, Aculops pelekassi, Eriophyes chibaensis, and Aceria tulipae; Tarsonemidae such as Polyphagotarsonemus latus and Steneotarsonemus pallidus; Astigmatae such as Tyrophagus putrescentiae and Rhizoglyphus robini; bee mites such as Varroa jacobsoni; ticks such as Boophilus microplus and Haemaphysalis longicornis; Psoroptidae such as Psoroptes ovis; Sarcoptidae such as Sarcoptes scabiei. Other harmful insects include crustaceans such as Armadillidium vulgare; nematodes such as Pratylenchus penetrans, Pratylenchus vulnus, Globodera rostochiensis, Heterodera glycines, Meloidogyne hapla, Meloidogyne incognita, and Bursaphelenchus xylophilus; and mollusks such as Pomacea canaliculata, Meghimatium bilineatum, Acusta despecta sieboldiana, and Euhadra peliomphala.

Hereinbelow, specific examples of the compounds to be used in the present invention which are represented by the general formula [I] are listed in Tables 1-1 to 1-72, and NMR spectral data for the compounds listed in Tables 1-1 to 1-72 are shown in Tables 2-1 to 2-25; the compounds to be used in the present invention are by no means limited to those listed in Tables 1-1 to 1-72. The compound numbers given in those tables will be referenced in the following description.

TABLE 1-1

| Compound No. | Structure | Physical property |
|---|---|---|
| 1 | 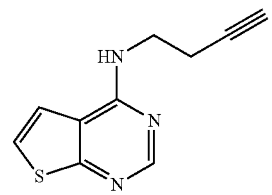 | m.p. 117~119° C. |
| 2 | 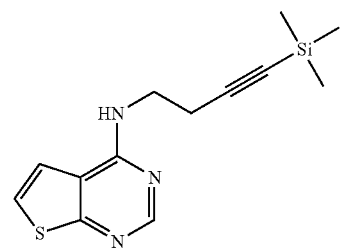 [SMILES: C[Si](C)(C)C#CCCNc1ncnc2sccc12] | m.p. 144~146° C. |
| 3 | 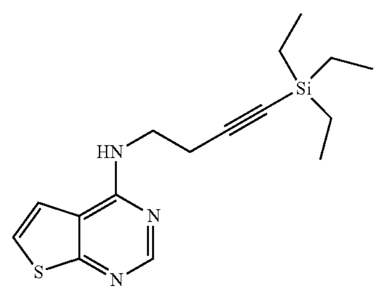 [SMILES: CC[Si](C#CCCNc1ncnc2sccc12)(CC)CC] | m.p. 152~154° C. |
| 4 | 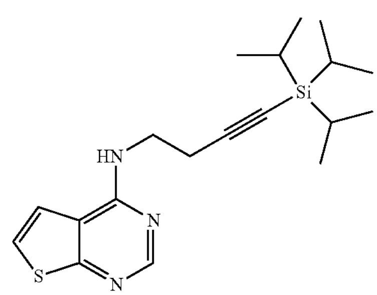 [SMILES: CC(C)[Si](C#CCCNc1ncnc2sccc12)(C(C)C)C(C)C] | m.p. 196~198° C. |
| 5 | 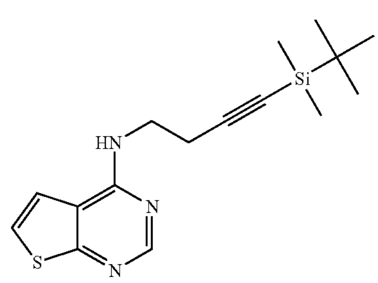 [SMILES: CC(C)(C)[Si](C)(C)C#CCCNc1ncnc2sccc12] | m.p. 190~192° C. |

TABLE 1-1-continued

| Compound No. | Structure | Physical property |
|---|---|---|
| 6 | HN-CH₂CH₂-C≡C-n-C₄H₉ attached to thieno[2,3-d]pyrimidin-4-yl | m.p. 66~68° C. |

TABLE 1-2

| Compound No. | Structure | Physical property |
|---|---|---|
| 7 | HN-CH₂CH₂-C≡C-CH(CH₃)₂ attached to thieno[2,3-d]pyrimidin-4-yl (isobutyl terminus) | m.p. 94~95° C. |
| 8 | HN-CH₂CH₂-C≡C-C(CH₃)₃ attached to thieno[2,3-d]pyrimidin-4-yl | m.p. 146~147° C. |
| 9 | HN-CH₂CH₂-C≡C-CH₂-Ph attached to thieno[2,3-d]pyrimidin-4-yl | m.p. 90~92° C. |
| 10 | HN-CH₂CH₂-C≡C-Ph attached to thieno[2,3-d]pyrimidin-4-yl | m.p. 129~132° C. |

TABLE 1-2-continued

| Compound No. | Structure | Physical property |
|---|---|---|
| 11 | HN-CH₂CH₂-C≡C-(2-F-C₆H₄) attached to thieno[2,3-d]pyrimidin-4-yl | m.p. 141~144° C. |
| 12 | HN-CH₂CH₂-C≡C-(3-F-C₆H₄) attached to thieno[2,3-d]pyrimidin-4-yl | m.p. 118~122° C. |

TABLE 1-3

| Compound No. | Structure | Physical property |
|---|---|---|
| 13 | HN-CH₂CH₂-C≡C-(4-F-C₆H₄) attached to thieno[2,3-d]pyrimidin-4-yl | m.p. 147~149° C. |
| 14 | HN-CH₂CH₂-C≡C-(2-Cl-C₆H₄) attached to thieno[2,3-d]pyrimidin-4-yl | m.p. 145~147° C. |
| 15 | HN-CH₂CH₂-C≡C-(3-Cl-C₆H₄) attached to thieno[2,3-d]pyrimidin-4-yl | m.p. 131~135° C. |

TABLE 1-3-continued

| Compound No. | Structure | Physical property |
|---|---|---|
| 16 | (thieno[2,3-d]pyrimidin-4-yl)-NH-CH₂CH₂-C≡C-(4-Cl-C₆H₄) | m.p. 130~132° C. |
| 17 | (thieno[2,3-d]pyrimidin-4-yl)-NH-CH₂CH₂-C≡C-(2-Me-C₆H₄) | Oily product |
| 18 | (thieno[2,3-d]pyrimidin-4-yl)-NH-CH₂CH₂-C≡C-(3-Me-C₆H₄) | m.p. 120~123° C. |

TABLE 1-4

| Compound No. | Structure | Physical property |
|---|---|---|
| 19 | (thieno[2,3-d]pyrimidin-4-yl)-NH-CH₂CH₂-C≡C-(4-Me-C₆H₄) | m.p. 125~127° C. |
| 20 | (thieno[2,3-d]pyrimidin-4-yl)-NH-CH₂CH₂-C≡C-(4-tBu-C₆H₄) | Resinoid product |
| 21 | (thieno[2,3-d]pyrimidin-4-yl)-NH-CH₂CH₂-C≡C-(2-OMe-C₆H₄) | m.p. 127~129° C. |
| 22 | (thieno[2,3-d]pyrimidin-4-yl)-NH-CH₂CH₂-C≡C-(3-OMe-C₆H₄) | m.p. 141~143° C. |
| 23 | (thieno[2,3-d]pyrimidin-4-yl)-NH-CH₂CH₂-C≡C-(4-OMe-C₆H₄) | Resinoid product |
| 24 | (thieno[2,3-d]pyrimidin-4-yl)-NH-CH₂CH₂-C≡C-(3,4-diOMe-C₆H₃) | m.p. 182~184° C. |

TABLE 1-5

| Compound No. | Structure | Physical property |
|---|---|---|
| 25 | (thieno[2,3-d]pyrimidin-4-yl)-NH-CH₂CH₂-C≡C-(2-CF₃-C₆H₄) | m.p. 116~117° C. |

TABLE 1-5-continued

| Compound No. | Structure | Physical property |
|---|---|---|
| 26 | (thieno[2,3-d]pyrimidin-4-yl)HN-CH2CH2-C≡C-(3-CF3-C6H4) | m.p. 123~125° C. |
| 27 | (thieno[2,3-d]pyrimidin-4-yl)HN-CH2CH2-C≡C-(4-CF3-C6H4) | m.p. 129~134° C. |
| 28 | (thieno[2,3-d]pyrimidin-4-yl)HN-CH2CH2-C≡C-(3,5-(CF3)2-C6H3) | m.p. 163~166° C. |
| 29 | (thieno[2,3-d]pyrimidin-4-yl)HN-CH2CH2-C≡C-(2-CO2Me-C6H4) | m.p. 113~114° C. |
| 30 | (thieno[2,3-d]pyrimidin-4-yl)HN-CH2CH2-C≡C-(3-CO2Me-C6H4) | m.p. 163~166° C. |

TABLE 1-6

| Compound No. | Structure | Physical property |
|---|---|---|
| 31 | (thieno[2,3-d]pyrimidin-4-yl)HN-CH2CH2-C≡C-(4-CO2Me-C6H4) | m.p. 145~146° C. |
| 32 | (thieno[2,3-d]pyrimidin-4-yl)HN-CH2CH2-C≡C-(2-OCF3-C6H4) | m.p. 81~83° C. |
| 33 | (thieno[2,3-d]pyrimidin-4-yl)HN-CH2CH2-C≡C-(3-OCF3-C6H4) | m.p. 98~101° C. |
| 34 | (thieno[2,3-d]pyrimidin-4-yl)HN-CH2CH2-C≡C-(4-OCF3-C6H4) | m.p. 96~99° C. |
| 35 | (thieno[2,3-d]pyrimidin-4-yl)HN-CH2CH2-C≡C-(2-CN-C6H4) | m.p. 197~198° C. |
| 36 | (thieno[2,3-d]pyrimidin-4-yl)HN-CH2CH2-C≡C-(3-CN-C6H4) | m.p. 187~188° C. |

TABLE 1-7

| Compound No. | Structure | Physical property |
|---|---|---|
| 37 | (thieno[2,3-d]pyrimidin-4-yl)HN-CH₂CH₂-C≡C-C₆H₄-CN (para) | m.p. 173~174° C. |
| 38 | (thieno[2,3-d]pyrimidin-4-yl)HN-CH₂CH₂-C≡C-C₆H₄-NO₂ (ortho) | m.p. 162~163° C. |
| 39 | (thieno[2,3-d]pyrimidin-4-yl)HN-CH₂CH₂-C≡C-C₆H₄-NO₂ (meta) | m.p. 171~172° C. |
| 40 | (thieno[2,3-d]pyrimidin-4-yl)HN-CH₂CH₂-C≡C-C₆H₄-NO₂ (para) | m.p. 184~185° C. |
| 41 | (thieno[2,3-d]pyrimidin-4-yl)HN-CH₂CH₂-C≡C-C₆H₃(2,4-F₂) | m.p. 177~178° C. |

TABLE 1-7-continued

| Compound No. | Structure | Physical property |
|---|---|---|
| 42 | (thieno[2,3-d]pyrimidin-4-yl)HN-CH₂CH₂-C≡C-C₆H₃(2,6-F₂) | m.p. 179~181° C. |

TABLE 1-8

| Compound No. | Structure | Physical property |
|---|---|---|
| 43 | (thieno[2,3-d]pyrimidin-4-yl)HN-CH₂CH₂-C≡C-C₆H₂(3,4,5-F₃) | m.p. 158~159° C. |
| 44 | (thieno[2,3-d]pyrimidin-4-yl)HN-CH₂CH₂-C≡C-C₆H₄-CH₂OH (ortho) | m.p. 131~132° C. |
| 45 | (thieno[2,3-d]pyrimidin-4-yl)HN-CH₂CH₂-C≡C-C₆H₄-CH₂OMe (ortho) | Resinoid product |
| 46 | (thieno[2,3-d]pyrimidin-4-yl)HN-CH₂CH₂-C≡C-C₆H₄-CH₂OEt (ortho) | Oily product |

TABLE 1-8-continued

| Compound No. | Structure | Physical property |
|---|---|---|
| 47 | 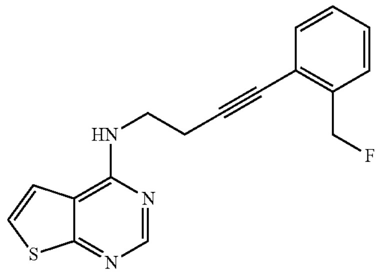 [SMILES: FCc1ccccc1C#CCCNc1ncnc2sccc12] | Oily product |

TABLE 1-9

| Compound No. | Structure | Physical property |
|---|---|---|
| 48 | 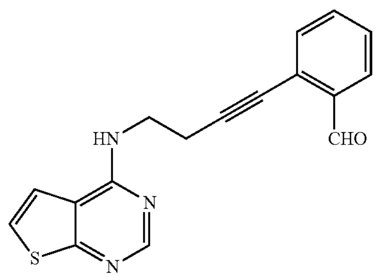 [SMILES: O=Cc1ccccc1C#CCCNc1ncnc2sccc12] | m.p. 162~163° C. |
| 49 | 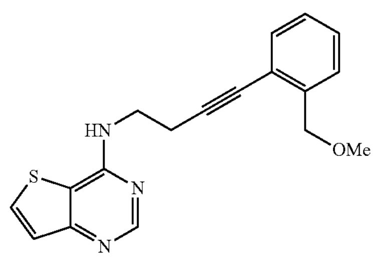 [SMILES: COCc1ccccc1C#CCCNc1ncnc2ccsc12] | Oily product |
| 50 | 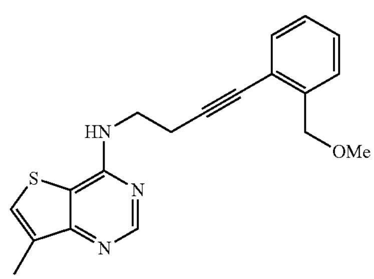 [SMILES: COCc1ccccc1C#CCCNc1ncnc2c(C)csc12] | Oily product |
| 51 | 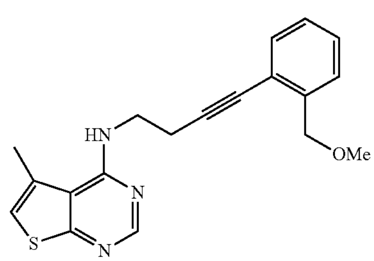 [SMILES: COCc1ccccc1C#CCCNc1ncnc2scc(C)c12] | Oily product |

TABLE 1-9-continued

| Compound No. | Structure | Physical property |
|---|---|---|
| 52 | 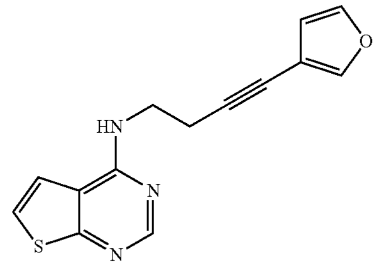 [SMILES: C(#Cc1ccoc1)CCNc1ncnc2sccc12] | m.p. 117~118° C. |
| 53 | 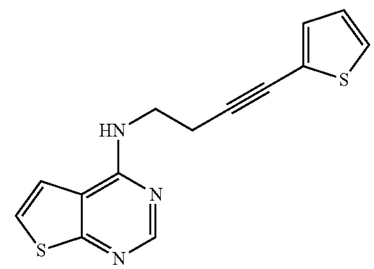 [SMILES: C(#Cc1cccs1)CCNc1ncnc2sccc12] | m.p. 127~128° C. |

TABLE 1-10

| Compound No. | Structure | Physical property |
|---|---|---|
| 54 | 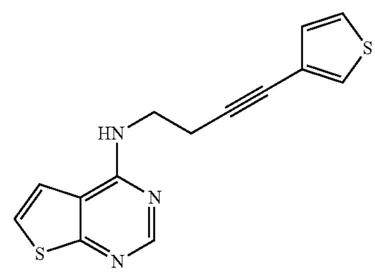 [SMILES: C(#Cc1ccsc1)CCNc1ncnc2sccc12] | m.p. 153~155° C. |
| 55 | 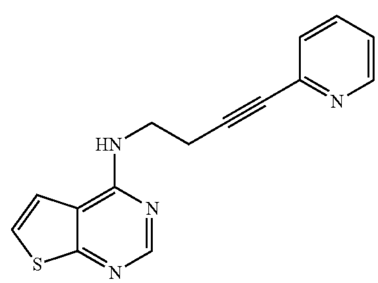 [SMILES: C(#Cc1ccccn1)CCNc1ncnc2sccc12] | m.p. 178~180° C. |
| 56 | 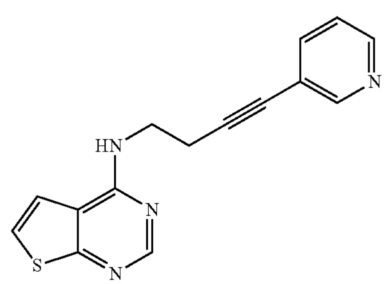 [SMILES: C(#Cc1cccnc1)CCNc1ncnc2sccc12] | m.p. 138~140° C. |

TABLE 1-10-continued

| Compound No. | Structure | Physical property |
|---|---|---|
| 57 | (thieno[2,3-d]pyrimidin-4-yl)NH-CH2CH2-C≡C-(pyridin-4-yl) | m.p. 140~141° C. |
| 58 | (thieno[2,3-d]pyrimidin-4-yl)NH-CH2CH2-C≡C-(pyrimidin-2-yl) | Resinoid product |
| 59 | (thieno[2,3-d]pyrimidin-4-yl)NH-CH2CH2-C≡C-(4,6-dimethylpyrimidin-2-yl) | m.p. 112~113° C. |

TABLE 1-11

| Compound No. | Structure | Physical property |
|---|---|---|
| 60 | (thieno[2,3-d]pyrimidin-4-yl)NH-CH2CH2-C≡C-(4,6-dimethoxypyrimidin-2-yl) | Resinoid product |
| 61 | (thieno[2,3-d]pyrimidin-4-yl)NH-CH2CH2-C≡C-(thiazol-5-yl) | m.p. 156~158° C. |
| 62 | (thieno[2,3-d]pyrimidin-4-yl)NH-CH2CH2-C≡C-(thiazol-2-yl) | m.p. 128~129° C. |
| 63 | (thieno[2,3-d]pyrimidin-4-yl)NH-CH2CH2-C≡C-(thiazol-4-yl) | m.p. 174° C. |
| 65 | (thieno[2,3-d]pyrimidin-4-yl)NH-CH2CH2-C≡C-(4-bromothiazol-2-yl) | m.p. 90~92° C. |

TABLE 1-12

| Compound No. | Structure | Physical property |
|---|---|---|
| 65 | (thieno[2,3-d]pyrimidin-4-yl)NH-CH2CH2-C≡C-(5-methylthiazol-4-yl) | m.p. 148~150° C. |

TABLE 1-12-continued

| Compound No. | Structure | Physical property |
|---|---|---|
| 66 | 2-methyl-thiazol-4-yl connected via C≡C-CH2-CH2-NH to thieno[2,3-d]pyrimidin-4-yl | m.p. 160~161° C. |
| 67 | 2-methoxy-thiazol-4-yl connected via C≡C-CH2-CH2-NH to thieno[2,3-d]pyrimidin-4-yl | m.p. 152~153° C. |
| 68 | 2-(fluoromethyl)-thiazol-4-yl connected via C≡C-CH2-CH2-NH to thieno[2,3-d]pyrimidin-4-yl | Resinoid product |
| 69 | 2-formyl-thiazol-4-yl connected via C≡C-CH2-CH2-NH to thieno[2,3-d]pyrimidin-4-yl | Resinoid product |

TABLE 1-13

| Compound No. | Structure | Physical property |
|---|---|---|
| 70 | 2-(hydroxymethyl)-thiazol-4-yl connected via C≡C-CH2-CH2-NH to thieno[2,3-d]pyrimidin-4-yl | m.p. 193° C. |
| 71 | 2-(((tert-butyldimethylsilyl)oxy)methyl)-thiazol-4-yl connected via C≡C-CH2-CH2-NH to thieno[2,3-d]pyrimidin-4-yl | Resinoid product |

TABLE 1-13-continued
| Compound No. | Structure | Physical property |
|---|---|---|
| 72 | 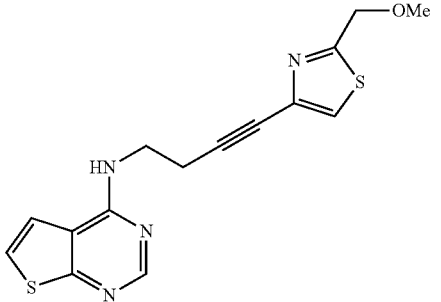 [SMILES: COCc1nc(C#CCCNc2ncnc3sccc23)cs1] | Resinoid product |
| 73 | 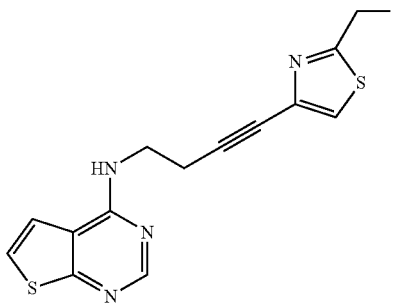 | m.p. 128~129° C. |
| 74 | 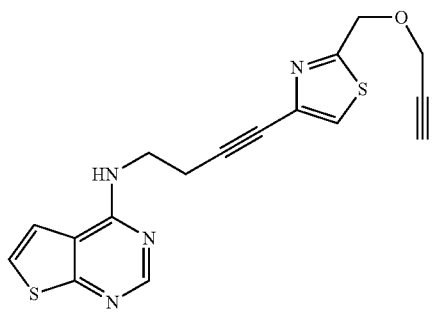 [SMILES: C#CCOCc1nc(C#CCCNc2ncnc3sccc23)cs1] | Oily product |
TABLE 1-14
| Compound No. | Structure | Physical property |
|---|---|---|
| 75 | 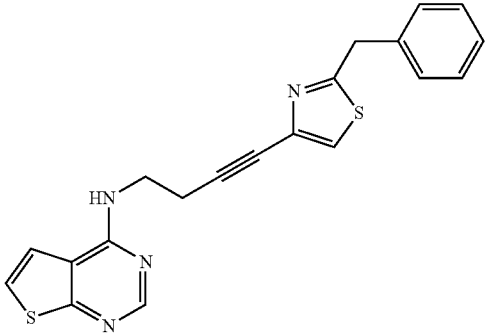 [SMILES: C(#Cc1csc(Cc2ccccc2)n1)CCNc1ncnc2sccc12] | Resinoid product |

TABLE 1-14-continued

| Compound No. | Structure | Physical property |
|---|---|---|
| 76 | 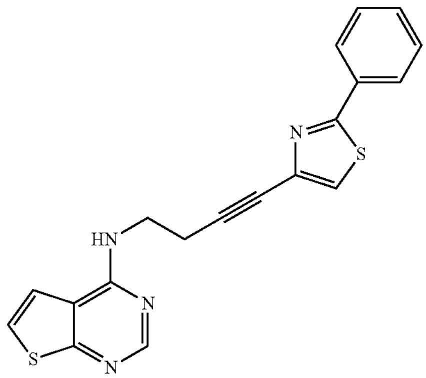 [SMILES: C(#Cc1csc(-c2ccccc2)n1)CCNc1ncnc2sccc12] | m.p. 134~136° C. |
| 77 | 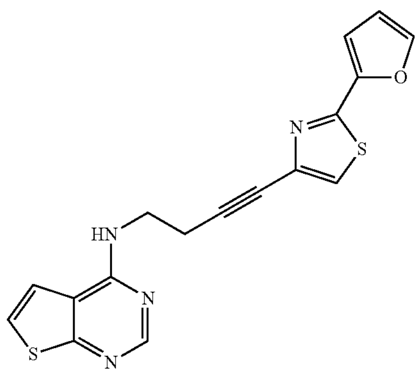 [SMILES: C(#Cc1csc(-c2ccco2)n1)CCNc1ncnc2sccc12] | m.p. 53~55° C. |
| 78 | 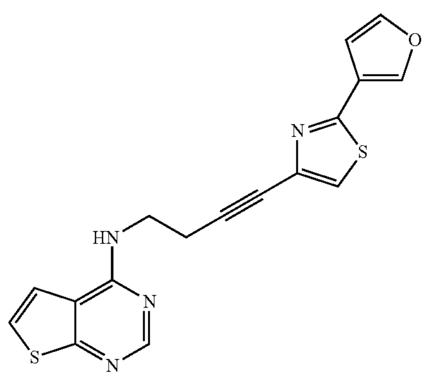 [SMILES: C(#Cc1csc(-c2ccoc2)n1)CCNc1ncnc2sccc12] | m.p. 140~142° C. |

TABLE 1-15

| Compound No. | Structure | Physical property |
|---|---|---|
| 79 | 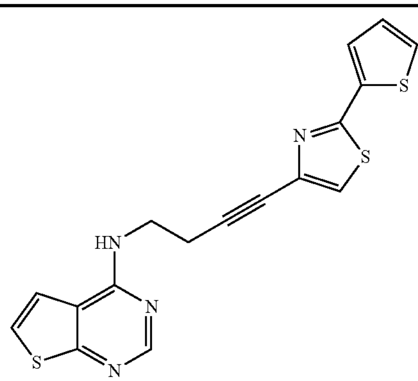 | Resinoid product |

TABLE 1-15-continued
| Compound No. | Structure | Physical property |
|---|---|---|
| 80 | 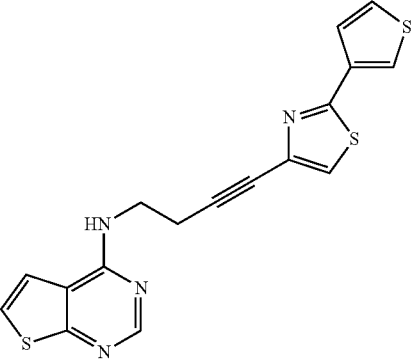 [SMILES: C(#Cc1csc(-c2ccsc2)n1)CCNc1ncnc2sccc12] | m.p. 55~56° C. |
| 81 | 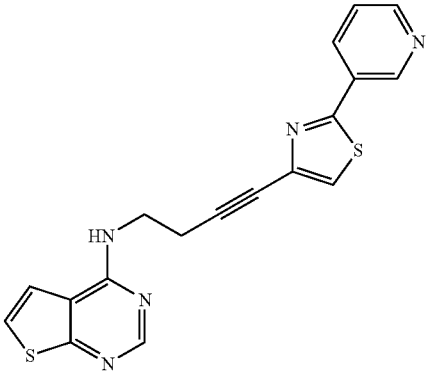 [SMILES: C(#Cc1csc(-c2cccnc2)n1)CCNc1ncnc2sccc12] | m.p. 175~177° C. |
| 82 | 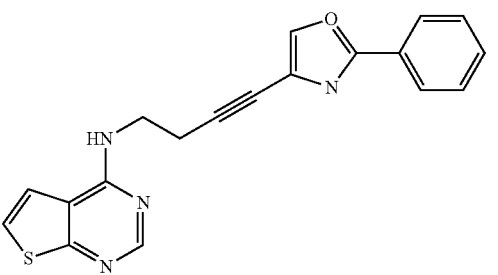 | m.p. 79~80° C. |
| 83 | 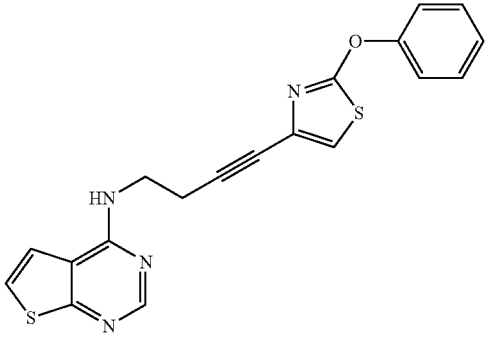 | Resinoid product |

TABLE 1-16

| Compound No. | Structure | Physical property |
|---|---|---|
| 84 | 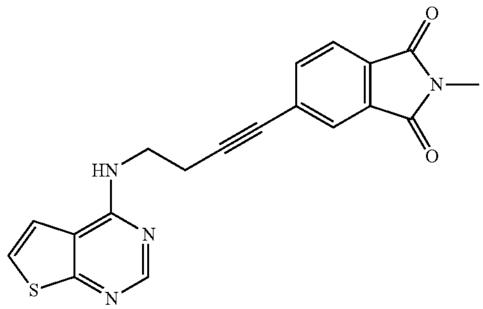 [SMILES: CN1C(=O)c2ccc(C#CCCNc3ncnc4sccc34)cc2C1=O] | m.p. 193~195° C. |
| 85 | 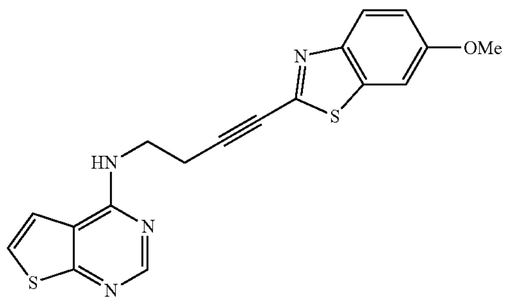 [SMILES: COc1ccc2nc(C#CCCNc3ncnc4sccc34)sc2c1] | Resinoid product |
| 86 | 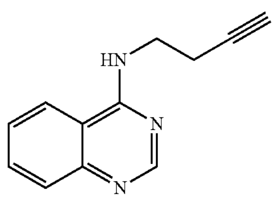 | m.p. 160~162° C. |
| 87 | 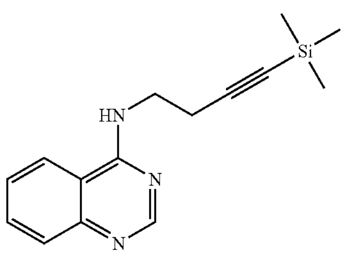 [SMILES: C[Si](C)(C)C#CCCNc1ncnc2ccccc12] | m.p. 159~161° C. |
| 88 | 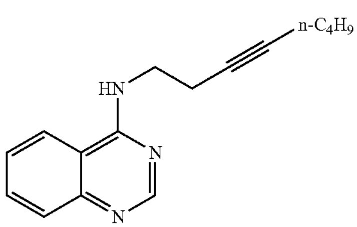 | m.p. 99~101° C. |
| 89 | 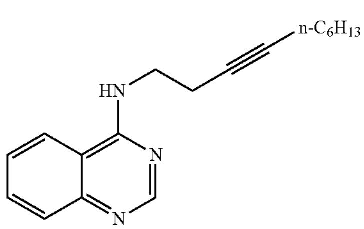 | m.p. 82~84° C. |

TABLE 1-17

| Compound No. | Structure | Physical property |
| --- | --- | --- |
| 90 | 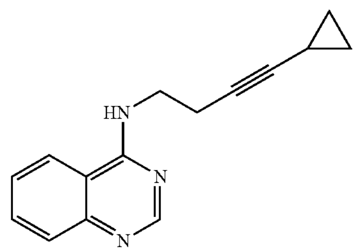 [SMILES: C(#CC1CC1)CCNc1ncnc2ccccc12] | m.p. 107~109° C. |
| 91 | 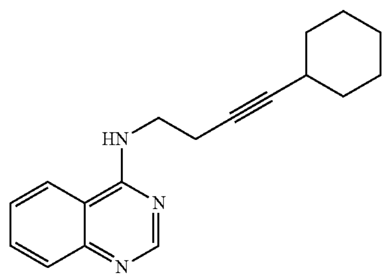 [SMILES: C(#CC1CCCCC1)CCNc1ncnc2ccccc12] | m.p. 155~157° C. |
| 92 | 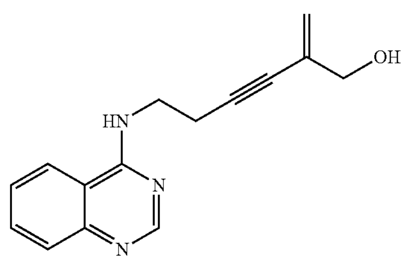 [SMILES: C=C(C#CCCNc1ncnc2ccccc12)CO] | m.p. 139° C. |
| 93 | 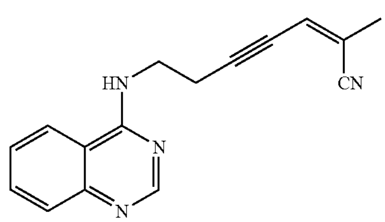 [SMILES: C/C(C#N)=C/C#CCCNc1ncnc2ccccc12] | m.p. 84~86° C. |
| 94 | 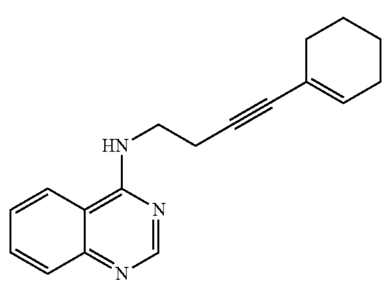 [SMILES: C(#CC1=CCCCC1)CCNc1ncnc2ccccc12] | m.p. 160~162° C. |
| 95 | 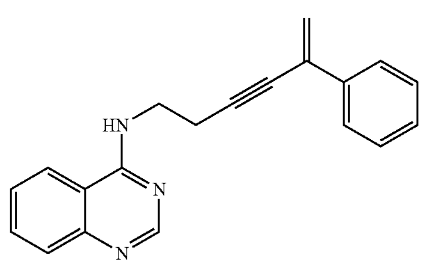 [SMILES: C=C(C#CCCNc1ncnc2ccccc12)c1ccccc1] | Oily product |

TABLE 1-18

| Compound No. | Structure | Physical property |
|---|---|---|
| 96 | quinazolin-4-yl-NH-CH2CH2-C≡C-phenyl | m.p. 120~122° C. |
| 97 | quinazolin-4-yl-NH-CH2CH2-C≡C-(2-Cl-phenyl) | Resinoid product |
| 98 | quinazolin-4-yl-NH-CH2CH2-C≡C-(4-I-phenyl) | m.p. 183~184° C. |
| 99 | quinazolin-4-yl-NH-CH2CH2-C≡C-(2-CH2F-phenyl) | Oily product |
| 100 | quinazolin-4-yl-NH-CH2CH2-C≡C-(2-CHF2-phenyl) | Oily product |

TABLE 1-18-continued

| Compound No. | Structure | Physical property |
|---|---|---|
| 101 | quinazolin-4-yl-NH-CH2CH2-C≡C-(2-CF3-phenyl) | m.p. 136~138° C. |

TABLE 1-19

| Compound No. | Structure | Physical property |
|---|---|---|
| 102 | quinazolin-4-yl-NH-CH2CH2-C≡C-(2-CN-phenyl) | m.p. 150~151° C. |
| 103 | quinazolin-4-yl-NH-CH2CH2-C≡C-(2-ethyl-phenyl) | m.p. 106~107° C. |
| 104 | quinazolin-4-yl-NH-CH2CH2-C≡C-(2-isopropyl-phenyl) | m.p. 90~91° C. |
| 105 | quinazolin-4-yl-NH-CH2CH2-C≡C-(2-(3-methylbut-3-enyl)-phenyl) | m.p. 92~94° C. |

TABLE 1-19-continued

| Compound No. | Structure | Physical property |
|---|---|---|
| 106 | (4-n-C₄H₉-phenyl)-C≡C-CH₂CH₂-NH-quinazolin-4-yl | m.p. 102~105° C. |
| 107 | (4-n-C₆H₁₂-phenyl)-C≡C-CH₂CH₂-NH-quinazolin-4-yl | m.p. 100~102° C. |

TABLE 1-20

| Compound No. | Structure | Physical property |
|---|---|---|
| 108 | (4-n-C₈H₁₇-phenyl)-C≡C-CH₂CH₂-NH-quinazolin-4-yl | Resinoid product |
| 109 | (4-cyclohexyl-phenyl)-C≡C-CH₂CH₂-NH-quinazolin-4-yl | m.p. 152~154° C. |
| 110 | (4-vinyl-phenyl)-C≡C-CH₂CH₂-NH-quinazolin-4-yl | Resinoid product |

TABLE 1-20-continued

| Compound No. | Structure | Physical property |
|---|---|---|
| 111 | 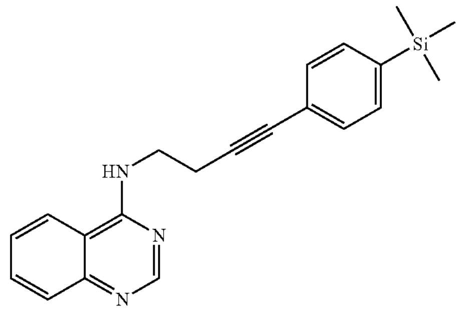 [SMILES: C[Si](C)(C)c1ccc(C#CCCNc2ncnc3ccccc23)cc1] | Resinoid product |
| 112 | 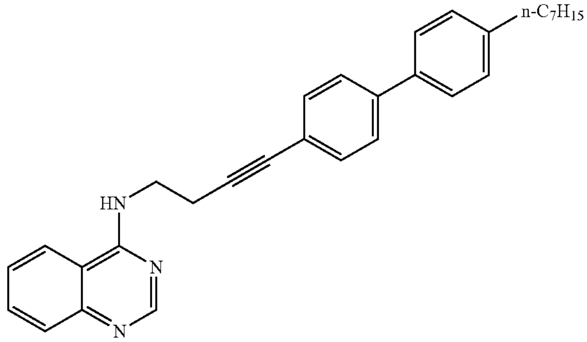 | n-C$_7$H$_{15}$ m.p. 144~146° C. |

TABLE 1-21

| Compound No. | Structure | Physical property |
|---|---|---|
| 113 | 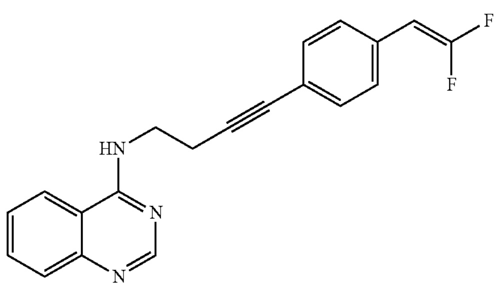 [SMILES: FC(F)=Cc1ccc(C#CCCNc2ncnc3ccccc23)cc1] | Oily product |
| 114 | 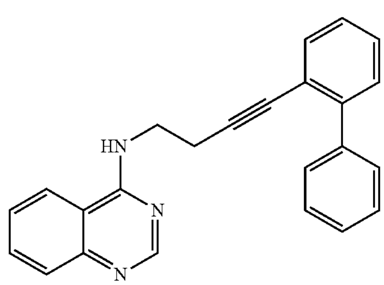 [SMILES: C(#Cc1ccccc1-c1ccccc1)CCNc1ncnc2ccccc12] | Oily product |

TABLE 1-21-continued

| Compound No. | Structure | Physical property |
|---|---|---|
| 115 | *quinazolin-4-yl-NH-CH₂CH₂-C≡C-(2-OMe-phenyl)* | Oily product |
| 116 | *quinazolin-4-yl-NH-CH₂CH₂-C≡C-(3-SMe-phenyl)* | m.p. 141~142° C. |
| 117 | *quinazolin-4-yl-NH-CH₂CH₂-C≡C-(4-SMe-phenyl)* | m.p. 147~148° C. |
| 118 | *quinazolin-4-yl-NH-CH₂CH₂-C≡C-(2-OEt-phenyl)* | m.p. 119~120° C. |

TABLE 1-22

| Compound No. | Structure | Physical property |
|---|---|---|
| 119 | *quinazolin-4-yl-NH-CH₂CH₂-C≡C-(2-OiPr-phenyl)* | Resinoid product |

TABLE 1-22-continued

| Compound No. | Structure | Physical property |
|---|---|---|
| 120 | 4-(quinazolin-4-ylamino)but-1-ynyl-phenyl-SO₂Me | m.p. 164~165° C. |
| 121 | 4-(quinazolin-4-ylamino)but-1-ynyl-phenyl-O-CH₂-OMe | m.p. 108~110° C. |
| 122 | 4-(quinazolin-4-ylamino)but-1-ynyl-phenyl-SO₂N(Me)₂ | m.p. 175~176° C. |
| 123 | 4-(quinazolin-4-ylamino)but-1-ynyl-phenyl-NHSO₂Me | Oily product |

TABLE 1-23

| Compound No. | Structure | Physical property |
|---|---|---|
| 124 | (quinazolin-4-yl)NH-CH2CH2-C≡C-C6H4-N(Me)SO2Me | Oily product |
| 125 | (quinazolin-4-yl)NH-CH2CH2-C≡C-C6H4-N(OMe)C(O)OMe | Resinoid product |
| 126 | (quinazolin-4-yl)NH-CH2CH2-C≡C-C6H4-C(O)NHMe | m.p. 212~214° C. |
| 127 | (quinazolin-4-yl)NH-CH2CH2-C≡C-C6H4-CO2H | Resinoid product |
| 128 | (quinazolin-4-yl)NH-CH2CH2-C≡C-C6H4-COMe | Resinoid product |

TABLE 1-24

| Compound No. | Structure | Physical property |
|---|---|---|
| 129 | quinazolin-4-yl-NH-CH₂CH₂-C≡C-C₆H₄-CO₂C₂H₅ (para) | m.p. 137~138° C. |
| 130 | quinazolin-4-yl-NH-CH₂CH₂-C≡C-C₆H₄-CH₂OH (ortho) | m.p. 156~157° C. |
| 131 | quinazolin-4-yl-NH-CH₂CH₂-C≡C-C₆H₄-CH₂OH (meta) | m.p. 113~115° C. |
| 132 | quinazolin-4-yl-NH-CH₂CH₂-C≡C-C₆H₄-CH₂OH (para) | m.p. 69~71° C. |
| 133 | quinazolin-4-yl-NH-CH₂CH₂-C≡C-C₆H₄-CH₂OMe (ortho) | m.p. 108~110° C. |

TABLE 1-25

| Compound No. | Structure | Physical property |
|---|---|---|
| 134 | [quinazolin-4-yl-NH-CH2CH2-C≡C-(2-OCHF2-benzyl)phenyl] | Resinoid product |
| 135 | [quinazolin-4-yl-NH-CH2CH2-C≡C-(3-CH2OMe)phenyl] | Resinoid product |
| 136 | [quinazolin-4-yl-NH-CH2CH2-C≡C-(4-CH2OMe)phenyl] | m.p. 107~109° C. |
| 137 | [quinazolin-4-yl-NH-CH2CH2-C≡C-(2-CH(OMe)-)phenyl], racemic | Oily product |
| 138 | [quinazolin-4-yl-NH-CH2CH2-C≡C-(2-CH(OH)(CF3)-)phenyl], racemic | m.p. 183~187° C. |

TABLE 1-26

| Compound No. | Structure | Physical property |
|---|---|---|
| 139 | 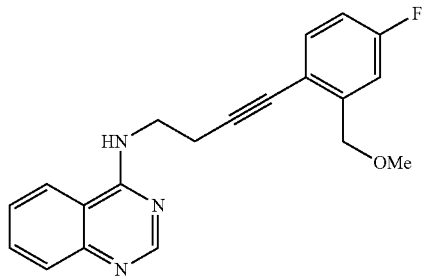 [SMILES: COCc1cc(F)ccc1C#CCCNc1ncnc2ccccc12] | m.p. 121~122° C. |
| 140 | 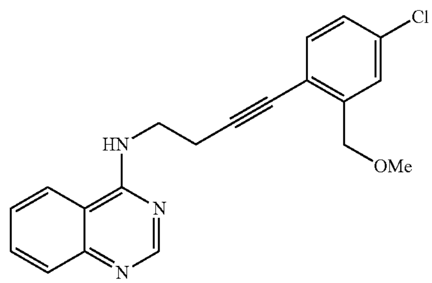 [SMILES: COCc1cc(Cl)ccc1C#CCCNc1ncnc2ccccc12] | m.p. 122~124° C. |
| 141 | 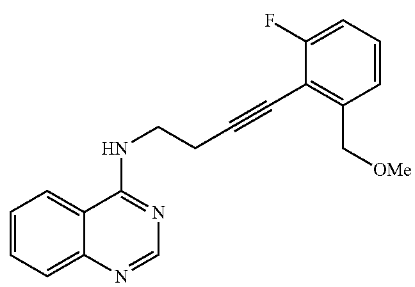 [SMILES: COCc1cccc(F)c1C#CCCNc1ncnc2ccccc12] | Oily product |
| 142 | 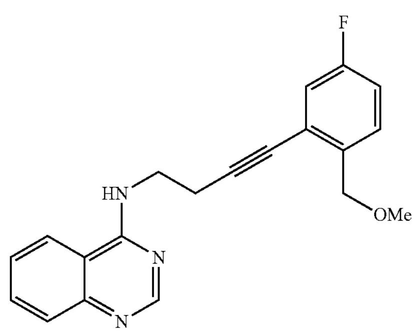 [SMILES: COCc1ccc(F)cc1C#CCCNc1ncnc2ccccc12] | m.p. 124~125° C. |
| 143 | 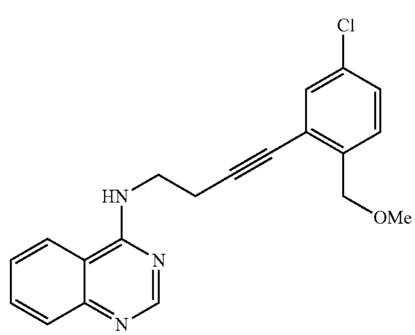 | Oily product |

TABLE 1-27
| Compound No. | Structure | Physical property |
|---|---|---|
| 144 | 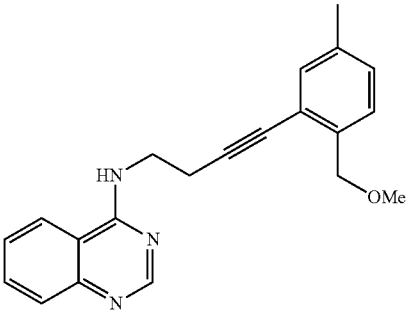 [SMILES: COCc1ccc(C)cc1C#CCCNc1ncnc2ccccc12] | Oily product |
| 145 | 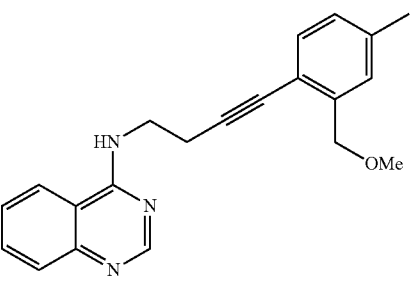 [SMILES: COCc1cc(C)ccc1C#CCCNc1ncnc2ccccc12] | m.p. 102~105° C. |
| 146 | 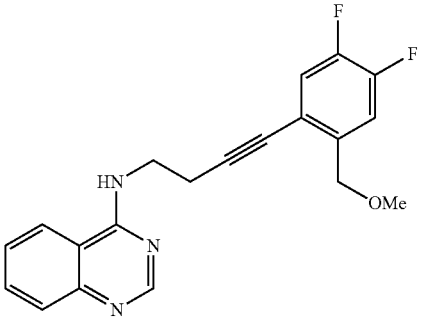 [SMILES: COCc1cc(F)c(F)cc1C#CCCNc1ncnc2ccccc12] | m.p. 121~125° C. |
| 147 | 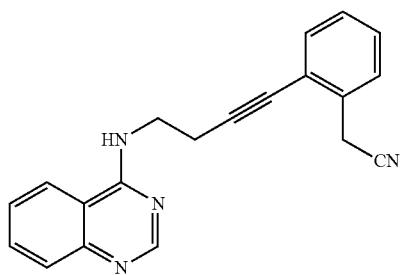 | m.p. 146~147° C. |
| 148 | 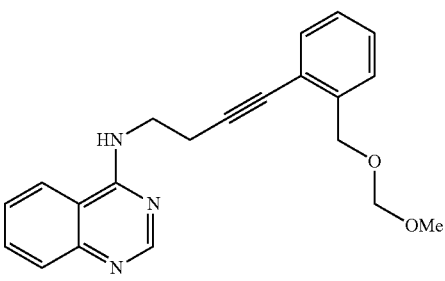 [SMILES: COCOCc1ccccc1C#CCCNc1ncnc2ccccc12] | Oily product |

TABLE 1-28

| Compound No. | Structure | Physical property |
| --- | --- | --- |
| 149 | 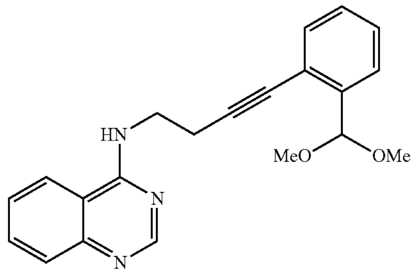 [SMILES: COC(OC)c1ccccc1C#CCCNc1ncnc2ccccc12] | Oily product |
| 150 | 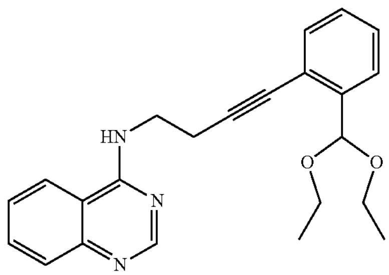 [SMILES: CCOC(OCC)c1ccccc1C#CCCNc1ncnc2ccccc12] | Oily product |
| 151 | 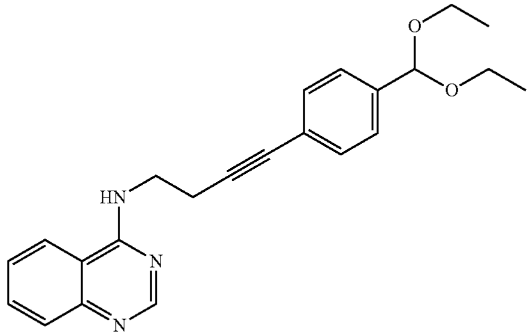 [SMILES: CCOC(OCC)c1ccc(C#CCCNc2ncnc3ccccc23)cc1] | m.p. 143~144° C. |
| 152 | 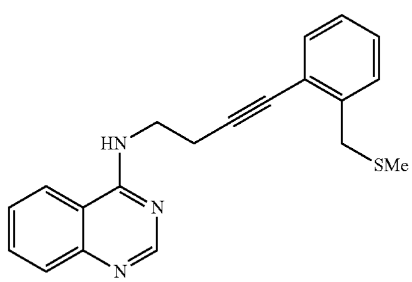 [SMILES: CSCc1ccccc1C#CCCNc1ncnc2ccccc12] | m.p. 131~133° C. |
| 153 | 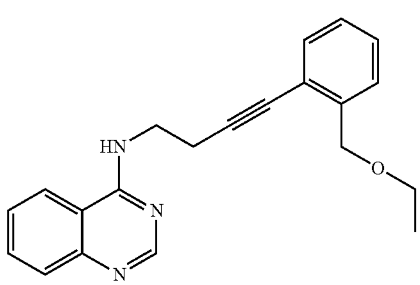 [SMILES: CCOCc1ccccc1C#CCCNc1ncnc2ccccc12] | Oily product |

TABLE 1-29

| Compound No. | Structure | Physical property |
|---|---|---|
| 154 | 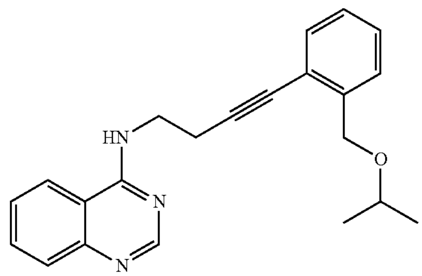 [SMILES: CC(C)OCc1ccccc1C#CCCNc1ncnc2ccccc12] | Resinoid product |
| 155 | 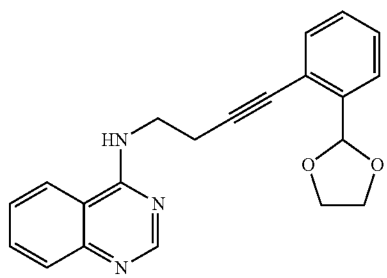 [SMILES: C(#Cc1ccccc1C1OCCO1)CCNc1ncnc2ccccc12] | Oily product |
| 156 | 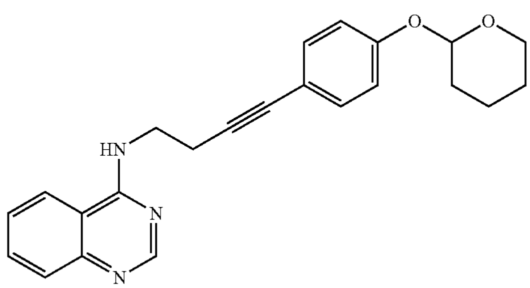 [SMILES: C(#Cc1ccc(OC2CCCCO2)cc1)CCNc1ncnc2ccccc12] | m.p. 163~165° C. |
| 157 | 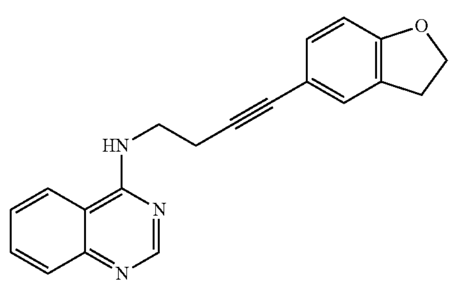 [SMILES: C(#Cc1ccc2c(c1)CCO2)CCNc1ncnc2ccccc12] | Resinoid product |
| 158 | 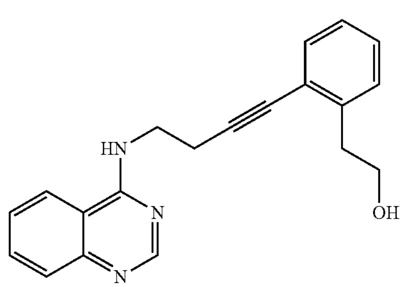 [SMILES: OCCc1ccccc1C#CCCNc1ncnc2ccccc12] | Resinoid product |

TABLE 1-30

| Compound No. | Structure | Physical property |
|---|---|---|
| 159 | 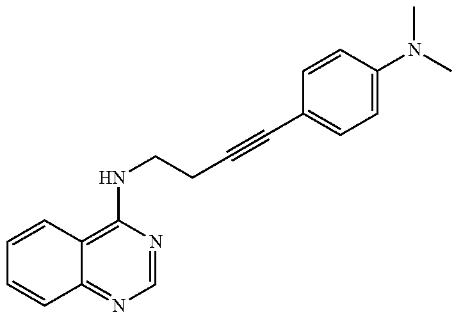 [SMILES: CN(C)c1ccc(C#CCCNc2ncnc3ccccc23)cc1] | Resinoid product |
| 160 | 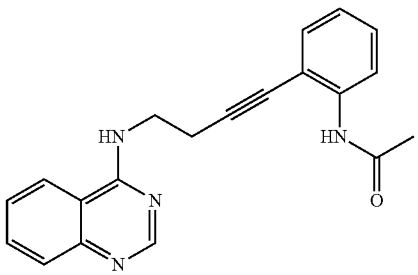 [SMILES: CC(=O)Nc1ccccc1C#CCCNc1ncnc2ccccc12] | m.p. 177~178° C. |
| 161 | 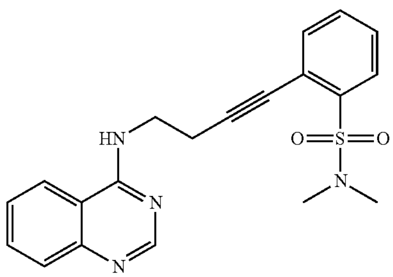 [SMILES: CN(C)S(=O)(=O)c1ccccc1C#CCCNc1ncnc2ccccc12] | m.p. 146~148° C. |
| 162 | 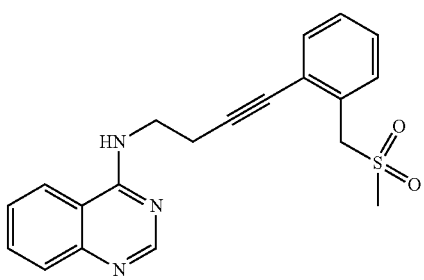 [SMILES: CS(=O)(=O)Cc1ccccc1C#CCCNc1ncnc2ccccc12] | Resinoid product |
| 163 | 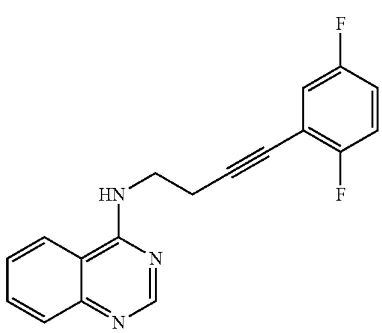 [SMILES: Cc1ccc(F)cc1C#CCCNc1ncnc2ccccc12] | m.p. 176~177° C. |

TABLE 1-31

| Compound No. | Structure | Physical property |
|---|---|---|
| 164 | quinazolin-4-yl-NH-CH2CH2-C≡C-(2-F,4-Cl-phenyl) | m.p. 198~199° C. |
| 165 | quinazolin-4-yl-NH-CH2CH2-C≡C-(2-CN,3-F-phenyl) | m.p. 163~164° C. |
| 166 | quinazolin-4-yl-NH-CH2CH2-C≡C-(3,4-di-F-phenyl) | m.p. 161~162° C. |
| 167 | quinazolin-4-yl-NH-CH2CH2-C≡C-(2-Me,5-F-phenyl) | Resinoid product |
| 168 | quinazolin-4-yl-NH-CH2CH2-C≡C-(2-CF3,5-F-phenyl) | m.p. 147~148° C. |

TABLE 1-32
| Compound No. | Structure | Physical property |
|---|---|---|
| 169 | 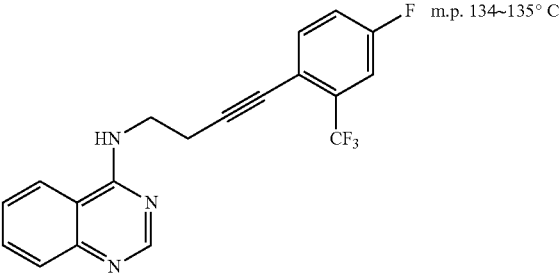 | m.p. 134~135° C. |
| 170 | 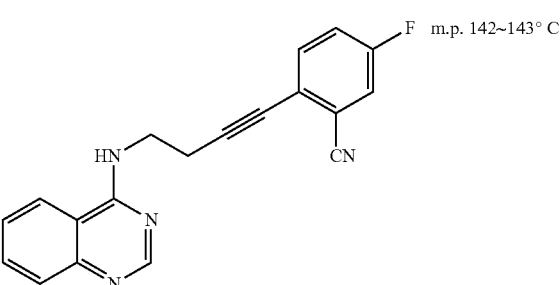 | m.p. 142~143° C. |
| 171 | 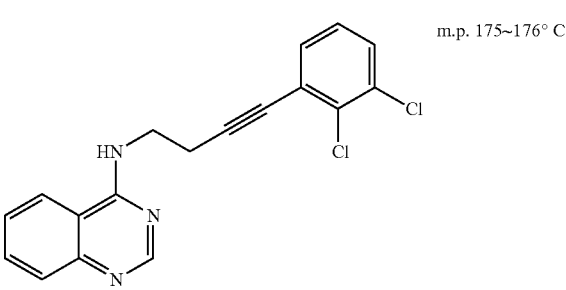 | m.p. 175~176° C. |
| 172 | 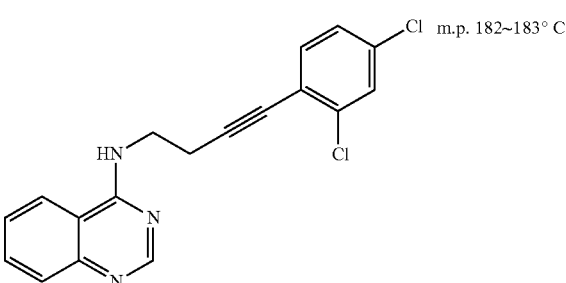 | m.p. 182~183° C. |
| 173 | 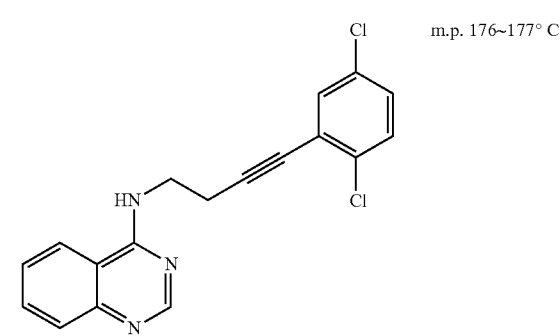 | m.p. 176~177° C. |

TABLE 1-33

| Compound No. | Structure | Physical property |
|---|---|---|
| 174 | N-(4-(2,6-dichlorophenyl)but-3-yn-1-yl)quinazolin-4-amine | m.p. 153~155° C. |
| 175 | N-(4-(3,4-dichlorophenyl)but-3-yn-1-yl)quinazolin-4-amine | m.p. 147~148° C. |
| 176 | N-(4-(2-chloro-5-(trifluoromethyl)phenyl)but-3-yn-1-yl)quinazolin-4-amine | m.p. 144~145° C. |
| 177 | N-(4-(3-chloro-4-(trifluoromethyl)phenyl)but-3-yn-1-yl)quinazolin-4-amine | m.p. 139~140° C. |
| 178 | N-(4-(4-chloro-2-(trifluoromethyl)phenyl)but-3-yn-1-yl)quinazolin-4-amine | m.p. 161~163° C. |

TABLE 1-34

| Compound No. | Structure | Physical property |
|---|---|---|
| 179 | 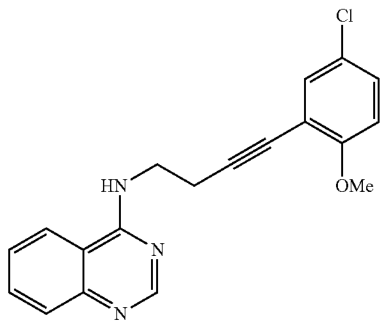 [SMILES: Fc1ccc(C(F)(F)F)c(C#CCCNc2ncnc3ccccc23)c1] | m.p. 147~149° C. |
| 180 | 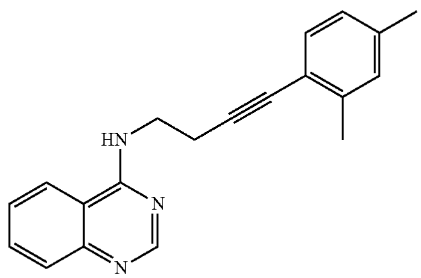 [SMILES: Cc1ccc(C#CCCNc2ncnc3ccccc23)c(C)c1] | m.p. 153~155° C. |
| 181 | 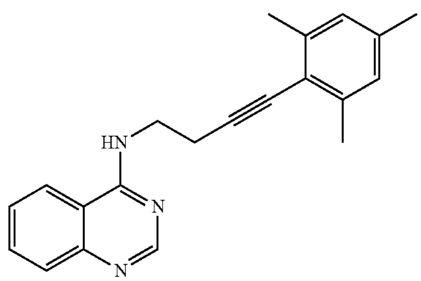 [SMILES: Cc1cc(C)c(C#CCCNc2ncnc3ccccc23)c(C)c1] | Oily product |
| 182 | 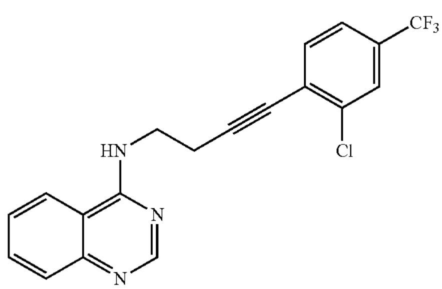 [SMILES: FC(F)(F)c1ccc(C#CCCNc2ncnc3ccccc23)c(Cl)c1] | m.p. 135~139° C. |
| 183 | 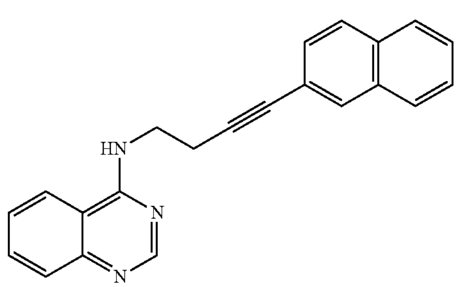 [SMILES: C(#Cc1ccc2ccccc2c1)CCNc1ncnc2ccccc12] | m.p. 159~160° C. |

TABLE 1-34-continued
| Compound No. | Structure | Physical property |
|---|---|---|
| 184 | 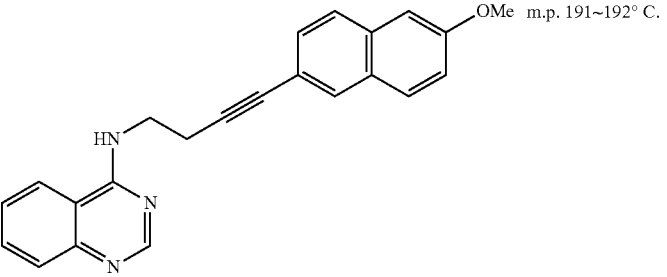 | m.p. 191~192° C. |
TABLE 1-35
| Compound No. | Structure | Physical property |
|---|---|---|
| 185 | 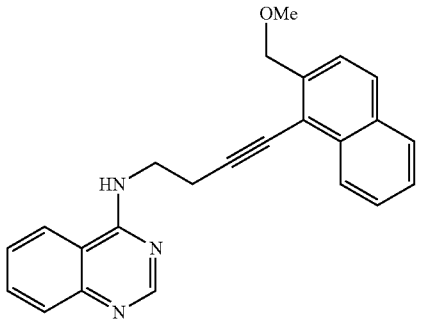 [SMILES: COCc1ccc2ccccc2c1C#CCCNc1ncnc2ccccc12] | Oily product |
| 186 | 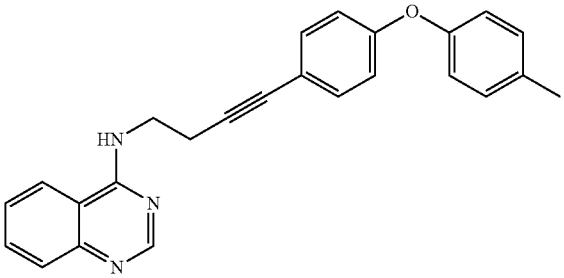 [SMILES: Cc1ccc(Oc2ccc(C#CCCNc3ncnc4ccccc34)cc2)cc1] | Oily product |
| 187 | 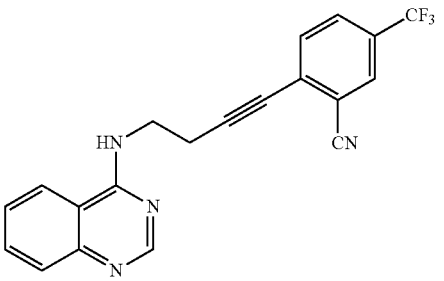 [SMILES: N#Cc1cc(C(F)(F)F)ccc1C#CCCNc1ncnc2ccccc12] | m.p. 181~182° C. |
| 188 | 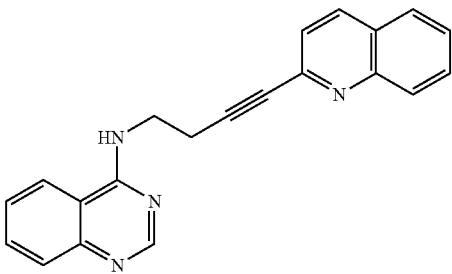 [SMILES: C(#Cc1ccc2ccccc2n1)CCNc1ncnc2ccccc12] | Resinoid product |

TABLE 1-35-continued
| Compound No. | Structure | Physical property |
|---|---|---|
| 189 | 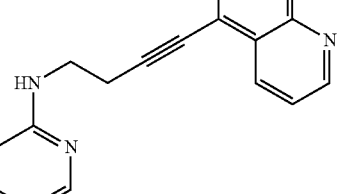 | Resinoid product |
| 190 | 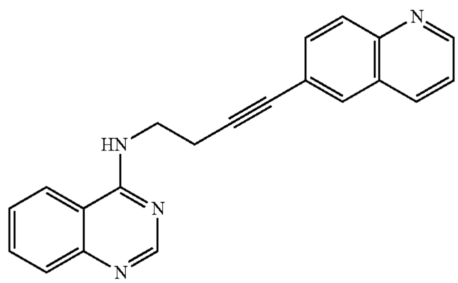 [SMILES: C(#Cc1ccc2ncccc2c1)CCNc1ncnc2ccccc12] | m.p. 183~186° C. |
TABLE 1-36
| Compound No. | Structure | Physical property |
|---|---|---|
| 191 | 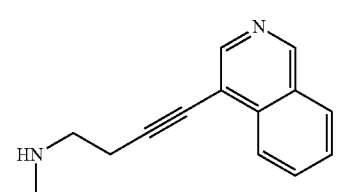 | Resinoid product |
| 192 | 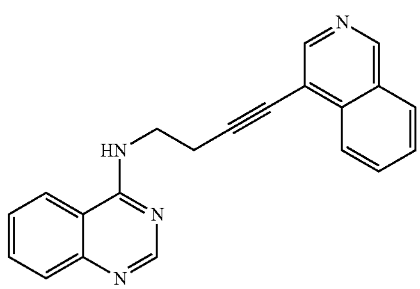 [SMILES: C(#Cc1cncc2ccccc12)CCNc1ncnc2ccccc12] | Resinoid product |
| 193 | 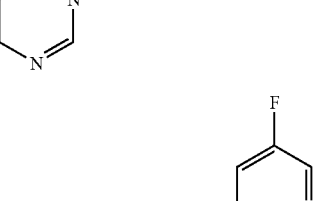 | m.p. 145~150° C. |

TABLE 1-36-continued

| Compound No. | Structure | Physical property |
|---|---|---|
| 194 | N-(4-(6-fluoropyridin-3-yl)but-3-yn-1-yl)quinazolin-4-amine | m.p. 157~158° C. |
| 195 | N-(4-(2-chloropyridin-3-yl)but-3-yn-1-yl)quinazolin-4-amine | m.p. 168~170° C. |

TABLE 1-37

| Compound No. | Structure | Physical property |
|---|---|---|
| 196 | N-(4-(2-chloropyridin-4-yl)but-3-yn-1-yl)quinazolin-4-amine | Resinoid product |
| 197 | N-(4-(5-(trifluoromethyl)pyridin-2-yl)but-3-yn-1-yl)quinazolin-4-amine | Resinoid product |
| 198 | N-(4-(6-(trifluoromethyl)pyridin-3-yl)but-3-yn-1-yl)quinazolin-4-amine | m.p. 134~139° C. |

TABLE 1-37-continued
| Compound No. | Structure | Physical property |
|---|---|---|
| 199 | 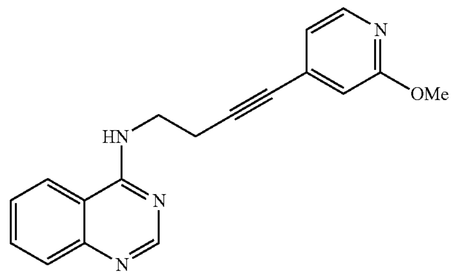 [SMILES: COc1cc(C#CCCNc2ncnc3ccccc23)ccn1] | m.p. 161~163° C. |
| 200 | 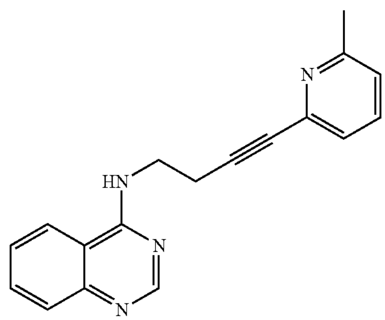 [SMILES: Cc1cccc(C#CCCNc2ncnc3ccccc23)n1] | Resinoid product |
| 201 | 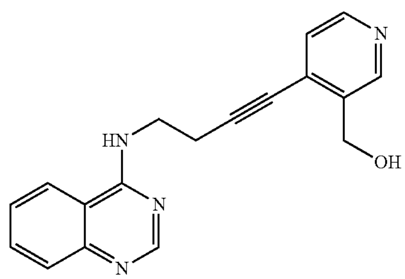 [SMILES: OCc1cnccc1C#CCCNc1ncnc2ccccc12] | m.p. 182~186° C. |
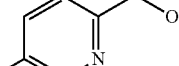
TABLE 1-38
| Compound No. | Structure | Physical property |
|---|---|---|
| 202 | 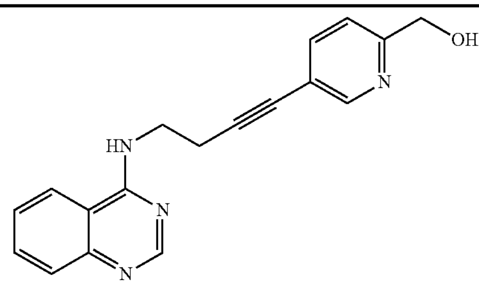 | m.p. 183~185° C. |
| 203 | 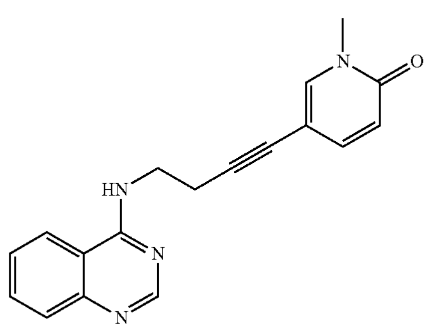 [SMILES: Cn1cc(C#CCCNc2ncnc3ccccc23)ccc1=O] | Oily product |

TABLE 1-38-continued

| Compound No. | Structure | Physical property |
| --- | --- | --- |
| 204 | 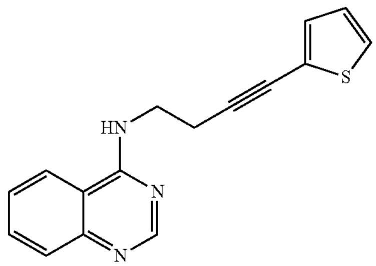 [SMILES: C(#Cc1cccs1)CCNc1ncnc2ccccc12] | m.p. 160~161° C. |
| 205 | 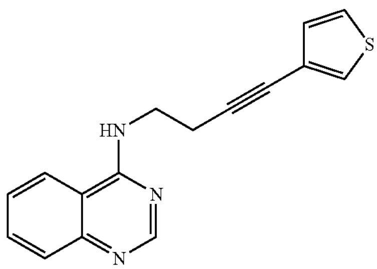 | m.p. 180~181° C. |
| 206 | 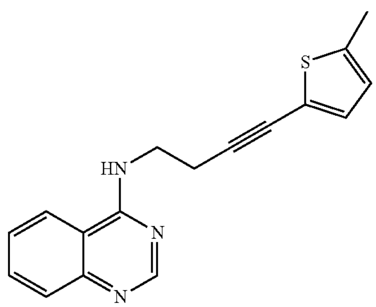 [SMILES: Cc1ccc(C#CCCNc2ncnc3ccccc23)s1] | m.p. 141~142° C. |
| 207 | 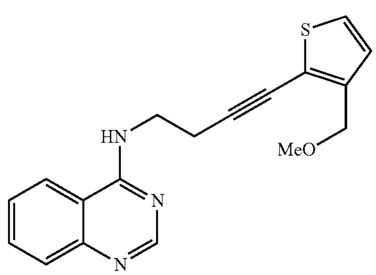 [SMILES: COCc1ccsc1C#CCCNc1ncnc2ccccc12] | Resinoid product |

TABLE 1-39

| Compound No. | Structure | Physical property |
| --- | --- | --- |
| 208 | 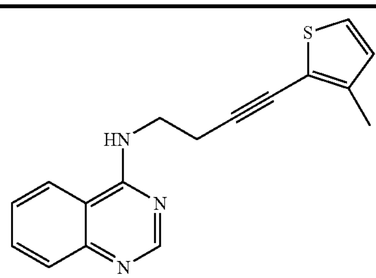 | m.p. 141~143° C. |

TABLE 1-39-continued

| Compound No. | Structure | Physical property |
|---|---|---|
| 209 | (quinazolin-4-yl)HN-CH₂CH₂-C≡C-(5-(hydroxymethyl)furan-3-yl) | m.p. 135~147° C. |
| 210 | (quinazolin-4-yl)HN-CH₂CH₂-C≡C-(thiazol-4-yl) | m.p. 204~207° C. |
| 211 | (quinazolin-4-yl)HN-CH₂CH₂-C≡C-(2-methylthiazol-4-yl) | m.p. 159~160° C. |
| 212 | (quinazolin-4-yl)HN-CH₂CH₂-C≡C-(2-methoxythiazol-4-yl) | m.p. 145~146° C. |

TABLE 1-40

| Compound No. | Structure | Physical property |
|---|---|---|
| 213 | 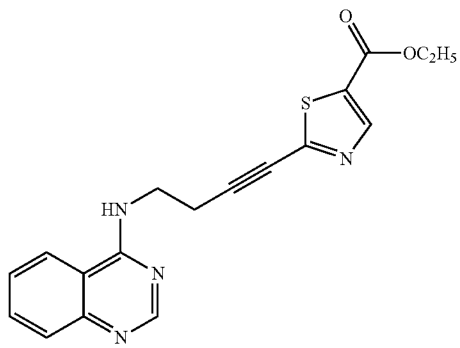 [SMILES: CCOC(=O)c1cnc(C#CCCNc2ncnc3ccccc23)s1] | m.p. 113~114° C. |
| 214 | 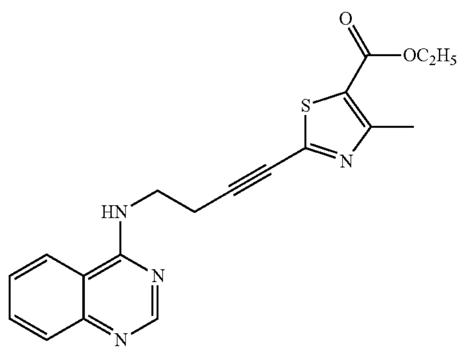 [SMILES: CCOC(=O)c1sc(C#CCCNc2ncnc3ccccc23)nc1C] | m.p. 139~140° C. |
| 215 | 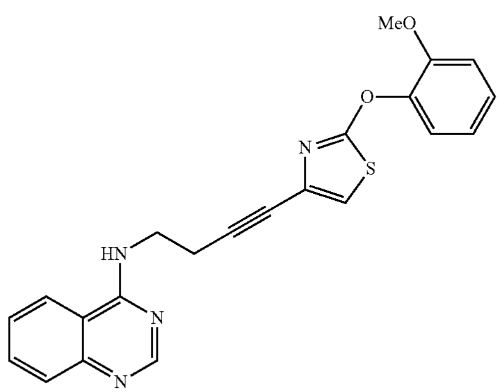 [SMILES: COc1ccccc1Oc1nc(C#CCCNc2ncnc3ccccc23)cs1] | Resinoid product |
| 216 | 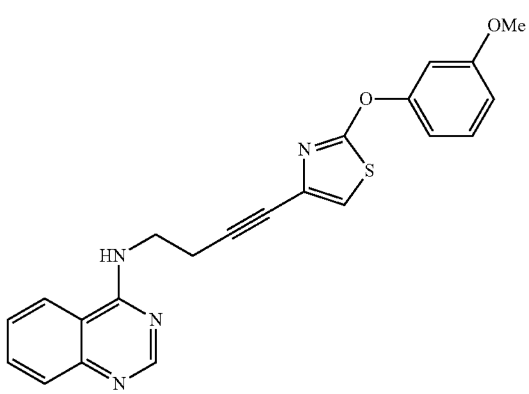 [SMILES: COc1cccc(Oc2nc(C#CCCNc3ncnc4ccccc34)cs2)c1] | m.p. 77~79° C. |

TABLE 1-40-continued

| Compound No. | Structure | Physical property |
|---|---|---|
| 217 | 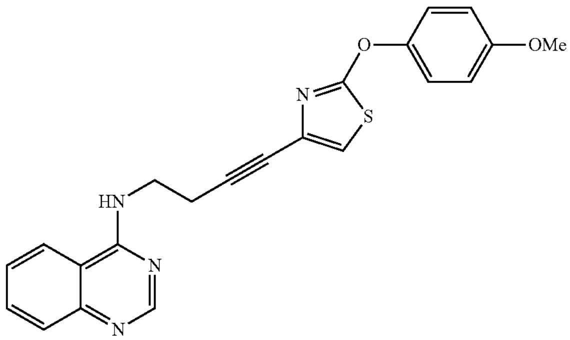 [SMILES: COc1ccc(Oc2nc(C#CCCNc3ncnc4ccccc34)cs2)cc1] | m.p. 150~152° C. |

TABLE 1-41

| Compound No. | Structure | Physical property |
|---|---|---|
| 218 | 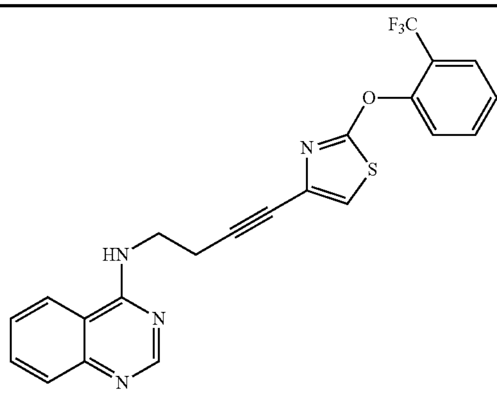 | m.p. 159~161° C. |
| 219 | 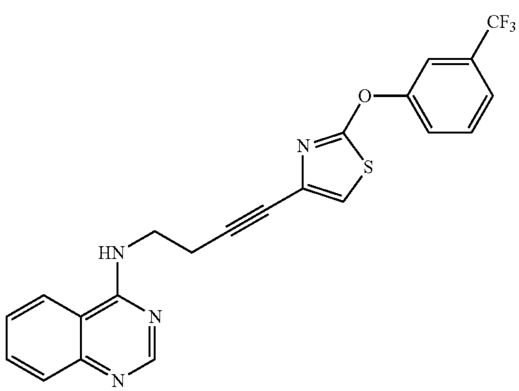 [SMILES: FC(F)(F)c1cccc(Oc2nc(C#CCCNc3ncnc4ccccc34)cs2)c1] | m.p. 106~108° C. |
| 220 | 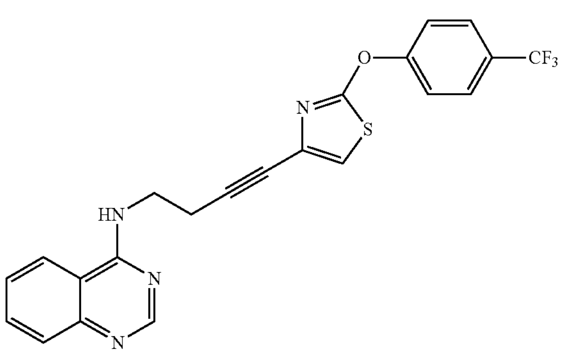 [SMILES: FC(F)(F)c1ccc(Oc2nc(C#CCCNc3ncnc4ccccc34)cs2)cc1] | m.p. 137~139° C. |

TABLE 1-41-continued
| Compound No. | Structure | Physical property |
|---|---|---|
| 221 | 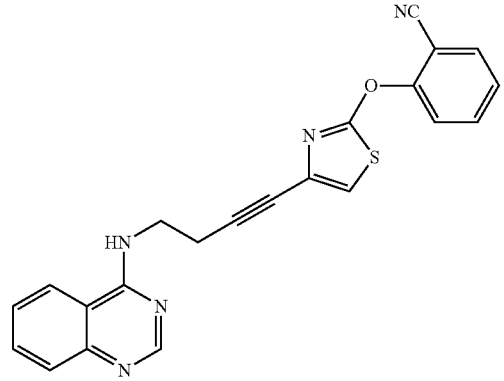 [SMILES: N#Cc1ccccc1Oc1nc(C#CCCNc2ncnc3ccccc23)cs1] | m.p. 185~186° C. |
| 222 | 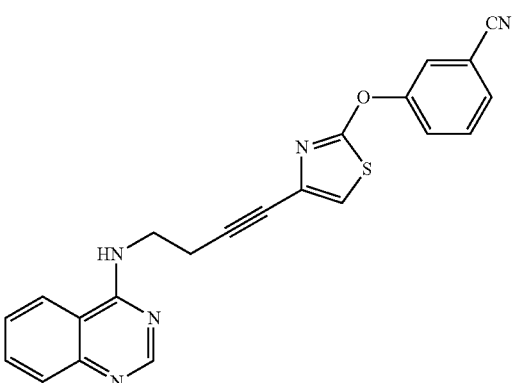 | m.p. 137~139° C. |
TABLE 1-42
| Compound No. | Structure | Physical property |
|---|---|---|
| 223 | 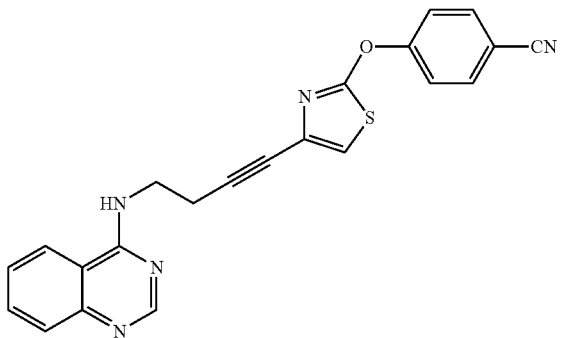 [SMILES: N#Cc1ccc(Oc2nc(C#CCCNc3ncnc4ccccc34)cs2)cc1] | m.p. 55~57° C. |

TABLE 1-42-continued

| Compound No. | Structure | Physical property |
|---|---|---|
| 224 | 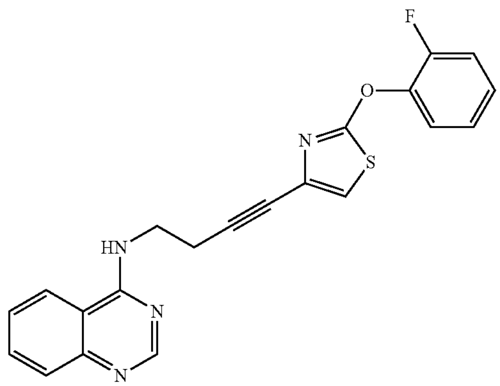 [SMILES: Fc1ccccc1Oc1nc(C#CCCNc2ncnc3ccccc23)cs1] | m.p. 136~138° C. |
| 225 | 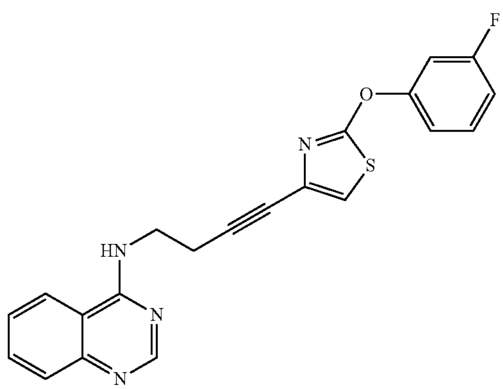 [SMILES: Fc1cccc(Oc2nc(C#CCCNc3ncnc4ccccc34)cs2)c1] | m.p. 134~136° C. |
| 226 | 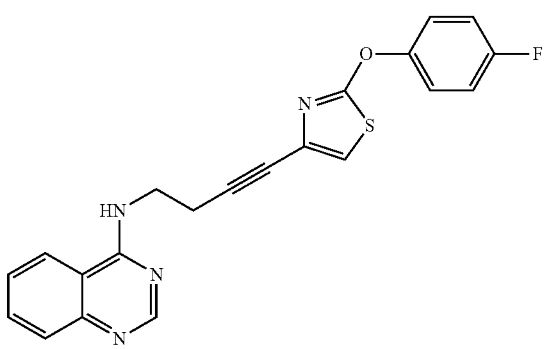 [SMILES: Fc1ccc(Oc2nc(C#CCCNc3ncnc4ccccc34)cs2)cc1] | m.p. 116~118° C. |
| 227 | 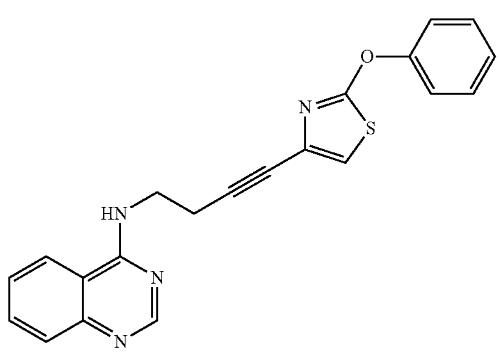 [SMILES: C(#Cc1csc(Oc2ccccc2)n1)CCNc1ncnc2ccccc12] | Resinoid product |

TABLE 1-43

| Compound No. | Structure | Physical property |
|---|---|---|
| 228 | (quinazolin-4-yl)amino-propynyl-(2-piperidin-1-yl-thiazol-4-yl) | Oily product |
| 229 | (thieno[2,3-d]pyrimidin-4-yl)amino-methyl-propynyl-phenyl, racemic | Resinoid product |
| 230 | (thieno[2,3-d]pyrimidin-4-yl)amino-methyl-propynyl-(4-fluorophenyl), racemic | m.p. 126~128° C. |
| 231 | (thieno[2,3-d]pyrimidin-4-yl)amino-methyl-propynyl-(2-chlorophenyl), racemic | Oily product |
| 232 | (thieno[2,3-d]pyrimidin-4-yl)amino-methyl-propynyl-(4-chlorophenyl), racemic | m.p. 110~115° C. |

TABLE 1-44

| Compound No. | Structure | Physical property |
|---|---|---|
| 233 | *N*-(4-(2-(trifluoromethyl)phenyl)but-3-yn-2-yl)thieno[2,3-d]pyrimidin-4-amine, racemic | Oily product |
| 234 | *N*-(4-(3-(trifluoromethyl)phenyl)but-3-yn-2-yl)thieno[2,3-d]pyrimidin-4-amine, racemic | Oily product |
| 235 | *N*-(4-(4-(trifluoromethyl)phenyl)but-3-yn-2-yl)thieno[2,3-d]pyrimidin-4-amine, racemic | m.p. 126~129° C. |
| 236 | *N*-(4-(2-methoxyphenyl)but-3-yn-2-yl)thieno[2,3-d]pyrimidin-4-amine, racemic | Resinoid product |
| 237 | *N*-(4-(2-(methylsulfonyl)phenyl)but-3-yn-2-yl)thieno[2,3-d]pyrimidin-4-amine, racemic | Oily product |

TABLE 1-44-continued
| Compound No. | Structure | Physical property |
|---|---|---|
| 238 | 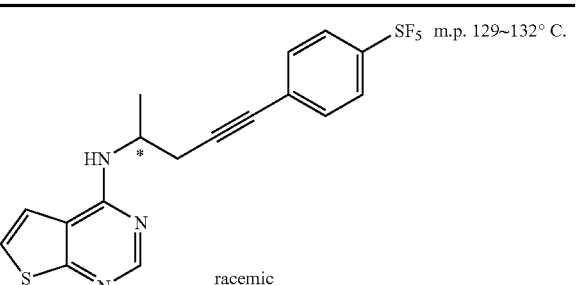 racemic | m.p. 129~132° C. |
TABLE 1-45
| Compound No. | Structure | Physical property |
|---|---|---|
| 239 | racemic | Oily product |
| 240 | racemic | Oily product |
| 241 | racemic | Oily product |
| 242 | racemic | Oily product |

TABLE 1-45-continued

| Compound No. | Structure | Physical property |
| --- | --- | --- |
| 243 | (thieno[2,3-d]pyrimidin-4-yl-NH-CH(CH3)-C≡C-(2-(hydroxymethyl)phenyl)), racemic | m.p. 141~142° C. |
| 244 | (thieno[2,3-d]pyrimidin-4-yl-NH-CH(CH3)-C≡C-(4-fluoro-2-(hydroxymethyl)phenyl)), racemic | m.p. 138~139° C. |

TABLE 1-46

| Compound No. | Structure | Physical property |
| --- | --- | --- |
| 245 | (thieno[2,3-d]pyrimidin-4-yl-NH-CH(CH3)-C≡C-(4-chloro-2-(hydroxymethyl)phenyl)), racemic | m.p. 125~126° C. |
| 246 | (thieno[2,3-d]pyrimidin-4-yl-NH-CH(CH3)-C≡C-(4-fluoro-2-methylphenyl)), racemic | Resinoid product |
| 247 | (thieno[2,3-d]pyrimidin-4-yl-NH-CH(CH3)-C≡C-(2-chloro-4-fluorophenyl)), racemic | Resinoid product |

TABLE 1-46-continued
| Compound No. | Structure | Physical property |
|---|---|---|
| 248 | 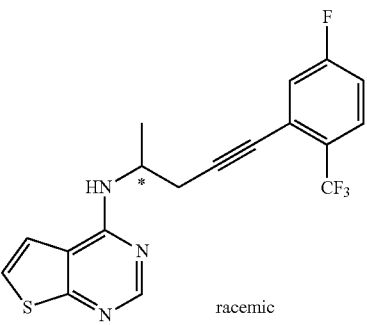 [SMILES: CC(CC#Cc1cc(F)ccc1C(F)(F)F)Nc1ncnc2sccc12] racemic | m.p. 118~120° C. |
| 249 | 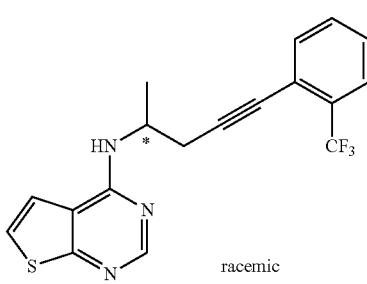 racemic | Oily product |
TABLE 1-47
| Compound No. | Structure | Physical property |
|---|---|---|
| 250 | 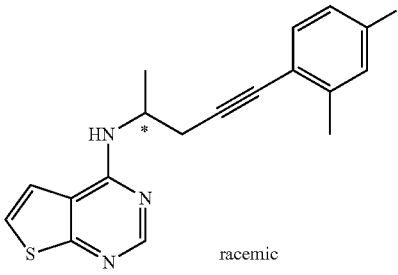 racemic | Oily product |
| 251 | 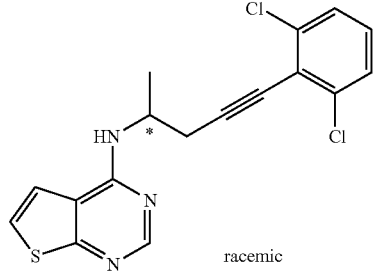 [SMILES: CC(CC#Cc1c(Cl)cccc1Cl)Nc1ncnc2sccc12] racemic | Oily product |
| 252 | 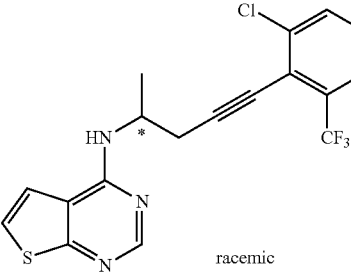 racemic | Resinoid product |

TABLE 1-47-continued
| Compound No. | Structure | Physical property |
|---|---|---|
| 253 | 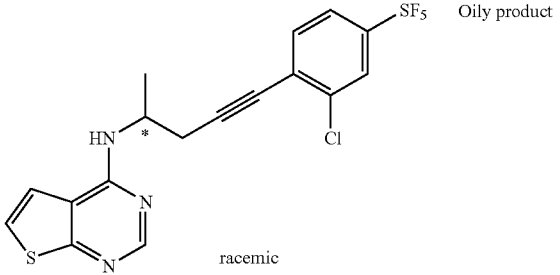 racemic | Oily product |
| 254 | 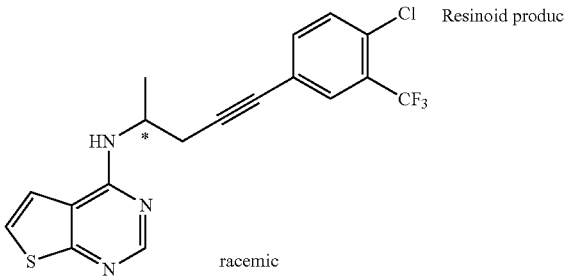 racemic | Resinoid product |
| 255 | 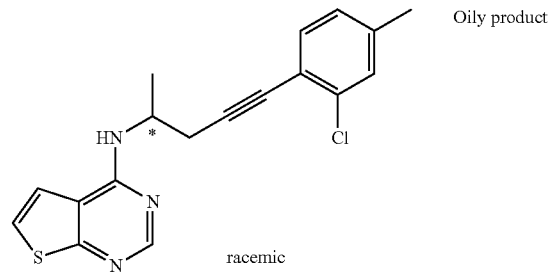 racemic | Oily product |
TABLE 1-48
| Compound No. | Structure | Physical property |
|---|---|---|
| 256 | 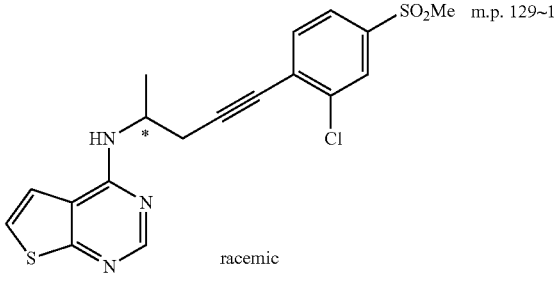 racemic | m.p. 129~134° C. |
| 257 | 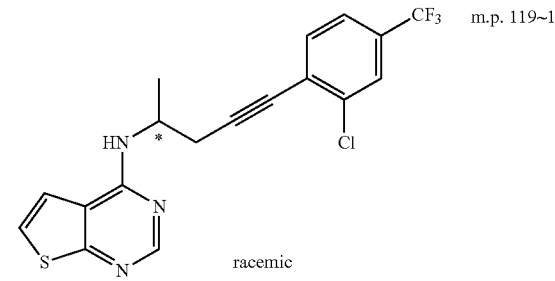 racemic | m.p. 119~123° C. |

TABLE 1-48-continued
| Compound No. | Structure | Physical property |
|---|---|---|
| 258 | 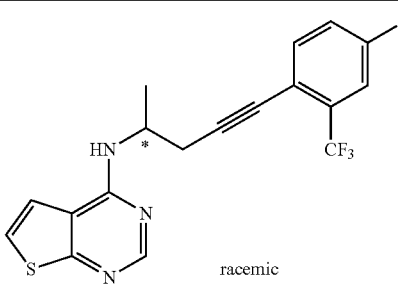 racemic | m.p. 115~117° C. |
| 259 | 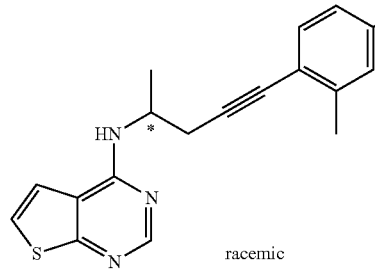 racemic | Oily product |
| 260 | 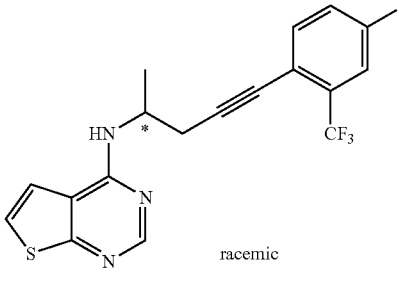 racemic | Oily product |
| 261 | 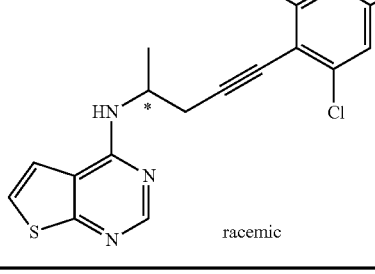 racemic | Resinoid product |
TABLE 1-49
| Compound No. | Structure | Physical property |
|---|---|---|
| 262 | 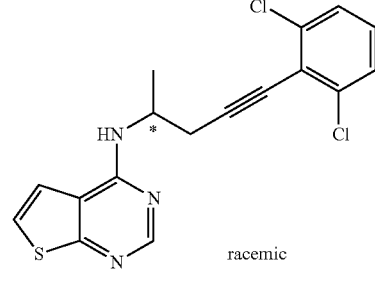 racemic | Oily product |

TABLE 1-49-continued
| Compound No. | Structure | Physical property |
|---|---|---|
| 263 | 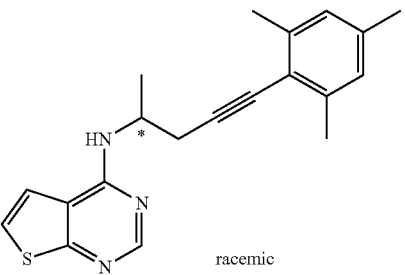 [SMILES: Cc1ccc(C#CCC(C)Nc2ncnc3sccc23)c(C)c1] racemic | Oily product |
| 264 | 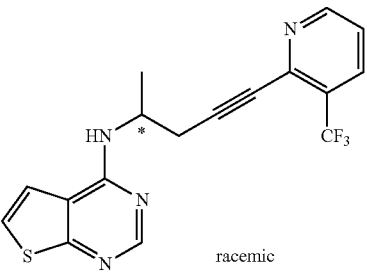 [SMILES: CC(CC#Cc1ncccc1C(F)(F)F)Nc1ncnc2sccc12] racemic | Oily product |
| 265 | 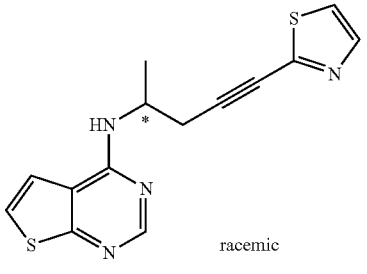 [SMILES: CC(CC#Cc1nccs1)Nc1ncnc2sccc12] racemic | Resinoid product |
| 266 | 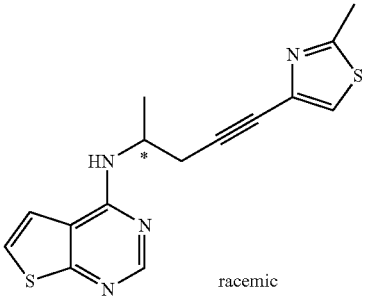 [SMILES: Cc1nc(C#CCC(C)Nc2ncnc3sccc23)cs1] racemic | Resinoid product |
| 267 | 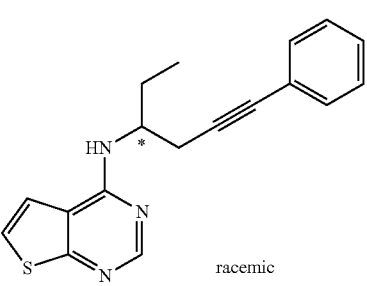 [SMILES: CCC(CC#Cc1ccccc1)Nc1ncnc2sccc12] racemic | Oily product |

TABLE 1-50
| Compound No. | Structure | Physical property |
|---|---|---|
| 268 | 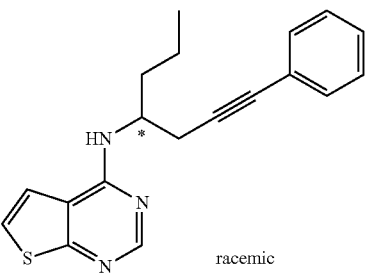 [SMILES: CCCC(CC#Cc1ccccc1)Nc1ncnc2sccc12] racemic | Oily product |
| 269 | 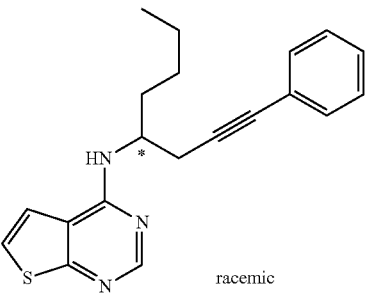 [SMILES: CCCCC(CC#Cc1ccccc1)Nc1ncnc2sccc12] racemic | Oily product |
| 270 | 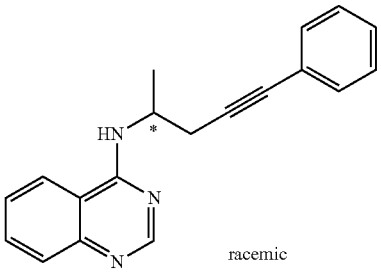 [SMILES: CC(CC#Cc1ccccc1)Nc1ncnc2ccccc12] racemic | m.p. 158~160° C. |
| 271 | 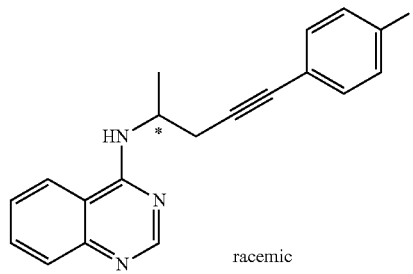 racemic | m.p. 154~157° C. |
| 272 | 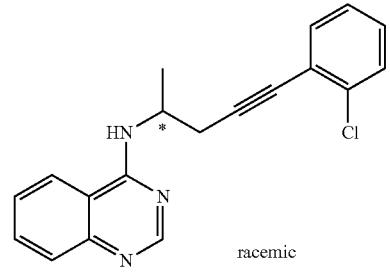 racemic | m.p. 158~159° C. |

TABLE 1-50-continued
| Compound No. | Structure | Physical property |
|---|---|---|
| 273 | 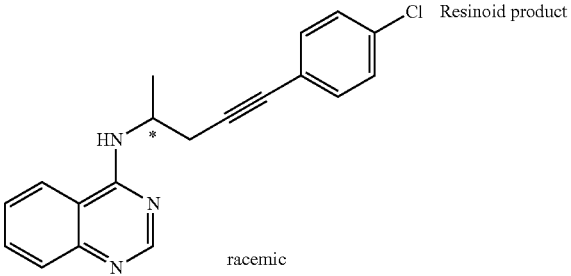 racemic | Resinoid product |
TABLE 1-51
| Compound No. | Structure | Physical property |
|---|---|---|
| 274 | 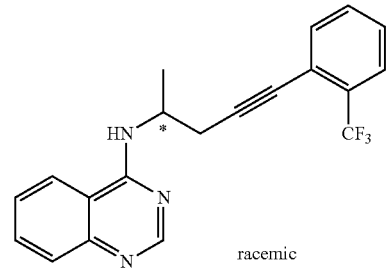 [SMILES: CC(CC#Cc1ccccc1C(F)(F)F)Nc1ncnc2ccccc12] racemic | Resinoid product |
| 275 | 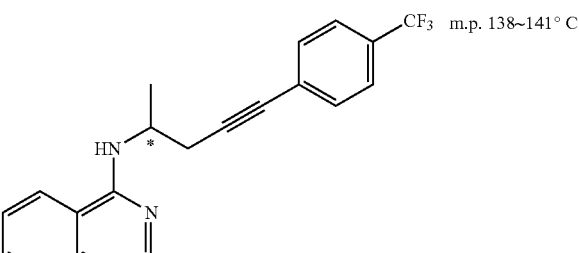 racemic | m.p. 138~141° C. |
| 276 | 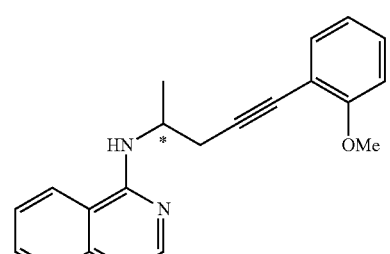 racemic | Oily product |
| 277 | 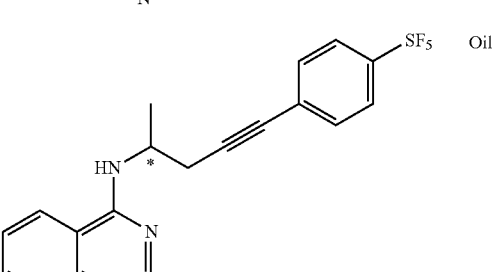 racemic | Oily product |

TABLE 1-51-continued

| Compound No. | Structure | Physical property |
|---|---|---|
| 278 | (quinazolin-4-yl)NH-CH(Me)-C≡C-(2-(CH2OMe)phenyl), racemic | Oily product |
| 279 | (quinazolin-4-yl)NH-CH(Me)-C≡C-(4-methylphenyl), racemic | m.p. 164~166° C. |

TABLE 1-52

| Compound No. | Structure | Physical property |
|---|---|---|
| 280 | (quinazolin-4-yl)NH-CH(Me)-C≡C-(2,4-bis(CF$_3$)phenyl), racemic | Oily product |
| 281 | (quinazolin-4-yl)NH-CH(Me)-C≡C-(2-Cl-4-(CF(CF$_3$)$_2$)phenyl), racemic | Oily product |
| 282 | (quinazolin-4-yl)NH-CH(Me)-C≡C-(2-Cl-4-CF$_3$-phenyl), racemic | Oily product |

TABLE 1-52-continued
| Compound No. | Structure | Physical property |
|---|---|---|
| 283 | 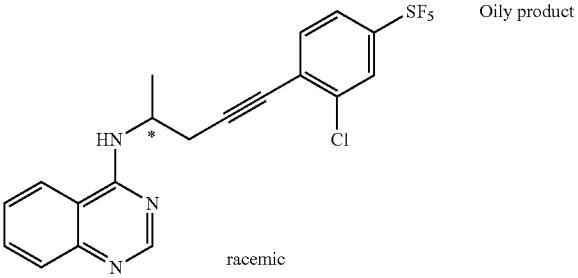 racemic | Oily product |
| 284 | 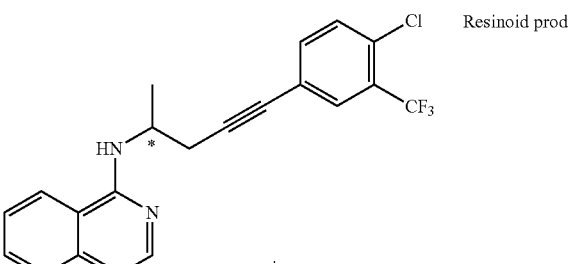 racemic | Resinoid product |
TABLE 1-53
| Compound No. | Structure | Physical property |
|---|---|---|
| 285 | 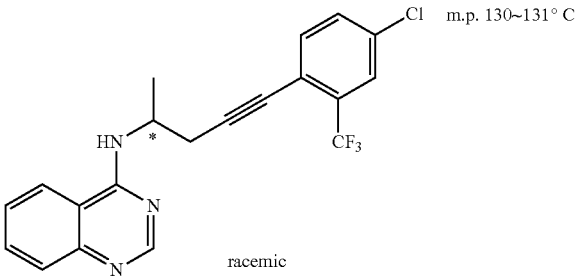 racemic | m.p. 130~131° C. |
| 286 | 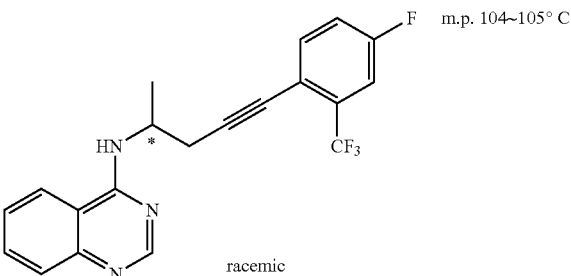 racemic | m.p. 104~105° C. |
| 287 | 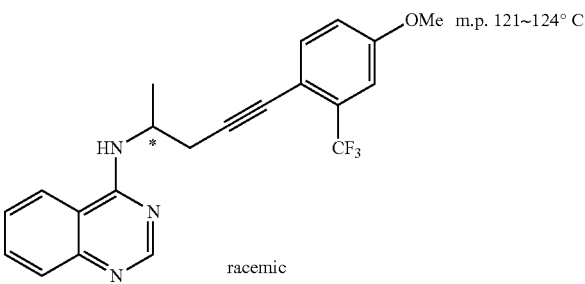 racemic | m.p. 121~124° C. |

TABLE 1-53-continued

| Compound No. | Structure | Physical property |
| --- | --- | --- |
| 288 | 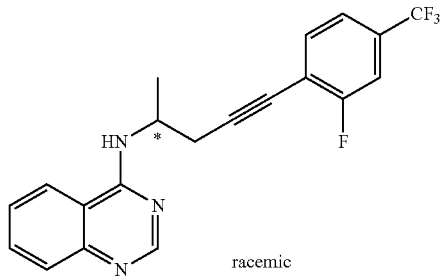 [SMILES: CC(CC#Cc1ccc(C(F)(F)F)cc1F)Nc1ncnc2ccccc12] | m.p. 110~112° C. |
| 289 | 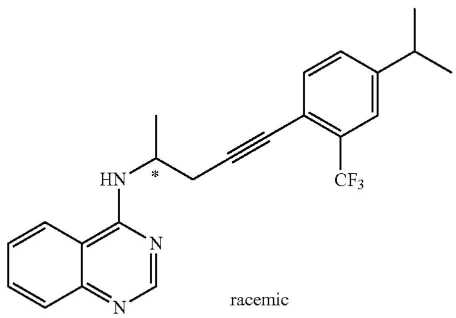 [SMILES: CC(CC#Cc1ccc(C(C)C)cc1C(F)(F)F)Nc1ncnc2ccccc12] | m.p. 130~131° C. |

TABLE 1-54

| Compound No. | Structure | Physical property |
| --- | --- | --- |
| 290 | 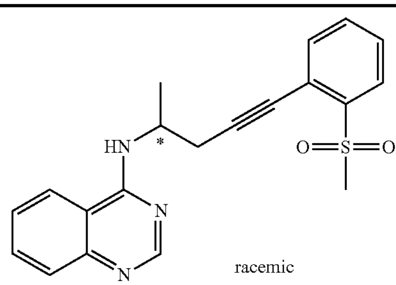 | Oily product |
| 291 | 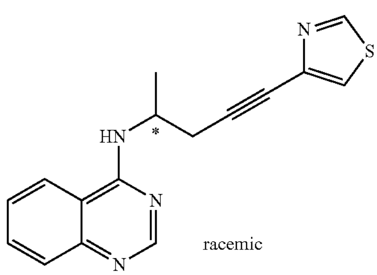 [SMILES: CC(CC#Cc1cscn1)Nc1ncnc2ccccc12] | m.p. 142~145° C. |
| 292 | 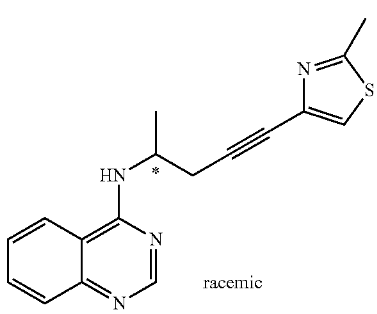 [SMILES: Cc1nc(C#CCC(C)Nc2ncnc3ccccc23)cs1] | Resinoid product |

TABLE 1-54-continued
| Compound No. | Structure | Physical property |
|---|---|---|
| 293 | 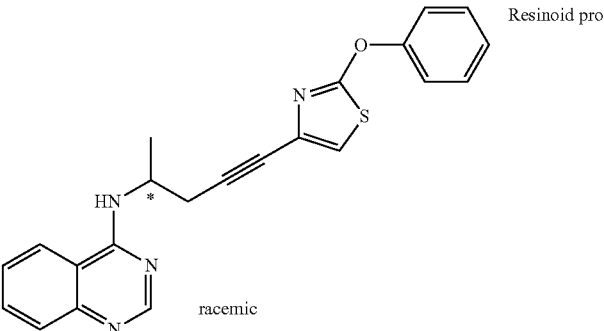 racemic | Resinoid product |
| 294 | 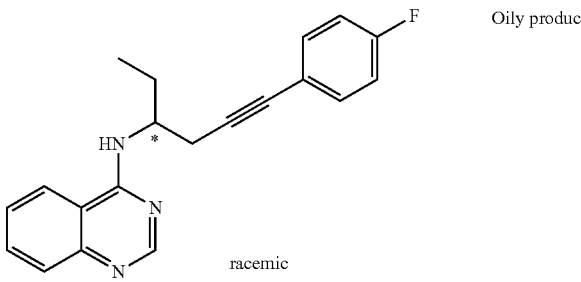 racemic | Oily product |
TABLE 1-55
| Compound No. | Structure | Physical property |
|---|---|---|
| 295 | 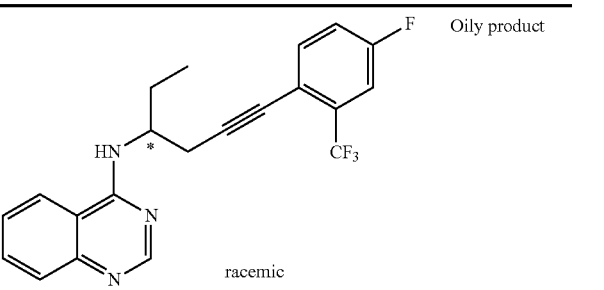 racemic | Oily product |
| 296 | 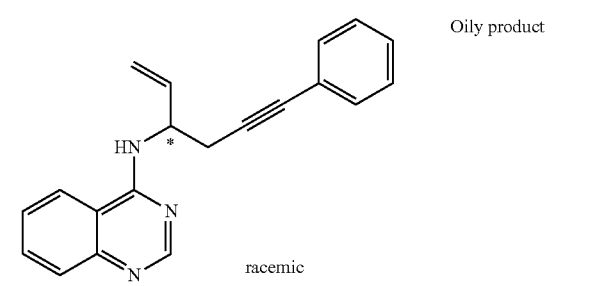 racemic | Oily product |
| 297 | 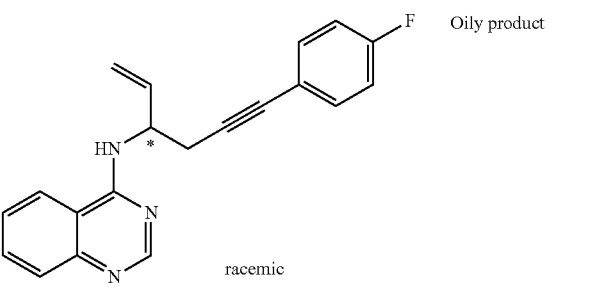 racemic | Oily product |

TABLE 1-55-continued
| Compound No. | Structure | Physical property |
|---|---|---|
| 298 | 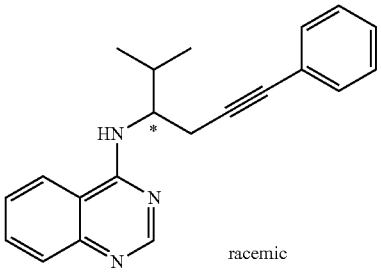 [SMILES: CC(C)C(CC#Cc1ccccc1)Nc1ncnc2ccccc12] racemic | Oily product |
| 299 | 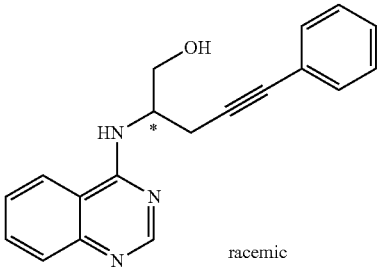 [SMILES: OCC(CC#Cc1ccccc1)Nc1ncnc2ccccc12] racemic | Oily product |
| 300 | 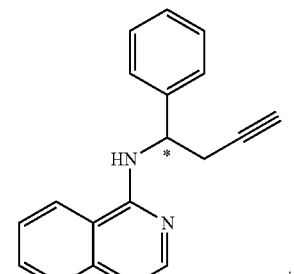 racemic | m.p. 127~129° C. |
TABLE 1-56
| Compound No. | Structure | Physical property |
|---|---|---|
| 301 | 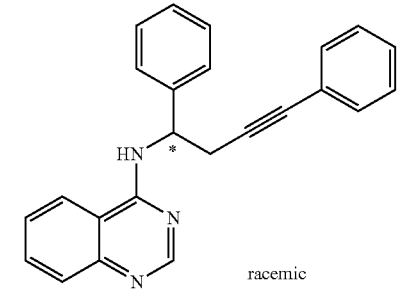 [SMILES: C(#Cc1ccccc1)CC(Nc1ncnc2ccccc12)c1ccccc1] racemic | m.p. 141~143° C. |
| 302 | 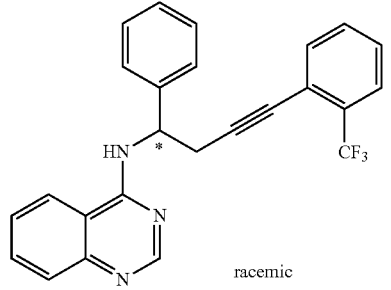 [SMILES: FC(F)(F)c1ccccc1C#CCC(Nc1ncnc2ccccc12)c1ccccc1] racemic | m.p. 150~152° C. |

TABLE 1-56-continued

| Compound No. | Structure | Physical property |
|---|---|---|
| 303 | (ethyl ester, quinazolin-4-ylamino, phenyl alkyne) racemic | Oily product |
| 304 | (ethyl ester, quinazolin-4-ylamino, 2-CF3-phenyl alkyne) racemic | Oily product |
| 305 | (N-methyl amide, quinazolin-4-ylamino, phenyl alkyne) racemic | Resinoid product |

TABLE 1-57

| Compound No. | Structure | Physical property |
|---|---|---|
| 306 | (8-fluoroquinazolin-4-yl)-NH-CH2CH2-C≡C-(2-CF3-phenyl) | m.p. 118~124° C. |
| 307 | (8-chloroquinazolin-4-yl)-NH-CH2CH2-C≡C-(2-CF3-phenyl) | m.p. 170~171° C. |

TABLE 1-57-continued
| Compound No. | Structure | Physical property |
|---|---|---|
| 308 | 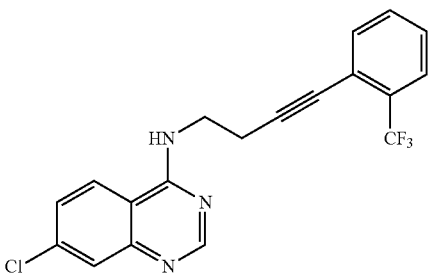 [SMILES: FC(F)(F)c1ccccc1C#CCCNc1ncnc2cc(Cl)ccc12] | m.p. 153~154° C. |
| 309 | 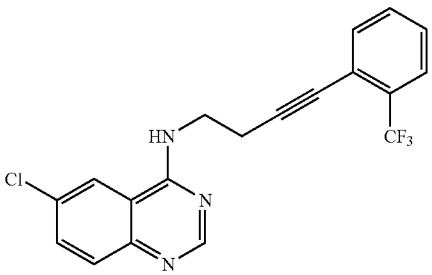 [SMILES: FC(F)(F)c1ccccc1C#CCCNc1ncnc2ccc(Cl)cc12] | m.p. 145~146° C. |
| 310 | 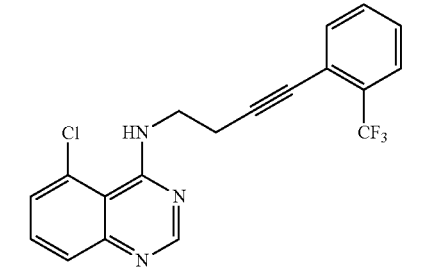 [SMILES: FC(F)(F)c1ccccc1C#CCCNc1ncnc2cccc(Cl)c12] | m.p. 95~97° C. |
| 311 | 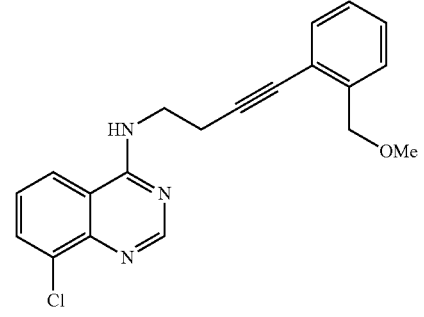 | 159° C. |
TABLE 1-58
| Compound No. | Structure | Physical property |
|---|---|---|
| 312 | 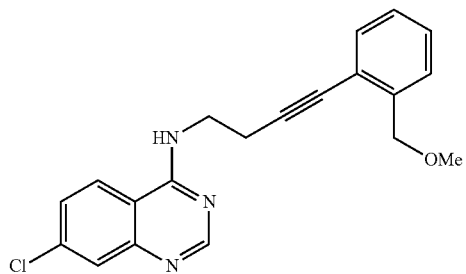 [SMILES: COCc1ccccc1C#CCCNc1ncnc2cc(Cl)ccc12] | m.p. 118~120° C. |

TABLE 1-58-continued
| Compound No. | Structure | Physical property |
|---|---|---|
| 313 | 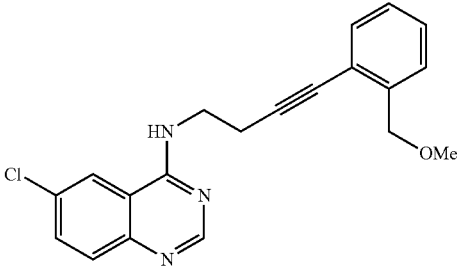 [SMILES: COCc1ccccc1C#CCCNc1ncnc2ccc(Cl)cc12] | Resinoid product |
| 314 | 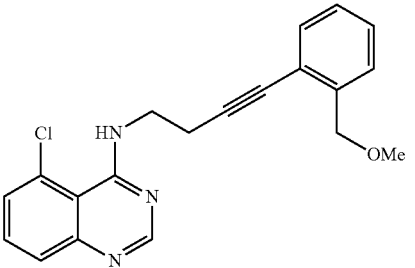 [SMILES: COCc1ccccc1C#CCCNc1ncnc2cccc(Cl)c12] | Oily product |
| 315 | 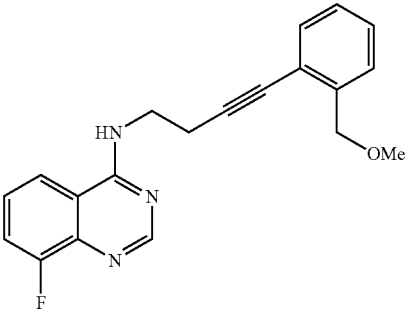 [SMILES: COCc1ccccc1C#CCCNc1ncnc2c(F)cccc12] | m.p. 143~144° C. |
| 316 | 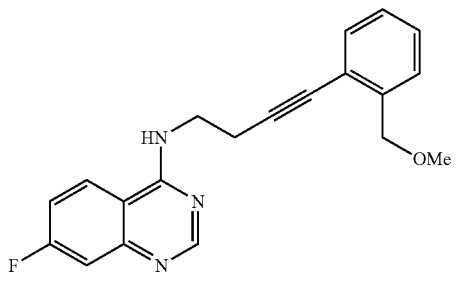 [SMILES: COCc1ccccc1C#CCCNc1ncnc2cc(F)ccc12] | m.p. 113~115° C. |
| 317 | 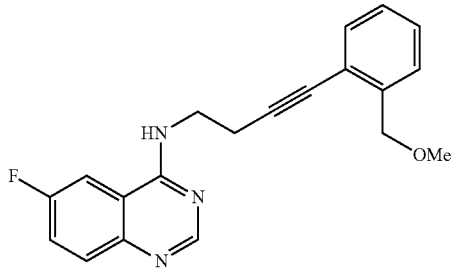 | m.p. 121~122° C. |

TABLE 1-59

| Compound No. | Structure | Physical property |
|---|---|---|
| 318 | 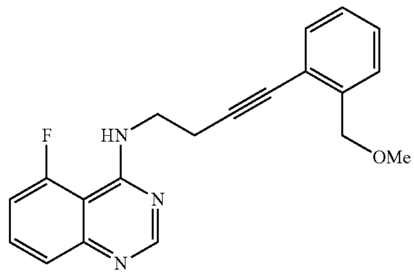 [SMILES: COCc1ccccc1C#CCCNc1ncnc2cccc(F)c12] | Resinoid product |
| 319 | 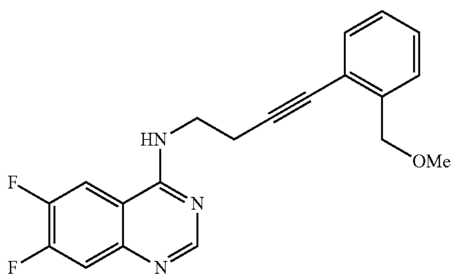 [SMILES: COCc1ccccc1C#CCCNc1ncnc2cc(F)c(F)cc12] | m.p. 117~119° C. |
| 320 | 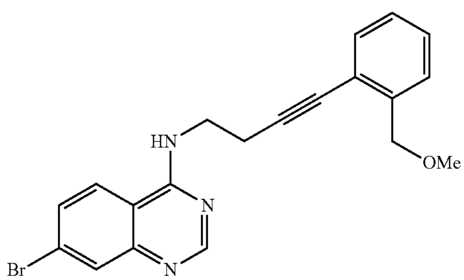 [SMILES: COCc1ccccc1C#CCCNc1ncnc2cc(Br)ccc12] | m.p. 111~114° C. |
| 321 | 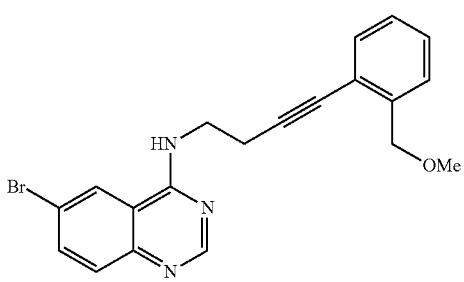 [SMILES: COCc1ccccc1C#CCCNc1ncnc2ccc(Br)cc12] | m.p. 118~120° C. |
| 322 | 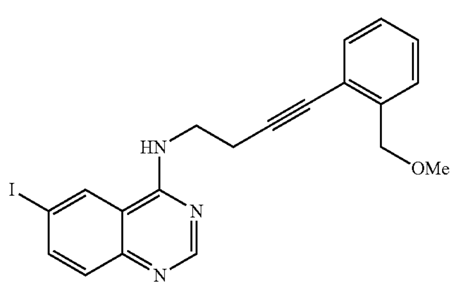 [SMILES: COCc1ccccc1C#CCCNc1ncnc2ccc(I)cc12] | m.p. 121~123° C. |

TABLE 1-59-continued
| Compound No. | Structure | Physical property |
|---|---|---|
| 323 | 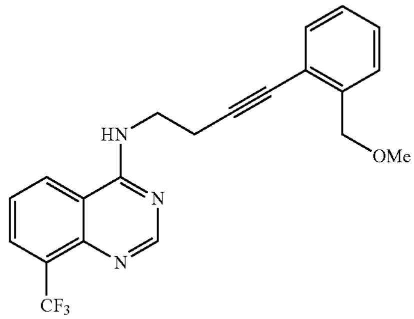 [SMILES: COCc1ccccc1C#CCCNc1ncnc2c(C(F)(F)F)cccc12] | Oily product |
TABLE 1-60
| Compound No. | Structure | Physical property |
|---|---|---|
| 324 | 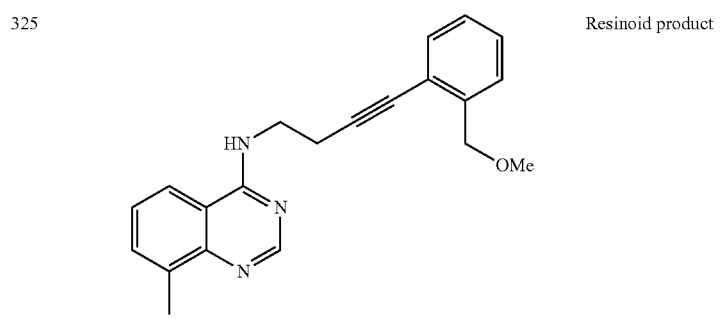 | m.p. 77~79° C. |
| 325 | 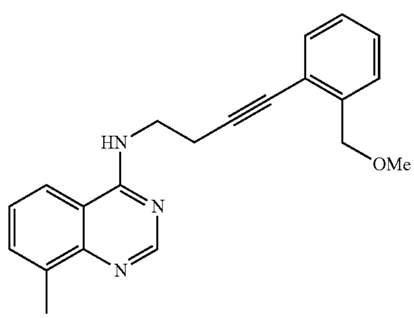 [SMILES: COCc1ccccc1C#CCCNc1ncnc2c(C)cccc12] | Resinoid product |
| 326 | 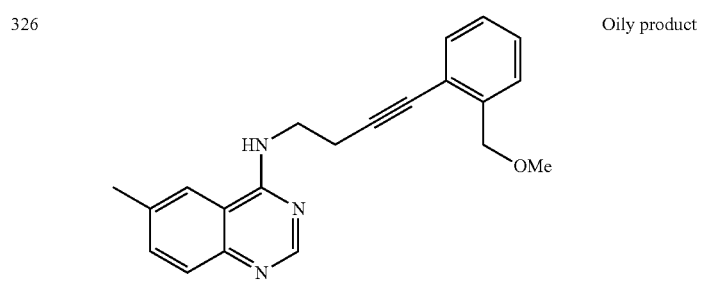 | Oily product |

TABLE 1-60-continued

| Compound No. | Structure | Physical property |
|---|---|---|
| 327 | 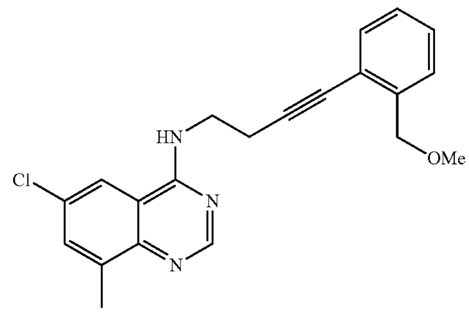 [SMILES: COCc1ccccc1C#CCCNc1ncnc2c(C)cc(Cl)cc12] | Oily product |
| 328 | 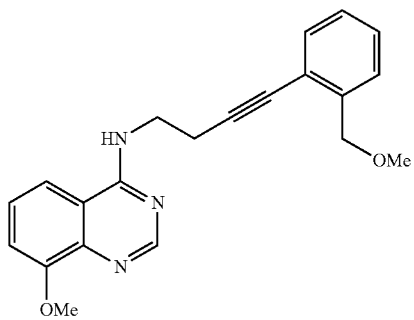 [SMILES: COCc1ccccc1C#CCCNc1ncnc2c(OC)cccc12] | Resinoid product |
| 329 | 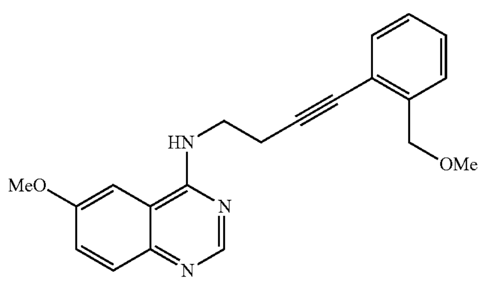 | Oily product |

TABLE 1-61

| Compound No. | Structure | Physical property |
|---|---|---|
| 330 | 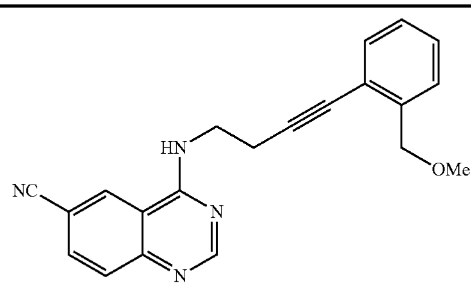 | Oily product |
| 331 | 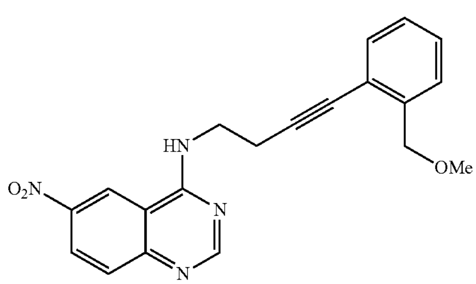 [SMILES: COCc1ccccc1C#CCCNc1ncnc2ccc([N+](=O)[O-])cc12] | Oily product |

TABLE 1-61-continued

| Compound No. | Structure | Physical property |
|---|---|---|
| 332 | MeS-quinazoline-NH-CH₂CH₂-C≡C-C₆H₄-CH₂OMe | Oily product |
| 333 | Ph-quinazoline-NH-CH₂CH₂-C≡C-C₆H₄-CH₂OMe | Resinoid product |
| 334 | (2-F-C₆H₄)-quinazoline-NH-CH₂CH₂-C≡C-C₆H₄-CH₂OMe | Resinoid product |
| 335 | (3-F-C₆H₄)-quinazoline-NH-CH₂CH₂-C≡C-C₆H₄-CH₂OMe | Resinoid product |

TABLE 1-62

| Compound No. | Structure | Physical property |
|---|---|---|
| 336 | (4-F-C₆H₄)-quinazoline-NH-CH₂CH₂-C≡C-C₆H₄-CH₂OMe | m.p. 168~170° C. |

TABLE 1-62-continued

| Compound No. | Structure | Physical property |
| --- | --- | --- |
| 337 | 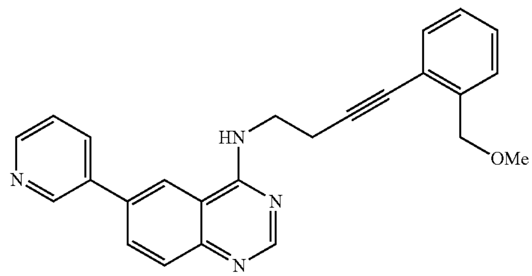 [SMILES: COCc1ccccc1C#CCCNc1ncnc2ccc(-c3cccnc3)cc12] | Resinoid product |
| 338 | 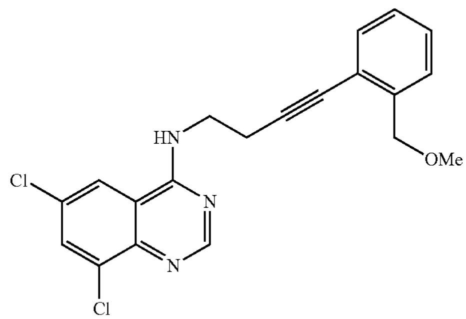 [SMILES: COCc1ccccc1C#CCCNc1ncnc2c(Cl)cc(Cl)cc12] | m.p. 161~162° C. |
| 339 | 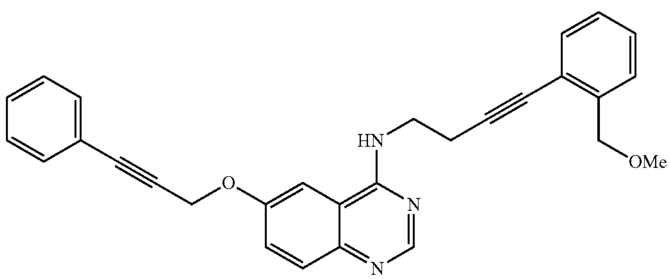 [SMILES: COCc1ccccc1C#CCCNc1ncnc2ccc(OCC#Cc3ccccc3)cc12] | Oily product |
| 340 | 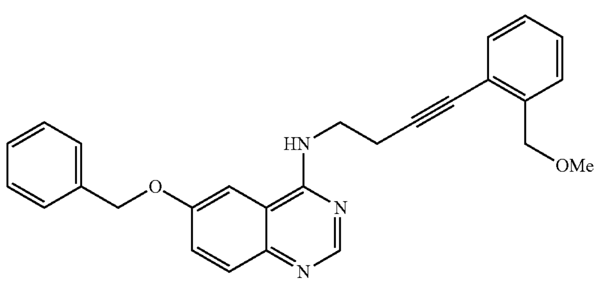 [SMILES: COCc1ccccc1C#CCCNc1ncnc2ccc(OCc3ccccc3)cc12] | Oily product |
| 341 | 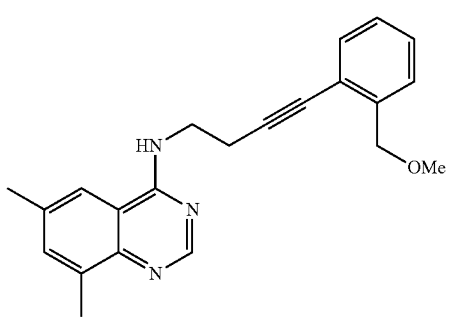 [SMILES: COCc1ccccc1C#CCCNc1ncnc2c(C)cc(C)cc12] | Oily product |

TABLE 1-63

| Compound No. | Structure | Physical property |
|---|---|---|
| 342 | 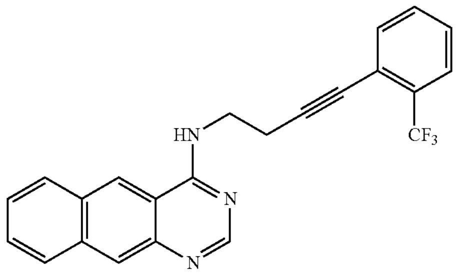 [SMILES: FC(F)(F)c1ccccc1C#CCCNc1ncnc2cc3ccccc3cc12] | >240° C. |
| 343 | racemic | m.p. 105~108° C. |
| 344 | racemic | Oily product |
| 345 | racemic | Resinoid product |
| 346 | racemic | Oily product |

TABLE 1-63-continued
| Compound No. | Structure | Physical property |
|---|---|---|
| 347 | 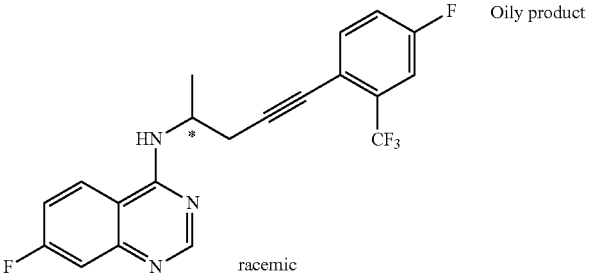 racemic | Oily product |
TABLE 1-64
| Compound No. | Structure | Physical property |
|---|---|---|
| 348 | 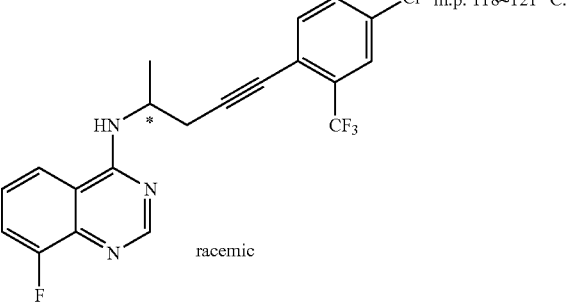 racemic | m.p. 118~121° C. |
| 349 | 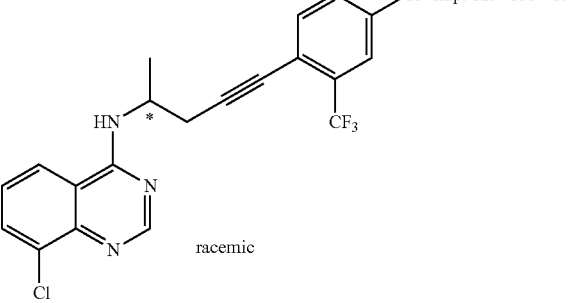 racemic | m.p. 129~135° C. |
| 350 | 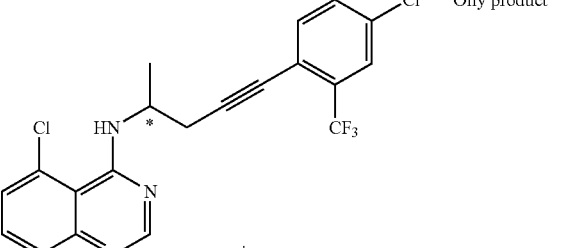 racemic | Oily product |

TABLE 1-64-continued

| Compound No. | Structure | Physical property |
|---|---|---|
| 351 | N-(quinazolin-4-yl, 8-CF3) amine with pent-3-yn-2-yl linker to 4-Cl-2-CF3-phenyl; racemic | Oily product |
| 352 | N-(quinazolin-4-yl, 8-OMe) amine with pent-3-yn-2-yl linker to 4-Cl-2-CF3-phenyl; racemic | m.p. 197~198° C. |

TABLE 1-65

| Compound No. | Structure | Physical property |
|---|---|---|
| 353 | N-(quinazolin-4-yl, 8-OMe) amine with pent-3-yn-2-yl linker to 4-F-2-CF3-phenyl; racemic | m.p. 160~161° C. |
| 354 | N-(quinazolin-4-yl, 8-Me) amine with pent-3-yn-2-yl linker to 4-Cl-2-CF3-phenyl; racemic | Oily product |

TABLE 1-65-continued

| Compound No. | Structure | Physical property |
|---|---|---|
| 355 | 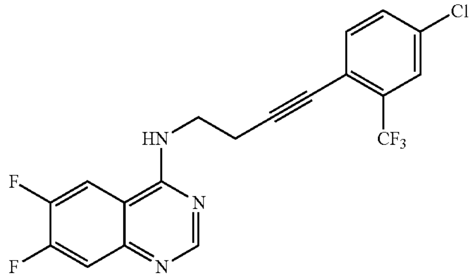 [SMILES: Fc1cc2ncnc(NCCC#Cc3ccc(Cl)cc3C(F)(F)F)c2cc1F] | Resinoid product |
| 356 | 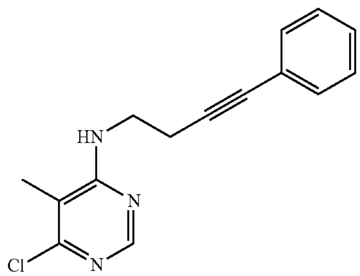 [SMILES: Cc1c(Cl)ncnc1NCCC#Cc1ccccc1] | m.p. 112~114° C. |
| 357 | 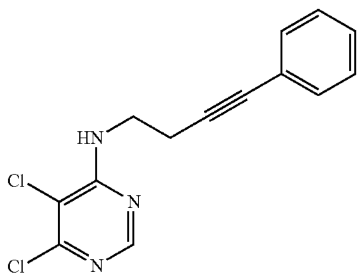 [SMILES: Clc1ncnc(NCCC#Cc2ccccc2)c1Cl] | m.p. 122~123° C. |

TABLE 1-66

| Compound No. | Structure | Physical property |
|---|---|---|
| 358 | 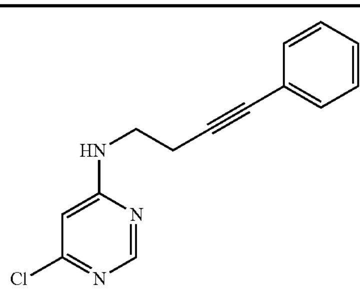 | m.p. 118~120° C. |
| 359 | 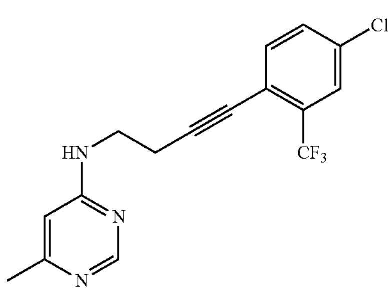 [SMILES: Cc1cc(NCCC#Cc2ccc(Cl)cc2C(F)(F)F)ncn1] | Oily product |

TABLE 1-66-continued

| Compound No. | Structure | Physical property |
|---|---|---|
| 360 | 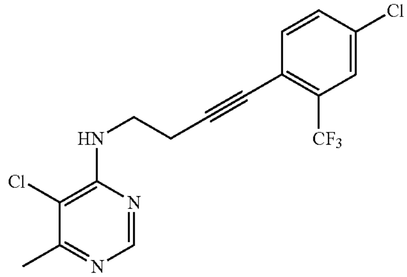 [SMILES: Cc1ncnc(NCCC#Cc2ccc(Cl)cc2C(F)(F)F)c1Cl] | m.p. 91~93° C. |
| 361 | 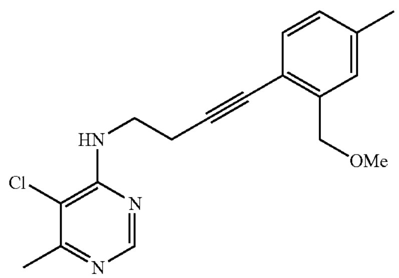 | Resinoid product |
| 362 | 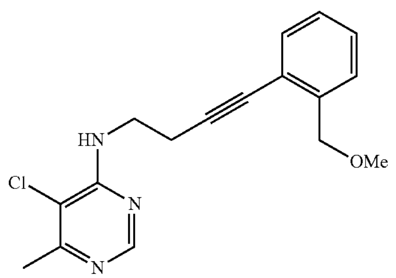 | Resinoid product |
| 363 | 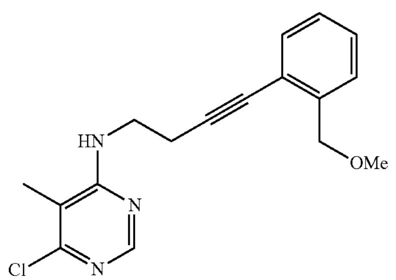 [SMILES: COCc1ccccc1C#CCCNc1ncnc(Cl)c1C] | Oily product |

TABLE 1-67

| Compound No. | Structure | Physical property |
|---|---|---|
| 364 | 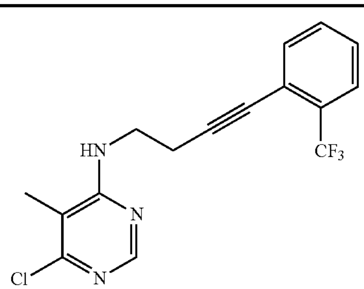 | Resinoid product |
| 365 | | Oily product |

TABLE 1-67-continued

| Compound No. | Structure | Physical property |
|---|---|---|
| 366 | 5-Br, 6-Cl pyrimidin-4-yl NH-CH2CH2-C≡C-(2-CH2OMe-phenyl) | Oily product |
| 367 | 5-Br, 6-Cl pyrimidin-4-yl NH-CH2CH2-C≡C-(2-CF3-phenyl) | m.p. 102~103° C. |
| 368 | 5-NH2, 6-Cl pyrimidin-4-yl NH-CH2CH2-C≡C-(2-CF3-phenyl) | Oily product |
| 369 | 5-NO2, 6-SO2Me pyrimidin-4-yl NH-CH2CH2-C≡C-(2-CF3-phenyl) | Resinoid product |

TABLE 1-68

| Compound No. | Structure | Physical property |
|---|---|---|
| 370 | 5-NO2, 6-Cl pyrimidin-4-yl NH-CH2CH2-C≡C-(2-CF3-phenyl) | Oily product |
| 371 | 5-NO2, 6-SMe pyrimidin-4-yl NH-CH2CH2-C≡C-(2-CF3-phenyl) | Resinoid product |
| 372 | 5-benzyl, 6-Cl pyrimidin-4-yl NH-CH2CH2-C≡C-phenyl | m.p. 157~158° C. |

TABLE 1-68-continued

| Compound No. | Structure | Physical property |
|---|---|---|
| 373 | 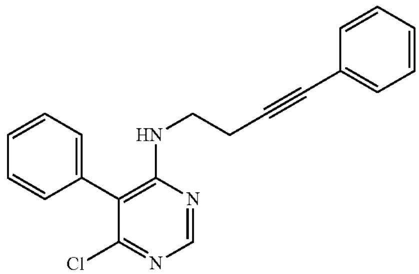 [SMILES: Clc1ncnc(NCCC#Cc2ccccc2)c1-c1ccccc1] | Resinoid product |
| 374 | racemic | Oily product |
| 375 | racemic | Oily product |

TABLE 1-69

| Compound No. | Structure | Physical property |
|---|---|---|
| 376 | racemic | m.p. 84–86° C. |

TABLE 1-69-continued

| Compound No. | Structure | Physical property |
|---|---|---|
| 377 | 5-chloro-6-(1-fluoroethyl)-N-(4-(4-chloro-2-(trifluoromethyl)phenyl)but-3-yn-1-yl)pyrimidin-4-amine (racemic) | Oily product |
| 378 | N-(4-phenylbut-3-yn-1-yl)-7H-purin-6-amine | m.p. 207~208° C. |
| 379 | N-(4-phenylbut-3-yn-1-yl)-7H-pyrrolo[2,3-d]pyrimidin-4-amine | Resinoid product |
| 380 | N-(4-(2-(methoxymethyl)phenyl)but-3-yn-1-yl)pyrido[2,3-d]pyrimidin-4-amine | m.p. 158~161° C. |

TABLE 1-70
| Compound No. | Structure | Physical property |
|---|---|---|
| 381 | 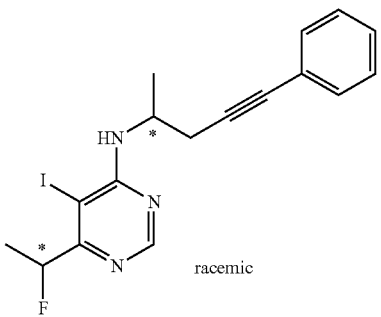 [SMILES: CC(CC#Cc1ccccc1)Nc1ncnc(C(C)F)c1I] racemic | Oily product |
| 382 | 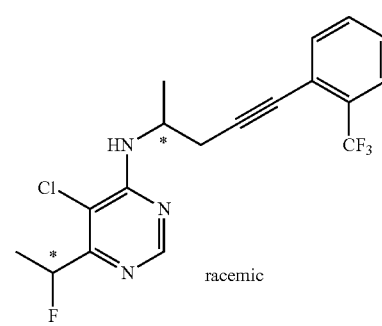 racemic | Oily product |
| 383 | 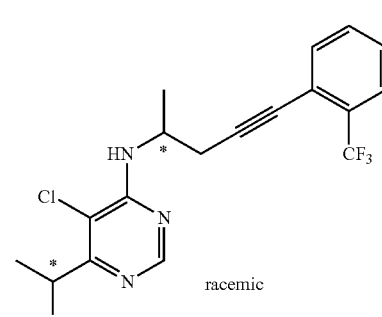 racemic | Oily product |
| 384 | 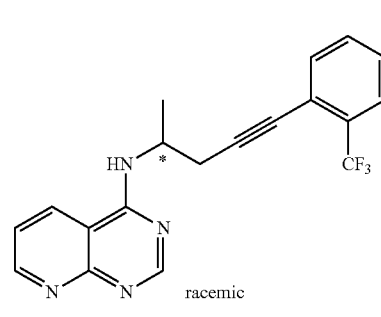 racemic | m.p. 176~180° C. |
| 385 | 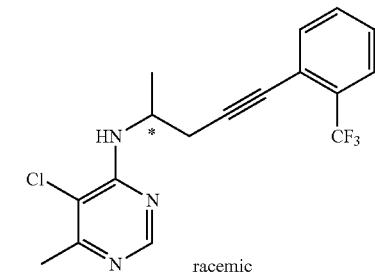 [SMILES: Cc1ncnc(NC(C)CC#Cc2ccccc2)c1Cl] racemic | Resinoid product |

TABLE 1-70-continued

| Compound No. | Structure | Physical property |
|---|---|---|
| 386 | (5-iodo-6-methylpyrimidin-4-yl)-NH-CH(CH₃)-C≡C-(4-chloro-2-trifluoromethylphenyl), racemic | Resinoid product |

TABLE 1-71

| Compound No. | Structure | Physical property |
|---|---|---|
| 387 | (5-bromo-6-methylpyrimidin-4-yl)-NH-CH(CH₃)-C≡C-(4-chloro-2-trifluoromethylphenyl), racemic | Resinoid product |
| 388 | (5-chloro-6-trifluoromethylpyrimidin-4-yl)-NH-CH(CH₃)-C≡C-(4-chloro-2-trifluoromethylphenyl), racemic | m.p. 96~98° C. |
| 389 | (5-chloro-6-methylpyrimidin-4-yl)-NH-CH(CH₃)-C≡C-phenyl, racemic | Resinoid product |

TABLE 1-72

| | | |
|---|---|---|
| 390 | 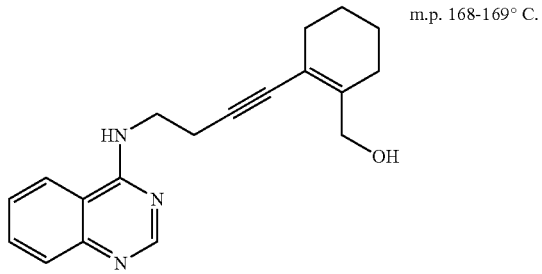 | m.p. 168-169° C. |
| 391 | 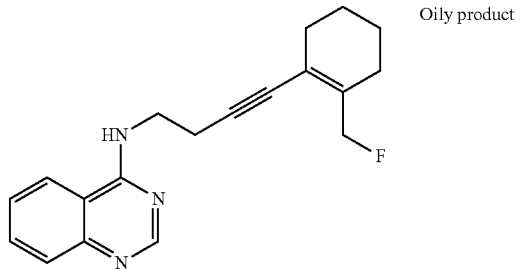 | Oily product |

TABLE 2-1

| Compound No. | δ value (ppm; solvent, CDCl₃; internal standard substance, TMS) |
|---|---|
| 1 | 2.05 (t, 1H), 2.60 (dt, 2H), 3.80 (q, 2H), 5.82 (brs, 1H), 7.18 (d, 2H), 7.28 (d, 2H), 8.51 (s, 1H) |
| 2 | 0.05 (s, 9H), 2.47 (t, 2H), 3.63 (q, 2H), 5.52 (brs, 1H), 6.97 (d, 2H), 7.13 (d, 2H), 8.35 (s, 1H) |
| 3 | 0.43-0.71 (m, 6H), 0.91-1.10 (m, 9H), 2.65 (t, 2H), 3.78 (q, 2H), 5.62 (brs, 1H), 7.10 (d, 2H), 7.29 (d, 2H), 8.50 (s, 1H) |
| 4 | 1.06 (s, 21H), 2.67 (t, 2H), 3.81 (q, 1H), 5.51 (brs, 1H), 7.08 (d, 2H), 7.28 (d, 2H), 8.51 (s, 1H) |
| 5 | 0.05 (s, 6H), 0.83 (s, 9H), 2.55 (t, 2H), 3.69 (q, 2H), 5.42 (brs, 1H), 7.00 (d, 2H), 7.19 (d, 2H), 8.41 (s, 1H) |
| 6 | 0.90 (t, 3H), 1.26-1.53 (m, 4H), 2.08-2.24 (m, 2H), 2.46-2.66 (m, 2H), 3.74 (q, 2H), 5.68 (brs, 1H), 7.14 (d, 2H), 7.29 (d, 2H), 8.51 (s, 1H) |
| 7 | 1.02 (d, 6H), 1.70-1.84 (m, 1H), 2.00-2.12 (m, 2H), 2.48-2.67 (m, 2H), 3.75 (q, 2H), 5.76 (brs, 1H), 7.14 (d, 2H), 7.28 (d, 2H), 8.50 (s, 1H) |
| 8 | 1.21 (s, 9H), 2.55 (t, 2H), 3.74 (q, 2H), 5.52 (brs, 1H), 7.12 (d, 2H), 7.29 (d, 2H), 8.51 (s, 1H) |
| 9 | 2.52-2.72 (m, 2H), 3.55-3.67 (m, 2H), 3.80 (q, 2H), 5.74 (brs, 1H), 6.97-7.35 (m, 7H), 8.46 (s, 1H) |
| 10 | 2.79 (t, 2H), 3.90 (q, 2H), 5.67 (brs, 1H), 7.18-7.46 (m, 7H), 8.53 (s, 1H) |
| 11 | 2.86 (t, 2H), 3.88 (q, 2H), 5.53 (brs, 1H), 6.96-7.40 (m, 6H), 8.52 (s, 1H) |
| 12 | 2.83 (t, 2H), 3.87 (q, 2H), 5.53 (brs, 1H), 6.90-7.60 (m, 6H), 8.53 (s, 1H) |
| 13 | 2.82 (t, 2H), 3.87 (q, 2H), 5.58 (brs, 1H), 6.88-7.44 (m, 6H), 8.53 (s, 1H) |
| 14 | 2.85 (t, 2H), 3.91 (q, 2H), 5.72 (brs, 1H), 7.10-7.48 (m, 6H), 8.52 (s, 1H) |
| 15 | 2.83 (t, 2H), 3.82 (q, 2H), 5.51 (brs, 1H), 6.96-7.63 (m, 6H), 8.53 (s, 1H) |

TABLE 2-2

| Compound No. | δ value (ppm; solvent, CDCl₃; internal standard substance, TMS) |
|---|---|
| 16 | 2.83 (t, 2H), 3.86 (q, 2H), 5.59 (brs, 1H), 7.07-7.41 (m, 6H), 8.52 (s, 1H) |
| 17 | 2.39 (s, 3H), 2.81 (d, 2H), 3.89 (q, 2H), 5.60 (brs, 1H), 7.13-7.68 (m, 6H), 8.52 (s, 1H) |

TABLE 2-2-continued

| Compound No. | δ value (ppm; solvent, CDCl₃; internal standard substance, TMS) |
|---|---|
| 18 | 2.27 (s, 3H), 2.80 (t, 2H), 3.85 (q, 2H), 5.56 (brs, 1H), 6.90-7.60 (m, 6H), 8.52 (s, 1H) |
| 19 | 2.31 (s, 3H), 2.80 (t, 2H), 3.86 (q, 2H), 6.07 (t, 1H), 7.01-7.31 (m, 6H), 8.52 (s, 1H) |
| 20 | 1.29 (s, 9H), 2.81 (t, 2H), 3.85 (q, 2H), 5.87 (brs, 1H), 7.11-7.31 (m, 6H), 8.52 (s, 1H) |
| 21 | 2.85 (t, 2H), 3.84 (s, 3H), 3.86 (q, 4H), 6.03 (brs, 1H), 6.79-6.96 (m, 2H), 7.14-7.41 (m, 4H), 8.52 (s, 1H) |
| 22 | 2.83 (t, 2H), 3.78 (s, 3H), 3.88 (q, 2H), 5.58 (brs, 1H), 6.78-7.33 (m, 6H), 8.53 (s, 1H) |
| 23 | 2.80 (t, 2H), 3.78 (s, 3H), 3.82 (q, 2H), 5.82 (t, 1H), 6.83 (d, 2H), 7.11-7.36 (m, 4H), 8.52 (s, 1H) |
| 24 | 2.82 (t, 2H), 3.85 (s, 3H), 3.87 (s, 3H), 3.90 (q, 2H), 5.72 (brs, 1H), 6.72-7.31 (m, 5H), 8.53 (s, 1H) |
| 25 | 2.86 (t, 2H), 3.90 (q, 2H), 5.62 (brs, 1H), 7.18-7.70 (m, 6H), 8.52 (s, 1H) |
| 26 | 2.85 (t, 2H), 3.87 (q, 2H), 5.62 (brs, 1H), 7.11-7.67 (m, 6H), 8.52 (s, 1H) |
| 27 | 2.83 (t, 2H), 3.87 (q, 2H), 7.10-7.62 (m, 6H), 8.53 (s, 1H) |
| 28 | 2.83 (t, 2H), 3.88 (q, 2H), 7.18-7.72 (m, 5H), 8.54 (s, 1H) |
| 29 | 2.80 (t, 2H), 3.88-4.08 (m, 5H), 6.94 (brs, 1H), 7.16-7.67 (m, 5H), 8.02 (d, 1H), 8.49 (s, 1H) |
| 30 | 2.85 (t, 2H), 3.80-4.00 (m, 5H), 7.12-7.54 (m, 4H), 7.92-8.07 (m, 2H), 8.53 (s, 1H) |
| 31 | 2.86 (t, 2H), 3.88 (q, 2H), 3.90 (s, 3H), 5.76 (brs, 1H), 7.13-7.46 (m, 4H), 7.95 (d, 2H), 8.53 (s, 1H) |
| 32 | 2.87 (t, 2H), 3.90 (q, 2H), 5.66 (brs, 1H), 7.06-7.51 (m, 6H), 8.52 (s, 1H) |

TABLE 2-3

| Compound No. | δ value (ppm; solvent, CDCl₃; internal standard substance, TMS) |
|---|---|
| 33 | 2.77 (t, 2H), 2.88 (q, 2H), 5.62 (brs, 1H), 7.12-7.33 (m, 6H), 8.53 (s, 1H) |
| 34 | 2.83 (t, 2H), 2.78 (q, 2H), 5.55 (brs, 1H), 7.08-7.45 (m, 6H), 8.52 (s, 1H) |
| 35 | 2.89 (t, 2H), 3.97 (q, 2H), 6.25 (brs, 1H), 7.22-7.61 (m, 6H), 8.50 (s, 1H) |
| 36 | 2.86 (t, 2H), 3.89 (q, 2H), 7.13-7.64 (m, 6H), 8.53 (s, 1H) |
| 37 | 2.88 (t, 2H), 3.88 (q, 2H), 7.17-7.82 (m, 6H), 8.51 (s, 1H) |
| 38 | 2.86 (t, 2H), 3.96 (q, 2H), 7.21-7.61 (m, 5H), 8.04 (d, 1H), 8.50 (s, 1H) |
| 39 | 2.85 (t, 2H), 3.91 (q, 2H), 5.58 (brs, 1H), 7.09-7.71 (m, 5H), 8.11 (d, 1H), 8.54 (s, 1H) |
| 40 | 2.90 (t, 2H), 3.92 (q, 2H), 5.48 (brs, 1H), 7.11-7.57 (m, 5H), 8.12 (d, 1H), 8.54 (s, 1H) |
| 41 | 2.85 (t, 2H), 3.87 (q, 2H), 5.55 (brs, 1H), 6.73-7.34 (m, 5H), 8.52 (s, 1H) |
| 42 | 2.90 (t, 2H), 3.92 (q, 2H), 5.65 (brs, 1H), 6.90-7.34 (m, 5H), 8.52 (s, 1H) |
| 43 | 2.83 (t, 2H), 3.92 (q, 2H), 5.50 (brs, 1H), 6.92-7.32 (m, 5H), 8.51 (s, 1H) |
| 44 | 2.82 (t, 2H), 3.90 (q, 2H), 4.78 (d, 2H), 6.10 (brs, 1H), 7.13-7.41 (m, 6H), 8.50 (s, 1H) |
| 45 | 2.83 (t, 2H), 3.33 (s, 3H), 3.90 (q, 2H), 4.60 (s, 2H), 6.15 (brs, 1H), 7.15-7.45 (m, 6H), 8.51 (s, 1H) |
| 46 | 1.22 (t, 3H), 2.83 (t, 2H), 3.50 (q, 2H), 3.92 (q, 2H), 4.65 (s, 2H), 6.20 (brs, 1H), 7.15-7.45 (m, 6H), 8.51 (s, 1H) |
| 47 | 2.86 (t, 2H), 3.92 (q, 2H), 5.25 (s, 1H), 5.74 (brs, 1H), 5.78 (s, 1H), 7.14-7.44 (m, 6H), 8.52 (s, 1H) |
| 48 | 2.90 (t, 2H), 3.92 (q, 2H), 7.24-7.89 (m, 6H), 8.45 (s, 1H), 10.37 (s, 1H) |
| 49 | 2.85 (t, 2H), 3.37 (s, 3H), 3.90 (q, 2H), 4.60 (s, 2H), 6.00 (brs, 1H), 7.18-7.71 (m, 6H), 8.64 (s, 1H) |

TABLE 2-4

| Compound No. | δ value (ppm; solvent, CDCl$_3$; internal standard substance, TMS) |
|---|---|
| 50 | 2.20 (s, 3H), 2.83 (t, 2H), 3.34 (s, 3H), 3.90 (q, 2H), 4.70 (s, 2H), 6.06 (brs, 1H), 7.10-7.62 (m, 5H), 8.66 (s, 1H) |
| 51 | 2.56 (s, 3H), 2.87 (t, 2H), 3.32 (s, 3H), 3.87 (q, 2H), 4.60 (s, 2H), 5.92 (brs, 1H), 6.80 (s, 1H), 7.17-7.48 (m, 4H), 8.44 (s, 1H) |
| 52 | 2.80 (t, 2H), 3.82 (q, 2H), 6.20 (brs, 1H), 6.34-6.36 (m, 1H), 7.12-7.57 (m, 4H), 8.50 (s, 1H) |
| 53 | 2.82 (t, 2H), 3.84 (q, 2H), 5.88 (brs, 1H), 6.87-7.30 (m, 5H), 8.52 (s, 1H) |
| 54 | 2.80 (t, 2H), 3.85 (q, 2H), 6.23 (brs, 1H), 7.02-7.38 (m, 5H), 8.52 (s, 1H) |
| 55 | 2.85 (t, 2H), 3.90 (q, 2H), 6.24 (brs, 1H), 7.12-7.72 (m, 5H), 8.48-8.57 (m, 2H) |
| 56 | 2.85 (t, 2H), 3.90 (q, 2H), 5.56 (brs, 1H), 7.12-7.34 (m, 4H), 7.58-7.78 (m, 1H), 8.45-8.68 (m, 3H) |
| 57 | 2.87 (t, 2H), 3.90 (q, 2H), 5.62 (brs, 1H), 7.12-7.35 (m, 4H), 8.45-8.58 (m, 3H) |
| 58 | 2.90 (t, 2H), 3.95 (q, 2H), 5.85 (brs, 1H), 7.15-7.27 (m, 3H), 8.50 (s, 1H), 8.75 (d, 2H) |
| 59 | 2.42 (s, 6H), 2.90 (t, 2H), 3.92 (q, 2H), 6.30 (brs, 1H), 6.97 (s, 1H), 7.24-7.32 (m, 4H), 8.50 (s, 1H) |
| 60 | 2.87 (t, 2H), 3.94 (q, 2H), 3.95 (s, 6H), 6.00 (s, 1H), 7.45 (d, 2H), 7.60 (d, 2H), 8.48 (s, 1H), 8.87 (s, 1H) |
| 61 | 2.86 (t, 2H), 3.88 (q, 2H), 5.52 (brs, 1H), 7.15 (d, 2H), 7.30 (d, 2H), 7.89 (s, 1H), 8.52 (s, 1H), 8.68 (s, 1H) |
| 62 | 3.86 (t, 2H), 3.90 (q, 2H), 5.86 (brs, 1H), 7.18-7.28 (m, 3H), 7.77 (d, 2H), 8.48 (s, 1H) |
| 63 | 2.88 (t, 3H), 3.90 (q, 2H), 6.04 (brs, 1H), 7.40 (d, 2H), 7.24 (s, 2H), 8.52 (s, 1H), 8.75 (d, 2H) |
| 64 | 2.90 (t, 2H), 3.82 (q, 2H), 6.16 (brs, 1H), 7.17-7.27 (m, 3H), 8.50 (s, 1H) |
| 65 | 2.51 (s, 3H), 2.88 (t, 2H), 3.91 (q, 2H), 5.92 (brs, 1H), 7.16-7.26 (m, 3H), 8.52 (s, 1H) |

TABLE 2-5

| Compound No. | δ value (ppm; solvent, CDCl$_3$; internal standard substance, TMS) |
|---|---|
| 66 | 2.38 (s, 3H), 2.88 (t, 2H), 3.90 (q, 2H), 6.04 (brs, 1H), 7.17-7.25 (m, 3H), 8.51 (s, 1H) |
| 67 | 2.82 (t, 2H), 3.90 (q, 2H), 4.09 (s, 3H), 5.74 (brs, 1H), 6.75 (s, 1H), 7.16 (d, 1H), 7.28 (d, 1H), 8.51 (s, 1H) |
| 68 | 2.85 (t, 3H), 3.88 (q, 2H), 5.33 (s, 1H), 5.85 (brs, 2H), 7.15-7.42 (m, 3H), 8.51 (s, 1H) |
| 69 | 2.90 (t, 3H), 3.91 (q, 2H), 5.75 (brs, 1H), 7.21-7.30 (m, 2H), 7.70 (s, 1H), 8.52 (s, 1H), 9.95 (s, 1H) |
| 70 | 2.79 (t, 2H), 3.70 (q, 2H), 4.67 (d, 2H), 6.00 (t, 1H), 7.51 (s, 2H), 7.65 (s, 1H), 8.37 (s, 1H) |
| 71 | 0.13 (s, 6H), 0.95 (s, 9H), 2.83 (t, 2H), 3.87 (q, 2H), 4.92 (s, 2H), 5.82 (brs, 1H), 7.22-7.31 (m, 3H), 8.51 (s, 1H) |
| 72 | 2.83 (t, 2H), 3.48 (s, 3H), 3.87 (q, 2H), 4.70 (s, 2H), 6.09 (brs, 1H), 7.23-7.41 (m, 3H), 8.51 (s, 1H) |
| 73 | 2.16 (s, 3H), 2.85 (t, 3H), 3.88 (q, 2H), 5.34 (s, 2H), 5.73 (brs, 1H), 7.15-7.36 (m, 3H), 8.51 (s, 1H) |
| 74 | 2.51 (t, 1H), 2.84 (t, 2H), 3.88 (q, 2H), 4.30 (d, 2H), 4.86 (s, 2H), 5.90 (brs, 1H), 7.17-7.35 (m, 3H), 8.51 (s, 1H) |
| 75 | 2.83 (t, 2H), 3.86 (q, 2H), 4.29 (s, 2H), 5.82 (brs, 1H), 7.13-7.30 (m, 8H), 8.51 (s, 1H) |
| 76 | 2.87 (t, 2H), 3.90 (q, 2H), 5.82 (brs, 1H), 7.14-7.51 (m, 6H), 7.90-8.00 (m, 2H), 8.52 (s, 1H) |
| 77 | 2.85 (t, 2H), 3.88 (q, 4H), 5.87 (brs, 1H), 6.83 (d, 1H), 7.16-7.31 (m, 4H), 7.47 (t, 1H), 8.01 (s, 1H), 8.52 (s, 1H) |
| 78 | 2.82 (t, 2H), 3.86 (q, 2H), 5.93 (brs, 1H), 7.16-7.59 (m, 5H), 7.85-7.90 (m, 1H), 8.52 (s, 1H) |
| 79 | 2.81 (t, 2H), 3.85 (q, 2H), 6.22 (t, 1H), 7.00-8.48 (m, 6H), 8.50 (s, 1H) |
| 80 | 2.82 (t, 2H), 3.88 (q, 2H), 5.93 (brs, 1H), 7.16-7.59 (m, 5H), 7.85-7.90 (m, 1H), 8.52 (s, 1H) |
| 81 | 2.89 (t, 2H), 3.92 (q, 2H), 5.77 (brs, 1H), 7.16-7.45 (m, 4H), 8.18-8.31 (m, 1H), 8.53 (s, 1H), 8.64-8.70 (m, 1H), 9.15 (s, 1H) |

TABLE 2-6

| Compound No. | δ value (ppm; solvent, CDCl$_3$; internal standard substance, TMS) |
|---|---|
| 82 | 2.86 (t, 2H), 3.90 (q, 2H), 5.85 (brs, 1H), 7.27 (s, 2H), 7.39-7.48 (m, 3H), 7.76 (s, 1H), 7.99-8.09 (m, 2H), 8.51 (s, 1H) |
| 83 | 2.77 (t, 2H), 3.82 (q, 2H), 5.85 (brs, 1H), 6.85 (s, 1H), 7.11-7.41 (m, 7H), 8.49 (s, 1H) |
| 84 | 2.90 (t, 2H), 3.15 (s, 3H), 3.92 (q, 2H), 7.10-7.80 (m, 5H), 8.52 (s, 1H) |
| 85 | 2.95 (t, 3H), 3.87 (s, 3H), 3.92 (q, 2H), 5.84 (brs, 1H), 7.10-7.92 (m, 5H), 8.50 (s, 1H) |
| 86 | 2.08 (t, 1H), 2.64 (dt, 2H), 3.85 (q, 2H), 6.19 (brs, 1H), 7.44-7.91 (m, 4H), 8.67 (s, 1H) |
| 87 | 0.17 (s, 9H), 2.67 (t, 2H), 3.83 (q, 2H), 6.12 (brs, 1H), 7.45-7.84 (m, 4H), 8.67 (s, 1H) |
| 88 | 0.89 (t, 3H), 1.27-1.54 (m, 4H), 2.12-2.21 (m, 2H), 2.60 (dt, 2H), 3.78 (q, 2H), 6.32 (brs, 1H), 7.28-7.81 (m, 4H), 8.67 (s, 1H) |
| 89 | 0.87 (t, 3H), 1.25-1.57 (m, 8H), 2.11-2.02 (m, 2H), 2.50-2.70 (m, 2H), 3.78 (q, 2H), 6.30 (brs, 1H), 7.19-7.81 (m, 4H), 8.67 (s, 1H) |
| 90 | 0.61-0.87 (m, 4H), 1.13-1.25 (m, 1H), 2.57 (dt, 2H), 3.76 (q, 2H), 6.17 (brs, 1H), 7.19-7.90 (m, 4H), 8.66 (s, 1H) |
| 91 | 1.26-1.79 (m, 10H), 2.39 (brs, 1H), 2.64 (t, 2H), 3.78 (q, 2H), 6.10 (brs, 1H), 7.45-7.90 (m, 4H), 8.66 (s, 1H) |
| 92 | 2.82 (t, 2H), 3.88 (q, 2H), 4.18 (s, 2H), 3.44 (d, 2H), 6.14 (brs, 1H), 7.41-7.82 (m, 4H), 8.66 (s, 1H) |
| 93 | 1.99-2.07 (m, 3H), 2.84-2.99 (m, 2H), 3.78-4.02 (m, 2H), 6.00-6.18 (m, 1H), 6.61 (brs, 1H), 7.10-7.99 (m, 4H), 8.67 (brs, 1H) |
| 94 | 1.53-1.66 (m, 4H), 2.03-2.10 (m, 4H), 2.74 (t, 2H), 3.83 (q, 2H), 6.04-6.16 (m, 2H), 7.19-7.82 (m, 4H), 8.67 (s, 1H) |
| 95 | 3.88 (t, 2H), 3.94 (q, 2H), 5.70 (d, 2H), 7.11-8.02 (m, 9H), 8.68 (s, 1H) |
| 96 | 2.88 (t, 2H), 3.92 (q, 2H), 6.18 (brs, 1H), 7.21-7.82 (m, 9H), 8.65 (s, 1H) |
| 97 | 2.92 (t, 2H), 3.95 (q, 2H), 6.22 (brs, 1H), 7.12-7.91 (m, 8H), 8.68 (s, 1H) |

TABLE 2-7

| Compound No. | δ value (ppm; solvent, CDCl$_3$; internal standard substance, TMS) |
|---|---|
| 98 | 2.90 (t, 2H), 4.00 (q, 2H), 7.00-8.35 (m, 9H), 8.65 (s, 1H) |
| 99 | 2.89 (t, 2H), 3.94 (q, 2H), 5.24 (s, 1H), 5.77 (s, 1H), 6.46 (brs, 1H), 7.26-7.83 (m, 8H), 8.68 (s, 1H) |
| 100 | 2.91 (t, 2H), 3.95 (q, 2H), 6.33 (brs, 1H), 6.95 (dd, 1H), 7.26-7.82 (m, 8H), 8.69 (s, 1H) |
| 101 | 2.91 (t, 2H), 3.95 (q, 2H), 6.10 (brs, 1H), 7.37-7.80 (m, 8H), 8.65 (s, 1H) |
| 102 | 2.94 (t, 2H), 4.05 (q, 2H), 7.37-7.80 (m, 8H), 8.66 (s, 1H) |
| 103 | 1.94 (s, 3H), 2.65-2.99 (m, 4H), 3.94 (q, 2H), 6.05 (brs, 1H), 7.19-7.83 (m, 8H), 8.69 (s, 1H) |
| 104 | 1.20 (d, 6H), 2.91 (t, 2H), 3.40 (m, 1H), 3.94 (q, 2H), 6.22 (brs, 1H), 6.96-7.80 (8H), 8.68 (s, 1H) |
| 105 | 1.72 (s, 3H), 2.59-2.98 (m, 4H), 2.88 (t, 2H), 3.88 (q, 2H), 4.67 (s, 2H), 6.09 (brs, 1H), 7.06-7.83 (m, 8H), 8.68 (s, 1H) |
| 106 | 0.82 (t, 3H), 1.16-1.68 (m, 4H), 2.55 (t, 2H), 3.84 (t, 2H), 3.88 (q, 2H), 6.11 (brs, 1H), 6.91-7.81 (m, 8H), 8.68 (s, 1H) |
| 107 | 0.85 (t, 3H), 1.13-1.72 (m, 8H), 2.56 (t, 2H), 3.85 (t, 2H), 3.92 (q, 2H), 6.14 (brs, 1H), 6.96-7.81 (m, 8H), 8.67 (s, 1H) |
| 108 | 0.85 (t, 3H), 1.05-1.67 (m, 12H), 2.59 (t, 2H), 2.86 (t, 2H), 3.90 (q, 2H), 6.09 (brs, 1H), 6.98-7.81 (m, 8H), 8.68 (s, 1H) |
| 109 | 1.11-1.88 (m, 12H), 2.22-2.70 (m, 1H), 2.82 (t, 2H), 3.90 (q, 2H), 6.10 (brs, 1H), 7.08-7.81 (m, 8H), 8.67 (s, 1H) |
| 110 | 2.88 (t, 2H), 3.91 (q, 2H), 5.26 (d, 1H), 5.72 (d, 1H), 6.39 (brs, 1H), 6.68 (dd, 2H), 7.26-8.00 (m, 8H), 8.68 (s, 1H) |
| 111 | 0.26 (s, 9H), 2.87 (t, 2H), 3.90 (q, 2H), 7.30-7.84 (m, 8H), 8.68 (s, 1H) |

TABLE 2-7-continued

| Compound No. | δ value (ppm; solvent, CDCl₃; internal standard substance, TMS) |
|---|---|
| 112 | 0.88 (t, 3H), 1.15-1.67 (m, 10H), 2.60 (t, 2H), 2.88 (t, 2H), 3.90 (q, 2H), 6.10 (brs, 1H), 7.20-7.84 (m, 12H), 8.69 (s, 1H) |
| 113 | 2.87 (t, 2H), 3.92 (q, 2H), 5.25 (dd, 1H), 6.24 (brs, 1H), 7.18-7.91 (m, 8H), 8.69 (s, 1H) |
| 114 | 2.73 (t, 2H), 3.75 (q, 2H), 5.83 (brs, 1H), 7.18-7.75 (m, 13H), 8.62 (s, 1H) |

TABLE 2-8

| Compound No. | δ value (ppm; solvent, CDCl₃; internal standard substance, TMS) |
|---|---|
| 115 | 3.70 (t, 2H), 3.55 (q, 2H), 3.92 (s, 3H), 6.10 (brs, 1H), 6.82-7.40 (m, 8H), 8.23 (s, 1H) |
| 116 | 2.45 (s, 3H), 2.86 (t, 2H), 3.92 (q, 2H), 6.27 (brs, 1H), 7.17-7.83 (m, 8H), 8.68 (s, 1H) |
| 117 | 2.47 (s, 3H), 2.86 (t, 2H), 3.91 (q, 2H), 6.18 (brs, 1H), 7.09-7.81 (m, 8H), 8.68 (s, 1H) |
| 118 | 1.40 (t, 3H), 2.84 (t, 2H), 3.87-4.06 (m, 4H), 6.20 (brs, 1H), 6.75-7.80 (m, 8H), 8.68 (s, 1H) |
| 119 | 1.30 (d, 6H), 3.84 (t, 2H), 3.90 (q, 2H), 4.55 (m, 1H), 6.43 (brs, 1H), 6.78-7.82 (m, 8H), 8.67 (s, 1H) |
| 120 | 2.98 (t, 2H), 3.04 (s, 3H), 3.93 (q, 2H), 7.44-7.92 (m, 8H), 8.69 (s, 1H) |
| 121 | 2.84 (t, 2H), 3.46 (s, 3H), 3.87 (q, 2H), 5.16 (s, 2H), 6.22 (d, 1H), 6.95 (d, 2H), 7.28-7.83 (m, 8H), 8.68 (s, 1H) |
| 122 | 2.70 (s, 6H), 2.92 (t, 2H), 3.94 (q, 2H), 6.40 (brs, 1H), 7.44-7.93 (m, 8H), 8.69 (s, 1H) |
| 123 | 2.02 (s, 1H), 2.82 (t, 2H), 3.00 (s, 3H), 3.88 (q, 2H), 6.14 (brs, 1H), 7.07-7.90 (m, 8H), 8.66 (s, 1H) |
| 124 | 2.80 (s, 3H), 2.86 (t, 2H), 3.26 (s, 3H), 3.90 (q, 2H), 6.64 (brs, 1H), 7.22-7.88 (m, 8H), 8.68 (s, 1H) |
| 125 | 2.72 (t, 2H), 3.74 (s, 6H), 3.82 (q, 2H), 7.37-7.97 (m, 8H), 8.53 (s, 1H) |
| 126 | 2.85 (s, 3H), 2.92 (t, 2H), 3.90 (q, 2H), 6.04 (brs, 1H), 7.31-7.80 (m, 9H), 8.64 (s, 1H) |
| 127 | 2.83 (t, 2H), 4.00 (q, 2H), 5.78 (brs, 1H), 7.35-8.08 (m, 8H), 8.37 (s, 1H) |
| 128 | 2.60 (s, 3H), 2.91 (t, 2H), 3.92 (q, 2H), 6.37 (brs, 1H), 7.20-7.87 (m, 8H), 8.58 (s, 1H) |
| 129 | 1.37 (t, 3H), 2.89 (t, 2H), 3.94 (q, 2H), 4.37 (q, 2H), 6.07 (brs, 1H), 7.38-7.98 (m, 8H), 8.65 (s, 1H) |
| 130 | 2.86 (t, 2H), 3.93 (q, 2H), 4.79 (s, 2H), 6.73 (brs, 1H), 7.18-7.90 (m, 8H), 8.60 (s, 1H) |

TABLE 2-9

| Compound No. | δ value (ppm; solvent, CDCl₃; internal standard substance, TMS) |
|---|---|
| 131 | 2.17 (brs, 1H), 2.79 (t, 2H), 3.84 (q, 2H), 4.55 (s, 2H), 6.17 (brs, 1H), 7.13-7.34 (m, 8H), 8.57 (s, 1H) |
| 132 | 2.87 (t, 2H), 3.93 (q, 2H), 4.68 (d, 2H), 6.15 (brs, 1H), 7.26-7.85 (m, 8H), 8.67 (s, 1H) |
| 133 | 2.92 (t, 2H), 3.32 (s, 3H), 4.03 (q, 2H), 4.58 (s, 2H), 7.16-7.81 (m, 7H), 8.27-8.35 (m, 2H) |
| 134 | 2.92 (t, 2H), 3.94 (q, 2H), 5.02 (s, 2H), 6.23 (t, 1H), 6.43 (brs, 1H), 7.22-7.91 (m, 8H), 8.69 (s, 1H) |
| 135 | 2.93 (t, 2H), 3.36 (s, 3H), 4.00 (t, 2H), 4.39 (s, 2H), 7.20-8.12 (m, 8H), 8.65 (s, 1H) |
| 136 | 2.85 (t, 2H), 3.37 (s, 3H), 3.83 (q, 2H), 4.41 (s, 2H), 6.84 (brs, 1H), 7.18-7.88 (m, 8H), 8.69 (s, 1H) |
| 137 | 1.40 (d, 3H), 2.91 (t, 2H), 3.20 (s, 3H), 3.95 (q, 2H), 4.71 (q, 1H), 6.85 (brs, 1H), 7.10-7.92 (m, 8H), 8.70 (brs, 1H) |
| 138 | 2.88 (t, 2H), 3.88 (t, 2H), 5.58 (q, 1H), 7.25-7.85 (m, 9H), 8.54 (s, 1H) |

TABLE 2-9-continued

| Compound No. | δ value (ppm; solvent, CDCl₃; internal standard substance, TMS) |
|---|---|
| 139 | 2.95 (t, 2H), 3.36 (s, 3H), 3.97 (brs, 2H), 4.54 (s, 2H), 6.79-7.84 (m, 8H), 8.24 (brs, 1H) |
| 140 | 2.88 (t, 2H), 3.36 (s, 3H), 3.98 (q, 2H), 4.54 (s, 2H), 6.32 (brs, 1H), 7.22-8.01 (m, 7H), 8.68 (s, 1H) |
| 141 | 2.93 (t, 2H), 3.36 (s, 3H), 3.96 (q, 2H), 4.57 (s, 2H), 6.50 (brs, 1H), 6.98-7.80 (m, 7H), 8.69 (brs, 1H) |
| 142 | 2.88 (t, 2H), 3.33 (s, 3H), 3.94 (q, 2H), 4.52 (s, 2H), 6.71 (brs, 1H), 6.96-7.90 (m, 7H), 8.68 (s, 1H) |
| 143 | 2.88 (t, 2H), 3.33 (s, 3H), 3.94 (q, 2H), 4.53 (s, 2H), 6.58 (brs, 1H), 7.27-8.01 (m, 7H), 8.67 (s, 1H) |
| 144 | 2.31 (s, 3H), 2.88 (t, 2H), 3.33 (s, 3H), 3.95 (q, 2H), 4.56 (s, 2H), 6.62 (brs, 1H), 7.14-8.01 (m, 7H), 8.67 (s, 1H) |
| 145 | 2.35 (s, 3H), 2.87 (t, 2H), 3.35 (s, 3H), 3.96 (q, 2H), 4.56 (s, 2H), 6.51 (brs, 1H), 6.99-7.87 (m, 7H), 8.67 (s, 1H) |
| 146 | 2.85 (t, 2H), 3.35 (s, 3H), 3.94 (q, 2H), 4.88 (s, 2H), 6.28 (brs, 1H), 7.08-7.82 (m, 6H), 8.70 (s, 1H) |

TABLE 2-10

| Compound No. | δ value (ppm; solvent, CDCl₃; internal standard substance, TMS) |
|---|---|
| 147 | 2.95 (t, 2H), 3.81 (s, 2H), 3.95 (q, 2H), 6.54 (brs, 1H), 7.15-7.79 (m, 8H), 8.67 (s, 1H) |
| 148 | 2.89 (t, 2H), 3.42 (s, 3H), 3.93 (q, 2H), 4.70 (s, 2H), 4.76 (s, 2H), 6.84 (brs, 1H), 7.18-7.90 (m, 8H), 8.68 (s, 1H) |
| 149 | 2.84 (t, 2H), 3.32 (s, 6H), 3.98 (q, 2H), 5.76 (s, 1H), 6.67 (brs, 1H), 7.13-8.00 (m, 8H), 8.67 (s, 1H) |
| 150 | 1.24 (t, 5H), 2.92 (t, 2H), 3.44 (q, 4H), 3.96 (q, 2H), 5.82 (s, 1H), 6.66 (brs, 1H), 7.10-7.97 (m, 8H), 8.67 (s, 1H) |
| 151 | 1.24 (t, 6H), 2.88 (t, 2H), 3.58 (q, 2H), 3.92 (q, 2H), 5.48 (s, 1H), 6.10 (brs, 1H), 7.34-8.02 (m, 8H), 8.69 (s, 1H) |
| 152 | 2.01 (s, 3H), 2.91 (t, 2H), 3.83 (s, 2H), 3.96 (q, 2H), 6.42 (brs, 1H), 7.25-7.83 (m, 8H), 8.68 (s, 1H) |
| 153 | 1.21 (t, 3H), 2.88 (t, 2H), 3.48 (q, 2H), 3.93 (q, 2H), 4.63 (s, 2H), 6.76 (brs, 1H), 7.17-7.94 (m, 8H), 8.68 (s, 1H) |
| 154 | 1.18 (d, 6H), 2.88 (t, 2H), 3.49-3.76 (m, 1H), 3.95 (q, 2H), 4.64 (s, 2H), 6.61 (brs, 1H), 7.18-7.81 (m, 8H), 8.68 (s, 1H) |
| 155 | 2.84 (t, 2H), 3.95 (q, 2H), 3.98-4.08 (m, 4H), 6.23 (s, 1H), 6.55 (brs, 1H), 7.24-7.98 (m, 8H), 8.66 (s, 1H) |
| 156 | 1.61-2.01 (m, 6H), 2.84 (t, 2H), 3.60 (m, 2H), 3.90 (q, 2H), 5.40 (m, 1H), 6.23 (brs, 1H), 6.91-7.90 (m, 8H), 8.68 (s, 1H) |
| 157 | 2.84 (t, 2H), 3.13 (t, 2H), 3.87 (q, 2H), 4.54 (s, 2H), 6.68 (d, 1H), 7.12-7.86 (m, 7H), 8.69 (s, 1H) |
| 158 | 2.88-3.15 (m, 4H), 3.86-4.01 (m, 4H), 4.40 (brs, 1H), 7.08-8.13 (m, 9H), 8.61 (s, 1H) |
| 159 | 2.87 (t, 2H), 2.94 (s, 6H), 3.88 (q, 2H), 6.60 (d, 1H), 7.22-7.79 (m, 8H), 8.67 (s, 1H) |
| 160 | 2.04 (s, 3H), 2.88 (t, 2H), 3.95 (q, 2H), 6.21 (brs, 1H), 6.93-7.84 (m, 8H), 8.22 (brs, 1H), 8.68 (s, 1H) |
| 161 | 2.77 (s, 6H), 2.83 (t, 2H), 3.97 (q, 2H), 7.15 (brs, 1H), 7.39-8.19 (m, 8H), 8.64 (s, 1H) |
| 162 | 2.80 (s, 3H), 2.84 (t, 2H), 3.87 (q, 2H), 4.35 (s, 2H), 6.22 (d, 1H), 7.30-7.88 (m, 8H), 8.66 (s, 1H) |

TABLE 2-11

| Compound No. | δ value (ppm; solvent, CDCl₃; internal standard substance, TMS) |
|---|---|
| 163 | 2.91 (t, 2H), 3.95 (q, 2H), 6.10 (brs, 1H), 6.91-7.84 (m, 7H), 8.69 (s, 1H) |
| 164 | 2.90 (t, 2H), 3.94 (q, 2H), 6.10 (brs, 1H), 7.00-7.83 (m, 7H), 8.68 (s, 1H) |
| 165 | 2.92 (t, 2H), 3.95 (q, 2H), 6.57 (brs, 1H), 7.20-7.90 (m, 7H), 8.67 (s, 1H) |
| 166 | 2.86 (t, 2H), 3.89 (q, 2H), 6.05 (brs, 1H), 7.00-7.84 (m, 7H), 8.68 (s, 1H) |
| 167 | 2.35 (s, 3H), 3.00 (t, 2H), 4.02 (q, 2H), 6.23 (brs, 1H), 7.04-8.27 (m, 7H), 8.71 (s, 1H) |

TABLE 2-11-continued

| Compound No. | δ value (ppm; solvent, CDCl$_3$; internal standard substance, TMS) |
| --- | --- |
| 168 | 2.91 (t, 2H), 3.96 (q, 2H), 6.10 (brs, 1H), 7.07-7.83 (m, 7H), 8.68 (s, 1H) |
| 169 | 2.88 (t, 2H), 3.94 (q, 2H), 6.33 (brs, 1H), 7.05-7.79 (m, 7H), 8.67 (s, 1H) |
| 170 | 2.90 (t, 2H), 3.95 (q, 2H), 7.37-7.83 (m, 7H), 8.68 (s, 1H) |
| 171 | 2.93 (t, 2H), 3.97 (q, 2H), 6.10 (brs, 1H), 7.03-7.84 (m, 7H), 8.67 (s, 1H) |
| 172 | 2.92 (t, 2H), 3.95 (q, 2H), 6.10 (brs, 1H), 7.13-7.81 (m, 7H), 8.68 (s, 1H) |
| 173 | 2.92 (t, 2H), 3.93 (q, 2H), 6.10 (brs, 1H), 7.28-7.81 (m, 7H), 8.68 (s, 1H) |
| 174 | 2.97 (t, 2H), 4.00 (q, 2H), 6.22 (brs, 1H), 7.05-7.83 (m, 7H), 8.68 (s, 1H) |
| 175 | 2.87 (t, 2H), 3.92 (q, 2H), 6.05 (brs, 1H), 7.13-7.84 (m, 7H), 8.69 (s, 1H) |
| 176 | 2.95 (t, 2H), 4.01 (q, 2H), 6.12 (brs, 1H), 7.18-7.82 (m, 7H), 8.69 (s, 1H) |
| 177 | 2.90 (t, 2H), 3.94 (q, 2H), 6.27 (brs, 1H), 7.19-7.84 (m, 7H), 8.69 (s, 1H) |
| 178 | 2.93 (t, 2H), 3.92 (s, 3H), 4.00 (q, 2H), 6.55 (brs, 1H), 7.12-7.75 (m, 7H), 8.66 (s, 1H) |

TABLE 2-12

| Compound No. | δ value (ppm; solvent, CDCl$_3$; internal standard substance, TMS) |
| --- | --- |
| 179 | 2.93 (t, 2H), 4.00 (q, 2H), 6.55 (brs, 1H), 7.16-7.79 (m, 7H), 8.60 (s, 1H) |
| 180 | 2.31 (s, 3H), 2.36 (s, 3H), 2.90 (t, 2H), 3.93 (q, 2H), 6.89-7.83 (m, 7H), 8.68 (s, 1H) |
| 181 | 2.15 (s, 3H), 2.35 (s, 6H), 2.94 (t, 2H), 3.92 (q, 2H), 6.84 (brs, 1H), 6.84-8.00 (m, 6H), 8.67 (s, 1H) |
| 182 | 2.99 (t, 2H), 4.00 (q, 2H), 7.37-8.15 (m, 8H), 8.66 (s, 1H) |
| 183 | 2.88 (t, 2H), 3.87 (q, 2H), 6.10 (brs, 1H), 6.87-7.84 (m, 11H), 8.68 (s, 1H) |
| 184 | 2.91 (t, 2H), 3.88 (q, 2H), 3.92 (s, 3H), 6.10 (brs, 1H), 7.09-7.84 (m, 10H), 8.69 (s, 1H) |
| 185 | 2.88 (t, 2H), 3.38 (s, 3H), 4.04 (q, 2H), 4.81 (s, 2H), 6.62 (brs, 1H), 7.37-8.30 (m, 10H), 8.70 (s, 1H) |
| 186 | 2.33 (s, 3H), 2.86 (t, 2H), 3.92 (q, 2H), 6.81-7.93 (m, 13H), 8.67 (s, 1H) |
| 187 | 2.96 (t, 2H), 4.08 (q, 2H), 6.97 (brs, 1H), 7.40-7.94 (m, 6H), 8.47-8.64 (m, 2H) |
| 188 | 3.62 (t, 2H), 3.90 (q, 2H), 6.80 (brs, 1H), 7.38-8.27 (m, 10H), 8.89 (s, 1H) |
| 189 | 2.95 (t, 2H), 3.74 (q, 2H), 7.02-8.58 (m, 12H) |
| 190 | 2.94 (t, 2H), 4.00 (q, 2H), 6.09 (brs, 1H), 7.29-8.15 (m, 9H), 8.71 (s, 1H), 8.92 (d, 1H) |
| 191 | 3.04 (t, 2H), 4.00 (q, 2H), 6.12 (brs, 1H), 7.21-8.88 (m, 10H) |
| 192 | 3.06 (t, 2H), 4.06 (q, 2H), 6.14 (brs, 1H), 7.38-8.14 (m, 8H), 8.64 (s, 1H), 8.72 (s, 1H), 9.16 (s, 1H) |
| 193 | 2.80 (t, 2H), 3.83 (q, 2H), 6.04 (brs, 1H), 7.25-8.44 (m, 7H), 8.69 (s, 1H) |
| 194 | 2.89 (t, 2H), 3.85 (q, 2H), 6.02 (brs, 1H), 6.79-8.26 (m, 7H), 8.69 (s, 1H) |
| 195 | 2.95 (t, 2H), 3.96 (q, 2H), 7.47-7.84 (m, 6H), 8.23-8.35 (m, 1H), 8.69 (s, 1H) |

TABLE 2-13

| Compound No. | δ value (ppm; solvent, CDCl$_3$; internal standard substance, TMS) |
| --- | --- |
| 196 | 2.85 (t, 2H), 3.88 (q, 2H), 6.06 (brs, 1H), 7.11-7.93 (m, 6H), 8.30 (d, 1H), 8.69 (s, 1H) |
| 197 | 2.95 (t, 2H), 3.92 (q, 2H), 6.15 (brs, 1H), 7.30-7.90 (m, 6H), 8.68 (s, 1H), 8.80 (s, 1H) |
| 198 | 2.92 (t, 2H), 3.95 (q, 2H), 6.05 (brs, 1H), 7.44-7.85 (m, 7H), 8.67 (s, 1H) |

TABLE 2-13-continued

| Compound No. | δ value (ppm; solvent, CDCl$_3$; internal standard substance, TMS) |
| --- | --- |
| 199 | 2.81 (t, 2H), 3.88 (q, 2H), 3.90 (q, 2H), 6.28 (brs, 1H), 6.72-6.84 (m, 2H), 7.25-8.13 (m, 5H), 8.68 (s, 1H) |
| 200 | 2.54 (s, 3H), 2.90 (t, 2H), 3.95 (q, 2H), 7.03-8.03 (m, 8H), 8.66 (s, 1H) |
| 201 | 2.85 (t, 2H), 3.82 (q, 2H), 4.52 (d, 2H), 5.32 (t, 1H), 7.28-7.87 (m, 5H), 8.25 (d, 1H), 8.52 (s, 1H), 8.65 (s, 1H) |
| 202 | 2.92 (t, 2H), 3.40 (t, 1H), 3.95 (q, 2H), 4.75 (d, 2H), 6.03 (brs, 1H), 7.47-7.84 (m, 6H), 8.57 (s, 1H), 8.69 (s, 1H) |
| 203 | 2.82 (t, 2H), 3.50 (s, 3H), 3.86 (t, 2H), 6.48 (d, 1H), 7.23-7.98 (m, 5H), 8.58 (s, 1H) |
| 204 | 2.86 (t, 2H), 3.92 (q, 2H), 6.10 (brs, 1H), 6.90-7.93 (m, 7H), 8.68 (s, 1H) |
| 205 | 2.80 (t, 2H), 3.85 (q, 2H), 6.23 (brs, 1H), 7.02-7.38 (m, 7H), 8.52 (s, 1H) |
| 206 | 2.44 (s, 3H), 2.88 (t, 2H), 3.91 (q, 2H), 6.55-6.90 (m, 3H), 7.26-7.91 (m, 4H), 8.68 (s, 1H) |
| 207 | 2.90 (t, 2H), 3.29 (s, 3H), 3.90 (q, 2H), 4.45 (s, 2H), 6.85 (brs, 1H), 6.97 (d, 1H), 7.13 (d, 1H), 7.39-7.84 (m, 4H), 8.68 (s, 1H) |
| 208 | 2.26 (s, 3H), 2.92 (t, 2H), 3.90 (q, 2H), 6.13 (brs, 1H), 6.80 (d, 1H), 7.08 (d, 1H), 7.38-7.91 (m, 4H), 8.68 (s, 1H) |
| 209 | 2.83 (t, 2H), 3.90 (q, 2H), 4.57 (s, 2H), 6.10 (brs, 1H), 7.46-7.83 (m, 6H), 8.67 (s, 1H) |
| 210 | 2.90 (t, 2H), 3.94 (q, 2H), 6.27 (brs, 1H), 7.26-7.82 (m, 5H), 8.67 (s, 1H), 8.74 (d, 1H) |
| 211 | 2.67 (s, 3H), 2.90 (t, 2H), 3.84 (q, 2H), 6.07 (brs, 1H), 7.25 (s, 1H), 7.46-7.84 (m, 4H), 8.67 (s, 1H) |

TABLE 2-14

| Compound No. | δ value (ppm; solvent, CDCl$_3$; internal standard substance, TMS) |
| --- | --- |
| 212 | 2.87 (t, 2H), 3.91 (q, 2H), 4.06 (s, 3H), 6.25 (brs, 1H), 7.17 (s, 1H), 7.38-7.91 (m, 4H), 8.68 (s, 1H) |
| 213 | 1.33 (t, 3H), 2.94 (t, 2H), 3.92 (q, 2H), 4.35 (q, 2H), 5.62 (brs, 1H), 7.20-7.35 (m, 2H), 8.32 (s, 1H), 8.53 (s, 1H) |
| 214 | 1.34 (t, 3H), 2.71 (s, 3H), 2.93 (t, 2H), 3.89 (q, 2H), 4.34 (q, 2H), 5.60 (brs, 1H), 7.13-7.34 (m, 2H), 8.52 (s, 1H) |
| 215 | 2.79 (t, 2H), 3.80 (s, 3H), 3.84 (q, 2H), 6.44 (brs, 1H), 6.81-7.83 (m, 9H), 8.64 (s, 1H) |
| 216 | 2.79 (t, 2H), 3.74 (s, 3H), 3.82 (q, 2H), 6.69-7.83 (m, 9H), 8.65 (s, 1H) |
| 217 | 2.80 (t, 2H), 3.77 (s, 3H), 3.83 (q, 2H), 6.81-7.88 (m, 9H), 8.64 (s, 1H) |
| 218 | 2.82 (t, 2H), 3.87 (q, 2H), 6.23 (brs, 1H), 6.92 (s, 1H), 7.25-7.89 (m, 8H), 8.65 (s, 1H) |
| 219 | 2.81 (t, 2H), 3.85 (q, 2H), 6.86 (brs, 1H), 6.91 (s, 1H), 7.25-7.88 (m, 8H), 8.66 (s, 1H) |
| 220 | 2.83 (t, 2H), 3.87 (q, 2H), 6.55 (brs, 1H), 6.93 (s, 1H), 7.27-7.88 (m, 8H), 8.66 (s, 1H) |
| 221 | 2.79 (t, 2H), 3.71 (q, 2H), 7.41-8.24 (m, 9H), 8.50 (s, 1H) |
| 222 | 2.82 (t, 2H), 3.85 (q, 2H), 6.93 (s, 1H), 7.17-7.88 (m, 8H), 8.65 (s, 1H) |
| 223 | 2.84 (t, 2H), 3.88 (q, 2H), 6.44 (brs, 1H), 6.97 (s, 1H), 7.27-7.81 (m, 9H), 8.66 (s, 1H) |
| 224 | 2.74 (t, 2H), 3.77 (q, 2H), 6.85-7.85 (m, 9H), 8.63 (s, 1H) |
| 225 | 2.83 (t, 2H), 3.88 (q, 2H), 6.32 (brs, 1H), 6.90-7.89 (m, 9H), 8.66 (s, 1H) |
| 226 | 2.81 (t, 2H), 3.85 (q, 2H), 6.65 (brs, 1H), 6.85-7.88 (m, 9H), 8.66 (s, 1H) |
| 227 | 2.78 (t, 2H), 3.82 (q, 2H), 6.84 (s, 1H), 7.26-7.87 (m, 9H), 8.65 (s, 1H) |
| 228 | 1.65-1.76 (m, 6H), 2.85 (t, 2H), 3.36-3.46 (m, 4H), 3.90 (q, 2H), 6.28 (brs, 1H), 6.27 (s, 1H), 7.25-8.00 (m, 4H), 8.65 (s, 1H) |

TABLE 2-15

| Compound No. | δ value (ppm; solvent, CDCl₃; internal standard substance, TMS) |
|---|---|
| 229 | 1.48 (d, 3H), 2.81 (dd, 2H), 4.62-4.79 (m, 1H), 5.43 (d, 1H), 7.10-7.40 (m, 7H), 8.49 (s, 1H) |
| 230 | 1.45 (d, 3H), 2.80 (d, 2H), 4.55-4.83 (m, 1H), 5.36 (d, 1H), 6.85-7.46 (m, 6H), 8.52 (s, 1H) |
| 231 | 1.50 (d, 3H), 2.87 (dd, 2H), 4.64-4.91 (m, 1H), 5.58 (d, 1H), 7.06-7.48 (m, 6H), 8.51 (s, 1H) |
| 232 | 1.46 (d, 3H), 2.81 (dd, 2H), 4.58-4.85 (m, 1H), 5.40 (d, 1H), 7.11-7.31 (m, 6H), 8.52 (s, 1H) |
| 233 | 1.48 (d, 3H), 2.90 (dd, 2H), 4.63-4.92 (m, 1H), 5.35 (d, 1H), 7.06-7.74 (m, 6H), 8.50 (s, 1H) |
| 234 | 1.50 (d, 3H), 2.84 (d, 2H), 4.63-4.78 (m, 1H), 5.33 (d, 1H), 7.12-7.62 (m, 6H), 8.53 (s, 1H) |
| 235 | 1.48 (d, 3H), 2.85 (d, 2H), 4.58-4.86 (m, 1H), 5.41 (d, 1H), 7.12-7.67 (m, 6H), 8.53 (s, 1H) |
| 236 | 1.54 (d, 3H), 2.84 (dd, 2H), 3.86 (s, 3H), 4.65-4.90 (m, 1H), 5.58 (brs, 1H), 6.80-7.42 (m, 6H), 8.50 (s, 1H) |
| 237 | 1.47 (d, 3H), 2.62 (dd, 2H), 3.09 (s, 3H), 4.83-4.93 (m, 1H), 6.40 (d, 1H), 7.23-7.64 (m, 4H), 8.04-8.15 (m, 1H), 8.53 (s, 1H) |
| 238 | 1.48 (d, 3H), 2.85 (d, 2H), 4.64-4.80 (m, 1H), 5.15 (brs, 1H), 7.10-7.73 (m, 6H), 8.52 (s, 1H) |
| 239 | 1.48 (d, 3H), 2.40 (s, 3H), 2.86 (dd, 2H), 4.64-4.80 (m, 1H), 5.48 (d, 1H), 7.05-7.42 (m, 6H), 8.52 (s, 1H) |
| 240 | 1.20 (t, 3H), 1.47 (d, 3H), 2.60 (q, 2H), 2.85 (dd, 2H), 4.56-4.83 (m, 1H), 5.38 (brs, 1H), 6.99-7.36 (m, 6H), 8.51 (s, 1H) |
| 241 | 1.24 (d, 6H), 1.47 (d, 3H), 2.77-2.97 (m, 3H), 4.62-4.77 (m, 1H), 5.40 (d, 1H), 7.10-7.37 (m, 6H), 8.51 (s, 1H) |
| 242 | 1.30 (dd, 6H), 1.52 (d, 3H), 4.45-4.89 (m, 2H), 5.67 (d, 1H), 6.78-7.42 (m, 6H), 8.50 (s, 1H) |
| 243 | 1.36 (d, 3H), 2.57-3.15 (m, 3H), 4.63-4.79 (m, 3H), 5.90 (d, 1H), 7.13-7.46 (m, 6H), 8.46 (s, 1H) |
| 244 | 1.49 (d, 3H), 2.83 (dd, 2H), 3.71 (s, 1H), 4.60-4.87 (m, 1H), 4.75 (s, 2H), 6.13 (d, 1H), 6.78-7.56 (m, 5H), 8.44 (s, 1H) |

TABLE 2-16

| Compound No. | δ value (ppm; solvent, CDCl₃; internal standard substance, TMS) |
|---|---|
| 245 | 1.49 (d, 3H), 2.90 (dd, 2H), 4.64-4.82 (m, 1H), 4.73 (s, 2H), 6.25 (d, 1H), 7.10-7.42 (m, 5H), 8.46 (s, 1H) |
| 246 | 1.48 (d, 3H), 2.38 (s, 3H), 2.85 (dd, 2H), 4.63-4.79 (m, 1H), 5.40 (d, 1H), 6.69-7.39 (m, 5H), 8.51 (s, 1H) |
| 247 | 1.51 (d, 3H), 2.89 (dd, 2H), 4.63-4.90 (m, 1H), 5.46 (d, 1H), 6.82-7.49 (m, 5H), 8.51 (s, 1H) |
| 248 | 1.48 (d, 3H), 2.89 (dd, 2H), 4.71-4.84 (m, 1H), 5.40 (d, 1H), 6.93-7.72 (m, 5H), 8.51 (s, 1H) |
| 249 | 1.48 (d, 3H), 2.88 (dd, 2H), 4.67-4.83 (m, 1H), 5.30 (brs, 1H), 7.09-7.61 (m, 5H), 8.51 (s, 1H) |
| 250 | 1.48 (d, 3H), 2.35 (s, 3H), 2.86 (dd, 2H), 4.63-4.79 (m, 1H), 5.41 (d, 1H), 7.01-7.31 (m, 5H), 8.52 (s, 1H) |
| 251 | 1.50 (d, 3H), 2.94 (dd, 2H), 4.68-4.95 (m, 1H), 5.60 (d, 1H), 7.04-7.52 (m, 5H), 8.51 (s, 1H) |
| 252 | 1.50 (d, 3H), 2.96 (dd, 2H), 4.67-4.94 (m, 1H), 5.53 (d, 1H), 7.11-7.63 (m, 5H), 8.51 (s, 1H) |
| 253 | 1.51 (d, 3H), 2.88 (dd, 2H), 4.64-4.91 (m, 1H), 5.32 (d, 1H), 7.10-7.81 (m, 5H), 8.52 (s, 1H) |
| 254 | 1.50 (d, 3H), 2.85 (dd, 2H), 4.64-4.72 (m, 1H), 5.74 (d, 1H), 7.29-7.66 (m, 5H), 8.51 (s, 1H) |
| 255 | 1.50 (d, 3H), 2.33 (s, 3H), 2.85 (dd, 2H), 4.67-4.84 (m, 1H), 5.51 (d, 1H), 6.95-7.44 (m, 5H), 8.50 (s, 1H) |
| 256 | 1.52 (d, 3H), 2.92 (dd, 2H), 3.06 (s, 3H), 4.71-4.87 (m, 1H), 5.33 (d, 1H), 7.10-7.99 (m, 5H), 8.52 (s, 1H) |
| 257 | 1.52 (d, 3H), 2.90 (dd, 2H), 4.70-4.86 (m, 1H), 5.56 (d, 1H), 7.13-7.65 (m, 5H), 8.52 (s, 1H) |
| 258 | 1.46 (d, 3H), 2.87 (dd, 2H), 4.70-4.83 (m, 1H), 5.32 (d, 1H), 7.09-7.63 (m, 5H), 8.51 (s, 1H) |
| 259 | 1.48 (d, 3H), 2.30 (s, 3H), 2.36 (s, 3H), 2.85 (dd, 2H), 4.63-4.79 (m, 1H), 5.42 (d, 1H), 6.88-7.30 (m, 5H), 8.51 (s, 1H) |
| 260 | 1.48 (d, 3H), 2.92 (dd, 2H), 4.69-4.83 (m, 1H), 5.28 (d, 1H), 7.09-7.92 (m, 5H), 8.51 (s, 1H) |

TABLE 2-17

| Compound No. | δ value (ppm; solvent, CDCl₃; internal standard substance, TMS) |
|---|---|
| 261 | 1.52 (d, 3H), 2.94 (dd, 2H), 4.66-4.93 (m, 1H), 5.62 (d, 1H), 7.05-7.31 (m, 4H), 8.51 (s, 1H) |
| 262 | 1.53 (d, 3H), 3.00 (dd, 2H), 4.65-4.95 (m, 1H), 5.40 (d, 1H), 7.00-7.58 (m, 4H), 8.52 (s, 1H) |
| 263 | 1.50 (d, 3H), 2.15 (s, 3H), 2.35 (s, 6H), 2.91 (t, 2H), 4.60-4.90 (m, 1H), 5.32 (brs, 1H), 6.85-7.30 (m, 4H), 8.51 (s, 1H) |
| 264 | 1.49 (d, 3H), 2.92 (dd, 2H), 4.71-4.86 (m, 1H), 5.57 (d, 1H), 7.15-7.42 (m, 3H), 7.92-8.01 (m, 1H), 8.50 (s, 1H), 8.68-8.74 (m, 1H) |
| 265 | 1.47 (d, 3H), 2.90 (dd, 2H), 4.66-4.80 (m, 1H), 5.33 (brs, 1H), 7.19-7.31 (m, 3H), 7.76-7.82 (m, 1H), 8.51 (s, 1H) |
| 266 | 1.47 (d, 3H), 2.67 (s, 3H), 2.86 (dd, 2H), 4.67-4.82 (m, 1H), 5.70 (brs, 1H), 7.19 (s, 1H), 7.37-7.81 (m, 4H), 8.67 (s, 1H) |
| 267 | 1.05 (t, 3H), 1.70-1.95 (m, 2H), 2.82 (dd, 2H), 4.49-4.59 (m, 1H), 5.42 (d, 1H), 7.05-7.41 (m, 7H), 8.50 (s, 1H) |
| 268 | 0.98 (t, 3H), 1.17-2.07 (m, 4H), 2.82 (dd, 2H), 4.52-4.74 (m, 1H), 5.42 (d, 1H), 7.12-7.43 (m, 7H), 8.51 (s, 1H) |
| 269 | 0.86-0.99 (m, 3H), 1.17-1.47 (m, 4H), 1.64-1.85 (m, 2H), 2.82 (dd, 2H), 4.49-4.71 (m, 1H), 5.31 (d, 1H), 7.11-7.46 (m, 7H), 8.50 (s, 1H) |
| 270 | 1.60 (d, 3H), 2.85 (dd, 2H), 4.63-4.85 (m, 1H), 5.83 (brs, 1H), 7.20-7.83 (m, 9H), 8.67 (s, 1H) |
| 271 | 1.48 (d, 3H), 2.85 (dd, 2H), 4.62-4.88 (m, 1H), 6.80 (brs, 1H), 6.86-7.88 (m, 8H), 8.66 (s, 1H) |
| 272 | 1.58 (d, 3H), 2.90 (dd, 2H), 4.74-4.91 (m, 1H), 6.00 (brs, 1H), 7.03-7.89 (m, 8H), 8.61 (s, 1H) |
| 273 | 1.48 (d, 3H), 2.85 (dd, 2H), 4.61-4.86 (m, 1H), 6.78 (brs, 1H), 7.14-7.84 (m, 8H), 8.67 (s, 1H) |
| 274 | 1.51 (d, 3H), 2.91 (dd, 2H), 4.80 (brs, 1H), 5.82 (brs, 1H), 7.16-7.81 (m, 8H), 8.66 (s, 1H) |
| 275 | 1.52 (d, 3H), 2.85 (dd, 2H), 4.64-4.83 (m, 1H), 6.80 (d, 1H), 7.31-7.81 (m, 8H), 8.68 (s, 1H) |

TABLE 2-18

| Compound No. | δ value (ppm; solvent, CDCl₃; internal standard substance, TMS) |
|---|---|
| 276 | 1.52 (d, 3H), 2.90 (dd, 2H), 4.83 (s, 3H), 4.62-4.95 (m, 1H), 6.15 (brs, 1H), 6.82-7.82 (m, 8H), 8.68 (s, 1H) |
| 277 | 1.52 (t, 3H), 2.88 (d, 2H), 4.55-4.92 (m, 1H), 5.84 (d, 1H), 7.37-7.91 (m, 8H), 8.69 (s, 1H) |
| 278 | 1.48 (d, 3H), 2.90 (dd, 2H), 3.33 (s, 3H), 4.60 (s, 2H), 4.74-4.92 (m, 1H), 6.34 (d, 1H), 7.19-7.90 (m, 8H), 8.67 (s, 1H) |
| 279 | 1.50 (d, 3H), 2.32 (s, 3H), 2.80 (dd, 2H), 4.52-4.85 (m, 1H), 6.78 (d, 2H), 7.76-7.82 (m, 8H), 8.66 (s, 1H) |
| 280 | 1.25 (d, 3H), 2.52 (dd, 2H), 3.86-4.08 (m, 1H), 6.81 (s, 1H), 7.26-7.99 (m, 7H), 8.50 (s, 1H) |
| 281 | 1.60 (d, 3H), 3.00 (dd, 2H), 4.85-5.00 (m, 1H), 7.19-8.25 (m, 8H), 8.65 (s, 1H) |
| 282 | 1.58 (d, 3H), 2.97 (dd, 2H), 4.71-5.00 (m, 1H), 6.52 (d, 1H), 7.26-7.97 (m, 8H), 8.59 (s, 1H) |
| 283 | 1.60 (d, 3H), 3.00 (dd, 2H), 4.75-5.08 (m, 1H), 7.26-8.43 (m, 8H), 8.64 (s, 1H) |
| 284 | 1.62 (d, 3H), 3.00 (d, 2H), 4.84-4.92 (m, 1H), 7.13-8.62 (m, 9H) |
| 285 | 1.50 (d, 3H), 2.90 (dd, 2H), 4.73-4.87 (m, 1H), 5.92 (d, 1H), 7.27-7.89 (m, 8H), 8.67 (s, 1H) |
| 286 | 1.50 (d, 3H), 2.90 (dd, 2H), 4.67-4.93 (m, 1H), 5.88 (d, 1H), 7.06-7.91 (7H), 8.67 (s, 1H) |
| 287 | 1.57 (d, 3H), 2.93 (dd, 2H), 3.87 (s, 3H), 3.76-5.05 (m, 1H), 6.90-6.85 (m, 8H), 8.70 (s, 1H) |
| 288 | 1.56 (d, 3H), 2.97 (dd, 2H), 4.65-5.02 (m, 1H), 6.93 (d, 1H), 7.36-8.05 (m, 7H), 8.65 (s, 1H) |
| 289 | 1.25 (d, 2H), 1.50 (d, 2H), 2.62-3.19 (m, 3H), 4.74-4.89 (m, 1H), 5.96 (m, 1H), 7.26-7.89 (m, 8H), 8.67 (s, 1H) |
| 290 | 1.55 (d, 3H), 2.58-3.38 (m, 2H), 3.05 (s, 3H), 4.72-5.08 (m, 1H), 6.76 (d, 1H), 7.28-8.17 (m, 8H), 8.64 (s, 1H) |
| 291 | 1.53 (d, 3H), 2.90 (dd, 2H), 4.65-4.92 (m, 1H), 5.95 (brs, 1H), 7.17-8.00 (m, 6H), 8.62 (s, 1H) |

TABLE 2-19

| Compound No. | δ value (ppm; solvent, CDCl₃; internal standard substance, TMS) |
|---|---|
| 292 | 1.43 (d, 3H), 2.67 (s, 3H), 2.86 (dd, 2H), 4.52-4.82 (m, 1H), 5.75 (d, 1H), 7.37-7.81 (m, 5H), 8.67 (s, 1H) |
| 293 | 1.50 (d, 3H), 2.85 (dd, 2H), 4.60-4.80 (m, 1H), 5.82 (brs, 1H), 6.85-7.80 (m, 5H), 8.62 (s, 1H) |
| 294 | 1.07 (t, 3H), 1.74-1.99 (m, 2H), 2.86 (dd, 2H), 4.42-4.78 (m, 1H), 5.94 (d, 1H), 6.87-7.90 (m, 8H), 8.67 (s, 1H) |
| 295 | 1.07 (t, 3H), 1.74-1.98 (m, 2H), 2.91 (dd, 2H), 4.44-4.78 (m, 1H), 5.96 (d, 1H), 7.04-7.91 (m, 7H), 8.67 (s, 1H) |
| 296 | 2.94 (d, 2H), 5.23-5.50 (m, 3H), 5.96-6.27 (m, 2H), 7.22-7.83 (m, 9H), 8.69 (s, 1H) |
| 297 | 2.93 (d, 2H), 5.23-5.50 (m, 3H), 5.96-6.33 (m, 2H), 6.86-7.90 (m, 8H), 8.70 (s, 1H) |
| 298 | 1.06 (d, 3H), 1.13 (d, 3H), 2.00-2.40 (m, 1H), 2.86 (d, 2H), 4.41-4.60 (m, 1H), 5.94 (d, 1H), 7.21-7.90 (m, 9H), 8.66 (s, 1H) |
| 299 | 2.95 (d, 2H), 3.96-4.12 (m, 2H), 4.50-4.68 (m, 1H), 6.70 (d, 1H), 7.02-7.83 (m, 9H), 8.64 (s, 1H) |
| 300 | 2.08 (t, 1H), 2.97 (dd, 2H), 5.73 (m, 1H), 6.42 (d, 1H), 7.01-7.90 (m, 9H), 8.64 (s, 1H) |
| 301 | 3.17 (d, 2H), 5.80 (m, 1H), 6.45 (d, 1H), 7.18-7.82 (m, 14H), 8.66 (s, 1H) |
| 302 | 3.25 (d, 2H), 5.86 (m, 1H), 6.47 (d, 1H), 7.18-7.87 (m, 13H), 8.66 (s, 1H) |
| 303 | 1.34 (t, 3H), 3.23 (dd, 2H), 4.34 (q, 2H), 5.14-5.32 (m, 1H), 6.87 (d, 1H), 7.21-7.93 (m, 9H), 8.67 (s, 1H) |
| 304 | 1.33 (t, 3H), 2.93-3.36 (m, 2H), 4.33 (q, 2H), 5.08-5.38 (m, 1H), 6.69 (d, 1H), 7.26-7.91 (m, 8H), 8.66 (s, 1H) |
| 305 | 2.78-3.42 (m, 2H), 2.84 (d, 3H), 4.92-5.17 (m, 1H), 6.65 (brs, 1H), 6.94 (d, 1H), 7.22-7.90 (m, 9H), 8.67 (s, 1H) |
| 306 | 2.90 (t, 2H), 3.95 (q, 2H), 6.28 (brs, 1H), 7.31-7.69 (m, 7H), 8.71 (s, 1H) |
| 307 | 2.86 (t, 2H), 3.91 (q, 2H), 6.18 (brs, 1H), 7.13-7.88 (m, 7H), 8.79 (s, 1H) |

TABLE 2-20

| Compound No. | δ value (ppm; solvent, CDCl₃; internal standard substance, TMS) |
|---|---|
| 308 | 2.89 (t, 2H), 3.95 (q, 2H), 6.10 (brs, 1H), 7.20-7.84 (m, 7H), 8.65 (s, 1H) |
| 309 | 2.86 (t, 2H), 3.91 (q, 2H), 6.05 (brs, 1H), 7.22-7.75 (m, 7H) 8.65 (s, 1H) |
| 310 | 2.91 (t, 2H), 3.93 (q, 2H), 7.19-7.70 (m, 7H), 8.10 (brs, 1H), 8.58 (s, 1H) |
| 311 | 2.87 (t, 2H), 3.50 (s, 3H), 3.96 (q, 2H), 4.60 (s, 2H), 6.59 (brs, 1H), 7.30-7.89 (m, 7H), 8.78 (s, 1H) |
| 312 | 2.86 (t, 2H), 3.35 (s, 3H), 3.94 (q, 2H), 4.60 (s, 2H), 6.58 (brs, 1H), 7.13-7.84 (m, 7H), 8.64 (s, 1H) |
| 313 | 2.91 (t, 2H), 3.38 (s, 3H), 3.94 (q, 2H), 4.60 (s, 2H), 7.12-7.71 (m, 7H), 8.55 (brs, 1H), 8.58 (s, 1H) |
| 314 | 2.89 (t, 2H), 3.36 (s, 3H), 3.94 (q, 2H), 4.60 (s, 2H), 7.12-7.76 (m, 7H), 8.55 (brs, 1H), 8.58 (s, 1H) |
| 315 | 2.87 (t, 2H), 3.35 (s, 3H), 3.96 (q, 2H), 4.60 (s, 2H), 6.60 (brs, 1H), 7.30-7.72 (m, 7H), 8.71 (s, 1H) |
| 316 | 2.86 (t, 2H), 3.35 (s, 3H), 3.96 (q, 2H), 4.60 (s, 2H), 6.53 (brs, 1H), 7.07-7.95 (m, 7H), 8.64 (s, 1H) |
| 317 | 2.85 (t, 2H), 3.37 (s, 3H), 3.96 (q, 2H), 4.62 (s, 2H), 6.58 (brs, 1H), 7.26-7.93 (m, 7H), 8.64 (s, 1H) |
| 318 | 2.90 (t, 2H), 3.38 (s, 3H), 3.94 (q, 2H), 4.60 (s, 2H), 6.96-7.69 (m, 8H), 8.62 (s, 1H) |
| 319 | 2.83 (t, 2H), 3.37 (s, 3H), 3.96 (q, 2H), 4.63 (s, 2H), 6.66 (brs, 1H), 7.21-7.89 (m, 6H), 8.62 (s, 1H) |
| 320 | 2.86 (t, 2H), 3.35 (s, 3H), 3.95 (q, 2H), 4.60 (s, 2H), 6.60 (brs, 1H), 7.21-8.02 (m, 7H), 8.64 (s, 1H) |
| 321 | 2.84 (t, 2H), 3.39 (s, 3H), 3.94 (q, 2H), 4.65 (s, 2H), 6.76 (brs, 1H), 7.21-8.22 (m, 6H), 8.70 (s, 1H) |
| 322 | 2.82 (t, 2H), 3.40 (s, 3H), 3.96 (q, 2H), 4.67 (s, 2H), 6.78 (brs, 1H), 7.21-8.36 (m, 6H), 8.66 (s, 1H) |
| 323 | 2.88 (t, 2H), 3.36 (s, 3H), 3.92 (q, 2H), 4.61 (s, 2H), 6.73 (brs, 1H), 7.18-8.12 (m, 7H), 8.72 (s, 1H) |

TABLE 2-21

| Compound No. | δ value (ppm; solvent, CDCl₃; internal standard substance, TMS) |
|---|---|
| 324 | 2.88 (t, 2H), 3.36 (s, 3H), 3.92 (q, 2H), 4.61 (s, 2H), 6.73 (brs, 1H), 7.18-8.12 (m, 7H), 8.72 (s, 1H) |
| 325 | 2.70 (s, 3H), 2.88 (t, 2H), 3.35 (s, 3H), 3.95 (q, 2H), 4.59 (s, 2H), 6.38 (brs, 1H), 7.15-7.61 (m, 7H), 8.73 (s, 1H) |
| 326 | 2.49 (s, 3H), 2.88 (t, 2H), 3.34 (s, 3H), 3.94 (q, 2H), 4.60 (s, 2H), 6.48 (brs, 1H), 7.22-8.01 (m, 7H), 8.63 (s, 1H) |
| 327 | 2.66 (s, 3H), 2.86 (t, 2H), 3.38 (s, 3H), 3.92 (q, 2H), 4.62 (s, 2H), 6.64 (brs, 1H), 7.18-7.82 (m, 6H), 8.68 (s, 1H) |
| 328 | 2.87 (t, 2H), 3.50 (s, 3H), 3.75 (s, 3H), 3.96 (q, 2H), 4.60 (s, 2H), 6.59 (brs, 1H), 7.30-7.89 (m, 7H), 8.78 (s, 1H) |
| 329 | 2.87 (t, 2H), 3.32 (s, 3H), 3.75 (s, 3H), 3.93 (q, 2H), 4.53 (s, 2H), 6.62 (brs, 1H), 7.00-7.82 (m, 7H), 8.59 (s, 1H) |
| 330 | 2.84 (t, 2H), 3.31 (s, 3H), 3.95 (q, 2H), 7.20-7.90 (m, 7H), 8.55 (s, 1H), 8.71 (s, 1H) |
| 331 | 2.83 (t, 2H), 3.41 (s, 3H), 4.00 (q, 2H), 4.70 (s, 2H), 7.14-7.44 (m, 4H), 7.85-9.17 (m, 4H) |
| 332 | 2.46 (s, 3H), 2.84 (t, 2H), 3.32 (s, 3H), 3.95 (q, 2H), 4.61 (s, 2H), 6.64 (brs, 1H), 7.26-8.09 (m, 7H), 8.61 (s, 1H) |
| 333 | 2.86 (t, 2H), 3.20 (s, 3H), 3.92 (q, 2H), 4.56 (s, 2H), 6.68 (brs, 1H), 7.24-8.03 (m, 12H), 8.67 (s, 1H) |
| 334 | 2.88 (t, 2H), 3.22 (s, 3H), 3.95 (q, 2H), 4.52 (s, 2H), 6.60 (brs, 1H), 7.08-8.01 (m, 11H), 8.69 (s, 1H) |
| 335 | 2.85 (t, 2H), 3.22 (s, 3H), 3.92 (q, 2H), 4.58 (s, 2H), 6.80 (brs, 1H), 7.18-8.05 (m, 11H), 8.66 (s, 1H) |
| 336 | 2.85 (t, 2H), 3.24 (s, 3H), 3.92 (q, 2H), 4.54 (s, 2H), 6.74 (brs, 1H), 7.00-7.96 (m, 11H), 8.67 (s, 1H) |
| 337 | 2.88 (t, 2H), 3.24 (s, 3H), 2.97 (q, 2H), 4.56 (s, 2H), 7.14-7.37 (m, 5H), 7.91-8.69 (m, 7H) |
| 338 | 2.83 (t, 2H), 3.34 (s, 3H), 3.97 (q, 2H), 4.64 (s, 2H), 6.90 (brs, 1H), 7.25-7.95 (m, 6H), 8.75 (s, 1H) |
| 339 | 2.86 (t, 2H), 3.35 (s, 3H), 3.92 (q, 2H), 4.59 (s, 2H), 4.83 (s, 2H), 6.74 (brs, 1H), 7.13-7.85 (m, 12H), 8.62 (s, 1H) |

TABLE 2-22

| Compound No. | δ value (ppm; solvent, CDCl₃; internal standard substance, TMS) |
|---|---|
| 340 | 2.85 (t, 2H), 3.31 (s, 3H), 3.93 (q, 2H), 4.58 (s, 2H), 4.95 (s, 2H), 6.66 (brs, 1H), 7.15-7.83 (m, 12H), 8.58 (s, 1H) |
| 341 | 2.45 (s, 3H), 2.66 (s, 3H), 2.84 (t, 2H), 3.43 (s, 3H), 3.94 (q, 2H), 4.60 (s, 2H), 7.25-8.00 (m, 6H), 8.68 (s, 1H) |
| 342 | 2.86 (t, 2H), 3.94 (q, 2H), 7.30-8.91 (m, 11H) |
| 343 | 1.50 (d, 3H), 2.90 (dd, 2H), 4.67-4.98 (m, 1H), 5.93 (brs, 1H), 7.16-7.76 (m, 7H), 8.70 (s, 1H) |
| 344 | 1.48 (d, 3H), 2.91 (dd, 2H), 4.65-4.97 (m, 1H), 6.16 (d, 1H), 7.09-7.90 (m, 6H), 8.63 (s, 1H) |
| 345 | 1.53 (d, 3H), 2.93 (dd, 2H), 4.60-4.96 (m, 1H), 6.14 (d, 1H), 7.26-7.62 (m, 5H), 7.81-7.98 (m, 1H), 8.64 (s, 1H) |
| 346 | 1.51 (d, 3H), 2.90 (dd, 2H), 4.63-4.93 (m, 1H), 6.98-7.69 (m, 6H), 8.61 (s, 1H) |
| 347 | 2.48 (d, 3H), 2.90 (dd, 2H), 4.80 (m, 1H), 5.81 (d, 1H), 7.09-7.79 (m, 6H), 8.64 (s, 1H) |
| 348 | 1.51 (d, 3H), 2.92 (dd, 2H), 4.73-4.88 (m, 1H), 5.97 (d, 1H), 7.27-7.63 (m, 6H), 8.70 (s, 1H) |
| 349 | 1.50 (d, 3H), 2.91 (dd, 2H), 4.67-4.93 (m, 1H), 5.94 (d, 1H), 7.23-7.88 (m, 6H), 8.77 (s, 1H) |
| 350 | 1.53 (d, 3H), 2.90 (dd, 2H), 4.65-4.92 (m, 1H), 7.20-8.23 (m, 7H), 8.59 (s, 1H) |
| 351 | 1.53 (d, 3H), 2.94 (dd, 2H), 4.69-4.98 (m, 1H), 6.53 (d, 1H), 7.26-7.61 (m, 4H), 8.04-8.18 (m, 2H), 8.62 (s, 1H) |
| 352 | 1.51 (d, 3H), 2.92 (dd, 2H), 4.06 (s, 3H), 4.62-4.98 (m, 1H), 5.93 (d, 1H), 7.05-7.63 (m, 6H), 8.69 (s, 1H) |
| 353 | 1.49 (d, 3H), 2.86 (dd, 2H), 4.08 (s, 3H), 4.80 (m, 1H), 5.88 (d, 2H), 7.04-7.61 (m, 6H), 8.70 (s, 1H) |
| 354 | 1.52 (d, 3H), 2.70 (s, 3H), 2.92 (dd, 2H), 4.81 (brs, 1H), 6.16 (brs, 1H), 7.26-7.61 (m, 6H), 8.73 (s, 1H) |
| 355 | 1.52 (d, 3H), 2.92 (dd, 2H), 4.62-4.97 (m, 1H), 6.02 (d, 1H), 7.38-7.79 (m, 5H), 8.63 (s, 1H) |

TABLE 2-23

| Compound No. | δ value (ppm; solvent, CDCl₃; internal standard substance, TMS) |
|---|---|
| 356 | 2.15 (s, 3H), 2.75 (t, 3H), 3.74 (q, 2H), 5.28 (brs, 1H), 7.19-7.43 (m, 5H), 8.29 (s, 1H) |
| 357 | 2.76 (t, 2H), 3.76 (q, 2H), 5.93 (brs, 1H), 7.23-7.46 (m, 5H), 8.30 (s, 1H) |
| 358 | 2.74 (t, 2H), 3.60 (q, 2H), 5.44 (brs, 1H), 6.40 (s, 1H), 7.23-7.45 (m, 5H), 8.37 (s, 1H) |
| 359 | 1.24 (d, 3H), 2.33 (s, 3H), 2.55 (d, 2H), 4.68-4.99 (m, 1H), 6.29 (s, 1H), 7.25-7.60 (m, 4H), 8.06 (s, 1H) |
| 360 | 2.47 (s, 3H), 2.79 (t, 2H), 3.78 (q, 2H), 5.74 (brs, 1H), 7.44-7.61 (m, 3H), 8.38 (s, 1H) |
| 361 | 2.34 (s, 3H), 2.47 (s, 3H), 2.79 (t, 2H), 3.41 (s, 3H), 3.76 (q, 2H), 4.57 (s, 2H), 5.80 (brs, 1H), 7.06-7.34 (m, 3H), 8.39 (s, 1H) |
| 362 | 2.46 (s, 3H), 2.80 (t, 2H), 3.41 (s, 3H), 3.76 (q, 2H), 4.60 (s, 2H), 5.85 (brs, 1H), 7.17-7.45 (m, 4H), 8.39 (s, 1H) |
| 363 | 2.04 (s, 3H), 2.78 (t, 2H), 3.38 (s, 3H), 3.77 (q, 2H), 4.58 (s, 2H), 5.43 (brs, 1H), 7.18-7.45 (m, 4H), 8.24 (s, 1H) |
| 364 | 2.08 (s, 3H), 2.79 (t, 2H), 3.79 (q, 2H), 5.26 (brs, 1H), 7.27-7.68 (m, 4H), 8.28 (s, 1H) |
| 365 | 2.10 (s, 3H), 2.78 (t, 2H), 3.40 (s, 3H), 3.80 (q, 2H), 6.10 (brs, 1H), 7.18-7.70 (m, 4H), 8.32 (s, 1H) |
| 366 | 2.82 (t, 2H), 3.40 (s, 3H), 3.78 (q, 2H), 4.58 (s, 2H), 6.02 (brs, 1H), 7.22-7.45 (m, 4H), 8.30 (s, 1H) |
| 367 | 2.82 (t, 2H), 3.78 (q, 2H), 6.04 (brs, 1H), 7.27-7.72 (m, 4H), 8.30 (s, 1H) |
| 368 | 2.80 (t, 2H), 3.47 (brs, 2H), 3.77 (q, 2H), 5.36 (brs, 1H), 7.33-7.68 (m, 4H), 8.07 (s, 1H) |
| 369 | 2.92 (s, 3H), 2.92 (t, 2H), 3.96 (q, 2H), 7.39-7.75 (m, 5H), 8.12 (s, 1H) |
| 370 | 2.80 (t, 2H), 3.89 (q, 2H), 7.34-7.83 (m, 5H), 8.41 (s, 1H) |
| 371 | 2.52 (s, 3H), 2.81 (t, 2H), 3.96 (q, 2H), 6.70 (brs, 1H), 7.42-7.58 (m, 4H), 8.40 (s, 1H) |

TABLE 2-24

| Compound No. | δ value (ppm; solvent, CDCl₃; internal standard substance, TMS) |
|---|---|
| 372 | 2.70 (t, 2H), 3.63 (q, 2H), 3.98 (s, 2H), 7.19-7.35 (m, 10H), 7.91 (s, 1H) |
| 373 | 2.66 (t, 2H), 3.62 (q, 2H), 5.20 (brs, 1H), 7.09-7.45 (m, 10H), 8.36 (d, 1H) |
| 374 | 1.65 (dd, 3H), 2.75 (t, 2H), 3.82 (q, 2H), 5.92-6.17 (m, 2H), 7.22-7.48 (m, 5H), 8.45 (s, 1H) |
| 375 | 1.70 (dd, 3H), 2.80 (t, 2H), 3.80 (q, 2H), 5.50-6.20 (m, 1H), 6.05 (brs, 1H), 7.15-7.38 (m, 5H), 8.50 (s, 1H) |
| 376 | 1.65 (dd, 3H), 2.75 (t, 2H), 3.71 (q, 2H), 5.50-6.25 (m, 1H), 5.90 (brs, 1H), 7.19-7.44 (m, 5H), 8.55 (s, 1H) |
| 377 | 1.68 (dd, 3H), 2.81 (t, 2H), 3.80 (q, 2H), 5.89 (dq, 1H), 5.91 (brs, 1H), 7.44-7.61 (m, 3H), 8.54 (s, 1H) |
| 378 | 2.75 (t, 2H), 3.75 (q, 2H), 7.30 (s, 5H), 7.72 (t, 1H), 8.08 (s, 1H), 8.22 (s, 1H) |
| 379 | 2.84 (t, 2H), 3.89 (q, 2H), 5.61 (t, 1H), 6.41 (d, 1H), 7.10 (d, 1H), 7.23-7.47 (m, 5H), 8.39 (s, 1H) |
| 380 | 2.88 (t, 2H), 3.34 (s, 3H), 3.94 (q, 2H), 4.59 (s, 2H), 7.25-7.39 (m, 7H), 8.43 (s, 1H), 9.00 (brs, 1H) |
| 381 | 1.45 (d, 3H), 1.70 (dd, 3H), 2.78 (dd, 2H), 4.35-4.68 (m, 1H), 5.40-6.20 (m, 2H), 5.85 (brs, 1H), 7.17-7.47 (m, 5H), 8.45 (s, 1H) |
| 382 | 1.44 (d, 3H), 1.80 (d, 3H), 2.82 (t, 2H), 4.40-4.72 (m, 1H), 5.65 (d, 1H), 6.13 (q, 1H), 7.26-7.62 (m, 3H), 8.53 (s, 1H) |
| 383 | 1.44 (d, 3H), 1.85 (d, 3H), 2.82 (t, 2H), 4.40-4.72 (m, 1H), 5.48 (q, 1H), 5.70 (d, 1H), 7.45-7.74 (m, 3H), 8.54 (s, 1H) |
| 384 | 1.54 (d, 3H), 2.95 (dd, 2H), 4.68-4.99 (m, 1H), 7.16-7.67 (m, 4H), 8.57 (dd, 1H), 8.88 (s, 1H), 9.01 (dd, 1H) |
| 385 | 1.43 (d, 3H), 2.45 (s, 3H), 2.80 (d, 2H), 4.38-4.64 (m, 1H), 5.48 (brs, 1H), 7.44-7.62 (m, 3H), 8.36 (s, 1H) |
| 386 | 1.42 (d, 3H), 2.57 (s, 3H), 2.78 (d, 2H), 4.32-4.62 (m, 1H), 5.50 (d, 1H), 7.45-7.61 (m, 3H), 8.30 (s, 1H) |
| 387 | 1.34 (d, 3H), 2.50 (s, 3H), 2.80 (d, 2H), 4.37-4.62 (m, 1H), 5.57 (d, 1H), 7.46-7.62 (m, 3H), 8.36 (s, 1H) |

TABLE 2-25

| Compound No. | δ value (ppm; solvent, CDCl₃; internal standard substance, TMS) |
|---|---|
| 388 | 1.34 (d, 3H), 2.80 (d, 2H), 4.37-4.62 (m, 1H), 5.57 (d, 1H), 7.46-7.62 (m, 3H), 8.36 (s, 1H) |
| 389 | 1.43 (d, 3H), 2.46 (s, 3H), 2.74 (dd, 2H), 4.42-4.59 (m, 1H), 5.55 (d, 1H), 7.22-7.47 (m, 5H), 8.34 (s, 1H) |
| 390 | 1.54 (brs, 4H), 2.15 (brs, 4H), 2.78 (t, 2H), 3.81 (q, 2H), 4.24 (s, 2H), 7.30-7.98 (m, 4H), 8.60 (s, 1H) |
| 391 | 1.60 (brs, 4H), 2.20 (brs, 4H), 2.80 (t, 2H), 3.85 (q, 2H), 5.00 (d, 2H), 6.20 (brs, 1H), 7.35-7.83 (m, 4H), 8.66 (s, 1H) |

The pest control composition of the present invention can be applied to plants by spraying, dusting, coating, or otherwise treating them with the active ingredients or alternatively, by treating with the active ingredients the plant seeds, the soil around the plant, or the soil, rice pads or the water for hydroponic culture where the seeds are to be sown. The application may be effected either before or after the plant is infected with pathogenic microorganisms.

The invention composition can be used in ordinary dosage forms, for example, as various formulations suitable for agrihorticultural pest control preparations, as exemplified by granules, dust granules, water-soluble powder, oil-miscible liquid, concentrated emulsion, microemulsion, suspoemulsion, soluble concentrate, wettable powder, emulsifiable concentrate, suspension concentrate, tablets, water-dispersible granules, microcapsules, aerosol, paste, hand-throwables, dust, smoke, fumigant, and so forth. These dosage forms can be obtained by ordinary methods which comprise mixing at least one invention compound with a suitable solid or liquid carrier, optionally in the presence of suitable aids (e.g., surfactant, solvent, and stabilizer) that help improve the dispersibility and other properties of the active ingredients.

Examples of solid carriers or diluents include vegetable substances (e.g., microcrystalline cellulose, starch, wood flour, cork, coffee husks, etc.), fibrous substances, artificial plastic powder, clays (e.g., kaolin, bentonite, clay, diatomaceous earth, synthetic hydrous silicon oxide, Fubasami clay, acid clay, etc.), talc and inorganic matter (e.g., vermiculite, pumice stone, sulfur powder, apatite, mica, sericite, quartz powder, activated charcoal, calcium carbonate, etc.), high-molecular weight compounds (e.g., polyvinyl chloride, petroleum resins, etc.), and chemical fertilizers (e.g., ammonium sulfate, ammonium phosphate, ammonium nitrate, ammonium chloride, calcium chloride, urea, etc.), and so forth. Liquid carriers and diluents include water, alcohols (e.g., methanol, ethanol, isopropanol, cyclohexanol, etc.), ketones (e.g., acetone, methyl ethyl ketone, cyclohexanone, etc.), ethers (e.g., ethyl cellosolve, butyl cellosolve, dioxane, etc.), aromatic hydrocarbons (e.g., benzene, toluene, xylene, ethylbenzene, methylnaphthalene, etc.), aliphatic hydrocarbons (e.g., kerosene, paraffin, etc.), esters (e.g., isopropyl acetate, benzyl acetate, etc.), nitriles, amides (e.g., N,N-dimethylformamide, dimethyl sulfoxide, etc.), halogenated hydrocarbons (chlorobenzene and trichloroethylene), and so forth.

Gaseous carriers, namely, propellants include, for example, carbon dioxide, butane gas, fluorocarbons, and so forth.

Examples of surfactants include various anionic and nonionic surfactants that are conventionally used in the field of agrochemical preparations. Anionic surfactants include, for example, sulfonic acid surfactants such as alkylsulfonic acids, α-olefinsulfonic acids, lignin sulfonic acid, alkylbenzenesulfonates, alkylnaphthalenesulfonates, naphthalenesulfonic acid/formalin condensdate, and dialkylsulfosuccinates, and salts thereof; sulfate surfactants such as polyoxyethylene alkylether sulfates, polyoxyethylene alkylallylether sulfates, polyoxyethylene styrylphenylether sulfate, polyoxyethylene phenylalkylallylether sulfates, polyoxyalkylene glycol sulfates, higher alcohol sulfates, fatty acid ester sulfates, and phenylphenol (EO) sulfate salts, and salts thereof; phosphate surfactans such as polyoxyethylene alkylether phosphates, polyoxyethylene alkylallyl phosphates, phenylphenol (EO) phosphate ester salts, polyoxyethylene phenylalkylallylether phosphates, higher alcohol phosphates, and polyoxyethylene tribenzylphenol phosphate, and salts thereof, as well as higher fatty acid salts, polycarboxylic acid-type surfactants and salts thereof, and so forth. Salts of the above-mentioned surfactants include salts with sodium, potassium, magnesium, calcium, ammonium, ethanolamine, diethanolamine, triethanolamine, and various other amines. Nonionic surfactants include, for example, polyoxyethylene alkylallylethers, polyoxyethylene styrylphenylether, polyoxyethylene alkylethers, polyoxyethylene phenylalkylallylethers, polyoxyethylene sorbitan fatty acid esters, polyoxyethylene glycol, polyoxyethylene alkyl esters, polyoxyethylene/polyoxypropylene block copolymers, polyoxyalkylene glycols, alkynediols (acetylene glycol), alkynylene polyoxyethylene diols, sorbitan fatty acid esters, alkylarylether/formalin condensates, and so forth.

Stabilizers include isopropyl phosphate salt mixtures, tricresyl phosphate, tall oil, epoxidized oils, surfactants, fatty acids, and esters thereof. In addition to the ingredients described above, the pest control composition of the present invention may be mixed with other antimicrobials, insecticides, herbicides, fertilizers, etc. to formulate preparations.

The amount in which the pest control composition of the present invention is to be applied varies with such factors as the types of pest control active compounds to be combined with, the disease or harmful insect to be controlled, occurrence tendency, the severity of damage, environmental conditions, and the dosage form to be used. One or more of the 4-(3-butynyl)aminopyrimidine derivatives represented by the general formula [I] and at least one of the existing agrihorticultural pest control compounds listed above are to be mixed with each other in ratios ranging from 1:0.1 to 1:100,000 by weight, and the resulting composition is typically applied in amounts of 0.1 g to 1 kg for 10 ares. In the case where the composition in the form of a soluble concentrate, an emulsifiable concentrate, a wettable powder, a flowable or the like is used as diluted with water, the concentration after dilution is typically in the range of 1 to 10,000 ppm.

The pest control composition according to the present invention may be used in such a way that individual compositions are applied independently, either simultaneously or sequentially; if desired, they may be used as formulated preparations. Furthermore, they may be mixed with microbicidal/fungicidal agents, bactericides, miticides, nematicides, insecticides, bioagrochemicals, herebicides, plant hormonal agents, plant growth regulators, synergistic agents, attractants, repellents, dyes, fertilizers, etc. and the resulting mixtures or preparations of mixtures with one or more species selected from among their active ingredients may be used as pest control agents, whereupon improved efficacy is attained from the synergism with the concomitant ingredient or ingredients.

The agri-horticultural pest control composition of the present invention permits mixing at least one 4-(3-butynyl) aminopyrimidine derivative with at least one agri-horticultural pest control compound. In one example, one 4-(3-butynyl)aminopyrimidine derivative is mixed with one of the existing agri-horticultural pest control compounds listed above to make a dual mixture; another possible example is a tri-component mixture.

The 4-(3-butynyl)aminopyrimidine derivative of the general formula [I] which is to be used in the present invention may, for example, be produced by reacting a chloropyrimidine derivative of the general formula [II] with a 3-butynylamine derivative of the general formula [III] in the presence of a base and a solvent, as outlined by the following reaction scheme.

[Formula 4]

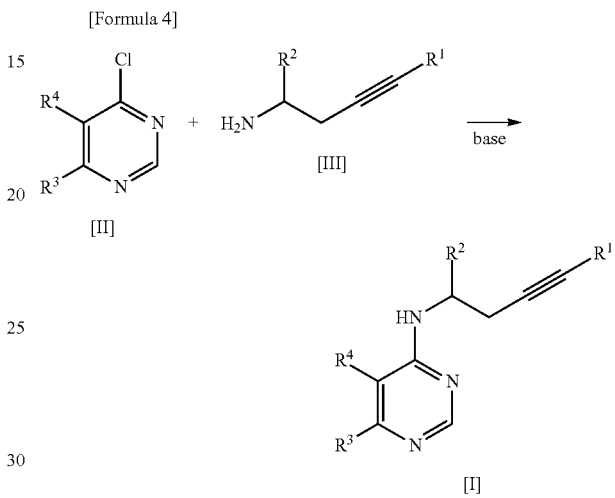

(where $R^1$, $R^2$, $R^3$, and $R^4$ have the same meanings as defined above.)

The solvents that can be used are not limited to any particular types as long as they are not directly involved in the reaction at issue; examples include: chlorinated or non-chlorinated aromatic, aliphatic or alicyclic hydrocarbons such as benzene, toluene, xylene, methylnaphthalene, petroleum ether, ligroin, hexane, chlorobenzene, dichlorobenzene, chloroform, dichloroethane, and trichloroethylene; ethers such as tetrahydrofuran, dioxane, and diethylether; nitriles such as acetonitrile and propionitrile; ketones such as acetone and methyl ethyl ketone; amide compounds such as N,N-dimethylformamide, N,N-dimethylacetamide, and N-methylpyrrolidone; sulfoxy compounds such as dimethyl sulfoxide; urea compounds such as N,N-dimethylimidazolidinone; sulfolane; and mixtures of these solvents. Particularly preferred are amide compounds such as N,N-dimethylformamide, N,N-dimethylacetamide, and N-methylpyrrolidone.

The solvents can be used in such amounts that the compound [II] accounts for 5-80 wt %, with 10-70 wt % being preferred.

The bases that can be used are not limited to any particular types and may include both organic and inorganic bases; exemplary organic bases are tertiary amines (e.g., triethylamine) and DBU, while exemplary inorganic bases are hydrides, hydroxides, carbonates, and hydrogencarbonates of alkali metals or alkaline earth metals; organic bases such as tertiary amines (e.g., triethylamine) and DBU are preferred.

The bases are used in amounts between 1.0 and 5.0 moles for 1.0 mole of the compound [II], with 1.2 to 2.0 moles being preferred.

The starting compounds are used in such amounts that the compound [III] accounts for 1.0 to 5.0 moles for 1.0 mole of the compound [II], with 1.0 to 1.2 moles being preferred.

The reaction temperature is not particularly limited but it is typically within the range from room temperature to not more than the boiling point of the solvent used; it is preferably between 60° C. and 110° C.

The reaction time varies with the above-mentioned concentrations and temperature but it typically ranges from 0.5 to 8 hours.

After the end of the reaction, the thus produced compound [I] is subjected to usual post-treatments such as extraction, concentration, and filtration; if necessary, it may be purified as appropriate by known means such as recrystallization and various chromatographic techniques.

If the thus produced compound [I] is alkyne-terminated (compound I-1 where $R^1$=H), the Sonogashira reaction or the like may be utilized to introduce a substituent.

[Formula 5]

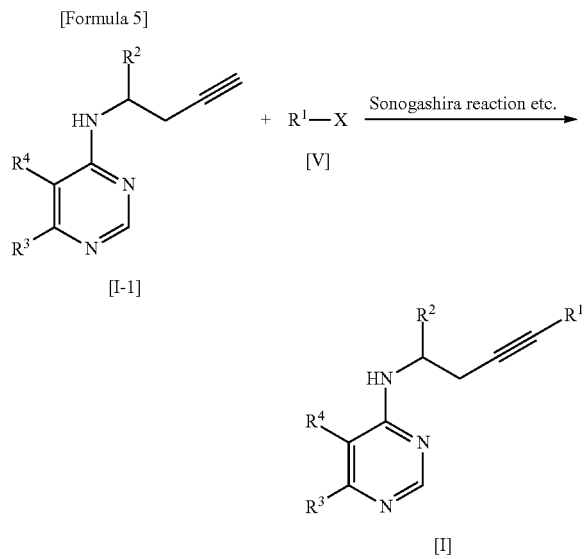

(where $R^1$ is phenyl, heteroaryl, or alkenyl; $R^2$, $R^3$, and $R^4$ have the same meanings as defined above.)

The compound [II] to be used in this synthesis method can be prepared by the method schematically shown below which is a modification of the method described in Non-Patent Document 1.

[Formula 6]

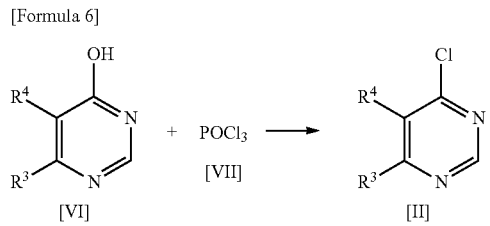

(where $R^3$ and $R^4$ have the same meanings as defined above.)

The 3-butynylamine derivative [III] to be used in the synthesis of interest is commercially available but, if necessary, it may be prepared by modifications of the methods described below. It should, however, be noted that the following methods are by no means intended to limit the scope of the present invention.

(Synthesis 1)

N-(3-Butynyl)phthalimide derivative [VIII] and a phenyl iodide or bromide, a heteroaryl iodide, bromide or chloride, or an alkenyl iodide or bromide [V] are subjected to the Sonogashira reaction and the product [IX] is then deprotected with hydrazine or base to produce 3-butynylamine derivative [III].

[Formula 7]

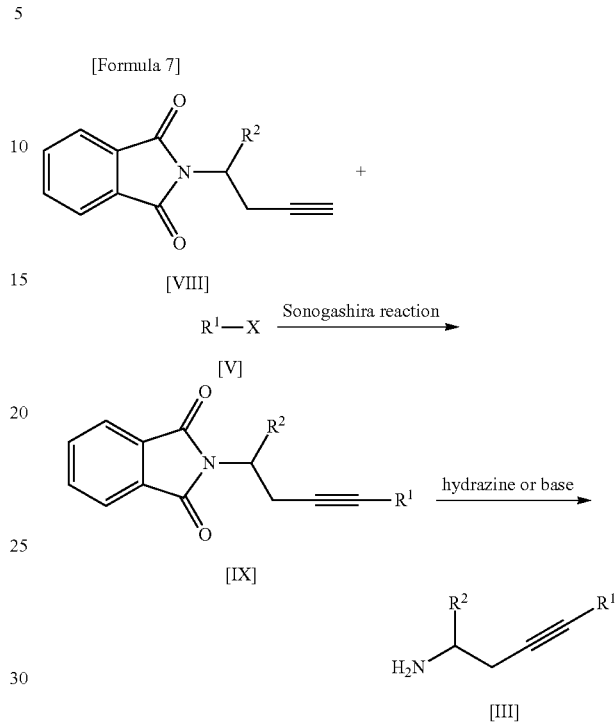

(where X is iodine, bromine, or chlorine; $R^1$ is phenyl, heteroaryl, or alkenyl; $R^2$ has the same meaning as defined above.)

(Synthesis 2)

From a substituted butynyl alcohol [X] and phthalimide [XI], a product [XIII] is synthesized by the Mitsunobu reaction and, as in Synthesis 1, subjected to the Sonogashira reaction and deprotection, whereby 3-butynylamine derivative [III] can be produced.

[Formula 8]

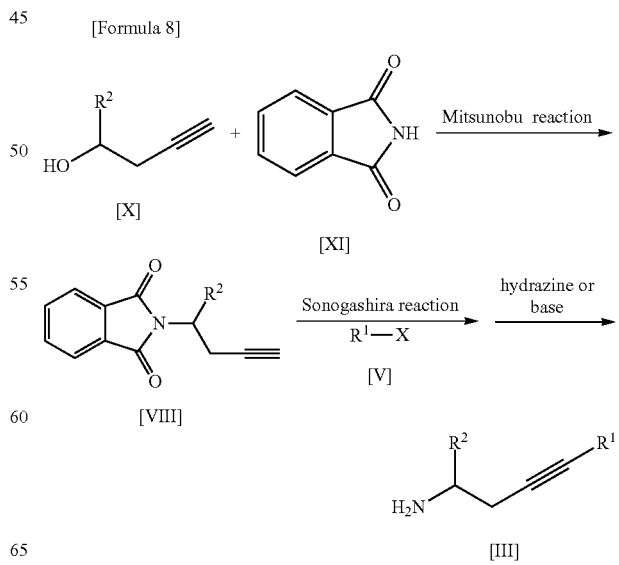

(where X is iodine, bromine, or chlorine; R¹ is phenyl, heteroaryl, or alkenyl; R² has the same meaning as defined above.)

(Synthesis 3)

Terminal alkyne [XII] is reacted with a Grignard reagent, then with ethylene oxide [XIII] to synthesize a 3-butynyl alcohol derivative [XIV]. Thereafter, this alcohol is subjected to the Mitsunobu reaction and deprotection, whereby 3-butynylamine derivative [III] can be produced.

[Formula 9]

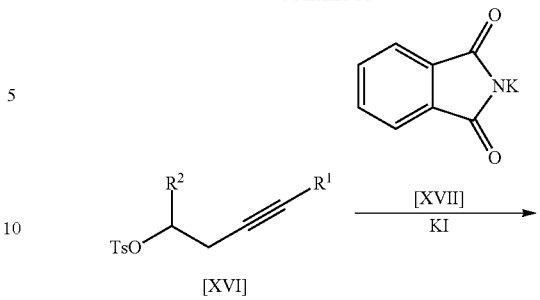

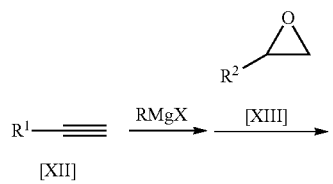

(where X is iodine, bromine, or chlorine; R¹ and R² have the same meanings as defined above.)

(Synthesis 4)

After protecting a substituted butynyl alcohol (X) with a tosyl group, alkyllithium is applied to generate an anion on the terminal alkyne carbon, in which a substituent is introduced through a nucleophilic substitution reaction to produce a product [XVI]. Thereafter, reaction with potassium phthalimide [XVII] is carried out in the presence of potassium iodide to give a product [IX]. By subsequent deprotection, 3-butynylamine derivative [III] can be produced.

[Formula 10]

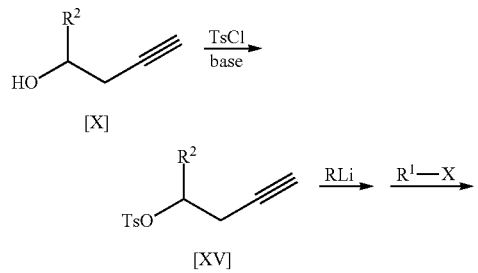

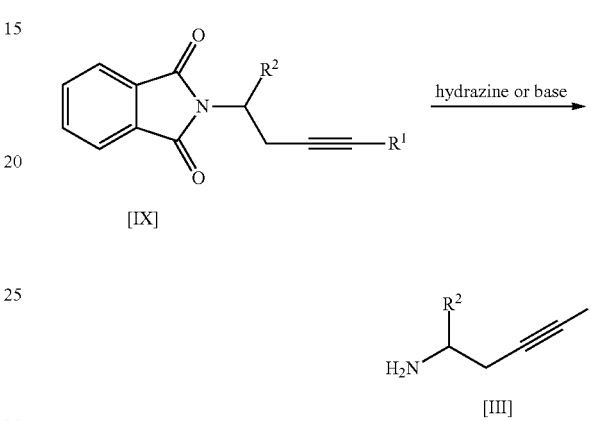

(where X is iodine, bromine, or chlorine; R¹ is trialkylsilyl; R² has the same meaning as defined above.)

(Synthesis 5)

A substituted butynyl alcohol [XIV] is protected with a tosyl group to form a compound [XVIII], which is reacted with sodium azide to form an azide compound [XIV]. Thereafter, the azide compound [XIV] is reduced with lithium aluminum hydride, whereby 3-butynylamine derivative [III] can be produced.

[Formula 11]

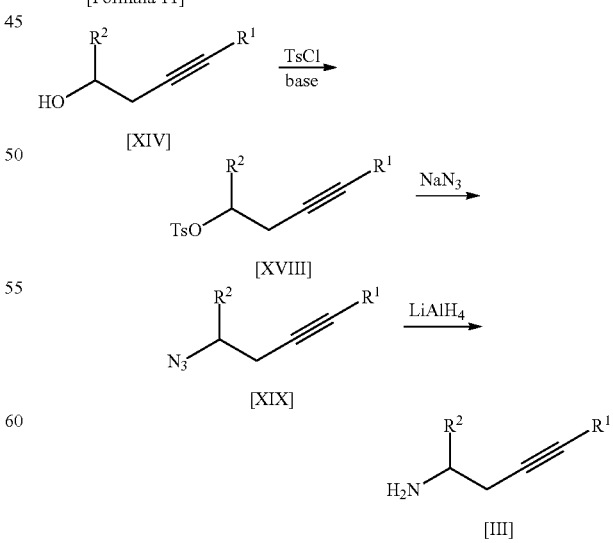

(where R¹ and R² have the same meanings as defined above.)

(Synthesis 6)

From 4-pentylamide [XX], a 3-butynylamine derivative [III] can be produced through Hoffmann rearrangement.

[Formula 12]

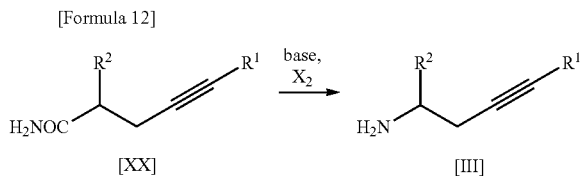

(where $R^1$ and $R^2$ have the same meanings as defined above.)

(Synthesis 7)

From acyl azide [XXI], a 3-butynylamine derivative [III] can be produced through Curtius rearrangement.

[Formula 13]

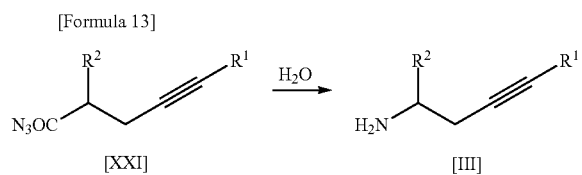

(1) Synthesis of Compound of the General Formula (I) where $R^1$=TMS, $R^2$=H, and $R^3$-$R^4$=Thiophene (Compound Identified as Compound No. 2 in Table 1)

Stage A: 3-Butynyl p-toluene sulfonate

To 500 ml of dichloromethane, 10.00 g of 3-butyn-1-ol and triethylamine (40 ml) was added and the resulting solution was cooled to 0° C. To the cooled solution, 30.00 g of p-toluenesulfonyl chloride was slowly added and following stifling overnight at room temperature, water was added to the reaction mixture, which was extracted twice with 200 ml of dichloromethane. The organic layer was washed twice with 200 ml of water and dried over magnesium sulfate. After filtering the magnesium sulfate, the organic layer was concentrated and the residue was purified by column chromatography (Wakogel C-200; hexane:ethyl acetate=6:1) to give 13.52 g of an O-tosyl compound.

Stage B: 4-Trimethylsilanyl-3-butynyl p-toluene sulfonate

A nitrogen-purged flask was charged with 130 ml of dry tetrahydrofuran and 6.45 g of the O-tosyl compound obtained in the foregoing stage and the resulting solution was cooled to −78° C. To the cooled solution, 18.9 ml of a 1.6 M n-butyllithium solution in hexane was slowly added dropwise. After the dropwise addition, the solution was stirred at −78° C. for 2 hours while 5.5 ml of trimethylsilyl chloride was slowly added dropwise. After the dropwise addition, the solution was stirred at −78° C. for 15 minutes and further stirred at room temperature for an hour. After the stirring, 150 ml of water was added to the reaction mixture and following two extractions with 150 ml of dichloromethane, drying was effected over magnesium sulfate. The organic layer was concentrated and the residue was dried under vacuum to give 8.37 g of a trimethylsilyl compound.

Stage C: 2-(4-trimethylsilanyl-3-butynyl)isoindole-1,3-dione

To 64 ml of N,N-dimethylformamide, 8.37 g of the trimethylsilyl compound obtained in the foregoing stage, 7.85 of potassium phthalimide and 0.46 g of potassium iodide were added and the resulting mixture was stirred at 140° C. for 2 hours. After cooling to room temperature, 100 ml of water was added to the reaction mixture, which was extracted twice with 100 ml of ethyl acetate. After being washed twice with 100 ml of water and once with 100 ml of saturated brine, the organic layer was dried over magnesium sulfate. After filtering the magnesium sulfate, the organic layer was concentrated and the residue was purified by column chromatography (Wakogel C-200; toluene:ethyl acetate=4:1) to give 3.28 g of a phthalimide compound.

Stage D: 4-Trimethylsilanyl-3-butynylamine

To 3.28 g of the phthalimide compound obtained in the foregoing stage, 121 ml of methanol and 2.25 g of hydrazine monohydrate (80%) were added and the mixture was stirred overnight. The reaction mixture was concentrated and the residue was suspended in 50 ml of chloroform and after filtering the insolubles, the filtrate was concentrated and dried under reduced pressure to give 1.72 g of amine.

Stage E: 4-(4-Trimethylsilanyl-3-butynylamino) thieno[2,3-d]pyrimidine

To 32 ml of N,N-dimethylformamide, 1.72 g of the amine obtained in the foregoing stage, 1.72 g of 4-chlorothieno[2,3-d]pyrimidine, and 1.7 ml of triethylamine were added and the mixture was stirred at 80° C. for 4 hours. After cooling the reaction mixture, 50 ml of water was added and two extractions were conducted with 50 ml of ethyl acetate. After being washed twice with 50 ml of water and once with 50 ml of saturated brine, the organic layer was dried over magnesium sulfate. After filtering the magnesium sulfate, the organic layer was concentrated and the residue was purified by column chromatography (Wakogel C-200; toluene:ethyl acetate=4:1) to give 1.83 g of the end product.

Similar production methods were employed to synthesize compounds identified as Compound Nos. 3-5 and 87 in Table 1.

(2) Synthesis of a Compound of the General Formula (I) where $R^1$=H, $R^2$=H, and $R^3$-$R^4$=Thiophene (Compound Identified as Compound No. 1 in Table 1)

A nitrogen-purged flask was charged with 16 ml of tetrahydrofuran, 0.37 g of the 4-(4-trimethylsilanyl-3-butynylamino)thieno[2,3-d]pyrimidine obtained in (1), and 2.1 ml of a 1 M tetrabutylammonium fluoride solution in tetrahydrofuran and the mixture was stirred at room temperature for 5 hours. After the stirring, 50 ml of a saturated aqueous solution of ammonium chloride was added and the mixture was extracted twice with 30 ml of dichloromethane. After being washed with 30 ml of saturated brine, the organic organic layer was dried over magnesium sulfate. After filtering the magnesium sulfate, the organic layer was concentrated and the residue was purified by column chromatography (Wakogel C-200; toluene:ethyl acetate=4:1) to give 0.20 of 4-(3-butynylamino)thieno[2,3-d]pyrimidine.

A similar production method was employed to synthesize a compound identified as Compound No. 86 in Table 1.

(3) Synthesis of a Compound of the General Formula (I) where $R^1$=Isobutyl, $R^2$=H, and $R^3$-$R^4$=Thiophene (Compound Identified as Compound No. 7 in Table 1)

Stage A: 6-Methyl-3-heptyn-1-ol

A nitrogen-purged flask was charged with 22 ml of dry tetrahydrofuran and 25 ml of a 1 Methylmagnesium bromide solution in tetrahydrofuran and to the resulting solution, 2.9 ml of 4-methylpentyne was slowly added dropwise. While the solution was stirred at room temperature for an hour, 25 ml of a 1.1 Methylene oxide solution in tetrahydrofuran was slowly added dropwise and the mixture was further stirred overnight at room temperature. To the reaction mixture, 100 ml of a saturated aqueous solution of ammonium chloride was added and following two extractions with 100 ml of diethyl ether, drying was effected over magnesium sulfate. After filtering the magnesium sulfate, the organic layer was concentrated and the resulting alcohol was used as such in the subsequent reaction (yield, 3.78 g.)

Stage B: 2-(6-Methyl-3-heptynyl)isoindole-1,3-dione

A nitrogen-purged flask was charged with 168 ml of dry tetrahydrofuran, 3.78 g of the alcohol obtained in the foregoing stage, 4.06 g of phthalimide, and 7.21 g of triphenylphosphine; to the resulting solution, 13.9 ml of diethyl azodicarboxylate (40% solution in toluene) was slowly added dropwise and the mixture was immediately stirred at room temperature for 24 hours. After concentrating the reaction mixture, 200 ml of water was added to the residue and two extractions were conducted with 150 ml of ethyl acetate. After being washed with 200 ml of water and 200 ml of saturated brine, the organic layer was dried over magnesium sulfate. After filtering the magnesium sulfate, the organic layer was purified by column chromatography (Wakogel C-200; toluene) to give 5.08 of a phthalimide compound.

Stage C: 6-Methyl-3-hetynylamine

To 5.08 g of the phthalimide compound obtained in the foregoing stage, 200 ml of methanol and 3.73 g of hydrazine monohydrate (80%) were added and the mixture was stirred overnight. After concentrating the reaction mixture, the residue was washed with 50 ml of chloroform and suspended in the washings chloroform; after filtering the insolubles, the filtrate was concentrated and dried under reduced pressure to give 1.65 g of amine.

Stage D: 4-(6-Methyl-3-heptynylamino)thieno[2,3-d]pyrimidine

To 42 ml of DMF, 1.65 g of the amine obtained in the foregoing stage, 2.13 g of 4-chlorothieno[2,3-d]pyrimidine, and 1.9 ml of triethylamine were added and the mixture was stirred at 85° C. for 4 hours. After cooling the reaction mixture, 100 ml of water was added and two extractions were conducted with 100 ml of ethyl acetate. After being washed twice with 100 ml of water and once with 100 ml of saturated brine, the organic layer was dried over magnesium sulfate. After filtering the magnesium sulfate, the organic layer was concentrated and the residue was purified by column chromatography (Wakogel C-200; toluene:ethyl acetate=4:1) to give 2.14 g of the end product.

Similar production methods were employed to synthesize compounds identified as Compound Nos. 6, 8, 9, 88-91 and 94 in Table 1.

(4) Synthesis of a Compound of the General Formula (I) where $R^1$=Phenyl, $R^2$=H, and $R^3$-$R^4$=Thiophene (Compound Identified as Compound No. 10 in Table 1)

To 535 mg of dichlorobis(triphenylphosphine)palladium, 145 mg of copper iodide, and 3.00 g of N-(3-butynyl)phthalimide were added 35 ml of tetrahydrofuran, 3.06 g of benzene iodide, and 9.0 ml of triethylamine in a nitrogen atmosphere, and the mixture was stirred under reflux for 4 hours. After the stirring, the reaction mixture was cooled to room temperature and the solids were filtered. After concentrating the filtrate, the residue was purified by column chromatography (Wakogel C-200; toluene:ethyl acetate=4:1) to give 3.70 g of a phthalimide compound.

Stage B: 4-Phenyl-3-butynylamine

To 3.70 g of the phthalimide compound obtained in the foregoing stage were added 135 ml of methanol and 2.52 g of hydrazine monohydrate (80%) and the mixture was stirred overnight. After the stirring, the reaction mixture was concentrated and the residue was suspended in 50 ml of chloroform; after filtering the insolubles, the filtrate was concentrated and dried under reduced pressure to give 1.94 g of amine.

Stage C: 4-(4-Phenyl-3-butynylamino)thieno[2,3-d]pyrimidine

To 31 ml of N,N-dimethylformamide were added 1.94 g of the amine obtained in the foregoing stage, 1.90 g of 4-chlorothieno[2,3-d]pyrimidine, and 1.9 ml of triethylamine and the mixture was stirred at 85° C. for 4 hours. After cooling the reaction mixture, 50 ml of water was added and two extractions were conducted with 50 ml of ethyl acetate. After being washed twice with 30 ml of water and once with 30 ml of saturated brine, the organic layer was dried over magnesium sulfate. After filtering the magnesium sulfate, the organic layer was concentrated and the residue was purified by column chromatography (Wakogel C-200; toluene:ethyl acetate=4:1) to give 1.68 g of the end product.

Similar production methods were employed to synthesize compounds identified as Compound Nos. 11-28, 32-54, 64-67, 84, 85, 96-100, 102-126, 128, 130-209, 211-214, 306-342, 355-380, 390, and 391 in Table 1.

(5) Synthesis of a Compound of the General Formula (I) where $R^1$=Phenyl, $R^2$=Methyl, and $R^3$-$R^4$=Thiophene (Compound Identified as Compound No. 229 in Table 1)

Stage A: 2-(1-Methyl-3-butynyl)isoindole-1,3-dione

A nitrogen-purged flask was charged with 400 ml of dry tetrahydrofuran, 5.00 g of 4-pentyn-2-ol, 9.65 g of phthalimide, and 17.13 g of triphenylphosphine and to the resulting solution, 30 ml of diethyl azodicarboxylate (40% solution in toluene) was slowly added dropwise and the mixture was immediately stirred at room temperature for 24 hours. After concentrating the reaction mixture, 300 ml of water was added to the residue and two extractions were conducted with 250 ml of ethyl acetate. After being washed with 200 ml of water and 200 ml of saturated brine, the organic layer was dried over magnesium sulfate. After filtering the magnesium sulfate, the organic layer was concentrated and the residue was purified by column chromatography (Wakogel C-200; toluene) to give 2.20 g of a phthalimide compound.

Stage B:
2-(1-Methyl-4-phenyl-3-butynyl)isoindole-1,3-dione

To 367 mg of dichlorobis(triphenylphosphine)palladium, 100 mg of copper iodide, and 2.20 g of the phthalimide obtained in the foregoing stage were added 24 ml of tetrahydrofuran, 2.11 g of iodobenzene, and 6.2 ml of triethylamine in a nitrogen atmosphnere and the mixture was stirred under reflux for 8 hours. After the stirring, the reaction mixture was cooled to room temperature and the solids were filtered. After concentrating the filtrate, the residue was purified by column chromatography (Wakogel C-200; toluene:ethyl acetate=9:1) to give 1.82 of a phthalimide compound.

Stage C: 1-Methyl-4-phenyl-3-butynylamine

To 1.82 g of the phthalimide compound obtained in the foregoing stage, 63 ml of methanol and 1.18 g of hydrazine monohydrate (80%) were added and the mixture was stirred overnight. After the stirring, the reaction mixture was concentrated and the residue was suspended in 30 ml of chloroform; after filtering the insolubles, the filtrate was concentrated and dried under reduced pressure so that amine was obtained quantitatively.

Stage D: 4-(1-Methyl-4-phenyl-3-butynylamino)thieno[2,3-d]pyrimidine

To 20 ml of N,N-dimethylformamide, the amine obtained in the foregoing stage, 1.02 g of 4-chlorothieno[2,3-d]pyrimidine, and 0.9 ml of triethylamine were added and the mixture was stirred at 85° C. for 4 hours. After cooling the reaction mixture, 30 ml of water was added and two extractions were conducted with 50 ml of ethyl acetate. After being washed twice with 30 ml of water and once with 30 ml of saturated brine, the organic layer was dried over magnesium suflate. After filtering the magnesium sulfate, the organic layer was concentrated and the residue was purified by column chromatography (Wakogel C-200; toluene:ethyl acetate=9:1) to give 0.46 g of the end product.

Similar production methods were employed to synthesize compounds identified as Compound Nos. 230-295, 298, 343-354, and 381-389 in Table 1.

(6) Synthesis of a Compound of the General Formula
(I) where $R^1$=4-Methoxycarbonylphenyl, $R^2$=H, and $R^3$-$R^4$=Thiophene (Compound Identified as Compound No. 29 in Table 1)

To 170 mg of dichlorobis(triphenylphosphine)palladium, 46 mg of copper iodide, and 0.97 g of the 4-[(3-butynyl)amino]thieno[2,3-d]pyrimidine obtained in (2) were added 11 ml of tetrahydrofuran, 1.25 g of methyl 4-iodobenzoate, and 2.9 ml of triethylamine in a nitrogen atmosphere, and the mixture was stirred under reflux for 4 hours. After the stirring, the reaction mixture was cooled to room temperature and the solids were filtered. After concentrating the filtrate, the organic layer was concentrated and the residue was purified by column chromatography (Wakogel C-200; toluene:ethyl acetate=1:1) to give 1.09 g of 4-[4-(thieno[2,3-d]pyrimidin-4-ylamino)-1-butynyl]benzoate.

Similar production methods were employed to synthesize compounds identified as Compound Nos. 30, 31, 92, 93, 95, 127, and 129 in Table 1.

(7) Synthesis of a Compound of the General Formula
(I) where $R^1$=2-Phenyl-4-Thiazolyl, $R^2$=H, and $R^3$-$R^4$=Thiophene (Compound Identified as Compound No. 76 in Table 1)

Stage A: 4-Bromo-2-phenylthiazole

A flask containing 238 mg of tetrakis(triphenylphosphine)palladium, 0.55 g of phenylboronic acid, and 1.00 g of 2,4-dibromothiazole was purged with nitrogen and then charged with 30 ml of toluene, 6.1 ml of ethanol, and 9.1 ml of a 2 M aqueous solution of sodium carbonate, and the mixture was stirred under reflux for 6 hours. After cooling to room temperature, 50 ml of water was added to the reaction mixture and two extractions were conducted with 50 ml of ethyl acetate. After being washed with 30 ml of saturated brine, the organic layer was dried over magnesium sulfate. After filtering the magnesium sulfate, the organic layer was concentrated and the residue was purified by column chromatography (Wakogel C-200; hexane:ethyl acetate=14:1) to give 0.71 g of 2-phenyl-4-bromothiazole.

Stage B: 2-[4-(2-Phenylthiazol-4-yl)-3-butynyl]isoindole-1,3-dione

To 221 mg of dichlorobis(triphenylphosphine)palladium, 60 mg of copper iodide, and 1.24 g of N-(3-butynyl)phthalimide were added 15 ml of tetrahydrofuran, 1.50 g of the 2-phenyl-4-bromothiazole obtained in the foregoing stage, and 3.8 ml of triethylamine in a nitrogen atmosphere, and the mixture was stirred under reflux for 4 hours. After the stifling, the reaction mixture was cooled to room temperature and the solids were filtered. After concentrating the filtrate, the residue was purified by column chromatography (Wakogel C-200; toluene:ethyl acetate=9:1) to give 1.24 g of a phthalimide compound.

Stage C: 4-(2-Phenylthiazol-4-yl)-3-butynylamine

To 1.24 g of the phthalimide compound obtained in the foregoing step, 35 ml of methanol and 0.65 g of hydrazine monohydrate (80%) were added and the mixture was stirred overnight. After the stirring, the reaction mixture was concentrated and the residue was suspended in 20 ml of chloroform; after filtering the insolubles, the filtrate was concentrated and dried under reduced pressure to give 0.96 g of amine.

Stage D: 4-[4-(2-Phenylthiazol-4-yl)-3-butynylamino]thieno[2,3-d]pyrimidine

To 13 ml of N,N-dimethylformamide, 0.96 g of the amine obtained in the foregoing stage, 0.68 g of 4-chlorothieno[2,3-d]pyrimidine, and 0.6 ml of triethylamine were added and the mixture was stirred at 85° C. for 4 hours. After cooling the reaction mixture, 25 ml of water was added and two extractions were conducted with 30 ml of ethyl acetate. After being washed twice with 30 ml of water and then once with 30 ml of saturated brine, the organic layer was dried over magnesium sulfate. After filtering the magnesium sulfate, the organic layer was concentrated and the residue was purified by col- Similar production methods were employed to synthesize compounds identified as Compound Nos. 77-82 in Table 1.

(8) Synthesis of a Compound of the General Formula (I) where $R^1$=(2-Benzyl)-4-Thiazolyl, $R^2$=H, and $R^3$-$R^4$=Thiophene (Compound Identified as Compound No. 75 in Table 1)

Stage A: 2-Benzyl-4-bromothiazole

A flask containing 267 mg of tetrakis(triphenylphosphine)palladium and 1.00 g of 2,4-dibromothiazole was purged with nitrogen and then charged with 9 ml of dry tetrahydrofuran and 9.9 ml of 0.5 M benzylzinc bromide in tetrahydrofuran, and the mixture was stirred at 70° C. for 6 hours. After cooling to room temperature, 30 ml of water was added to the reaction mixture and two extractions were conducted with 30 ml of ethyl acetate. After being washed twice with 30 ml of water and then once with 30 ml of saturated brine, the organic layer was dried over magnesium sulfate. After filtering the magnesium sulfate, the organic layer was concentrated and the residue was purified by column chromatography (Wakogel C-200; hexane:ethyl acetate=14:1) to give 0.36 g of 2-benzyl-4-bromothiazole.

Stage B: 2-[4-(2-Benzylthiazol-4-yl)-3-butynyl] isoindole-1,3-dione

To 143 mg of dichlorobis(triphenylphosphine)palladium, 38 mg of copper iodide, and 0.80 g of N-(3-butynyl)phthalimide were added 9 ml of tetrahydrofuran, 1.02 g of the 2-benzyl-4-bromothiazole obtained in the foregoing stage, and 2.3 ml of triethylamine in a nitrogen atmosphere, and the mixture was stirred under reflux for 4 hours. After the stirring, the reaction mixture was cooled to room temperature and the solids were filtered. After concentrating the filtrate, the residue was purified by column chromatography (Wakogel C-200; toluene:ethyl acetate=9:1) to give 1.00 g of a phthalimide compound.

Stage C: 4-(2-Benzylthiazol-4-yl)-3-butynylamine

To 1.00 g of the phthalimide compound obtained in the foregoing stage, 26 ml of methanol and 0.50 g of hydrazine monohydrate (80%) were added and the mixture was stirred overnight. After the stirring, the reaction mixture was concentrated and the residue was suspended in 25 ml of chloroform; after filtering the insolubles, the filtrate was concentrated and dried under reduced pressure to give 0.12 g of amine.

Stage D: 4-[4-(2-Benzylthiazol-4-yl)-3-butynyl) amino]thieno[2,3-d]pyrimidine

To 1.5 ml of N,N-dimethylformamide were added 0.12 g of the amine obtained in the foregoing stage, 0.08 g of 4-chlorothieno[2,3-d]pyrimidine, and 0.1 ml of triethylamine, and the mixture was stirred at 85° C. for 4 hours. After cooling the reaction mixture, 15 ml of water was added and two extractions were conducted with 20 ml of ethyl acetate. After being washed twice with 20 ml of water and then once with 20 ml of saturated brine, the organic layer was dried overe magnesium sulfate. After filtering the magnesium sulfate, the organic layer was concentrated and the residue was purified by column chromatography (Wakogel C-200; toluene:ethyl acetate=2:1) to give 0.70 g of the end product.

Similar production methods were employed to synthesize compounds identified as Compound Nos. 77-82 in Table 1.

(9) Synthesis of a Compound of the General Formula (I) where $R^1$=2-Phenoxy-4-Thiazolyl, $R^2$=H, and $R^3$-$R^4$=Thiophene (Compound Identified as Compound No. 83 in Table 1)

Stage A: 4-Bromo-2-phenoxythiazole

To 75 ml of N,N-dimethylformamide were added 3.00 g of 2,4-dibromothiazole, 1.74 g of phenol, and 3.44 g of potassium carbonate, and the mixture was stirred at 140° C. for 6 hours. After cooling to room temperature, 100 ml of water was added to the reaction mixture and two extractions were conducted with 100 ml of ethyl acetate. After being washed twice with 100 ml of water and once with 50 ml of saturated brine, the organic layer was dried over magnesium sulfate. After filtering the magnesium sulfate, the organic layer was concentrated and the residue was purified by column chromatography (Wakogel C-200; hexane:ethyl acetate=9:1) to give 2.86 g of an ether compound.

Stage B: 2-[4-(2-Phenoxythiazol-4-yl)-3-butynyl] isoindole-1,3-dione

To 99 mg of dichlorobis(triphenylphosphine)palladium, 109 mg of copper iodide, and 2.24 g of N-(3-butynyl)phthalimide were added 26 ml of tetrahydrofuran, 2.86 g of the ether compound obtained in the foregoing stage, and 6.9 ml of triethylamine in a nitrogen atmosphere, and the mixture was stirred under reflux for 4 hours. After the stirring, the reaction mixture was cooled to room temperature and the solids were filtered. After concentrating the filtrate, the residue was purified by column chromatography (Wakogel C-200; toluene: ethyl acetate=9:1) to give 3.50 g of a phthalimide compound.

Stage C: 4-(2-Phenoxythiazol-4-yl)-3-butynylamine

To 3.50 g of the phthalimide compound obtained in the foregoing stage were added 90 ml of methanol and 1.76 g of hydrazine monohydrate (80%) and the mixture was stirred overnight. After the stirring, the reaction mixture was concentrated and the residue was suspended in 40 ml of chloroform; after filtering the insolubles, the filtrate was concentrated and dried under reduced pressure to give 2.24 g of amine.

Stage D: 4-[4-(2-Phenoxythiazol-4-yl)-3-butynyl) amino]thieno[2,3-d]pyrimidine

To 27 ml of N,N-dimethylformamide were added 2.24 g of the amine obtained in the foregoing stage, 1.45 g of 4-chlorothieno[2,3-d]pyrimidine, and 1.3 ml of triethylamine, and the mixture was stirred at 85° C. for 4 hours. After cooling the reaction mixture, 50 ml of water was added and two extractions were conducted with 50 ml of ethyl acetate. After being washed twice with 50 ml of water and then once with 30 ml of saturated brine, the organic layer was dried overe magnesium sulfate. After filtering the magnesium sulfate, the organic layer was concentrated and the residue was purified by column chromatography (Wakogel C-200; toluene:ethyl acetate=1:1) to give 2.79 g of the end product.

Similar production methods were employed to synthesize compounds identified as Compound Nos. 215-228 in Table 1.

(10) Synthesis of a Compound of the General Formula (I) where $R^1$=4-Thiazolyl, $R^2$=H, and $R^3$-$R^4$=Thiophene (Compound Identified as Compound No. 61 in Table 1)

Stage A: 2-(4-Thiazolyl-3-butynyl)isoindole-1,3-dione

To 1184 mg of dichlorobis(triphenylphosphine)palladium, 322 mg of copper iodide, and 6.64 g of N-(3-butynyl)phthalimide were added 78 ml of tetrahydrofuran, 5.49 g of 4-bromothiazole, and 20.3 ml of triethylamine in a nitrogen atmosphere, and the mixture was stirred under reflux for 5 hours. After the stirring, the reaction mixture was cooled to room temperature and the solids were filtered. After concentrating the filtrate, the residue was purified by column chromatography (Wakogel C-200; toluene:ethyl acetate=4:1) to give 6.35 g of a phthalimide compound.

Stage B: 4-Thiazolyl-3-butynylamine

To 6.35 g of the phthalimide compound obtained in the foregoing stage, 115 ml of ethanol, 115 ml of water, and 115 ml of an ion-exchange resin (Diaion WA21J Resin) were added, and the mixture was stirred at 90° C. for 2 hours. After cooling to room temperature, the ion-exchange resin was filtered and the reaction mixture was concentrated under reduced pressure to give 2.48 g of amine.

Stage C: 4-[(4-Thiazolyl-3-butynyl)amino]thieno[2,3-d]pyrimidine

To 50 ml of N,N-dimethylformamide were added 2.48 g of the amine obtained in the foregoing stage, 2.60 g of 4-chlorothieno[2,3-d]pyrimidine, and 2.3 ml of triethylamine, and the mixture was stirred at 85° C. for 2.5 hours. After cooling the reaction mixture, 1 L of water was added and the precipitating solids were filtered; the filtrate was washed twice with 100 ml of water and thereafter dried under vacuum to give 3.00 g of the end product.

Similar production methods were employed to synthesize compounds identified as Compound Nos. 55-60, 62, 63, 68-74, 101, and 210 in Table 1.

(11) Synthesis of a Compound of the General Formula (I) where $R^1$=H, $R^2$=Phenyl, and $R^3$-$R^4$=Benzene (Compound Identified as Compound No. 300 in Table 1)

Stage A: 1-Phenyl-3-butynylamine

To a solution having 2.97 g of benzaldehyde dissolved in 4 ml of tetrahydrofuran, 1 M lithium bistrimethylsilylamide in tetrahydrofuran was added dropwise at 0° C. in a nitrogen atmosphere. The resulting solution was stirred at 0° C. for 15 minutes, then at room temperature for an hour. The product was designated solution A.

To 6.03 g of a zinc powder were added 4 ml of tetrahydrofuran and 0.63 g of 1,2-dibromoethane, and the mixture was stirred under reflux for an hour. After the stifling, the mixture was cooled to room temperature and a solution of chlorotrimethylsilane in tetrahydrofuran (0.37 g chlorotrimethylsilane+8 ml tetrahydrofuran) was added at room temperature. The resulting solution was cooled to −10° C., at which temperature a solution of propargyl bromide in tetrahydrofuran (10.00 g propargyl bromide+8 ml tetrahydrofuran) was added dropwise and the resulting mixture was stirred for an additional 1.5 hours. To the stirred solution, separately prepared solution A was added dropwise at −10° C.; after the dropwise addition, the temperature was gradually raised to room temperature, at which the mixture was stirred overnight. After cooling the reaction mixture to 0° C., 20 ml of a saturated solution of potassium carbonate was added and, further, 65 ml of water and 30 ml of methyl t-butyl ether were added. After being separated from the organic layer, the aqueous layer was extracted five more times with 30 ml of methyl t-butyl ether. The combined organic layers were concentrated and the residue was dried under vacuum. Water was added to the resulting residue and two extractions were conducted with 30 ml of methyl t-butyl ether; after being washed twice with 30 ml of water and once with 30 ml of saturated brine, the organic layer was dried over magnesium sulfate. After filtering the magnesium sulfate, the filtrate was concentrated and dried under vacuum to give 3.38 g of amine.

Stage B: 4-[(1-Phenyl-3-butynyl)amino]quinazoline

To 11 ml of N,N-dimethylformamide were added 0.49 g of the amine obtained in the foregoing stage, 0.50 g of 4-chloroquinazoline, and 0.7 ml of triethylamine, and the mixture was stirred at 85° C. for 3 hours. After cooling the reaction mixture, 50 ml of water was added and two extractions were conducted with 20 ml of ethyl acetate. After being washed twice with 20 ml of water and then once with 20 ml of saturated brine, the organic layer was dried over magnesium sulfate. After filtering the magnesium sulfate, the organic layer was concentrated and the residue was purified by column chromatography (Wakogel C-200; toluene:ethyl acetate=1:1) to give 0.69 g of the end product.

(12) Synthesis of a Compound of the General Formula (I) where $R^1$=Phenyl, $R^2$=Phenyl, and $R^3$-$R^4$=Benzene (Compound Identified as Compound No. 301 in Table 1)

To 278 mg of dichlorobis(triphenylphosphine)palladium, 71 mg of copper iodide, and 2.00 g of the 4-[(1-phenyl-3-butynyl)amino]quinazoline obtained in (11) were added 17 ml of tetrahydrofuran, 1.49 g of iodobenzene, and 4.5 ml of triethylamine in a nitrogen atmosphere, and the mixture was stirred under reflux for 3 hours. After the stirring, the reaction mixture was cooled to room temperature and the solids were filtered. After concentrating the filtrate, the residue was purified by column chromatography (Wakogel C-200; toluene: ethyl acetate=4:1) to give 1.03 g of 4-[(1,4-diphenyl-3-butynyl)amino]quinazoline.

A similar production method was employed to synthesize a compound identified as Compound No. 302 in Table 1.

(13) Synthesis of a Compound of the General Formula (I) where $R^1$=Phenyl, $R^2$=Ethoxycarbonyl, and $R^3$-$R^4$=Benzene (Compound Identified as Compound No. 303 in Table 1)

Stage A: N-(Diphenylmethylene)-2-(3-phenyl)propargyl glycine ethyl ester

A nitrogen-purged flask was charged with 50 ml of acetonitrile, 3.00 g of N-(diphenylmethylene)glycine ethyl ester, 2.60 g of 3-phenylpropargyl bromide, 2.32 g of potassium carbonate, and 381 mg of tetrabutylammonium hydrogen sulfate, and the mixture was stirred at 70° C. for 24 hours. After cooling the reaction mixture to room temperature, 100 ml of ethyl acetate was added and the mixture was filtered through Celite; thereafter, the filtrate was concentrated and purified by means of flash chromatography (Isolera™ manufactured by Biotage AB) to give 2.00 g of N-(diphenylmethylene)-2-(3-phenyl)propargyl glycine ethyl ester.

Stage B: 2-(3-Phenyl)propargyl glycine ethyl ester

A nitrogen-purged flask was charged with 20 ml of diethyl ether, 1.80 g of the alcohol obtained in the foregoing alcohol, and 20 ml of 1 N HCl, and the mixture was immediately stirred at room temperature for 24 hours. To the reaction mixture, 30 ml of an aqueous solution of sodium hydrogencarbonate was added; thereafter, the mixture was extracted twice with 50 ml of ethyl acetate and dried over sodium sulfate. After filtering the sodium sulfate, the organic layer was concentrated and purified by means of flash chromatography (Isolera™ manufactured by Biotage AB) to give 985 mg of 2-(3-phenyl)propargyl glycine ethyl ester.

Stage C: 4-[2-Ethoxycarbonyl-4-phenyl-3-butynylamino]quinazoline

To 15 ml of N,N-dimethylformamide were added 985 mg of the amine obtained in the foregoing stage, 720 mg of 4-chloroquinazoline, and 1 ml of triethylamine, and the mixture was stirred at 80° C. for 4 hours. After cooling the reaction mixture, 40 ml of water was added and two extractions were conducted with 70 ml of ethyl acetate. After being washed twice with 40 ml of saturated brine, the organic layer was dried over sodium sulfate. After filtering the sodium sulfate, the organic layer was concentrated and purified by means of flash chromatography (Isolera™ manufactured by Biotage AB) to give 1.10 g of the end product.

A similar production method was employed to synthesize a compound identified as Compound No. 304 in Table 1.

(14) Synthesis of a Compound of the General Formula (I) where $R^1$=Phenyl, $R^2$=Hydroxymethyl, and $R^3$-$R^4$=Benzene (Compound No. 299 in Table 1)

To 10 ml of tetrahydrofuran were added 200 mg of 4-[2-ethoxycarbonyl-4-phenyl-3-butynylamino]quinazoline and 1 ml of a lithium dimethylaminoborohydride solution (1 M in tetrahydrofuran), and the mixture was stirred at room temperature for an hour. To the reaction mixture, 20 ml of 1 N HCl was added and the mixture was stirred for 10 minutes. The reaction mixture was neutralized with an added aqueous solution of sodium hydrogencarbonate; thereafter, two extractions were conducted with 40 ml of ethyl acetate, followed by drying over sodium sulfate. After filtering the sodium sulfate, the organic layer was concentrated and purified by means of flash chromatography (Isolera™ manufactured by Biotage AB) to give 37 mg of 4-[2-hydroxymethyl-4-phenyl-3-butynylamino]quinazoline.

(15) Synthesis of a Compound of the General Formula (I) where $R^1$=Phenyl, $R^2$=Methylaminocarbonyl, and $R^3$-$R^4$=Benzene (Compound Identified as Compound No. 305 in Table 1)

To 5 ml of tetrahydrofuran were added 130 mg of 4-[2-ethoxycarbonyl-4-phenyl-3-butynylamino]quinazoline and 3 ml of a 40% solution of methylamine in methanol, and the mixture was stirred at 60° C. for an hour, then at room temperature for 24 hours. The reaction mixture was concentrated and purified by means of flash chromatography (Isolera™ manufactured by Biotage AB) to give 113 mg of 4-[2-methylaminocarbonyl-4-phenyl-3-butynylamino]quinazoline.

(16) Synthesis of a Compound of the General Formula (I) where $R^1$=Phenyl, $R^2$=Vinyl, and $R^3$-$R^4$=Benzene (Compound Identified as Compound No. 296 in Table 1)

Stage A: 2-Vinyl-4-phenyl-3-butynol

A nitrogen-purged flask was charged with 40 ml of dry tetrahydrofuran and 20 ml of a 1.6 M n-butyllithium solution at −78° C. and the mixture was stirred for 30 minutes. To the resulting solution, 3.5 ml of a trifluoroboron-tetrahydrofuran complex was slowly added dropwise. The resulting solution was stirred at −78° C. for an additional 15 minutes, during which 2.00 g of 1,3-butadiene monoepoxide was slowly added dropwise and the mixture was further stirred at −78° C. for 3 hours. To the resulting reaction mixture, 50 ml of a saturated aqueous solution of ammonium chloride was added; the mixture was then extracted once with 100 ml of ethyl acetate and dried over sodium sulfate. After filtering the sodium sulfate, the organic layer was concentrated and purified by means of flash chromatography (Isolera™ manufactured by Biotage AB) to give 1.80 g of 2-vinyl-4-phenyl-3-butynol.

Stage B: 2-(2-Vinyl-4-phenyl-3-butynyl)isoindole-1,3-dione

A nitrogen-purged flask was charged with 55 ml of toluene, 1.80 g of 2-vinyl-4-phenyl-3-butynol, 1.93 g of phthalimide, and 3.45 g of triphenylphosphine; to the resulting solution, 5.30 g of diethylazodicarboxylate (40% in toluene) was slowly added dropwise and the temperature of the mixture was raised to room temperature, at which it was stirred for 24 hours. After concentrating the reaction mixture, 200 ml of diethyl ether was added to the residue and the precipitating solids were recovered by filtration. The residue was concentrated and purified by means of flash chromatography (Isolera™ manufactured by Biotage AB) to give 1.00 g of 2-(2-vinyl-4-phenyl-3-butynyl)isoindole-1,3-dione.

Stage C: 2-Vinyl-4-phenyl-3-butynylamine

To 1.00 g of 2-(2-vinyl-4-phenyl-3-butynyl)isoindole-1,3-dione were added 20 ml of methanol and 10 ml of a methylamine solution (40% in methanol), and the mixture was stirred at 60° C. for an hour. The reaction mixture was concentrated and washed successively with 50 ml of ethyl acetate and 50 ml of diethyl ether; thereafter, the filtrate was concentrated to give 550 mg of amine as a crude product.

Stage D: 4-[2-Vinyl-4-phenyl-3-butynylamino]quinazoline

To 15 ml of DMF were added 550 mg of 2-vinyl-4-phenyl-3-butynylamine, 500 mg of 4-chloroquinazoline, and 636 μl of triethylamine, and the mixture was stirred at 80° C. for 5 hours. After cooling the reaction mixture, 20 ml of water was added and two extractions were conducted with 50 ml of ethyl acetate. After being washed twice with 50 ml of saturated brine, the organic layer was dried over sodium sulfate. After filtering the sodium sulfate, the organic layer was concentrated and purified by means of flash chromatography (Isolera™ manufactured by Biotage AB) to give 750 mg of the end product.

A similar production method was employed to synthesize a compound identified as Compound No. 297 in Table 1.

It should be noted here that 4-chlorothieno[2,3-d]pyrimidine, 4-chlorothieno[3,2-d]pyrimidine, 4-chloro-7-methylthieno[3,2-d]pyrimidine, 4-chloroquinazoline, 4,6-dichloro-5-methylpyrimidine, 6-chloropurine, 6-chloro-7-deazapurine, 4,6-dichloropyrimidine, 4-chloro-6-methylpyrimidine, and 4,6-dichloro-5-nitropyrimidine were commercial products whereas 4,6-dichloro-5-phenylpyrimidine was produced by a modification of the method described in WO 2006/138734, 4,5-dichloro-6-(1-fluoroethyl)pyrimidine by a modification of the method described in JP 2000-7662 A, and 4-chloro-5-iodo-6-(1-fluoroethyl)pyrimidine by a modification of the method described in JP 2002-275164 A.

When the agri-horticultural pest control compositions of the present invention are to be used, the active ingredients may be employed in suitable dosage forms as appropriate for the specific purpose of use. Typically, the active ingredients may be diluted with inert liquid or solid carriers, optionally together with surfactants and other additives, so that they can be applied in various forms of preparations such as dust, wettable powder, emulsifiable concentrate, and granules.

Suitable carriers include, for example, solid carriers such as talc, bentonite, clay, kaolin, diatomaceous earth, white carbon, vermiculite, slaked lime, quartz sand, ammonium sulfate, urea, etc. and liquid carriers such as isopropyl alcohol, xylene, cyclohexanone, methylnaphthalene, etc. Surfactants and dispersants include, for example, dinaphthylmethanesulfonic acid salts, alcohol sulfate ester salts, alkylarylsulfonic acid salts, lignin sulfonic acid salts, polyoxyethylene glycol ether, polyoxyethylene alkylaryl ethers, polyoxyethylene sorbitan monoalkylates, etc. Aids include carboxymethyl cellulose. These preparations are sprayed after being diluted to suitable concentrations or they may be applied directly.

If necessary, the agri-horticultural pest control compositions of the present invention may be used in combination with insecticides, other antimicrobials, herbicides, plant growth regulators, fertilizers, and so forth.

EXAMPLES

On the following pages, representative examples of the agri-horticultural pest control composition of the present invention are given to show how it is formulated into specific preparations. In the following description, all percentages are based on weight.
[Preparations]
Preparation 1: Emulsifiable Concentrate Ten parts of the invention compound was dissolved in 45 parts of 1,2-dimethyl-4-ethylbenzene and 35 parts of 1-methyl-2-pyrrolidinone; to the resulting solution, 10 parts of Sorpol 3005X (the trade name of a surfactant manufactured by TOHO Chemical Industry Co., Ltd.) was added and mixed under stirring to make a 10% emulsifiable concentrate.
Preparation 2: Wettable Powder Ten parts of the invention compound was added to a mixture of 2 parts of sodium lauryl sulfate, 4 parts of sodium lignin sulfonate, 20 parts of white carbon and 64 parts of clay, and the individual ingredients were mixed under stirring with a juice mixer to make a 10% wettable powder.
Preparation 3: Granules To 5 parts of the invention compound were added 2 parts of sodium dodecylbenzenesulfonate, 2 parts of carboxymethyl cellulose, 2 parts of sodium lauryl sulfate, 10 parts of bentonite and 79 parts of clay, and the individual ingredients were mixed under thorough stirring. After adding a suitable amount of water, the mixture was further stirred, granulated with a granulator, and dried with circulating air to make 5% granules.
Preparation 4: Dust One part of the invention was dissolved in 2 parts of soybean oil; to the solution, parts of white carbon, 0.3 parts of acidic isopropyl phosphate (PAP) amd 91.7 parts of clay were added and mixed under stifling with a juice mixer to make a 1% dust.
Preparation 5: Flowable Twenty parts of the invention compound was mixed with 20 parts of water containing 2 parts, 1 part and 0.2 parts, respectively, of polyoxyethylene alkyl ether, dialkyl sulfosuccinate sodium, and 1,2-benzisothiazolin-3-one and the mixture was wet-ground with DYNO-MILL; thereafter, the particles were mixed with 60 parts of water containing 8 parts and 0.32 parts, respectively, of propylene glycol and xanthan gum to make a 20% aqueous suspension.
Preparation 6: Water Dispersible Granules To 20 parts of the invention were added 2 parts of sodium lauryl sulfate, 3 parts of sodium alkyl naphthalenesulfonate, 5 parts of dextrin, 20 parts of white carbon and 50 parts of clay, and the individual ingredients were mixed under thorough stifling. After adding a suitable amount of water, the mixture was further stifled, granulated with a granulator, and dried with circulating air to make 20% water dispersible granules.

In the next place, the agri-horticultural pest control compositions of the present invention were subjected to efficacy tests to specifically show how they are effective.

The outstanding efficacy of the agri-horticultural pest control compositions of the present invention is apparent from the tests described below. To be more specific, the individual active compounds show efficacy to some extent but their combinations show even greater efficacies than when the effects of the individual active compounds are merely added together; in other words, synergism is achieved.

The expected efficacies of the combinations of the individual active compounds can be determined using Colby's formula, which is described below [Colby, S. R. "Calculating synergistic and antagonistic responses of herbicide combinations," Weeds 15, 20-22 (1967)]:

$$\text{Colby's formula: } E=A+B-(A\times B/100)$$

E is the predicted efficacy (control index) with reference to the untreated control when using the mixture of the active compound X at the concentration x and the active compound Y at the concentration y;
A is the efficacy (control index) with respect to the untreated control when using the active compound X at the concentration x;
B is the efficacy (control index) with respect to the untreated control when using the active compound B at the concentration y.

If the agri-horticultural pest control composition of the present invention has a greater efficacy than the value of E as calculated by Colby's formula, it then follows that the combination of the active ingredients shows synergism. Hereinbelow, the synergism exhibited by the agri-horticultural pest control compositions of the present invention is described specifically by reference to test results.
[Tests]
Test 1: Control Effect Against Powdery Mildew on Cucumber Potted young seedlings of cucumber (variety: SAGAMI HANJIRO; in two-leaf stage) were sprayed with invention compounds formulated in accordance with Preparations and the existing antimicrobial active compounds listed in Table 3 (all compounds are identified by associated letters of the alphabet) after they were diluted with water to predetermined concentrations so that they would serve as active compounds; a spray gun was used to provide a spray rate of 15 ml per pot. After air-drying, the seedlings were inoculated with conida of *Sphaerotheca fuliginea* by spraying a suspension of the conida. Thereafter, the seedlings were cultivated for 14 days in a greenhouse and the percentage of diseased area was investigated for each leaf; based on the result of this investigation, the control index was calculated using the following formula:

Control index={(percentage of diseased area on the untreated control–percentage of diseased area on treated sample)/percentage of diseased area on the untreated control}×100

The results are shown in Table 3 and Tables 4-1 to 4-5.

TABLE 3

Efficacies of individual active compounds

| Test compound | Test concentration (ppm) | Control index |
|---|---|---|
| 99 | 0.5 | 53 |
| 100 | 0.5 | 55 |
| 101 | 0.5 | 56 |
| 133 | 0.5 | 49 |
| 139 | 0.5 | 51 |
| 140 | 0.5 | 48 |
| 145 | 0.5 | 45 |
| 390 | 0.5 | 51 |
| 391 | 0.5 | 48 |
| Aa: Chlorothalonil | 5 | 48 |
| Nb: Chinomethionate | 10 | 38 |
| Ab: Iminoctadine albesilate | 2 | 41 |
| Hd: Triflumizole | 10 | 39 |
| Hb: Tebuconazole | 10 | 42 |
| Ha: Difenoconazole | 10 | 27 |
| Hc: Triadimefon | 100 | 21 |
| He: Fenpropimorph | 100 | 12 |
| Ea: Azoxystrobin | 100 | 21 |
| Ed: Pyraclostrobin | 100 | 22 |
| Ec: Trifloxystrobin | 100 | 24 |
| Eb: Kresoxim-methyl | 100 | 29 |
| Nc: Cyflufenamid | 1 | 49 |
| Da: Penthiopyrad | 1 | 51 |
| Nd: Flutianil | 1 | 42 |
| Ia: Quinoxyfen | 1 | 39 |
| Ca: Thiophanate-methyl | 2 | 40 |
| Fa: Diflumetorim | 1 | 42 |
| Ma: Acibenzolar-S-methyl | 10 | 38 |

TABLE 4-1

Efficacies of mixtures

| Test compound | Test concentration (ppm) | Observed value Control index | Calculated value Control index (E) |
|---|---|---|---|
| 99 + Aa | 0.5 + 5 | 90 | 76 |
| 99 + Nb | 0.5 + 10 | 89 | 71 |
| 99 + Ab | 0.5 + 2 | 85 | 72 |
| 99 + Hd | 0.5 + 10 | 91 | 71 |
| 99 + Hb | 0.5 + 10 | 83 | 73 |
| 99 + Ha | 0.5 + 10 | 70 | 66 |
| 99 + Hc | 0.5 + 100 | 71 | 63 |
| 99 + He | 0.5 + 100 | 65 | 59 |
| 99 + Ea | 0.5 + 100 | 75 | 63 |
| 99 + Ed | 0.5 + 100 | 72 | 63 |
| 99 + Ec | 0.5 + 100 | 73 | 64 |
| 99 + Eb | 0.5 + 100 | 78 | 67 |
| 99 + Nc | 0.5 + 1 | 89 | 76 |
| 99 + Da | 0.5 + 1 | 90 | 77 |

TABLE 4-1-continued

Efficacies of mixtures

| Test compound | Test concentration (ppm) | Observed value Control index | Calculated value Control index (E) |
|---|---|---|---|
| 99 + Nd | 0.5 + 1 | 84 | 73 |
| 99 + Ia | 0.5 + 1 | 86 | 71 |
| 99 + Ca | 0.5 + 2 | 93 | 72 |
| 99 + Fa | 0.5 + 1 | 82 | 73 |
| 99 + Ma | 0.5 + 10 | 90 | 71 |
| 100 + Aa | 0.5 + 5 | 86 | 77 |
| 100 + Nb | 0.5 + 10 | 91 | 72 |
| 100 + Ab | 0.5 + 2 | 89 | 73 |
| 100 + Hd | 0.5 + 10 | 83 | 73 |
| 100 + Hb | 0.5 + 10 | 80 | 74 |
| 100 + Ha | 0.5 + 10 | 71 | 67 |
| 100 + Hc | 0.5 + 100 | 69 | 64 |
| 100 + He | 0.5 + 100 | 65 | 60 |
| 100 + Ea | 0.5 + 100 | 70 | 64 |
| 100 + Ed | 0.5 + 100 | 72 | 65 |
| 100 + Ec | 0.5 + 100 | 71 | 66 |

TABLE 4-2

Efficacies of mixtures

| Test compound | Test concentration (ppm) | Observed value Control index | Calculated value Control index (E) |
|---|---|---|---|
| 100 + Eb | 0.5 + 100 | 74 | 68 |
| 100 + Nc | 0.5 + 1 | 90 | 77 |
| 100 + Da | 0.5 + 1 | 89 | 78 |
| 100 + Nd | 0.5 + 1 | 88 | 74 |
| 100 + Ia | 0.5 + 1 | 91 | 73 |
| 100 + Ca | 0.5 + 2 | 90 | 73 |
| 100 + Fa | 0.5 + 1 | 90 | 74 |
| 100 + Ma | 0.5 + 10 | 92 | 72 |
| 101 + Aa | 0.5 + 5 | 92 | 77 |
| 101 + Nb | 0.5 + 10 | 87 | 73 |
| 101 + Ab | 0.5 + 2 | 85 | 74 |
| 101 + Hd | 0.5 + 10 | 91 | 73 |
| 101 + Hb | 0.5 + 10 | 89 | 74 |
| 101 + Ha | 0.5 + 10 | 75 | 68 |
| 101 + Hc | 0.5 + 100 | 73 | 65 |
| 101 + He | 0.5 + 100 | 79 | 61 |
| 101 + Ea | 0.5 + 100 | 77 | 65 |
| 101 + Ed | 0.5 + 100 | 80 | 66 |
| 101 + Ec | 0.5 + 100 | 70 | 67 |
| 101 + Eb | 0.5 + 100 | 78 | 69 |
| 101 + Nc | 0.5 + 1 | 90 | 78 |
| 101 + Da | 0.5 + 1 | 89 | 78 |
| 101 + Nd | 0.5 + 1 | 85 | 74 |
| 101 + Ia | 0.5 + 1 | 88 | 73 |
| 101 + Ca | 0.5 + 2 | 90 | 74 |
| 101 + Fa | 0.5 + 1 | 89 | 74 |
| 101 + Ma | 0.5 + 10 | 89 | 73 |
| 133 + Aa | 0.5 + 5 | 82 | 73 |
| 133 + Nb | 0.5 + 10 | 75 | 68 |
| 133 + Ab | 0.5 + 2 | 80 | 70 |

TABLE 4-3

Efficacies of mixtures

| Test compound | Test concentration (ppm) | Observed value Control index | Calculated value Control index (E) |
|---|---|---|---|
| 133 + Hd | 0.5 + 10 | 79 | 69 |
| 133 + Hb | 0.5 + 10 | 79 | 70 |
| 133 + Ha | 0.5 + 10 | 75 | 63 |
| 133 + Hc | 0.5 + 100 | 73 | 60 |
| 133 + He | 0.5 + 100 | 66 | 55 |
| 133 + Ea | 0.5 + 100 | 70 | 60 |
| 133 + Ed | 0.5 + 100 | 70 | 60 |
| 133 + Ec | 0.5 + 100 | 70 | 61 |

TABLE 4-3-continued

Efficacies of mixtures

| Test compound | Test concentration (ppm) | Observed value Control index | Calculated value Control index (E) |
|---|---|---|---|
| 133 + Eb | 0.5 + 100 | 68 | 64 |
| 133 + Nc | 0.5 + 1 | 85 | 74 |
| 133 + Da | 0.5 + 1 | 89 | 75 |
| 133 + Nd | 0.5 + 1 | 86 | 70 |
| 133 + Ia | 0.5 + 1 | 79 | 69 |
| 133 + Ca | 0.5 + 2 | 76 | 69 |
| 133 + Fa | 0.5 + 1 | 83 | 70 |
| 133 + Ma | 0.5 + 10 | 83 | 68 |
| 139 + Aa | 0.5 + 5 | 87 | 75 |
| 139 + Nb | 0.5 + 10 | 92 | 70 |
| 139 + Ab | 0.5 + 2 | 85 | 71 |
| 139 + Hd | 0.5 + 10 | 88 | 70 |
| 139 + Hb | 0.5 + 10 | 79 | 72 |
| 139 + Ha | 0.5 + 10 | 78 | 64 |
| 139 + Hc | 0.5 + 100 | 73 | 61 |
| 139 + He | 0.5 + 100 | 74 | 57 |
| 139 + Ea | 0.5 + 100 | 72 | 61 |
| 139 + Ed | 0.5 + 100 | 79 | 62 |
| 139 + Ec | 0.5 + 100 | 77 | 63 |
| 139 + Eb | 0.5 + 100 | 78 | 65 |
| 139 + Nc | 0.5 + 1 | 89 | 75 |
| 139 + Da | 0.5 + 1 | 85 | 76 |

TABLE 4-4

Efficacies of mixtures

| Test compound | Test concentration (ppm) | Observed value Control index | Calculated value Control index (E) |
|---|---|---|---|
| 139 + Nd | 0.5 + 1 | 83 | 72 |
| 139 + Ia | 0.5 + 1 | 80 | 70 |
| 139 + Ca | 0.5 + 2 | 83 | 71 |
| 139 + Fa | 0.5 + 1 | 90 | 72 |
| 139 + Ma | 0.5 + 10 | 89 | 70 |
| 140 + Aa | 0.5 + 5 | 83 | 73 |
| 140 + Nb | 0.5 + 10 | 79 | 68 |
| 140 + Ab | 0.5 + 2 | 75 | 69 |
| 140 + Hd | 0.5 + 10 | 75 | 68 |
| 140 + Hb | 0.5 + 10 | 78 | 70 |
| 140 + Ha | 0.5 + 10 | 73 | 62 |
| 140 + Hc | 0.5 + 100 | 70 | 59 |
| 140 + He | 0.5 + 100 | 69 | 54 |
| 140 + Ea | 0.5 + 100 | 72 | 59 |
| 140 + Ed | 0.5 + 100 | 74 | 59 |
| 140 + Ec | 0.5 + 100 | 78 | 60 |
| 140 + Eb | 0.5 + 100 | 79 | 63 |
| 140 + Nc | 0.5 + 1 | 87 | 73 |
| 140 + Da | 0.5 + 1 | 89 | 75 |
| 140 + Nd | 0.5 + 1 | 88 | 70 |
| 140 + Ia | 0.5 + 1 | 83 | 68 |
| 140 + Ca | 0.5 + 2 | 80 | 69 |
| 140 + Fa | 0.5 + 1 | 89 | 70 |
| 140 + Ma | 0.5 + 10 | 77 | 68 |
| 145 + Aa | 0.5 + 5 | 83 | 71 |
| 145 + Nb | 0.5 + 10 | 75 | 66 |
| 145 + Ab | 0.5 + 2 | 80 | 68 |
| 145 + Hd | 0.5 + 10 | 78 | 66 |
| 145 + Hb | 0.5 + 10 | 77 | 68 |
| 145 + Ha | 0.5 + 10 | 75 | 60 |

TABLE 4-5

Efficacies of mixtures

| Test compound | Test concentration (ppm) | Observed value Control index | Calculated value Control index (E) |
|---|---|---|---|
| 145 + Hc | 0.5 + 100 | 68 | 57 |
| 145 + He | 0.5 + 100 | 70 | 52 |
| 145 + Ea | 0.5 + 100 | 68 | 57 |
| 145 + Ed | 0.5 + 100 | 65 | 57 |
| 145 + Ec | 0.5 + 100 | 70 | 58 |
| 145 + Eb | 0.5 + 100 | 68 | 61 |
| 145 + Nc | 0.5 + 1 | 80 | 72 |
| 145 + Da | 0.5 + 1 | 85 | 73 |
| 145 + Nd | 0.5 + 1 | 79 | 68 |
| 145 + Ia | 0.5 + 1 | 81 | 66 |
| 145 + Ca | 0.5 + 2 | 79 | 67 |
| 145 + Fa | 0.5 + 1 | 85 | 68 |
| 145 + Ma | 0.5 + 10 | 79 | 66 |
| 390 + Aa | 0.5 + 5 | 87 | 75 |
| 390 + Nb | 0.5 + 10 | 93 | 70 |
| 390 + Ab | 0.5 + 2 | 85 | 71 |
| 390 + Hd | 0.5 + 10 | 89 | 70 |
| 390 + Hb | 0.5 + 10 | 79 | 72 |
| 390 + Ha | 0.5 + 10 | 79 | 64 |
| 390 + Hc | 0.5 + 100 | 73 | 61 |
| 390 + He | 0.5 + 100 | 75 | 57 |
| 390 + Ea | 0.5 + 100 | 72 | 61 |
| 390 + Ed | 0.5 + 100 | 79 | 62 |
| 390 + Ec | 0.5 + 100 | 78 | 63 |
| 390 + Eb | 0.5 + 100 | 78 | 65 |
| 390 + Nc | 0.5 + 1 | 90 | 75 |
| 390 + Da | 0.5 + 1 | 85 | 76 |
| 390 + Nd | 0.5 + 1 | 83 | 72 |
| 390 + Ia | 0.5 + 1 | 80 | 70 |
| 390 + Ca | 0.5 + 2 | 83 | 71 |
| 390 + Fa | 0.5 + 1 | 91 | 72 |
| 390 + Ma | 0.5 + 10 | 89 | 70 |
| 391 + Aa | 0.5 + 5 | 86 | 73 |
| 391 + Nb | 0.5 + 10 | 80 | 68 |
| 391 + Ab | 0.5 + 2 | 75 | 69 |
| 391 + Hd | 0.5 + 10 | 77 | 68 |
| 391 + Hb | 0.5 + 10 | 78 | 70 |
| 391 + Ha | 0.5 + 10 | 75 | 62 |
| 391 + Hc | 0.5 + 100 | 71 | 59 |
| 391 + He | 0.5 + 100 | 69 | 54 |
| 391 + Ea | 0.5 + 100 | 73 | 59 |
| 391 + Ed | 0.5 + 100 | 75 | 59 |
| 391 + Ec | 0.5 + 100 | 79 | 60 |
| 391 + Eb | 0.5 + 100 | 79 | 63 |
| 391 + Nc | 0.5 + 1 | 88 | 73 |
| 391 + Da | 0.5 + 1 | 89 | 75 |
| 391 + Nd | 0.5 + 1 | 88 | 70 |
| 391 + Ia | 0.5 + 1 | 84 | 68 |
| 391 + Ca | 0.5 + 2 | 81 | 69 |
| 391 + Fa | 0.5 + 1 | 89 | 70 |
| 391 + Ma | 0.5 + 10 | 78 | 68 |

As is clear from Tables 4-1 and 4-5 above, the mixtures of the invention compounds and the existing antimicrobial active compounds had larger observed values than the calculated values E, supporting the synergism of the combinations.

Potted young seedlings of cucumber (variety: SAGAMI HANJIRO; in two-and-a-half leaf stage) were sprayed with invention agri-horticulatural pest control compositions formulated in accordance with Preparations and the existing antimicrobial active compounds listed in Table 5 (all compounds are identified by associated letters of the alphabet) after they were diluted with water to predetermined concentrations so that they would serve as active compounds; a spray gun was used to provide a spray rate of 15 ml per pot. After air-drying, the seedlings were inoculated with conida of *Pseudoperonospora cubensis* by spraying a suspension of the conida. Immediately thereafter, the seedlings were held for a day under the conditions of 21° C. and 100% humidity. The seedlings were then placed at room temperature and 3 days later, the percentage of diseased area was investigated for each leaf; based on the result of this investigation, the control index was calculated as in Test 1.

The results are shown in Table 5 and Tables 6-1 to 6-3.

TABLE 5

Efficacies of individual active compounds

| Test compound | Test concentration (ppm) | Observed value Control index |
|---|---|---|
| 99 | 0.05 | 46 |
| 100 | 0.05 | 42 |
| 101 | 0.05 | 38 |
| 133 | 0.05 | 41 |
| 139 | 0.05 | 43 |
| 140 | 0.05 | 45 |
| 145 | 0.05 | 37 |
| 390 | 0.05 | 38 |
| 391 | 0.05 | 41 |
| Aa: Chlorothalonil | 0.5 | 49 |
| Ac: Manzeb | 1 | 52 |
| Fb: Cyazofamid | 0.1 | 50 |
| Fc: Amisulbrom | 0.1 | 37 |
| Na: Cymoxanil | 10 | 45 |
| Eb: Kresoxim-methyl | 1 | 42 |
| Ea: Azoxystrobin | 1 | 45 |
| Ba: Metalaxyl M | 10 | 35 |
| Jc: Mandipropamid | 0.5 | 21 |
| Jb: Benthiavalicarb-isopropyl | 0.5 | 12 |
| Ja: Dimethomorph | 5 | 21 |

TABLE 6-1

Efficacies of mixtures

| Test compound | Test concentration (ppm) | Observed value Control index | Calculated value Control index (E) |
|---|---|---|---|
| 99 + Aa | 0.05 + 0.5 | 80 | 72 |
| 99 + Ac | 0.05 + 1 | 79 | 74 |
| 99 + Fb | 0.05 + 0.1 | 80 | 73 |
| 99 + Fc | 0.05 + 0.1 | 79 | 66 |
| 99 + Na | 0.05 + 10 | 78 | 70 |
| 99 + Eb | 0.05 + 1 | 73 | 69 |
| 99 + Ea | 0.05 + 1 | 78 | 70 |
| 99 + Ba | 0.05 + 10 | 72 | 65 |
| 99 + Jc | 0.05 + 0.5 | 69 | 57 |
| 99 + Jb | 0.05 + 0.5 | 66 | 52 |
| 99 + Ja | 0.05 + 5 | 68 | 57 |
| 100 + Aa | 0.05 + 0.5 | 75 | 70 |
| 100 + Ac | 0.05 + 1 | 78 | 72 |
| 100 + Fb | 0.05 + 0.1 | 76 | 71 |
| 100 + Fc | 0.05 + 0.1 | 70 | 63 |
| 100 + Na | 0.05 + 10 | 72 | 68 |
| 100 + Eb | 0.05 + 1 | 73 | 66 |
| 100 + Ea | 0.05 + 1 | 75 | 68 |
| 100 + Ba | 0.05 + 10 | 69 | 62 |
| 100 + Jc | 0.05 + 0.5 | 62 | 54 |
| 100 + Jb | 0.05 + 0.5 | 59 | 49 |
| 100 + Ja | 0.05 + 5 | 58 | 54 |
| 101 + Aa | 0.05 + 0.5 | 75 | 68 |
| 101 + Ac | 0.05 + 1 | 78 | 70 |
| 101 + Fb | 0.05 + 0.1 | 75 | 69 |
| 101 + Fc | 0.05 + 0.1 | 69 | 61 |
| 101 + Na | 0.05 + 10 | 71 | 66 |
| 101 + Eb | 0.05 + 1 | 70 | 64 |
| 101 + Ea | 0.05 + 1 | 73 | 66 |
| 101 + Ba | 0.05 + 10 | 68 | 60 |

TABLE 6-2

Efficacies of mixtures

| Test compound | Test concentration (ppm) | Observed value Control index | Calculated value Control index (E) |
|---|---|---|---|
| 101 + Jc | 0.05 + 0.5 | 69 | 51 |
| 101 + Jb | 0.05 + 0.5 | 57 | 45 |
| 101 + Ja | 0.05 + 5 | 60 | 51 |
| 133 + Aa | 0.05 + 0.5 | 74 | 70 |
| 133 + Ac | 0.05 + 1 | 79 | 72 |
| 133 + Fb | 0.05 + 0.1 | 80 | 71 |
| 133 + Fc | 0.05 + 0.1 | 73 | 63 |
| 133 + Na | 0.05 + 10 | 74 | 68 |
| 133 + Eb | 0.05 + 1 | 71 | 66 |
| 133 + Ea | 0.05 + 1 | 78 | 68 |
| 133 + Ba | 0.05 + 10 | 69 | 62 |
| 133 + Jc | 0.05 + 0.5 | 60 | 53 |
| 133 + Jb | 0.05 + 0.5 | 58 | 48 |
| 133 + Ja | 0.05 + 5 | 62 | 53 |
| 139 + Aa | 0.05 + 0.5 | 75 | 71 |
| 139 + Ac | 0.05 + 1 | 79 | 73 |
| 139 + Fb | 0.05 + 0.1 | 78 | 72 |
| 139 + Fc | 0.05 + 0.1 | 69 | 64 |
| 139 + Na | 0.05 + 10 | 74 | 69 |
| 139 + Eb | 0.05 + 1 | 76 | 67 |
| 139 + Ea | 0.05 + 1 | 78 | 69 |
| 139 + Ba | 0.05 + 10 | 74 | 63 |
| 139 + Jc | 0.05 + 0.5 | 69 | 55 |
| 139 + Jb | 0.05 + 0.5 | 60 | 50 |
| 139 + Ja | 0.05 + 5 | 59 | 55 |
| 140 + Aa | 0.05 + 0.5 | 83 | 72 |
| 140 + Ac | 0.05 + 1 | 80 | 74 |
| 140 + Fb | 0.05 + 0.1 | 83 | 73 |
| 140 + Fc | 0.05 + 0.1 | 68 | 65 |
| 140 + Na | 0.05 + 10 | 75 | 70 |

TABLE 6-3

Efficacies of mixtures

| Test compound | Test concentration (ppm) | Observed value Control index | Calculated value Control index (E) |
|---|---|---|---|
| 140 + Eb | 0.05 + 1 | 72 | 68 |
| 140 + Ea | 0.05 + 1 | 78 | 70 |
| 140 + Ba | 0.05 + 10 | 67 | 64 |
| 140 + Jc | 0.05 + 0.5 | 62 | 57 |
| 140 + Jb | 0.05 + 0.5 | 60 | 52 |
| 140 + Ja | 0.05 + 5 | 63 | 57 |
| 145 + Aa | 0.05 + 0.5 | 74 | 68 |
| 145 + Ac | 0.05 + 1 | 76 | 70 |
| 145 + Fb | 0.05 + 0.1 | 73 | 69 |
| 145 + Fc | 0.05 + 0.1 | 68 | 60 |
| 145 + Na | 0.05 + 10 | 70 | 65 |
| 145 + Eb | 0.05 + 1 | 72 | 63 |
| 145 + Ea | 0.05 + 1 | 70 | 65 |
| 145 + Ba | 0.05 + 10 | 65 | 59 |
| 145 + Jc | 0.05 + 0.5 | 60 | 50 |
| 145 + Jb | 0.05 + 0.5 | 55 | 45 |
| 145 + Ja | 0.05 + 5 | 59 | 50 |
| 390 + Aa | 0.05 + 0.5 | 75 | 68 |
| 390 + Ac | 0.05 + 1 | 78 | 70 |
| 390 + Fb | 0.05 + 0.1 | 76 | 69 |
| 390 + Fc | 0.05 + 0.1 | 69 | 61 |
| 390 + Na | 0.05 + 10 | 72 | 66 |
| 390 + Eb | 0.05 + 1 | 70 | 64 |
| 390 + Ea | 0.05 + 1 | 74 | 66 |
| 390 + Ba | 0.05 + 10 | 69 | 60 |
| 390 + Jc | 0.05 + 0.5 | 69 | 51 |
| 390 + Jb | 0.05 + 0.5 | 58 | 45 |
| 390 + Ja | 0.05 + 5 | 60 | 51 |
| 391 + Aa | 0.05 + 0.5 | 74 | 70 |
| 391 + Ac | 0.05 + 1 | 79 | 72 |
| 391 + Fb | 0.05 + 0.1 | 83 | 71 |
| 391 + Fc | 0.05 + 0.1 | 75 | 63 |
| 391 + Na | 0.05 + 10 | 76 | 68 |
| 391 + Eb | 0.05 + 1 | 72 | 66 |
| 391 + Ea | 0.05 + 1 | 79 | 68 |
| 391 + Ba | 0.05 + 10 | 70 | 62 |

TABLE 6-3-continued

Efficacies of mixtures

| Test compound | Test concentration (ppm) | Observed value Control index | Calculated value Control index (E) |
|---|---|---|---|
| 391 + Jc | 0.05 + 0.5 | 62 | 53 |
| 391 + Jb | 0.05 + 0.5 | 58 | 48 |
| 391 + Ja | 0.05 + 5 | 64 | 53 |

(Note)
The two letters of the alphabet in Tables 6-1 to 6-3 have the same meanings as in Table 5.

As is clear from Tables 6-1 and 6-3 above, the mixtures of the invention compounds and the existing antimicrobial active compounds had larger observed values than the calculated values E, supporting the synergism of the combinations.

Test 3: Insecticidal Effect on *Aphis gossypii*

Invention compounds and the existing insecticidal active compounds shown in Table 7 (hereinbelow, the compound names are identified by associated letters of the alphabet) were diluted with water to predetermined concentrations so that they would serve as active ingredients. Cucumber leaves with a diameter of 3 cm were placed on plastic cups filled with 0.5% soft agar and five adult aphids were released to feed on the leaves. After standing overnight, the adult insects were removed and the number of nymph as an offspring was counted; each of the prepared liquid samples of insecticide was sprayed in 0.4 ml portions and two days later, the number of dead insects was countd to calculate the mortality rate. The expected efficacies of the combinations of the individual active compounds were calculated by Colby's formula.

The results are shown in Table 7 and Tables 8-1 and 8-2.

TABLE 7

Efficacies of individual active compounds

| Test compound | Test concentration (ppm) | Observed value Mortality rate |
|---|---|---|
| 99 | 0.1 | 44 |
| 100 | 0.1 | 40 |
| 101 | 0.1 | 36 |
| 133 | 0.1 | 39 |
| 139 | 0.1 | 41 |
| 140 | 0.1 | 43 |
| 145 | 0.1 | 35 |
| 390 | 0.1 | 41 |
| 391 | 0.1 | 43 |
| P: Acephate | 10 | 47 |
| Q: Imidacloprid | 0.01 | 50 |
| R: Tolfenpyrad | 0.5 | 48 |
| S: Acrinathrin | 0.1 | 35 |
| T: Flonicamid | 1 | 43 |
| U: Pyrifluquinazon | 0.01 | 40 |

TABLE 8-1

Efficacies of mixtures

| Test compound | Test concentration (ppm) | Observed value Mortality rate | Calculated value Mortality rate (E) |
|---|---|---|---|
| 99 + P | 0.1 + 10 | 82 | 71 |
| 99 + Q | 0.1 + 0.01 | 81 | 73 |
| 99 + R | 0.1 + 0.5 | 82 | 64 |
| 99 + S | 0.1 + 0.1 | 81 | 72 |
| 99 + T | 0.1 + 1 | 80 | 56 |
| 99 + U | 0.1 + 0.01 | 80 | 74 |
| 100 + P | 0.1 + 10 | 82 | 69 |
| 100 + Q | 0.1 + 0.01 | 81 | 71 |
| 100 + R | 0.1 + 0.5 | 82 | 61 |
| 100 + S | 0.1 + 0.1 | 81 | 70 |
| 100 + T | 0.1 + 1 | 80 | 53 |
| 100 + U | 0.1 + 0.01 | 75 | 72 |
| 101 + P | 0.1 + 10 | 82 | 67 |
| 101 + Q | 0.1 + 0.01 | 81 | 69 |
| 101 + R | 0.1 + 0.5 | 82 | 58 |
| 101 + S | 0.1 + 0.1 | 81 | 68 |
| 101 + T | 0.1 + 1 | 80 | 49 |
| 101 + U | 0.1 + 0.01 | 75 | 71 |
| 133 + P | 0.1 + 10 | 82 | 69 |
| 133 + Q | 0.1 + 0.01 | 81 | 71 |
| 133 + R | 0.1 + 0.5 | 82 | 60 |
| 133 + S | 0.1 + 0.1 | 81 | 70 |
| 133 + T | 0.1 + 1 | 80 | 52 |
| 133 + U | 0.1 + 0.01 | 79 | 72 |
| 139 + P | 0.1 + 10 | 82 | 70 |
| 139 + Q | 0.1 + 0.01 | 81 | 72 |
| 139 + R | 0.1 + 0.5 | 82 | 62 |
| 139 + S | 0.1 + 0.1 | 81 | 71 |
| 139 + T | 0.1 + 1 | 75 | 53 |
| 139 + U | 0.1 + 0.01 | 75 | 73 |

TABLE 8-2

Efficacies of mixtures

| Test compound | Test concentration (ppm) | Observed value Mortality rate | Calculated value Mortality rate (E) |
|---|---|---|---|
| 140 + P | 0.1 + 10 | 82 | 71 |
| 140 + Q | 0.1 + 0.01 | 81 | 73 |
| 140 + R | 0.1 + 0.5 | 82 | 63 |
| 140 + S | 0.1 + 0.1 | 81 | 72 |
| 140 + T | 0.1 + 1 | 75 | 55 |
| 140 + U | 0.1 + 0.01 | 80 | 74 |
| 145 + P | 0.1 + 10 | 82 | 67 |
| 145 + Q | 0.1 + 0.01 | 81 | 69 |
| 145 + R | 0.1 + 0.5 | 82 | 58 |
| 145 + S | 0.1 + 0.1 | 81 | 68 |
| 145 + T | 0.1 + 1 | 80 | 49 |
| 145 + U | 0.1 + 0.01 | 75 | 70 |
| 390 + P | 0.1 + 10 | 83 | 70 |
| 390 + Q | 0.1 + 0.01 | 81 | 72 |
| 390 + R | 0.1 + 0.5 | 82 | 62 |
| 390 + S | 0.1 + 0.1 | 82 | 71 |
| 390 + T | 0.1 + 1 | 75 | 53 |
| 390 + U | 0.1 + 0.01 | 75 | 73 |
| 391 + P | 0.1 + 10 | 85 | 71 |
| 391 + Q | 0.1 + 0.01 | 82 | 73 |
| 391 + R | 0.1 + 0.5 | 83 | 63 |
| 391 + S | 0.1 + 0.1 | 81 | 72 |
| 391 + T | 0.1 + 1 | 76 | 55 |
| 391 + U | 0.1 + 0.01 | 82 | 74 |

As is clear from Tables 8-1 and 8-1 above, the mixtures of the invention compounds and the existing insecticidal active compounds had larger observed values than the calculated values E, supporting the synergism of the combinations.

INDUSTRIAL APPLICABILITY

The agri-horticultural pest control compositions of the present invention which comprise one or more of 4-(3-butynyl)aminopyrimidine derivatives represented by the general formula [I] in combination with one or more existing antimicrobial active compounds and/or insecticidal active compounds show outstanding control effect on various plant diseases and pests; in particular, they need be used in only low doses to exhibit outstanding control effect on powdery mildew, downy mildew, and aphids, so they have an extremely high level of safety to useful crops. These effects can be attributed to the fact that the agri-horticultural pest control compositions of the present invention as a combination formulation have observed values greater than the values of E as calculated from Colby's formula, supporting the synergism of the combination. The present invention therefore has extremely high utility in the contemplated technical field.

What is claimed is:

1. An agri-horticultural pest control composition which comprises as active ingredients one or more compounds represented by the formula [I] and one or more agri-horticultural antimicrobial compounds or agri-horitcultural insecticidal compounds selected from among the following (1) to (39):

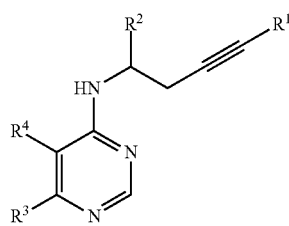

where $R^1$ is selected from among:
a) a monocyclic or bicyclic ring optionally containing 0-3 hetero atoms, as selected from the group consisting of phenyl, benzyl, oxazolyl, isoxazolyl, furyl, benzofuryl, isobenzofuryl, dihydrobenzofuryl, thiazolyl, isothiazolyl, naphthyl, pyrimidinyl, pyrazinyl, quinoxalyl, quinazolyl, pyridyl, quinolyl, isoquinolyl, benzothiazolyl, benzisothiazolyl, pyrrolyl, indolyl, isoindolyl, benzoxazolyl, benzisooxazolyl, thienyl, benzothienyl, imidazolyl, benzimidazolyl, pyrazolyl, and pyridonyl;
b) a linear or branched alkyl having 1-6 carbon atoms, a linear or branched alkenyl having 2-8 carbon atoms, a linear or branched alkynyl having 2-8 carbon atoms, a cycloalkyl having 3-8 carbon atoms, or a cycloalkenyl having 3-8 carbon atoms;
c) —$SiR^5R^6R^7$ (where $R^5$, $R^6$ and $R^7$ are a linear or branched alkyl having 1-6 carbon atoms, a linear or branched haloalkyl having 1-3 carbon atoms which is substituted by one halogen atom, a linear or branched cyanoalkyl having 1-3 carbon atoms which is substituted by one cyano group, and phenyl, provided that two or all of these may be the same substituent or all may be different substituents);
d) a hydrogen atom;
in the case of a) or b), $R^1$ may be substituted by —C(O)OR, —C(O)R, —R, —OR, —SR, —$SO_2R$, —OC(O)R, —C(O)NHR, —$C(O)NR_2$, —$NHSO_2R$, —$NRSO_2R$, —NHR, —$NR_2$, —NHC(O)R, —NRC(O)R, —NHC(O)OR, —NRC(O)OR, —N(OR)C(O)OR, —$NHSO_2R$, —$NRSO_2R$, —$SO_2NHR$, —$SO_2NR_2$ (where R is a linear or branched alkyl having 1-8 carbon atoms, a linear or branched alkenyl having 2-8 carbon atoms, a linear or branched alkynyl having 2-8 carbon atoms, or a cycloalkyl having 3-8 carbon atoms), —$SiR^5R^6R^7$, —$OSiR^5R^6R^7$ (where $R^5$, $R^6$ and $R^7$ are a linear or branched alkyl having 1-6 carbon atoms, a linear or branched haloalkyl having 1-3 carbon atoms which is substituted by one halogen atom, a linear or branched cyanoalkyl having 1-3 carbon atoms which is substituted by one cyano group, and phenyl, provided that two or all of these may be the same substituent or all may be different substituents), haloalkyl (a linear or branched alkyl group having 1-4 carbon atoms which is substituted by 1-9 halogen atoms which may be the same or different), haloalkenyl (a linear or branched alkenyl group having 2-6 carbon atoms which is substituted by 1-4 halogen atoms which may be the same or different), haloalkoxy (a linear or branched alkoxy group having 1-4 carbon atoms which is substituted by 1-9 halogen atoms which may be the same or different), acylalkoxy (a linear or branched alkoxy group having 1-3 carbon atoms which is substituted by one or two acyl groups represented by (a linear or branched aliphatic hydrocarbon group having 1-8 carbon atoms)-CO—), acyloxyalkyl (a linear or branched alkyl group having 1-3 carbon atoms which is substituted by one or two acyloxy groups represented by (a linear or branched aliphatic hydrocarbon group having 1-8 carbon atoms)-CO—O—), alkylsulfonylalkyl (a linear or branched alkyl group having 1-3 carbon atoms which is substituted by one or two linear or branched alkylsulfonyl groups having 1-8 carbon atoms), siloxyalkyl (a linear or branched alkyl group having 1-3 carbon atoms which is substituted by one or two —$OSiR^5R^6R^7$ (where $R^5$, $R^6$ and $R^7$ are a linear or branched alkyl having 1-6 carbon atoms, a linear or branched haloalkyl having 1-3 carbon atoms which is substituted by one halogen atom, a linear or branched cyanoalkyl having 1-3 carbon atoms which is substituted by one cyano group, and phenyl, provided that two or all of these may be the same substituent or all may be different substituents)), hydroxyalkyl (a linear or branched alkyl group having 1-3 carbon atoms which is substituted by one or two hydroxyl groups), alkoxyalkyl (a linear or branched alkyl group having 1-3 carbon atoms which is substituted by one or two linear or branched alkoxy groups having 1-8 carbon atoms), haloalkoxyalkyl (a linear or branched alkyl group having 1-3 carbon atoms which is substituted by one or two linear or branched haloalkoxy groups having 1-4 carbon atoms which are substituted by 1-9 halogen atoms which may be the same or different), alkylthioalkyl (a linear or branched alkyl group having 1-3 carbon atoms which is substituted by one or two linear or branched alkylthio groups having 1-8 carbon atoms), dialkoxyacetal (a dialkoxymethyl group having two linear or branched alkoxy groups with 1-8 carbon atoms substituted on the methyl group), alkoxyalkoxy (a linear or branched alkoxy group having 1-3 carbon atoms which is substituted by one or two linear or branched alkoxy groups having 1-8 carbon atoms), cyanoalkyl (a linear or branched alkyl group having 1-3 carbon atoms which is substituted by one or two cyano groups), halogen, cyano, nitro, amino, hydroxy, pentahalosulfanyl, benzyl, benzyloxy, phenyl, phenoxy, pyridyl, oxazolyl, furyl, thiazolyl, naphthyl, pyrimidinyl, thienyl, benzothiazolyl, benzoxazolyl, benzodioxolyl, imide, formyl (—CHO), carboxyl (—COOH), formamide (—NHCHO), cyclic ether, and cyclic amine;

$R^2$ represents a hydrogen atom, —R, —OR, —C(O)OR, —C(O)NHR, —$CONR_2$ (where R is a linear or branched alkyl having 1-8 carbon atoms, a linear or branched alkenyl having 2-8 carbon atoms, a linear or branched alkynyl having 2-8 carbon atoms, or a cycloalkyl having 3-8 carbon atoms), hydroxyalkyl (a linear or branched alkyl group having 1-3 carbon atoms which is substituted by 1 or 2 hydroxyl groups), alkoxyalkyl (a linear or branched alkyl group having 1-3 carbon atoms which is substituted by 1 or 2 alkoxy groups having 1-8 carbon atoms), haloalkoxyalkyl (a linear or branched alkyl groups having 1-3 carbon atoms which is substituted by 1 or 2 linear or branched haloalkoxy groups having 1-4 carbon atoms which are substituted by 1-9 halogen atoms which may be the same or different), phenyl, heteroaryl, halogen, cyano, haloalkyl (a linear or branched alkyl group having 1-4 carbon atoms which is substituted by 1-9 halogen atoms which may be the same or different), or haloalkoxy (a linear or branched alkoxy group having 1-4 carbon atoms which is substituted by 1-9 halogen atoms which may be the same or different);

$R^4$, taken together with $R^3$ and two carbon atoms of the pyrimidine ring, forms a benzene ring;

(1) chlorothalonil, dithianon, captan, folpet, iminoctadine albesilate, iminoctadine triacetate, ferbam, nabam, maneb, mancozeb, metiram, propineb, polycarbamate, thiram, ziram, zineb, cupric oxide, copper hydroxide, copper oxychloride, copper sulfate (anhydride), copper sulfate, and sulphur;

(2) metalaxyl, metalaxyl-M, oxadixyl, bupirimate, hymexazol, and oxolinic acid;

(3) benomyl, carbendazim, diethofencarb, thiophanate-methyl, zoxamide, pencycuron, and fluopicolide;

(4) furametpyr, penthiopyrad, thifluzamide, boscalid, oxycarboxin, carboxin, fluopyram, flutolanil, mepronil, sedaxane, isopyrazam, penflufen, bixafen, and fluxapyroxad;

(5) azoxystrobin, picoxystrobin, kresoxim-methyl, trifloxystrobin, orysastrobin, metominostrobin, pyraclostrobin, famoxadone, fenamidone, pyribencarb, dimoxystrobin, pyrametostrobin, and pyraoxystrobin;

(6) diflumetorim, cyazofamid, amisulbrom, meptyl dinocap, fluazinam, and ferimzone;

(7) cyprodinil, mepanipyrim, pyrimethanil, blasticidin-S, streptomycin, and kasugamycin;

(8) azaconazole, bitertanol, bromuconazole, cyproconazole, difenoconazole, epoxiconazole, fenbuconazole, furconazole, hexaconazole, imibenconazole, metconazole, myclobutanil, penconazole, propiconazole, simeconazole, tebuconazole, triadimefon, triadimenol, triticonazole, imazalil, triflumizole, pefurazoate, prochloraz, fenarimol, fenhexamid, fenpropimorph, piperalin, and spiroxamine;

(9) iprodione, myclozolin, procymidone, vinclozolin, quinoxyfen, fludioxonil, and proquinazid;

(10) iprobenfos, isoprothiolane, quintozene, propamocarb, and prothiocarb;

(11) validamycin, polyoxin B, dimethomorph, iprovalicarb, benthiavalicarb, mandipropamid, flumorph, and valifenalate;

(12) pyroquilon, tricyclazole, carpropamid, diclocymet, and fenoxanil;

(13) acibenzolar-S-methyl, probenazole, isotianil, and laminarin;

(14) cymoxanil, fosetyl-Al, triazoxide, methasulfocarb, flusulfamide, chinomethionat, ethaboxam, cyflufenamid, flutianil, metrafenone, tebufloquin, pyridylamidine, enestroburin, fluopyram, and pyrifenone;

(15) *Agrobacterium radiobacter, Bacillus subtilis, Erwinia carotovora, Pseudomonas fluorescens, Talaromyces flavus*, and *Trichoderma atroviride*;

(16) aldicarb, benfuracarb, carbaryl, carbofuran, carbosulfan, fenobucarb, methiocarb, methomyl, oxamyl, and thiodicarb;

(17) acephate, chlorpyrifos, diazinon, dimethoate, malathion, methamidophos, monocrotophos, parathion-methyl, profenofos, terbufos, and imicyafos;

(18) endosulfan, ethiprole, fipronil, and acetoprole;

(19) bifenthrin, cypermethrin, esfenvalerate, etofenprox, lambda-cyhalothrin, tefluthrin, DDT, and methoxychlor;

(20) acetamiprid, clothianidin, dinotefuran, imidacloprid, nitenpyram, thiacloprid, and thiamethoxam;

(21) spinetoram, and spinosad;

(22) abamectin, emamectin benzoate, milbemectin, and lepimectin;

(23) kinoprene, methoprene, fenoxycarb, and pyriproxyfen;

(24) methyl bromide, and chloropicrin;

(25) pymetrozine, and flonicamid;

(26) clofentezine, hexythiazox, and etoxazole;

(27) *Bacillus thuringiensis*;

(28) diafenthiuron, azocyclotin, cyhexatin, fenbutatin oxide, propargite, and tetradifon;

(29) chlorfenapyr;

(30) bensultap, cartap, and thiocyclam;

(31) chlorfluazuron, diflubenzuron, flufenoxuron, hexaflumuron, lufenuron, novaluron, teflubenzuron, triflumuron, buprofezin, bistrifluron, and noviflumuron;

(32) cyromazine, chromafenozide, halofenozide, methoxyfenozide, and tebufenozide;

(33) amitraz;

(34) fenazaquin, fenpyroximate, pyrimidifen, pyridaben, tebufenpyrad, tolfenpyrad, rotenone, hydramethylnon, and acequinocyl;

(35) aluminium phosphide;

(36) indoxacarb, and metaflumizone;

(37) spirodiclofen, spiromesifen, and spirotetramat;

(38) chlorantraniliprole, flubendiamide, and cyantraniliprole;

(39) azadirachtin, benzoximate, bifenazate, chinomethionat, dicofol, pyridalyl, pyrifluquinazon, and fluensulfone.

2. The agri-horticultural pest control composition according to claim 1 which comprises as active ingredients one or more compounds represented by the formula [I] recited in claim 1 and one or more antimicrobial active compounds selected from the group consisting of chlorothalonil, chinomethionate, iminoctadine albesilate, triflumizol, tebuconazole, difenoconazole, triadimefon, fenpropimorph, azoxystrobin, pyraclostrobin, trifloxystrobin, kresoxim-methyl, cyflufenamid, penthiopyrad, flutianil, quinoxyfen, thiophanate-methyl, diflumetorim, and acibenzolar-S-methyl.

3. The agri-horticultural pest control composition according to claim 1 which comprises as active ingredients one or more compounds represented by the formula [I] recited in claim 1 and one or more antimicrobial active compounds selected from the group consisting of chlorothalonil, manzeb, cyazofamid, amisulbrom, cymoxanil, kresoxim-methyl, azoxystrobin, metalaxyl M, mandipropamid, benthiavalicarb-isopropyl, and dimethomorph.

4. The agri-horticultural pest control composition according to claim 1 which comprises as active ingredients one or more compounds represented by the formula [I] recited in claim 1 and one or more insecticidal active compounds selected from the group consisting of acephate, imidacloprid, tolfenpyrad, acrinathrin, flonicamid, and pyrifluquinazon.

5. The agri-horticultural pest control composition according to claim 1, wherein the compound as an active ingredient is selected from the group consisting of compounds represented by the following formulae [II] to [X]:

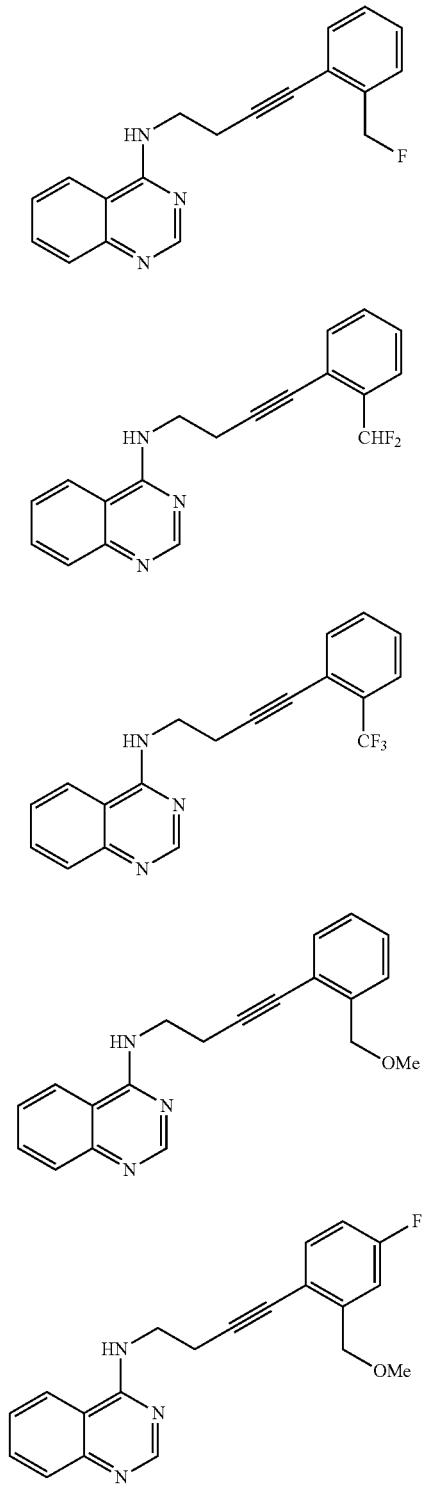
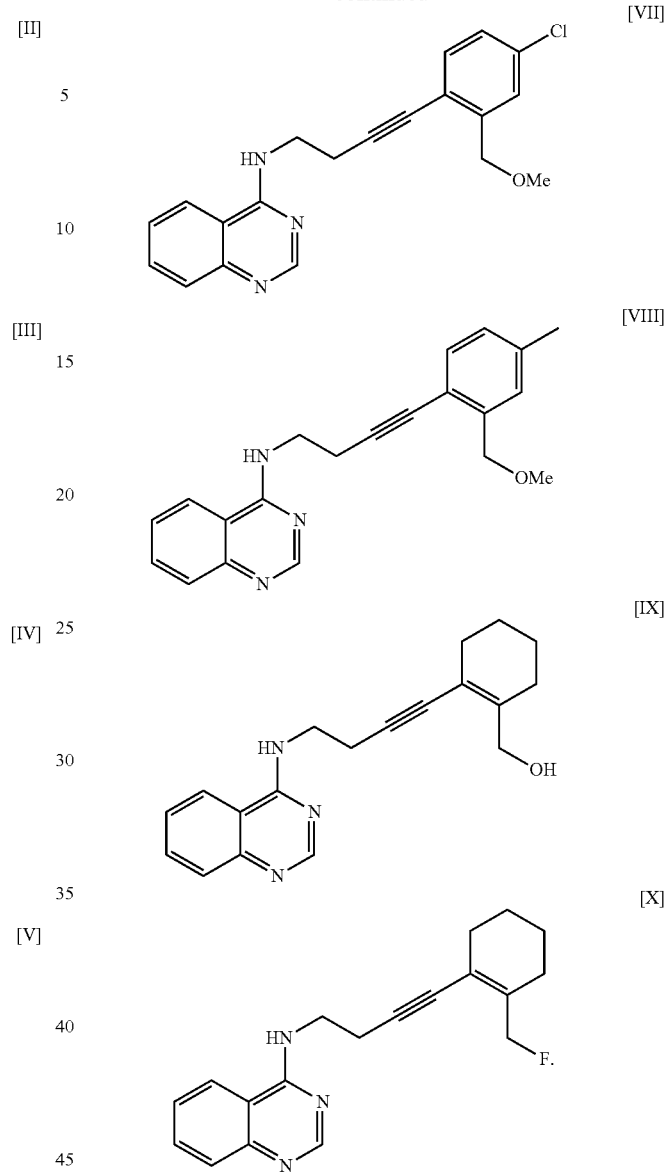

6. A method for controlling plant disease damage caused by a pathogenic microorganism with the agri-horticultural pest control composition as defined in claim 1, the method comprising:
   applying the composition as defined in claim 1 to a plant by spraying, dusting, or coating; or
   treating with the composition as defined in claim 1 a plant seed, a soil around a plant, or a soil, a rice pad or water for hydroponic culture where seeds are to be sown;
   wherein the application or treatment is effected either before or after the plant is infected with the pathogenic microorganism.

* * * * *

UNITED STATES PATENT AND TRADEMARK OFFICE
CERTIFICATE OF CORRECTION

PATENT NO. : 9,089,139 B2
APPLICATION NO. : 13/979306
DATED : July 28, 2015
INVENTOR(S) : Masaaki Sakai et al.

It is certified that error appears in the above-identified patent and that said Letters Patent is hereby corrected as shown below:

TITLE PAGE: ITEM (75), line 1, should read:

(75) Inventors: Masaaki Sakai, Ibaraki (JP);

Signed and Sealed this
Twenty-ninth Day of December, 2015

Michelle K. Lee
*Director of the United States Patent and Trademark Office*